US012539336B2

(12) United States Patent
Yang et al.

(10) Patent No.: US 12,539,336 B2

(45) Date of Patent: Feb. 3, 2026

(54) ANTIBODY, LINKERS, PAYLOAD, CONJUGATES AND APPLICATIONS THEREOF

(71) Applicant: GeneQuantum Healthcare (Suzhou) Co., Ltd., Jiang-su (CN)

(72) Inventors: Dong Yang, Jiang-su (KR); Mingyu Hu, Jiang-su (CN); Yajun Sun, Jiang-su (CN); Paul H. Song, Jiang-su (CN); Hanwen Xu, Jiang-su (CN); Gang Qin, Jiangsu (CN)

(73) Assignee: GENEQUANTUM HEALTHCARE (SUZHOU) CO., LTD., Jiang-Su (CN)

( * ) Notice: Subject to any disclaimer, the term of this patent is extended or adjusted under 35 U.S.C. 154(b) by 0 days.

(21) Appl. No.: 18/620,025

(22) Filed: Mar. 28, 2024

(65) Prior Publication Data

US 2025/0064953 A1 Feb. 27, 2025

Related U.S. Application Data

(63) Continuation of application No. PCT/CN2023/107444, filed on Jul. 14, 2023.

(30) Foreign Application Priority Data

Jul. 15, 2022 (WO) ................ PCT/CN2022/106014
Apr. 4, 2023 (WO) ................ PCT/CN2023/086107
Apr. 13, 2023 (WO) ................ PCT/CN2023/088115
Jul. 14, 2023 (WO) ................ PCT/CN2023/107444

(51) Int. Cl.

*A61K 47/68* (2017.01)
*A61K 31/437* (2006.01)
*A61K 47/65* (2017.01)
*C07K 16/30* (2006.01)

(52) U.S. Cl.

CPC ........ *A61K 47/6803* (2017.08); *A61K 31/437* (2013.01); *A61K 47/65* (2017.08); *C07K 16/30* (2013.01); *C07K 2317/565* (2013.01)

(58) Field of Classification Search

None

See application file for complete search history.

(56) References Cited

U.S. PATENT DOCUMENTS

| | | | |
|---|---|---|---|
| 5,834,476 | A | 11/1998 | Terasawa et al. |
| 7,517,964 | B2 | 4/2009 | Govindan et al. |
| 9,849,176 | B2 | 12/2017 | Govindan et al. |
| 9,872,923 | B2 | 1/2018 | Grawunder |

(Continued)

FOREIGN PATENT DOCUMENTS

| | | | |
|---|---|---|---|
| AU | 2021289927 | A1 | 1/2023 |
| AU | 2021359457 | A1 | 5/2023 |

(Continued)

OTHER PUBLICATIONS

Anti-Trop-2 antibody hRS7 VH region Seq Id 58, Supplemental Complex Repository for Examiners (SCORE): (Year: 2021).*

(Continued)

*Primary Examiner* — Karl J Puttlitz

(74) *Attorney, Agent, or Firm* — Ballard Spahr LLP

(57) ABSTRACT

The present disclosure relates to an antibody, a payload and a linker molecule for targeting molecule-drug conjugate, and the corresponding conjugate, the preparation and use thereof.

2 Claims, 12 Drawing Sheets

Specification includes a Sequence Listing.

(56) References Cited

U.S. PATENT DOCUMENTS

| | | | |
|---|---|---|---|
| 9,999,668 | B2 | 6/2018 | Govindan et al. |
| 10,195,288 | B2 | 2/2019 | Masuda et al. |
| 10,864,277 | B2 | 12/2020 | Grawunder et al. |
| 11,040,084 | B2 | 6/2021 | Qin et al. |
| 11,364,301 | B2 | 6/2022 | Grawunder et al. |
| 11,453,870 | B2 | 9/2022 | Qin et al. |
| 11,578,297 | B2 | 2/2023 | Qin et al. |
| 11,814,394 | B2 | 11/2023 | Yang et al. |
| 11,826,432 | B2 | 11/2023 | Qin et al. |
| 11,999,748 | B2 | 6/2024 | Qin et al. |
| 2011/0321183 | A1 | 12/2011 | Ploegh et al. |
| 2015/0297748 | A1 | 10/2015 | Masuda et al. |
| 2016/0193355 | A1 | 7/2016 | Qin et al. |
| 2016/0333112 | A1 | 11/2016 | Naito et al. |
| 2017/0035906 | A1 | 2/2017 | Naito et al. |
| 2017/0112944 | A1 | 4/2017 | Qin et al. |
| 2020/0129639 | A1 | 4/2020 | Levengood |
| 2021/0177929 | A1 | 6/2021 | Qin et al. |
| 2021/0187114 | A1 | 6/2021 | Qin et al. |
| 2021/0221907 | A1 | 7/2021 | Hou et al. |
| 2021/0347894 | A1 | 11/2021 | Ying et al. |
| 2021/0353764 | A1 | 11/2021 | Xu et al. |
| 2021/0401924 | A1 | 12/2021 | Qin et al. |
| 2022/0251494 | A1 | 8/2022 | Qin et al. |
| 2022/0251530 | A1 | 8/2022 | Qin et al. |
| 2022/0378927 | A1 | 12/2022 | Grawunder et al. |
| 2022/0378928 | A1 | 12/2022 | Zhu et al. |
| 2022/0378930 | A1 | 12/2022 | Song et al. |
| 2022/0395581 | A1 | 12/2022 | Qin et al. |
| 2022/0403360 | A1 | 12/2022 | Qin et al. |
| 2022/0411436 | A1 | 12/2022 | Zhu et al. |
| 2023/0054458 | A1 | 2/2023 | Yang et al. |
| 2023/0086097 | A1 | 3/2023 | Zhang et al. |
| 2023/0097252 | A1 | 3/2023 | Qin et al. |
| 2023/0101266 | A1 | 3/2023 | Qin et al. |
| 2023/0101735 | A1 | 3/2023 | Yang et al. |
| 2023/0140397 | A1 | 5/2023 | Ying et al. |
| 2023/0159875 | A1 | 5/2023 | Qin et al. |
| 2023/0165969 | A1 | 6/2023 | Yue et al. |
| 2023/0226207 | A1 | 7/2023 | Zhu et al. |
| 2023/0241242 | A1 | 8/2023 | Liang et al. |
| 2023/0381332 | A1 | 11/2023 | Zhu et al. |
| 2024/0018159 | A1 | 1/2024 | Yang et al. |
| 2024/0066141 | A1 | 2/2024 | Qin et al. |
| 2024/0174686 | A1 | 5/2024 | Zhang et al. |

FOREIGN PATENT DOCUMENTS

| | | | | | |
|---|---|---|---|---|---|
| CA | 3209426 | | | 8/2022 | |
| CN | 104755494 | A | | 7/2015 | |
| CN | 110167355 | A | | 8/2019 | |
| CN | 111689980 | A | | 9/2020 | |
| CN | 112125915 | | | 12/2020 | |
| CN | 202110159956.6 | | | 2/2021 | |
| CN | 202110533304.4 | | | 5/2021 | |
| CN | 202110718245.8 | | | 6/2021 | |
| CN | 202110936768.X | | | 8/2021 | |
| CN | 202111355330.9 | | | 11/2021 | |
| CN | 113816969 | A | | 12/2021 | |
| CN | 113827736 | A | | 12/2021 | |
| CN | 113943310 | A | | 1/2022 | |
| CN | 114569739 | A | | 6/2022 | |
| CN | 115103691 | A | | 9/2022 | |
| EP | 0495432 | A1 | | 7/1992 | |
| EP | 0 700 914 | A1 | | 3/1996 | |
| EP | 3725798 | A1 | | 10/2020 | |
| EP | 4095148 | A1 | | 11/2022 | |
| EP | 4129345 | A1 | | 2/2023 | |
| EP | 4130006 | A1 | | 2/2023 | |
| EP | 4130045 | A1 | | 2/2023 | |
| EP | 4162954 | A1 | | 4/2023 | |
| JP | 3359955 | B2 | | 3/1994 | |
| WO | WO 2003/074566 | A2 | | 9/2003 | |
| WO | WO 2005/051976 | A2 | | 6/2005 | |
| WO | WO 2010/087994 | A2 | | 8/2010 | |
| WO | WO 2014/057687 | A1 | | 4/2014 | |
| WO | WO 2014/177042 | A1 | | 11/2014 | |
| WO | WO 2015/047510 | A1 | | 4/2015 | |
| WO | WO 2015/115091 | A1 | | 8/2015 | |
| WO | WO 2015/165413 | A1 | | 11/2015 | |
| WO | WO 2018/112253 | A1 | | 6/2018 | |
| WO | WO 2020/016662 | A2 | | 1/2020 | |
| WO | WO 2020/063673 | A1 | | 4/2020 | |
| WO | WO 2020/063676 | A1 | | 4/2020 | |
| WO | WO 2021/007435 | A1 | | 1/2021 | |
| WO | WO 2021/052402 | A1 | | 3/2021 | |
| WO | WO 2021/115426 | A1 | | 6/2021 | |
| WO | WO 2021/147993 | A1 | | 7/2021 | |
| WO | WO-2021136475 | A1 | * | 7/2021 | ............. A61K 47/65 |
| WO | WO-2021136483 | A1 | * | 7/2021 | ......... A61K 47/6803 |
| WO | WO 2021/190581 | A1 | | 9/2021 | |
| WO | WO 2021/190583 | A1 | | 9/2021 | |
| WO | WO 2021/190586 | A1 | | 9/2021 | |
| WO | WO 2021/190602 | A1 | | 9/2021 | |
| WO | WO 2021/249228 | A1 | | 12/2021 | |
| WO | WO 2022/056696 | A1 | | 3/2022 | |
| WO | WO 2022/068878 | A1 | | 4/2022 | |
| WO | WO 2022/078259 | A1 | | 4/2022 | |
| WO | WO 2022/078260 | A1 | | 4/2022 | |
| WO | WO 2022/078279 | A1 | | 4/2022 | |
| WO | WO 2022/099762 | A1 | | 5/2022 | |
| WO | PCT/CN2022/101787 | | | 6/2022 | |
| WO | WO 2022/133722 | A1 | | 6/2022 | |
| WO | WO-2022159984 | A1 | * | 7/2022 | ......... A61K 47/6803 |
| WO | WO 2022/160156 | A1 | | 8/2022 | |
| WO | WO 2022/166762 | A1 | | 8/2022 | |
| WO | WO 2022/170676 | A1 | | 8/2022 | |
| WO | WO 2022/188740 | A1 | | 9/2022 | |
| WO | WO 2022/188743 | A1 | | 9/2022 | |
| WO | WO 2022/219331 | A1 | | 10/2022 | |
| WO | WO-2022218331 | A1 | * | 10/2022 | ........... A61K 31/165 |
| WO | WO 2022/236136 | A1 | | 11/2022 | |
| WO | WO 2022/253284 | A1 | | 12/2022 | |
| WO | PCT/CN2023/081140 | | | 3/2023 | |
| WO | PCT/CN2023/088092 | | | 4/2023 | |
| WO | WO-2023088235 | A1 | * | 5/2023 | ....... A61K 47/68037 |
| WO | WO 2023/143319 | A1 | | 8/2023 | |
| WO | WO 2023/143320 | A1 | | 8/2023 | |
| WO | WO 2024/012566 | A2 | | 1/2024 | |
| WO | WO-2024002154 | A1 | * | 1/2024 | ............. A61K 47/65 |
| WO | WO 2024/012569 | A1 | | 3/2024 | |

OTHER PUBLICATIONS

Anti-Trop-2 antibody hRS7 VL region, Seq Id 11; Supplemental Complex Repository for Examiners (Year: 2021).*

CAS No. 2019_1191462_1491917839_1, Entered Jun. 20, 2019.

Polson et al. (2009) "Antibody Drug Conjugates for the Treatment of Non-Hodgkin's Lymphoma: Target and Linker-Drug Selection," *Cancer Res.* 69(6): 2358-2364.

Ta et al. (2012) "Enzymatic Antibody Tagging: Toward a Universal Biocompatible Targeting Tool" *Trends Cardiovasc. Med.* 22(4).

U.S. Appl. No. 18/053,459 U.S. Pat. No. 11,814,394, filed Nov. 8, 2022 (Nov. 14, 2023), Dong Yang (GeneQuantum Healthcare (Suzhou) Co., Ltd.).

U.S. Appl. No. 18/453,748 (US 2024/0018159 A1), filed Aug. 22, 2023 (Jan. 18, 2024), Dong Yang (GeneQuantum Healthcare (Suzhou) Co., Ltd.).

P230101858, Jul. 15, 2022, Dong Yang (GeneQuantum Healthcare (Suzhou) Co., Ltd.).

PCT/CN2022/106014, Jul. 15, 2022, Dong Yang (GeneQuantum Healthcare (Suzhou) Co., Ltd.).

PCT/CN2023/086107, Apr. 3, 2023, Dong Yang (GeneQuantum Healthcare (Suzhou) Co., Ltd.).

PCT/CN2023/088115, Apr. 13, 2023, Dong Yang (GeneQuantum Helathcare (Suzhou) Co., Ltd.).

PCT/CN2023/107444 (WO 2024/012566 A2), filed Jul. 14, 2023 (Jan. 18, 2024), Dong Yang (GeneQuantum Healthcare (Suzhou) Co., Ltd.).

PCT/CN2021/130896, Nov. 16, 2021, ,Gang Qin (GeneQuantum Healthcare (Suzhou) Co., Ltd.).

(56) References Cited

OTHER PUBLICATIONS

PCT/CN2022/131904 (WO 2023/088235 A1), filed Nov. 15, 2022 (May 25, 2023), Gang Qin (GeneQuantum Healthcare (Suzhou) Co., Ltd.).
U.S. Appl. No. 18/711,006, Qin et al.
Sugimori, M. et al., “Synthesis and Antitumor Activity of Ring A- and F-Modified Hexacyclic Camptothecin Analogues,” Journal of Medicinal Chemistry, 1998, 41, 2308-2318.
Tamura, A. et al., “Re-evaluation and functional classification of non-synonymous single nucleotide polymorphisms of the human ATP-binding cassette transporter ABCG2,” Cancer Science, 2007, 98 (2), 231-239.
Wani, M. et al., “Plant Antitumor Agents. 23.1 Synthesis and Antileukemic Activity of Camptothecin Analogues,” Journal of Medicinal Chemistry, 1986, 29, 2358-2363.
Yaegashi, T. et al., “Synthesis and Antitumor Activity of 20(S)-Camptothecin Derivatives. A-Ring-Substituted 7-Ehtylcamptothecins and Their E-Ring-Modified Water-Soluble Derivatives,” Chemical and Pharmaceutical Bulletin, 1994, 42 (12), 2518-2525.
U.S. Appl. No. 18/879,386, Qin et al.

* cited by examiner

ANTIBODY, LINKERS, PAYLOAD, CONJUGATES AND APPLICATIONS THEREOF

CROSS-REFERENCE TO RELATED APPLICATIONS

This application is a continuation of International Application No. PCT/CN2023/107444, filed on Jul. 14, 2023, which claims the benefit of International Application No. PCT/CN2023/088115, filed on Apr. 13, 2023, International Application No. PCT/CN2023/086107, filed on Apr. 4, 2023, and International Application No. PCT/CN2022/106014, filed on Jul. 15, 2022, the contents of which are incorporated herein by reference in their entireties.

SEQUENCE LISTING STATEMENT

The Sequence Listing submitted on Apr. 9, 2024 as a xml file named "07570_0010U1_Sequence listing.xml" created on Apr. 9, 2024, and having a size of 44,179 bytes is hereby incorporated by reference pursuant to 37 C.F.R. §§ 1.831-1.835.

TECHNICAL FIELD

The present disclosure relates to the biopharmaceutical field, in particular, to an antibody, a payload and a linker for preparing targeting molecule-drug conjugates, and the corresponding conjugates, the preparing process and use thereof.

BACKGROUND

TROP2 is a transmembrane protein and was found to be overexpressed in several cancer types, including endometrial cancer, prostate cancer, pancreatic cancer, colon cancer, stomach cancer, oral cancer, glioma, making it a natural candidate for the development of targeted therapies. TROP2 acts as a regulator in cellular self-renewal, proliferation and transformation. Experiments have shown that TROP2 can promote tumor growth, and tumor cell proliferation is disturbed when the TROP2 gene is knocked out. The limited tissue expression of TROP2 reduces the toxicity of the treatment, which is also the advantage of targeting TROP2 therapy. Multiple TROP2 targeting ADC have been proposed, such as DS-1062, TRODELVY, BAT8003. These therapeutic agents have significantly improved the survival of TROP2 positive cancer patients.

DS-1062 is an antibody-conjugated drug developed by Daiichi Sankyo using its proprietary DXd ADC technology. It is composed of a monoclonal antibody targeting the Trop2 protein linked to DXd. The data, including more NSCLC patients, shows that DS-1062 exhibits good dose-dependent anticancer activity. As the dose was increased, more NSCLC patients' tumors shrank. TRODELVY is the first FDA-approved ADC specifically for relapsed or refractory metastatic TNBC and the first FDA-approved anti-TROP2 ADC. It consists of an antibody targeting TROP2 linked to SN-38, the active metabolite of the chemotherapeutic drug irinotecan.

However, new ADC drugs targeting TROP2 are still in great demand, and high-safety ADCs are also one of the development directions of the new drugs.

SUMMARY

In a first aspect, provided is a compound of formula (I):

formula (I)

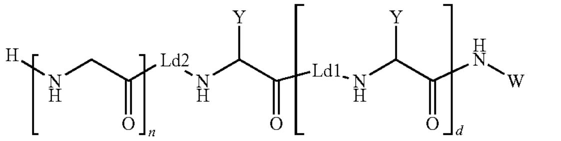

wherein,

W is hydrogen, LKb or —$C_2H_4$-$(PEG)_t$-(CO)$NH_2$;

Y is hydrogen or is LKa-LKb;

provided that W and Y are not simultaneously hydrogen;

each LKa is independently selected from

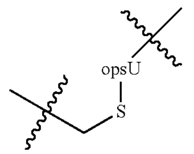

and

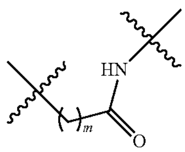

;

opSu is

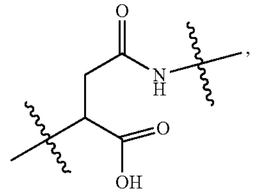

,

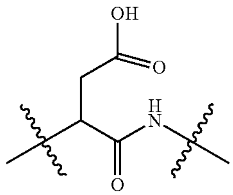

or a mixture thereof;

each LKb is independently $L^2$-$L^1$-B;

each B is independently a terminal group $R^{10}$, or a combination of the following 1), 2) and 3): 1) a self-immolative spacer Sp1; 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—; and 3) a terminal group $R^{10}$;

$R^{10}$ is hydrogen, or a group which can leave when reacting with a group in the payload;

$L^1$ is Cleavable sequence 1 comprising an amino acid sequence which can be cleaved by enzyme, and Cleavable sequence 1 comprises 1-10 amino acids;

$L^2$ is a bond; or a $C_{2-20}$ alkylene wherein one or more —$CH_2$— structures in the alkylene is optionally replaced by —$CR^3R^4$—, —O—, —(CO)—, —$S(=O)_2$—, —$NR^5$—, —$N^{\oplus}R^6R^7$—, $C_{4-10}$ cycloalkylene, $C_{4-10}$ heterocyclylene, phenylene; wherein the cycloalkylene, heterocyclylene and phenylene are each independently unsubstituted or substituted with at least one substituent selected from halogen, —$C_{1-10}$ alkyl, —$C_{1-10}$ haloalkyl, —$C_{1-10}$ alkylene-NH—$R^8$ and —$C_{1-10}$ alkylene-O—$R^9$;

Ld2 and each Ld1 are independently a bond; or selected from —NH—$C_{1-20}$ alkylene-(CO)—, —NH—$(PEG)_i$-(CO)—, or is a natural amino acid or oligomeric natural amino acids having a degree of polymerization of 2-10 independently unsubstituted or substituted with -$(PEG)_j$-$R^{11}$ on the side chain;

-$(PEG)_t$-, -$(PEG)_i$- and -$(PEG)_1$- are each a PEG fragment, which comprises the denoted number of consecutive —(O—$C_2H_4$)— structure units or consecutive —($C_2H_4$—O)— structure units, with an optional additional $C_{1-10}$ alkylene at one terminal;

$R^1$, $R^2$, $R^3$, $R^4$, $R^5$, $R^6$, $R^7$, $R^8$, $R^9$ are each independently selected from hydrogen, halogen, —$C_{1-10}$ alkyl, —$C_{1-10}$ haloalkyl, $C_{4-10}$ cycloalkylene; or $R^1$ and $R^2$ together with the carbon atom to which they are attached form a 3-6 membered cycloalkyl group; or $R^3$ and $R^4$ together with the carbon atom to which they are attached form a 3-6 membered cycloalkyl group;

$R^{11}$ is $C_{1-10}$ alkyl;

m is any integer of 1 to 3;

n is any integer of 2 to 20;

d is 0, or is any integer of 1 to 6; each i is independently an integer of 0-100, preferably 0 to 20; preferably each i is independently an integer of 0 to 12; more preferably 0 to 8; particularly 4;

each j is independently an integer of 1-100, preferably 1 to 20; preferably each j is independently an integer of 1 to 12; more preferably 8 to 12; particularly 8 or 12;

each t is independently an integer of 1-100, preferably 1 to 20; preferably each t is independently an integer of 1 to 12; more preferably 8 to 12; particularly 8 or 12.

In a second aspect, provided is a compound having the structure of formula (II)

formula (II)

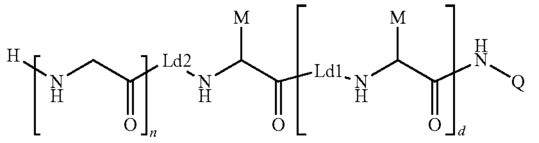

wherein

Q is hydrogen, —$C_2H_4$-$(PEG)_r$-(CO)$NH_2$ or LKb-P;

M is hydrogen or LKa-LKb-P;

provided that Q and M are not simultaneously hydrogen;

P is a payload which is linked to the B moiety or $L^1$ moiety of the compound of formula (I);

n, d, Ld1, Ld2, t, LKa and LKb are as defined in formula (I);

preferably, M is hydrogen or LKa-$L^2$-$L^1$-B—P; wherein each B is independently absent, or is a combination of the following 1) and 2): 1) a self-immolative spacer Sp1; and 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—;

preferably, Sp1 is selected from PABC, acetal, heteroacetal and the combination thereof; more preferably, Sp1 is acetal, heteroacetal or PABC; further preferably, the heteroacetal is selected from N,O— heteroacetal; more preferably, Sp1 is —O—$CH_2$—U— or —NH—$CH_2$—U—; wherein the —O— or the —NH— is connected to Cleavable sequence 1, and U is absent, or is O, S or NH, preferably O or S.

In a third aspect, provided is an anti-TROP2 antibody or antigen-binding fragment thereof, comprising a heavy chain variable region ($V_H$) and a light chain variable region ($V_L$), wherein the $V_H$ comprises:

(i) HCDR1 comprising the amino acid sequence of S $X_1$AGMN, wherein $X_1$ is N or A;

(ii) HCDR2 comprising the amino acid sequence of WINTDSGEPTYTDDFKG (SEQ ID NO: 10) or WINTYTGEPTYTDDFKG (SEQ ID NO: 8); and (iii) HCDR3 comprising the amino acid sequence of GGFGSSYWYFDV (SEQ ID NO: 11); and/or the $V_L$ comprises:

(i) LCDR1 comprising the amino acid sequence of KASQDVSIAVA (SEQ ID NO:13) or KASQDVSTAVA (SEQ ID NO:14);

(ii) LCDR2 comprising the amino acid sequence of SASYRYT (SEQ ID NO:15); and (iii) LCDR3 comprising the amino acid sequence of QQHYITPLT (SEQ ID NO: 16).

In a fourth aspect, provided is a cytotoxin having the structure of formula (i):

(i)

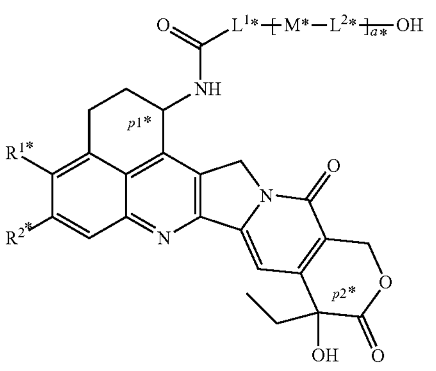

wherein, a* is 0 or 1;

the carbon atoms marked with p1* and p2* each is asymmetric center, and the asymmetric center is S configured, R configured or racemic;

$L^1$* is selected from $C_{1-6}$ alkylene, which is unsubstituted or substituted with one substituent selected from halogen, —OH and —$NH_2$;

M* is —$CH_2$—, —NH— or —O—;

$L^2$* is $C_1$-3 alkylene;

$R^1$* and $R^2$* are each independently selected from hydrogen, $C_{1-6}$ alkyl, halogen and $C_{1-6}$ alkoxy.

In a fifth aspect, provided is a conjugate having the structure of formula (III):

formula (III)

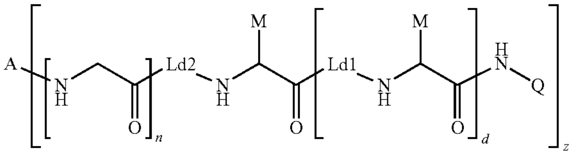

wherein,

Q is hydrogen, —$C_2H_4$-$(PEG)_t$-(CO)$NH_2$ or LKb-P;

M is hydrogen or LKa-LKb-P;

each LKa is independently selected from

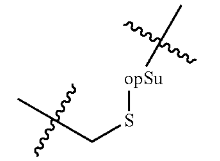 and 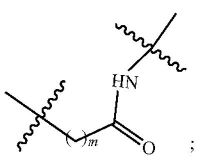 ;

opSu is

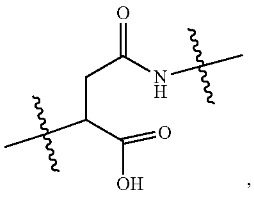 , 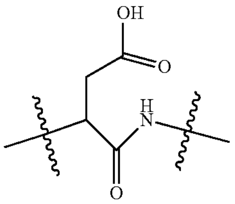

or a mixture thereof;

each LKb is independently $L^2$-$L^1$-B;

m, n, d, Ld1, Ld2, t, LKa and LKb are as defined in formula (I);

each B is independently absent, or is a combination of the following 1) and 2): 1) a self-immolative spacer Sp1; and 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—; preferably, B is —NH—$CH_2$—U—, absent, —NH—$CH_2$—U—$(CR^1R^2)_g$—(CO)— or NH—$CH_2$—U—$(CH_2)_g$—(CO)—;

provided that Q and M are not simultaneously hydrogen;

P is a payload which is linked to the B moiety or $L^1$ moiety of the compound of formula (I);

each $L^1$ is independently Cleavable sequence 1 comprising an amino acid sequence which can be cleaved by enzyme, and Cleavable sequence 1 comprises 1-10 amino acids;

each $L^2$ is independently a bond; or a $C_{2-20}$ alkylene wherein one or more —$CH_2$— structures in the alkylene is optionally replaced by —$CR^3R^4$—, —O—, —(CO)—, —S(=O)$_2$—, —$NR^5$—, —$N^{\oplus}R^6R^7$—, $C_{4-10}$ cycloalkylene, $C_{4-10}$ heterocyclylene, phenylene; wherein the cycloalkylene, heterocyclylene and phenylene are each independently unsubstituted or substituted with at least one substituent selected from halogen, —$C_{1-10}$ alkyl, —$C_{1-10}$ haloalkyl, —$C_{1-10}$ alkylene-NH—$R^8$ and —$C_{1-10}$ alkylene-O—$R^9$;

-$(PEG)_t$-, -$(PEG)_i$- and -$(PEG)_j$- are each a PEG fragment, which comprises the denoted number of consecutive —(O—$C_2H_4$)— structure units or consecutive —($C_2H_4$—O)— structure units, with an optional additional $C_{1-10}$ alkylene at one terminal;

$R^1$, $R^2$, $R^3$, $R^4$, $R^5$, $R^6$, $R^7$, $R^8$, $R^9$ are each independently selected from hydrogen, halogen, —$C_{1-10}$ alkyl, —$C_{1-10}$ haloalkyl, $C_{4-10}$ cycloalkylene; or $R^1$ and $R^2$ together with the carbon atom to which they are attached form a 3-6 membered cycloalkyl group; or $R^3$ and $R^4$ together with the carbon atom to which they are attached form a 3-6 membered cycloalkyl group;

each i is independently an integer of 0-100, preferably 0 to 20; preferably each i is independently an integer of 0 to 12; more preferably 0 to 8; particularly 4;

each j is independently an integer of 1-100, preferably 1 to 20; preferably each j is independently an integer of 1 to 12; more preferably 8 to 12; particularly 8 or 12;

each t is independently an integer of 1-100, preferably 1 to 20; preferably each t is independently an integer of 1 to 12; more preferably 8 to 12; particularly 8 or 12;

each g is independently an integer of 1-10, for example, 1, 2, 3, 4, 5, 6, 7;

A is anti-TROP2 antibody or antigen-binding fragment thereof which is linked to the $G_n$ moiety of the compound of formula (I); G is Glycine;

z is an integer of 1 to 20.

In a sixth aspect, provided is a use of anti-TROP2 antibody or antigen-binding fragment or the pharmaceutical composition thereof in the manufacture of a medicament for preventing or treating a disease; wherein the disease is a tumor.

In seventh aspect, provided is polynucleotide encoding antibody or antigen-binding fragment thereof.

In eighth aspect, provided is a vector comprising the polynucleotide.

In ninth aspect, provided is a host cell comprising the polynucleotide or the vector.

In tenth aspect, provided is a method of producing the antibody or antigen-binding fragment thereof, comprising:

(i) culturing the host cell under conditions suitable for the expression of the antibody or antigen-binding fragment thereof, and (ii) recovering the antibody or antigen-binding fragment thereof from the host cell or the cell culture thereof.

In another aspect, provided is pharmaceutical composition comprising a prophylactically or therapeutically effective amount of a conjugate, and at least one pharmaceutically acceptable carrier.

In another aspect, provided is pharmaceutical composition comprising a prophylactically or therapeutically effective amount of an antibody or antigen-binding fragment, and at least one pharmaceutically acceptable carrier.

In another aspect, provided is use of the conjugate, the antibody, or the pharmaceutical composition in the manufacture of a medicament for preventing or treating a disease; wherein the disease is a tumor.

In another aspect, provided is a method for treating a subject suffering a disease or preventing disease progression, comprises administering the conjugate, the antibody, or the pharmaceutical composition; and the disease is a tumor.

In one embodiment, the tumor is TROP2-associated tumor.

In some embodiments, the disease is a tumor. In some embodiments, the disease includes TROP2-positive tumor. In some embodiments, the disease includes tumor overexpressing TROP2 or tumor with TROP2 gene mutation. In some embodiments, the disease is selected from the group consisting of: fibrosarcoma, myxosarcoma, liposarcoma, chondrosarcoma, osteogenic sarcoma, chordoma, angiosarcoma, endotheliosarcoma, lymphangiosarcoma, lymphangioendothelial sarcoma, synovioma, mesothelioma, Ewing's tumor, leiomyosarcoma, rhabdomyosarcoma, colon cancer, pancreatic cancer, breast cancer, thyroid cancer, endometrial cancer, melanoma, ovarian cancer, prostate cancer, squamous cell carcinoma, basal cell carcinoma, adenocarcinoma, sweat gland carcinoma, sebaceous carcinoma, papillary carcinoma, papillary adenocarcinoma, cystadenocarcinoma, medullary carcinoma, bronchial carcinoma, renal cell carcinoma, liver cancer, bile duct cancer, choriocarcinoma, seminoma, embryonal carcinoma, Wilms' tumor, cervical cancer, testicular tumor, lung cancer, small cell lung cancer, bladder cancer, epithelial cancer, glioma, astrocytoma, medulloblastoma, craniopharyngioma, ependymoma, pinealoma, hemangioblastoma, acoustic neuroma, oligodendroglioma, meningioma, neuroblastoma and retinoblastoma. In one embodiment, the TROP2-associated tumor is selected from breast cancer, gastric cancer, lung cancer, ovarian cancer, and urothelial cancer.

In another aspect, provided is antibody drug conjugate comprises the antibody.

DETAILED DESCRIPTION

Figure 1A:
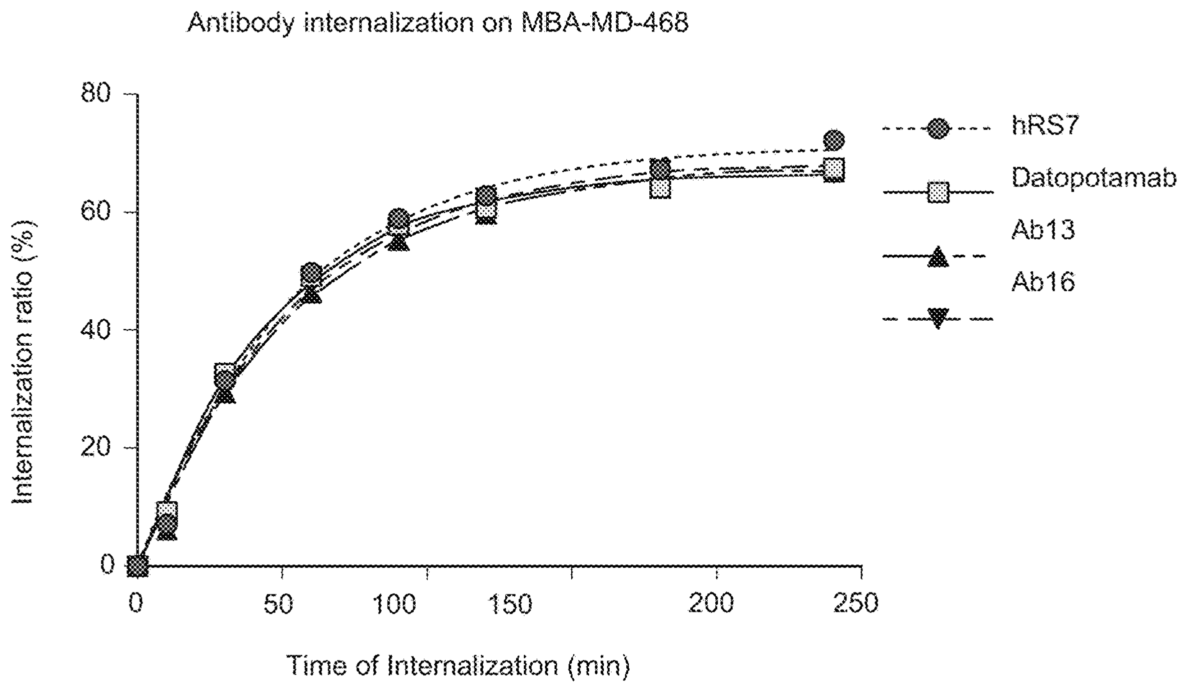
FIG. 1A shows the antibody internalization on MBA-MD-468.

The specific embodiments are provided below to illustrate technical contents of the present disclosure. Those skilled in the art can easily understand other advantages and effects of the present disclosure through the contents disclosed in the specification. The present disclosure can also be implemented or applied through other different specific embodiments. Various modifications and variations can be made by those skilled in the art without departing from the spirit of the present disclosure.

Definitions

Unless otherwise defined hereinafter, all technical and scientific terms used herein have the same meaning as commonly understood by those skilled in the art. The techniques used herein refer to those that are generally understood in the art, including the variants and equivalent substitutions that are obvious to those skilled in the art. While the following terms are believed to be readily comprehensible by those skilled in the art, the following definitions are set forth to better illustrate the present disclosure. When a trade name is present herein, it refers to the corresponding commodity or the active ingredient thereof. All patents, published patent applications and publications cited herein are hereby incorporated by reference.

When a certain amount, concentration, or other value or parameter is set forth in the form of a range, a preferred range, or a preferred upper limit or a preferred lower limit, it should be understood that it is equivalent to specifically revealing any range formed by combining any upper limit or preferred value with any lower limit or preferred value, regardless of whether the said range is explicitly recited. Unless otherwise stated, the numerical ranges listed herein are intended to include the endpoints of the range and all integers and fractions (decimals) within the range. For example, the expression "i is an integer of 1 to 20" means that i is any integer of 1 to 20, for example, i can be 1, 2, 3, 4, 5, 6, 7, 8, 9, 10, 11, 12, 13, 14, 15, 16, 17, 18, 19 or 20. Other similar expressions such as j, k and g should also be understood in a similar manner.

Unless the context clearly dictates otherwise, singular forms like "a" and "the" include the plural forms. The expression "one or more" or "at least one" may mean 1, 2, 3, 4, 5, 6, 7, 8, 9 or more.

The terms "about" and "approximately", when used in connection with a numerical variable, generally mean that the value of the variable and all values of the variable are within experimental error (for example, within a 95% confidence interval for the mean) or within =10% of a specified value, or a wider range.

The term "stoichiometric ratio" means matching various substances according to a certain amount by weight. For example, in the present disclosure, the active ingredient is mixed with a filler, a binder, and a lubricant in a designated weight ratio.

The term "optional" or "optionally" means the event described subsequent thereto may, but not necessarily happen, and the description includes the cases wherein said event or circumstance happens or does not happen.

The expressions "comprising", "including", "containing" and "having" are open-ended, and do not exclude additional unrecited elements, steps, or ingredients. The expression "consisting of" excludes any element, step, or ingredient not designated. The expression "consisting essentially of" means that the scope is limited to the designated elements, steps or ingredients, plus elements, steps or ingredients that are optionally present that do not substantially affect the essential and novel characteristics of the claimed subject matter. It should be understood that the expression "comprising" encompasses the expressions "consisting essentially of" and "consisting of".

As used herein, the term "antibody" is used in a broad way and particularly includes intact monoclonal antibodies, polyclonal antibodies, monospecific antibodies, multispecific antibodies (e.g., bispecific antibodies), and antibody fragments, as long as they have the desired biological activity. The antibody may be of any subtype (such as IgG, IgE, IgM, IgD, and IgA) or subclass, and may be derived from any suitable species. In some embodiments, the antibody is of human or murine origin. The antibody may also be a fully human antibody, humanized antibody or chimeric antibody prepared by recombinant methods.

Monoclonal antibodies are used herein to refer to antibodies obtained from a substantially homogeneous population of antibodies, i.e., the individual antibodies constituting the population are identical except for a small number of possible natural mutations. Monoclonal antibodies are highly specific for a single antigenic site. The word "monoclonal" refers to that the characteristics of the antibody are derived from a substantially homogeneous population of antibodies and are not to be construed as requiring some particular methods to produce the antibody.

An intact antibody or full-length antibody essentially comprises the antigen-binding variable region(s) as well as the light chain constant region(s) (CL) and heavy chain constant region(s) (CH), which could include CH1, CH2, CH3 and CH4, depending on the subtype of the antibody. An antigen-biding variable region (also known as a fragment variable region, Fv fragment) typically comprises a light chain variable region (VL) and a heavy chain variable region (VH). A constant region can be a constant region with a native sequence (such as a constant region with a human native sequence) or an amino acid sequence variant thereof. The variable region recognizes and interacts with the target antigen. The constant region can be recognized by and interacts with the immune system.

An antibody fragment may comprise a portion of an intact antibody, preferably its antigen-binding region or variable region. Examples of antibody fragments include Fab, Fab', F(ab')2, Fd fragment consisting of VH and CH1 domains, Fv fragment, single-domain antibody (dAb) fragment, and isolated complementarity determining region (CDR). The Fab fragment is an antibody fragment obtained by papain digestion of a full-length immunoglobulin, or a fragment having the same structure produced by, for example, recombinant expression. A Fab fragment comprises a light chain (comprising a VL and a CL) and another chain, wherein the said other chain comprises a variable domain of the heavy chain (VH) and a constant region domain of the heavy chain (CH1). The F(ab')2 fragment is an antibody fragment obtained by pepsin digestion of an immunoglobulin at pH 4.0-4.5, or a fragment having the same structure produced by, for example, recombinant expression. The F(ab')2 fragment essentially comprises two Fab fragments, wherein each heavy chain portion comprises a few additional amino acids, including the cysteines that form disulfide bonds connecting the two fragments. A Fab' fragment is a fragment comprising one half of a F(ab')2 fragment (one heavy chain and one light chain). The antibody fragment may comprise a plurality of chains joined together, for example, via a disulfide bond and/or via a peptide linker. Examples of antibody fragments also include single-chain Fv (scFv), Fv, dsFv, diabody, Fd and Fd' fragments, and other fragments, including modified fragments. An antibody fragment typically comprises at least or about 50 amino acids, and typically at least or about 200 amino acids. An antigen-binding fragment can include any antibody fragment that, when inserted into an antibody framework (e.g., by substitution of the corresponding region), can result in an antibody that immunospecifically binds to the antigen.

Antibodies according to the present disclosure can be prepared using techniques well known in the art, such as the following techniques or a combination thereof: recombinant techniques, phage display techniques, synthetic techniques, or other techniques known in the art. For example, a genetically engineered recombinant antibody (or antibody mimic) can be expressed by a suitable culture system (e.g., *E. coli* or mammalian cells). The engineering can refer to, for example, the introduction of a ligase-specific recognition sequence at its terminals.

Cytotoxin refers to a substance that inhibits or prevents the expression activity of a cell, cellular function, and/or causes destruction of cells. The cytotoxins currently used in ADCs are more toxic than chemotherapeutic drugs. Examples of cytotoxins include, but are not limited to, drugs that target the following targets: microtubule cytoskeleton, DNA, RNA, kinesin-mediated protein transport, regulation of apoptosis. The drug that targets microtubule cytoskeleton may be, for example, a microtubule-stabilizing agent or a tubulin polymerization inhibitor. Examples of microtubule-stabilizing agents include but are not limited to taxanes. Examples of tubulin polymerization inhibitors include but are not limited to maytansinoids, auristatins, vinblastines, colchicines, and dolastatins. The DNA-targeting drug can be, for example, a drug that directly disrupts the DNA structure or a topoisomerase inhibitor. Examples of drugs that directly disrupt DNA structure include but are not limited to DNA double strand breakers, DNA alkylating agents, DNA intercalators. The DNA double strand breakers can be, for example, an enediyne antibiotic, including but not limited to dynemicin, esperamicin, neocarzinostatin, uncialamycin, and the like. The DNA alkylating agent may be, for example, a DNA bis-alkylator (i.e. DNA-cross linker) or a DNA mono-alkylator. Examples of DNA alkylating agents include but are not limited to pyrrolo[2,1-c][1,4] benzodiazepine (PBD) dimer, 1-(chloromethyl)-2,3-dihydrogen-1H-benzo[e]indole (CBI) dimer, CBI-PBD heterodimer, dihydroindolobenzodiazepine (IGN) dimer, duocarmycin-like compound, and the like. Examples of topoisomerase inhibitors include but are not limited to exatecan and derivatives thereof (such as DX8951f, DXd-(1) and DXd-(2), the structures of which are depicted below), camptothecins and anthracyclines. The RNA-targeting drug may be, for example, a drug that inhibits splicing, and examples thereof include but are not limited to pladienolide. Drugs that target kinesin-mediated protein transport can be, for example, mitotic kinesin inhibitors including, but not limited to, kinesin spindle protein (KSP) inhibitors.

A spacer is a structure that is located between different structural modules and can spatially separate the structural modules. The definition of spacer is not limited by whether it has a certain function or whether it can be cleaved or degraded in vivo. Examples of spacers include but are not limited to amino acids and non-amino acid structures, wherein non-amino acid structures can be, but are not limited to, amino acid derivatives or analogues. "Spacer sequence" refers to an amino acid sequence serving as a spacer, and examples thereof include but are not limited to a single amino acid, a sequence containing a plurality of amino acids, for example, a sequence containing two amino acids such as GA, etc., or, for example, GGGGS, GGGGSGGGGS, GGGGSGGGGSGGGGS, etc. Self-immolative spacers are covalent assemblies tailored to correlate the cleavage of two chemical bonds after activation of a protective part in a precursor: Upon stimulation, the protective moiety (such as a cleavable sequence) is removed, which generates a cascade of disassembling reactions leading to the temporally sequential release of smaller molecules. Examples of self-immolative spacers include but not limited to PABC (p-benzyloxycarbonyl), acetal, heteroacetal and the combination thereof.

The term "alkyl" refers to a straight or branched saturated aliphatic hydrocarbon group consisting of carbon atoms and hydrogen atoms, which is connected to the rest of the molecule through a single bond. The alkyl group may contain 1 to 20 carbon atoms, referring to $C_1$-$C_{20}$ alkyl group, for example, $C_1$-$C_4$ alkyl group, $C_1$-$C_3$ alkyl group, $C_1$-$C_2$ alkyl, $C_3$ alkyl, $C_4$ alkyl, $C_3$-$C_6$ alkyl. Non-limiting examples of alkyl groups include but are not limited to methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethyl butyl, 1,1-dimethylbutyl, 2,3-dimethylbutyl, 1,3-dimethylbutyl or 1,2-dimethylbutyl, or their isomers. A bivalent radical refers to a group obtained from the corresponding monovalent radical by removing one hydrogen atom from a carbon atom with free valence electron(s). A bivalent radical has two connecting sites which are connected to the rest of the molecule. For example, an "alkylene" or an "alkylidene" refers to a saturated divalent hydrocarbon group, either straight or branched. Examples of alkylene groups include but are not limited to methylene ($—CH_2—$), ethylene ($—C_2H_4—$), propylene ($—C_3H_6—$), butylene ($—C_4H_8—$), pentylene ($—C_5H_{10}—$), hexylene ($—C_6H_{12}—$), 1-methylethylene ($—CH(CH_3)CH_2—$), 2-methylethylene ($—CH_2CH(CH_3)—$), methylpropylene, ethylpropylene, and the like.

As used herein, when a group is combined with another group, the connection of the groups may be linear or branched, provided that a chemically stable structure is formed. The structure formed by such a combination can be connected to other moieties of the molecule via any suitable atom in the structure, preferably via a designated chemical bond. For example, when two or more of the bivalent groups selected from: $—CR^1R^2—C_{4-10}$ alkylene, $C_{4-10}$ cycloalkylene, $C_{4-10}$ heterocyclylene and —(CO)— are combined together to form a combination, the two or more of the bivalent groups may form a linear connection with each other, such as $—CR^1R^2—C_{1-10}$ alkylene-(CO)—, $—CR^1R^2—C_{4-10}$ cycloalkylene-(CO)—, $—CR^1R^2—C_{4-10}$ cycloalkylene-$C_{1-10}$ alkylene-(CO)—, $—CR^1R^2—CR^{1'}R^{2'}—$(CO)—, $—CR^1R^2—CR^{1'}R^{2'}—CR^{1''}R^{2''}—$(CO)—, etc. The resulting bivalent structure can be further connected to other moieties of the molecule.

As used herein, the expressions "antibody-conjugated drug" and "antibody-drug conjugate" has the same meaning.

Compound of Formula (I)

In one aspect, provided is a compound of formula (I):

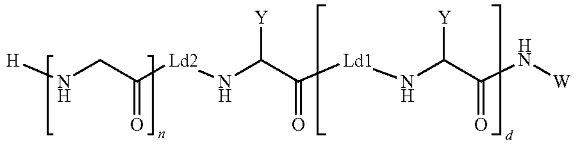

wherein,

W is hydrogen, LKb or $—C_2H_4$-$(PEG)_i$-$(CO)NH_2$;

Y is hydrogen or is LKa-LKb;

provided that W and Y are not simultaneously hydrogen;

each LKa is independently selected from

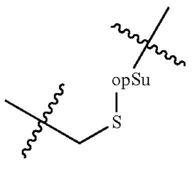

and

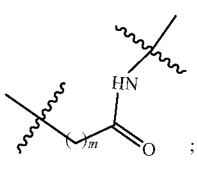

;

opSu is

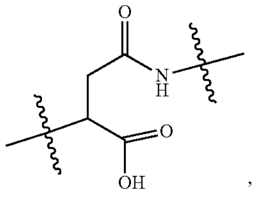

,

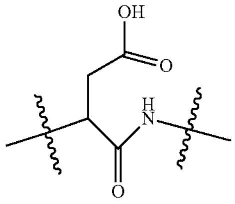

or a mixture thereof;

each LKb is independently $L^2$-$L^1$-B;

each B is independently a terminal group $R^{10}$, or a combination of the following 1), 2) and 3): 1) a self-immolative spacer Sp1; 2) a bond, or one of or a combination of two or more of the bivalent groups selected from: $—CR^1R^2—$, $C_{1-10}$ alkylene, $C_{4-10}$ cycloalkylene, $C_{4-10}$ heterocyclylene and —(CO)—; and 3) a terminal group $R^{10}$;

$R^{10}$ is hydrogen, or a group which can leave when reacting with a group in the payload;

each $L^1$ is independently Cleavable sequence 1 comprising an amino acid sequence which can be cleaved by enzyme, and Cleavable sequence 1 comprises 1-10 amino acids;

each $L^2$ is independently a bond; or a $C_{2-20}$ alkylene wherein one or more $—CH_2—$ structures in the alkylene is optionally replaced by $—CR^3R^4—$, —O—, —(CO)—, $—S(=O)_2—$, $—NR^5—$, $—N^{\oplus}R^6R^7—$, $C_{4-10}$ cycloalkylene, $C_{4-10}$ heterocyclylene, phenylene; wherein the cycloalkylene, heterocyclylene and phenylene are each independently unsubstituted or substituted with at least one substituent selected from halogen, $—C_{1-10}$ alkyl, $—C_{1-10}$ haloalkyl, $—C_{1-10}$ alkylene-$NH—R^8$ and $—C_{1-10}$ alkylene-$O—R^9$;

Ld2 and each Ld1 are independently a bond; or selected from $—NH—C_{1-20}$ alkylene-(CO)—, $—NH—(PEG)_i$-(CO)—, or is a natural amino acid or oligomeric natural amino acids having a degree of polymerization of 2-10 independently unsubstituted or substituted with -$(PEG)_j$-$R^{11}$ on the side chain;

$(PEG)_i$-, -$(PEG)_i$- and -$(PEG)_1$- are each a PEG fragment, which comprises the denoted number of consecutive $—(O—C_2H_4)—$ structure units or consecutive $—(C_2H_4—O)—$ structure units, with an optional additional $C_{1-10}$ alkylene at one terminal;

$R^1$, $R^2$, $R^3$, $R^4$, $R^5$, $R^6$, $R^7$, $R^8$, $R^9$ are each independently selected from hydrogen, halogen, $—C_{1-10}$ alkyl, $—C_{1-10}$ haloalkyl, $C_{4-10}$ cycloalkylene; or $R^1$ and $R^2$ together with the carbon atom to which they are attached form a 3-6 membered cycloalkyl group; or $R^3$ and $R^4$ together with the carbon atom to which they are attached form a 3-6 membered cycloalkyl group;

$R^{11}$ is $C_{1-10}$ alkyl;

m is any integer of 1 to 3;

n is any integer of 2 to 20;

d is 0, or is any integer of 1 to 6;

each i is independently an integer of 0-100, preferably 0 to 20; preferably each i is independently an integer of 0 to 12; more preferably 0 to 8; particularly 4;

each j is independently an integer of 1-100, preferably 1 to 20; preferably each j is independently an integer of 1 to 12; more preferably 8 to 12; particularly 8 or 12;

each t is independently an integer of 1-100, preferably 1 to 20; preferably each t is independently an integer of 1 to 12; more preferably 8 to 12; particularly 8 or 12.

In one embodiment, $L^2$ is selected from: $-(CH_2)_p-(CH_2)_2(CO)-$, p is 0, or an integer of 1 to 5;

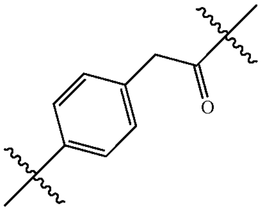
;

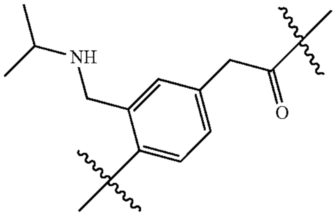
;

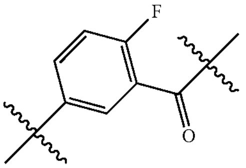
,

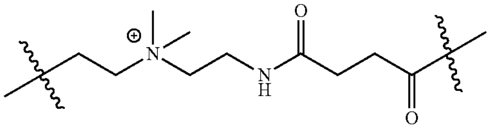
;

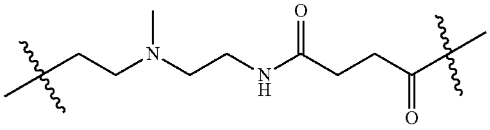
;

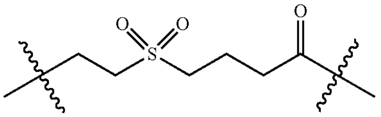
;

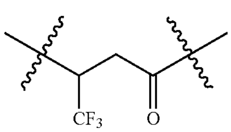
;

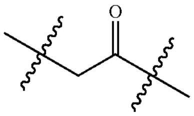
;

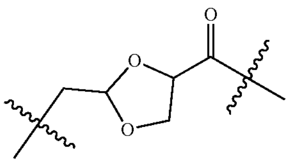
;

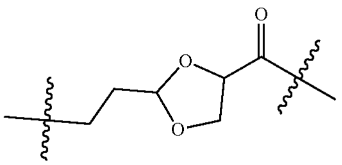
;

-continued

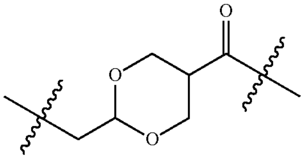
;

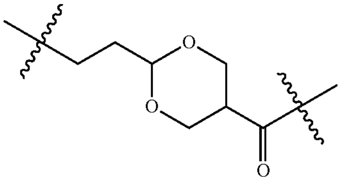
; and

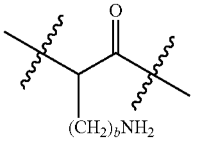
, b is an integer of 1 to 10.

In one embodiment, p is 0 to 3; preferably 3.

In one embodiment, $L^2$ is selected from: $-(C_2H_4-O)_p-(CH_2)_2(CO)-$, p is an integer of 1 to 5; more preferably p is 2 or 4.

In one embodiment, the carbonyl group in each of the above structure of $L^2$ is connected to $L^1$, and the other linking site is connected to opSu.

In one embodiment, the carbonyl group in each of the above structure of $L^2$ is connected to $L^1$, and the other linking site is connected to an amide.

Ld2 and each Ld1 are independently a bond or

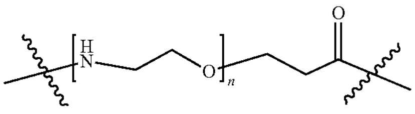
or

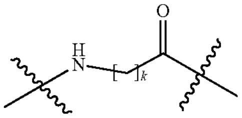
or

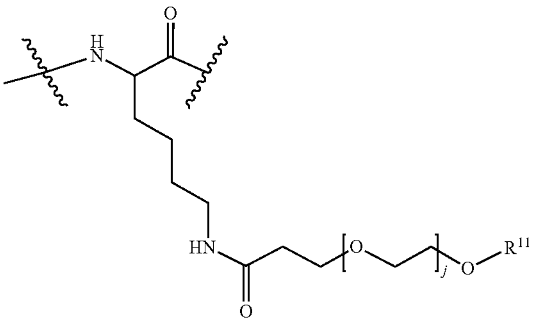
or

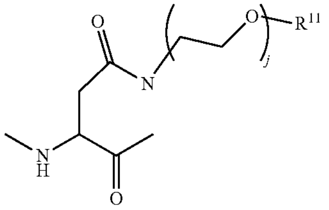
or

-continued

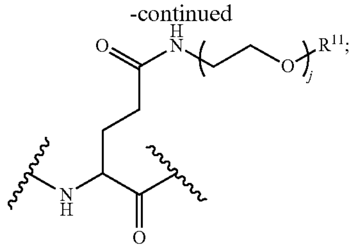

each i is independently an integer of 0-100;

each j and k are independently an integer of 1-100.

In one embodiment, each i is independently an integer of 0 to 20. In one embodiment, each i is independently an integer of 0 to 12.

In one embodiment, each j and k are independently an integer of 1 to 20. In one embodiment, each j and k are independently an integer of 1 to 12.

In one embodiment, each i is independently an integer of 0 to 8; particularly 4.

In one embodiment, each j is independently an integer of 8 to 12; particularly 8 or 12.

In one embodiment, each k is independently an integer of 1 to 7; particularly 1, or 3 or 5.

In one embodiment, Ld2 and each Ld1 are independently a bond; or a $C_{1-20}$ alkylene with an amino and a carbonyl at the two terminals respectively, or a PEG fragment of a certain length (denoted as -(PEG)$_i$-) with an amino and a carbonyl at the two terminals respectively, or one or more natural amino acids independently unsubstituted or substituted with a PEG fragment of a certain length (denoted as -(PEG)$_j$-) on the side chain.

In one embodiment, -(PEG)$_i$- comprises —(O—$C_2H_4$)$_i$— or —($C_2H_4$—O)$_i$—, and an optional additional $C_{1-10}$ alkylene at one terminal; -(PEG)$_j$-, comprises —(O—$C_2H_4$)$_j$— or —($C_2H_4$—O)$_j$—, and an optional additional $C_{1-10}$ alkylene at one terminal. In one embodiment, -(PEG)$_i$- comprises —$C_2H_4$—(O—$C_2H_4$)$_i$— or —($C_2H_{4-0}$)$_i$—$C_2H_4$—.

It is to be understood that when there are two or more Ld1, B, $L^2$ or $L^1$ structures in the molecule, the structure of each Ld1, B, $L^2$ or $L^1$ is selected independently. When there are two or more $R^x$ (x being 1, 2, 3, 4, 5, 6, 7, 8, 9, etc.) in the molecule, each $R^x$ is selected independently. In some embodiments, the "x"s in the molecule are denoted with or without additional apostrophe (') or apostrophes (such as '', ''', '''', etc.), for example R, $R^{1'}$, $R^{1''}$, $R^{1'''}$, $R^{2'}$, $R^{2''}$, $R^{2'''}$, etc, wherein each $R^x$, with or without additional apostrophe or apostrophes, are selected independently. The other $R^x$s such as $R^3$, $R^4$, $R^5$, $R^6$, $R^7$, $R^8$, $R^9$, and "Ld1"s, "B"s, "$L^2$"s and "$L^1$"s should be understood in a similar way. In some embodiments, the "i"s in the molecule are denoted with or without additional numbers, for example i1, i2, i3, i4, etc., wherein the numbers do not indicate any sequence, but are used merely to differentiate the "i"s. And each "i"s, with or without additional numbers, are selected independently.

In one embodiment, Cleavable sequence 1 is selected from Gly-Gly-Phe-Gly, Phe-Lys, Val-Cit, Val-Lys, Gly-Phe-Leu-Gly, Ala-Leu-Ala-Leu, Ala-Ala-Ala and the combination thereof; preferably, Cleavable sequence 1 is Gly-Gly-Phe-Gly.

In one embodiment, W is hydrogen.

In one embodiment, W is —$C_2H_4$-(PEG)$_t$-(CO)$NH_2$, wherein t is independently an integer of 1-100, preferably 1 to 20; preferably each t is independently an integer of 1 to 12; more preferably 8 to 12; particularly 8 or 12.

In one embodiment, $R^{11}$ is $C_{1-6}$ alkyl, preferably methyl.

In one embodiment, n is an integer of 2 to 5, especially 3.

In one embodiment, d is 0, or is any integer of 1 to 4; preferably 0, 1, 2 or 3.

Thiosuccinimide is unstable under physiological conditions and is liable to reverse Michael addition which leads to cleavage at the conjugation site. Moreover, when another thiol compound is present in the system, thiosuccinimide may also undergo thiol exchange with the other thiol compound. Both of these reactions cause the fall-off of the payload and result in toxic side effects. In the present disclosure, when applied in the linker, the ring-opened succinimide structure no longer undergoes reverse Michael addition or thiol exchange, and thus the product is more stable. Method of ring opening reaction can be found in WO2015165413A1.

The compound comprising ring-opened succinimide moiety can be purified by semi-preparative/preparative HPLC or other suitable separation means to obtain with high purity and defined composition, regardless of the efficiency of the succinimide ring opening reaction.

Moiety Comprising Recognition Sequence of the Ligase Acceptor or Donor Substrate In one embodiment, the G, moiety of the compound of formula (I) is a recognition sequence of a ligase acceptor substrate, which facilitates enzyme-catalyzed coupling of compound of formula (I) with the targeting molecule under the catalysis of the ligase. The targeting molecule optionally modified and comprises the corresponding recognition sequence of a ligase acceptor substrate.

In one embodiment, the ligase is a transpeptidase. In one embodiment, the ligase is selected from the group consisting of a natural transpeptidase, an unnatural transpeptidase, variants thereof, and the combination thereof. Unnatural transpeptidase enzymes can be, but are not limited to, those obtained by engineering of natural transpeptidase. In a preferred embodiment, the ligase is selected from the group consisting of a natural Sortase, an unnatural Sortase, and the combination thereof. The species of natural Sortase include Sortase A, Sortase B, Sortase C, Sortase D, Sortase *L. plantarum*, etc. (detailed description can be found in US20110321183A1, which is incorporated herein by reference). The type of ligase corresponds to the ligase recognition sequence and is thereby used to achieve specific conjugation between different molecules or structural fragments.

In some embodiments, the ligase is a Sortase selected from Sortase A, Sortase B, Sortase C, Sortase D and Sortase *L. plantarum*. In these embodiments, the recognition sequence of the ligase acceptor substrate is selected from the group consisting of oligomeric Glycine, oligomeric alanine, and a mixture of oligomeric Glycine/alanine having a degree of polymerization of 3-10. In a particular embodiment, the recognition sequence of the ligase acceptor substrate is $G_n$, wherein G is Glycine (Gly), and n is an integer of 2 to 10.

In another particular embodiment, the ligase is Sortase A from *Staphylococcus aureus*. Accordingly, the ligase recognition sequence may be typical recognition sequence of the enzyme as LPXTG. In yet another particular embodiment, the recognition sequence of the ligase donor substrate is LPXTGJ, and the recognition sequence of the ligase acceptor substrate is $G_n$, wherein X can be any single amino acid that is natural or unnatural; J is absent, or is an amino acid fragment comprising 1-10 amino acids, optionally labeled. In one embodiment, J is absent. In yet another embodiment, J is an amino acid fragment comprising 1-10 amino acids, wherein each amino acid is independently any natural or unnatural amino acid. In another embodiment, J is $G_m$, wherein m is an integer of 1 to 10. In yet another particular embodiment, the recognition sequence of the ligase donor substrate is LPETG. In another particular embodiment, the recognition sequence of the ligase donor substrate is LPETGG.

In one embodiment, the ligase is Sortase B from *Staphylococcus aureus* and the corresponding donor substrate recognition sequence can be NPQTN. In another embodiment, the ligase is Sortase B from *Bacillus anthracis* and the corresponding donor substrate recognition sequence can be NPKTG.

In yet another embodiment, the ligase is Sortase A from *Streptococcus pyogenes* and the corresponding donor substrate recognition sequence can be LPXTGJ, wherein J is as defined above. In another embodiment, the ligase is Sortase subfamily 5 from *Streptomyces coelicolor*, and the corresponding donor substrate recognition sequence can be LAXTG.

In yet another embodiment, the ligase is Sortase A from *Lactobacillus plantarum* and the corresponding donor substrate recognition sequence can be LPQTSEQ.

The ligase recognition sequence can also be other totally new recognition sequence for transpeptidase optimized by manual screening.

Moiety Comprising Reactive Group

Reactive Group for Connection with Payload

In one embodiment, B is a terminal group $R^{10}$, and the Cleavable sequence 1 in $L^1$ is connected to the payload. In such case, B is absent in the resulting molecule of the connection of Cleavable sequence 1 with the payload. In one embodiment, B is used for connection to the payload. For connection with the payload, the compound of formula (I) comprises a reactive group. In one embodiment, B in the compound of formula (I) is connected to the payload through an amide bond or an ester bond or an ether bond. In one embodiment, the reactive group in B in formula (I) is independently a reactive group for condensation reaction, nucleophilic addition or electrophilic addition (such as reactive C═O moiety, reactive C═C—C═O moiety, amino group, amine group, hydroxy group or thiol group), or a reactive group for substitution reaction (such as a leaving group attached to an O, C, N or S atom). In one embodiment, the reactive group in B is independently selected from carboxyl group, active ester, aldehyde group, amino group, amine group, hydroxy group and thiol group. In a specific embodiment, the reactive group in B which is used to connect to the payload is independently selected from amino group, amine group, hydroxy group, thiol group, carboxyl group and active ester.

In one embodiment, the reactive group in B is independently amino group, amine group or hydroxy group, which reacts with corresponding groups (such as carboxyl group, sulfonic acid group, phosphoryl group with free —OH end, active ester, acid chloride or isocyanate group) in the payload. In another embodiment, the reactive group in B is independently carboxyl group or active ester, which reacts with corresponding groups (such as amino group, amine group or hydroxy group) in the payload.

In one embodiment, the reactive group in B is independently amino group, hydroxy group or thiol group, which reacts with corresponding groups (such as halogen, hydroxy group, aldehyde group) in the payload. In another embodiment, the reactive group in B is independently hydroxy group, which reacts with corresponding groups (such as halogen or hydroxy group) in the payload.

In one embodiment, each B is independently $R^{10}$, or a combination of the following 1), 2) and 3): 1) a self-immolative spacer Sp1; 2) a bond, or one of or a combination of two or more of the bivalent groups selected from: $—CR^1R^2—$, $C_{1-10}$ alkylene and —(CO)—; and 3) a terminal group $R^{10}$.

In one embodiment, Sp1 is selected from PABC, acetal, heteroacetal and the combination thereof. In one embodiment, Sp1 is acetal, heteroacetal or PABC. In one embodiment, the heteroacetal is selected from N,O— heteroacetal. In one embodiment, Sp1 is $—O—CH_2—U—$, or $—NH—CH_2—U—$ wherein the —O— or the —NH— is connected to Cleavable sequence 1; U is absent or is O, S or NH, preferably O or S. In one embodiment, U is absent, or is O, S or NH, preferably O or S.

In one embodiment, B is $R^{10}$, $—NH—CH_2—U—R^{10}$, $—NH—CH_2—U—(CR^1R^2)_g—(CO)—R^{10}$ or $—NH—CH_2—U—(CH_2)_g—(CO)—R^{10}$.

In one embodiment, $R^{10}$ is hydrogen, hydroxy or

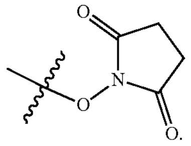 [SMILES: *ON1C(=O)CCC1=O]

In one embodiment, $R^{10}$ is hydrogen. In one embodiment, $R^{10}$ is hydroxy or

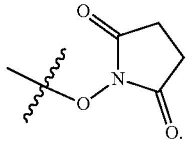 [SMILES: *ON1C(=O)CCC1=O]

In one embodiment, $R^{10}$ represents the part of structure which would not appear in the product molecule resulting from the reaction of B with the payload.

Specific Embodiment of the Formula (I) Compound

In one embodiment, W is hydrogen, each LKa is

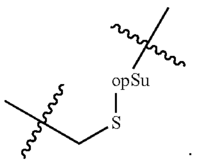

.

In one embodiment, formula (I) has the structure of formula (I-a)

formula (I-a)

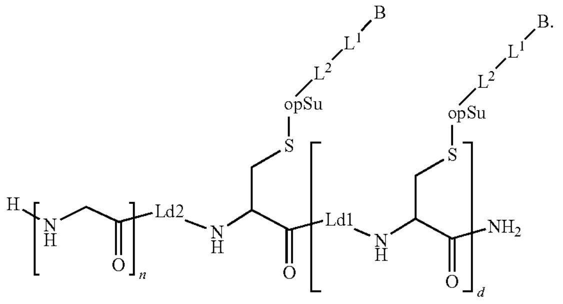

In one embodiment, each LKa is

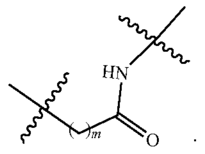 [SMILES: *CC(=O)N*]

In one embodiment, formula (I) has the structure of formula (I-b)

formula (I-b)

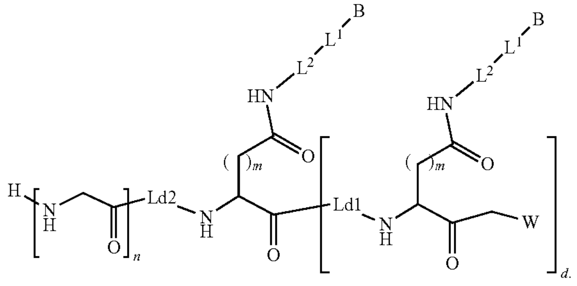

In one embodiment, Ld2 is a bond, d is 0. In one embodiment, the compound of formula (I-a) is as follows:

(I-a-0-1)

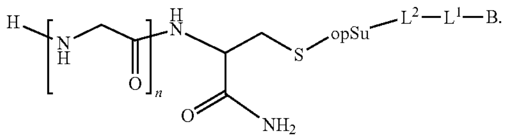

In one embodiment, d is 0, Ld2 is

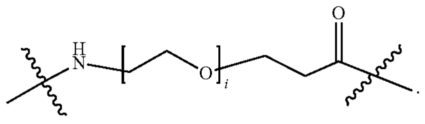

In one embodiment, the compound of formula (I-a) is as follows:

(I-a-0-2)

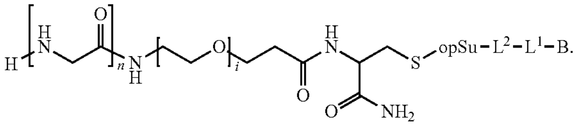

In one embodiment, d is 1, 2 or 3, Ld2 and each Ld1 are independently selected from

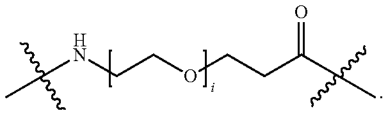

In one embodiment, the compound of formula (I-a) is as follows:

(I-a-0-3)
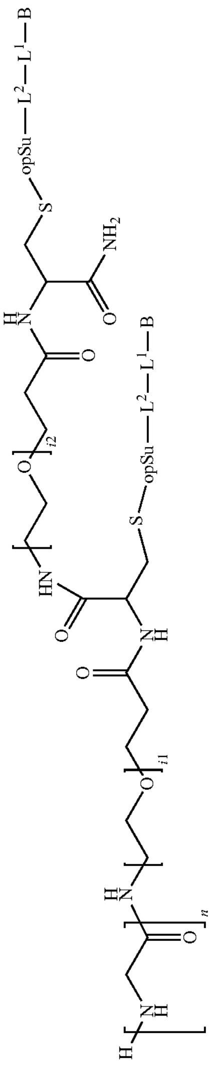
(I-a-0-4)
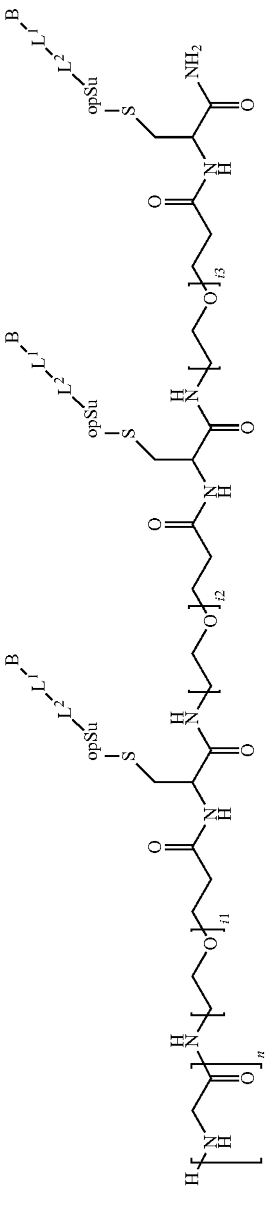
or
(I-a-0-5)
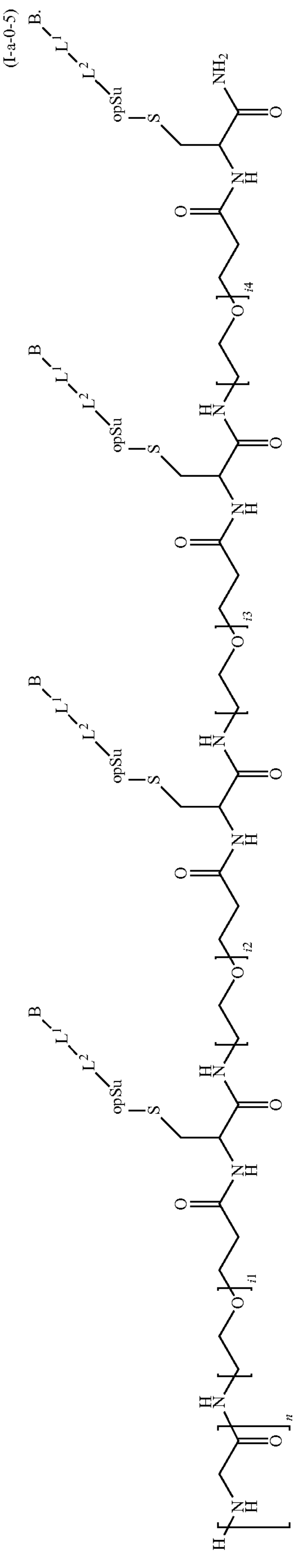

In one embodiment, Ld2 is
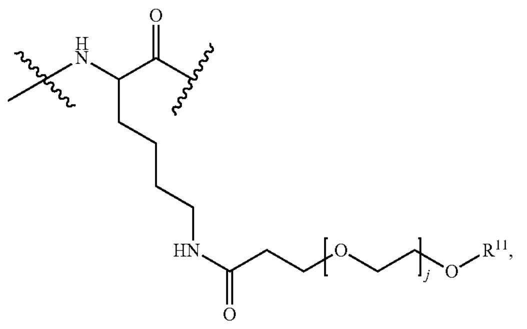
is 0. In one embodiment, the compound of formula (I-a) is as follows:
(I-a-1-1)
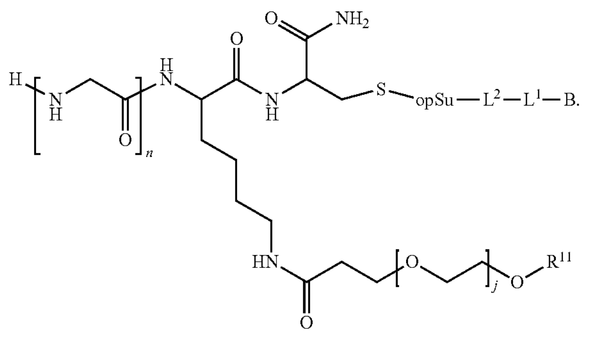
In one embodiment, d is 1, 2 or 3, Ld2 is
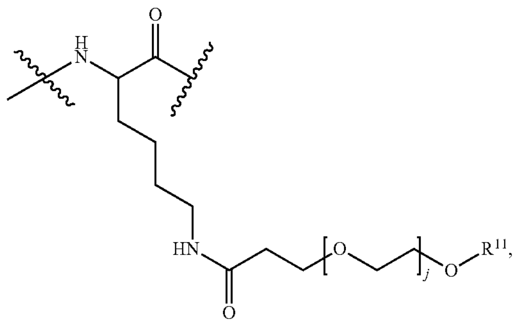
and each Ld1 is independently selected from
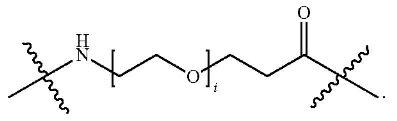
In one embodiment, the compound of formula (I-a) is as follows:
(I-a-1-2)
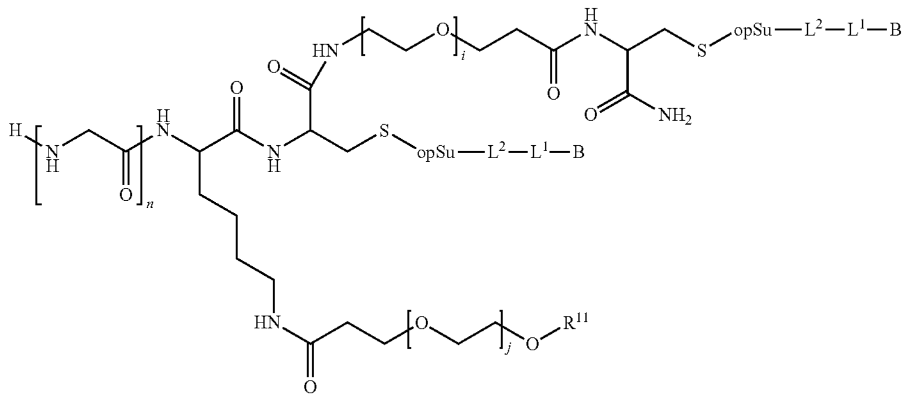

-continued
(I-a-1-3)
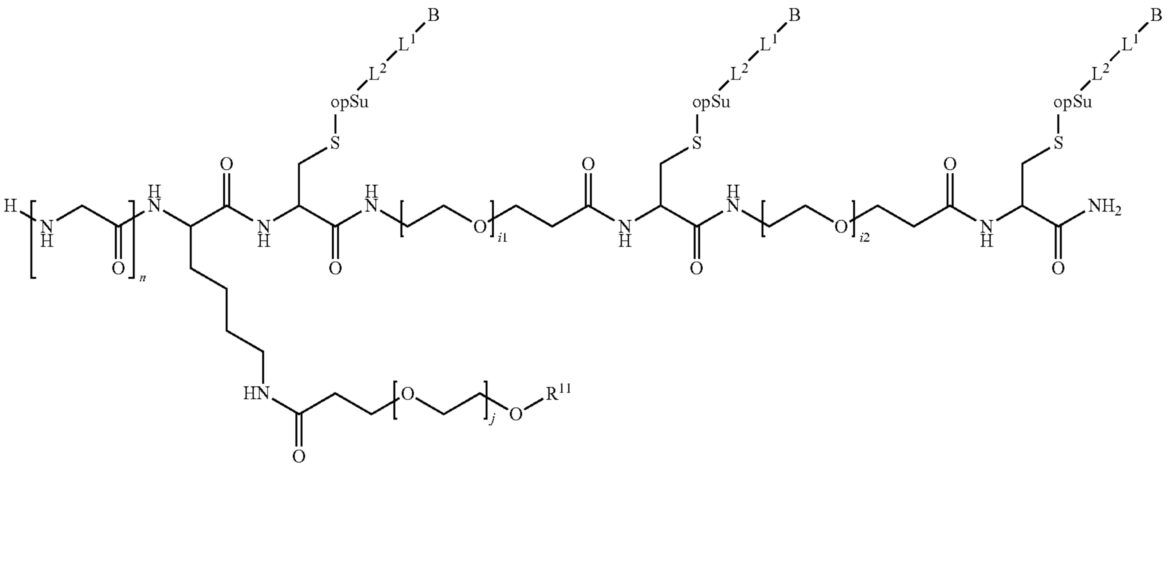
or
(I-a-1-4)
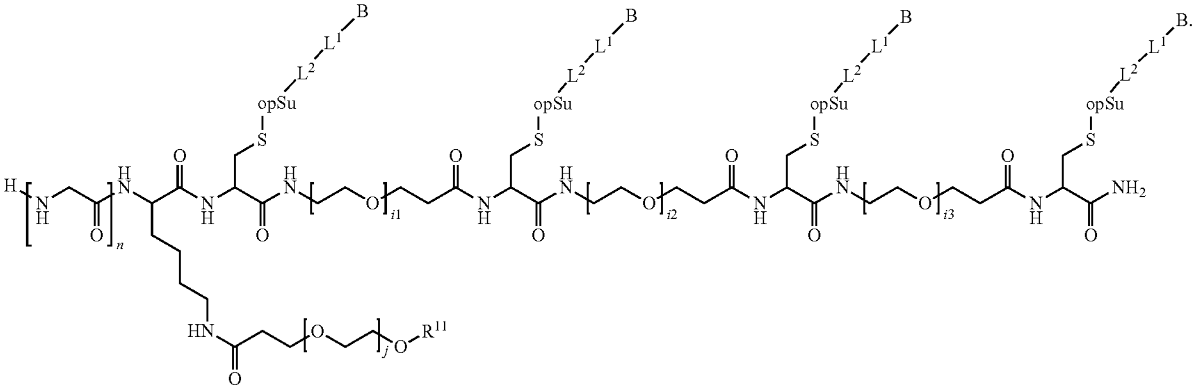
In one embodiment, d is 1, W is hydrogen, Ld2 is
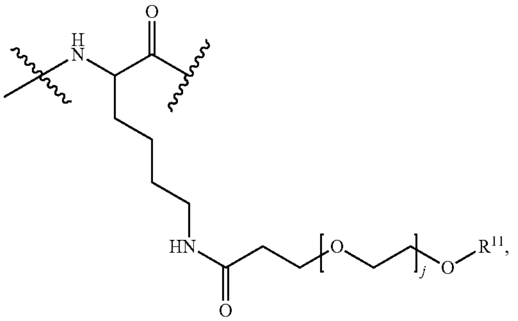
and each Ld1 is independently selected from
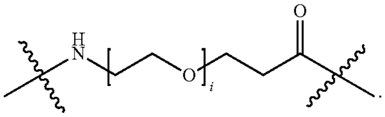
In one embodiment, the compound of formula (I-b) is as follows:

(I-b-1)
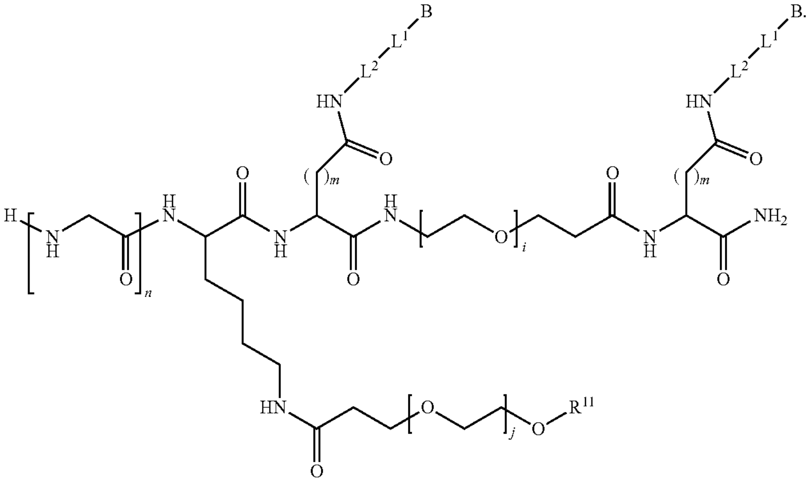
In one embodiment, d is 1, W is $—C_2H_4-(PEG)_t-C(O)NH_2$, Ld2 is a bond, and each Ld1 is independently selected from
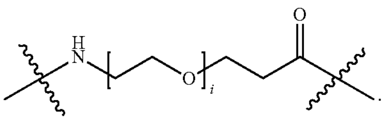
In one embodiment, the compound of formula (I-b) is as follows:
(I-b-0)
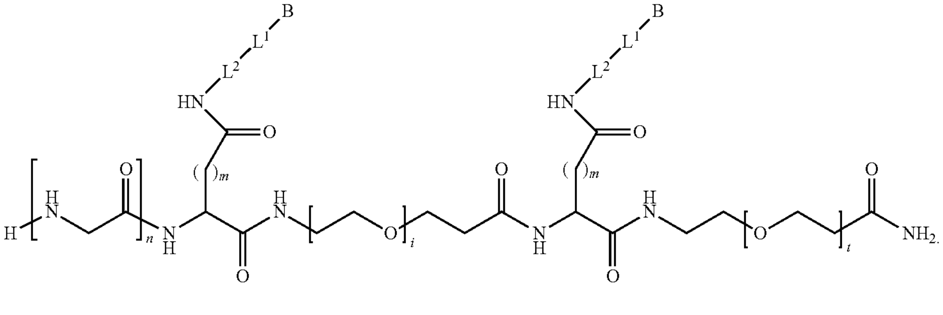
In one embodiment, n is 3, $L^2$ is $—(CH_2)_p—(CH_2)_2(CO)—$, p is 3, $L^1$ is GGFG, B is $—NH—CH_2—U—R^{10}$ or $—R^{10}$ or $—NH—CH_2—U—(CR^1R^2)—(CO)—R^{10}$, U is O, g is 1. In one embodiment, I-a-0-1 has the structure of:
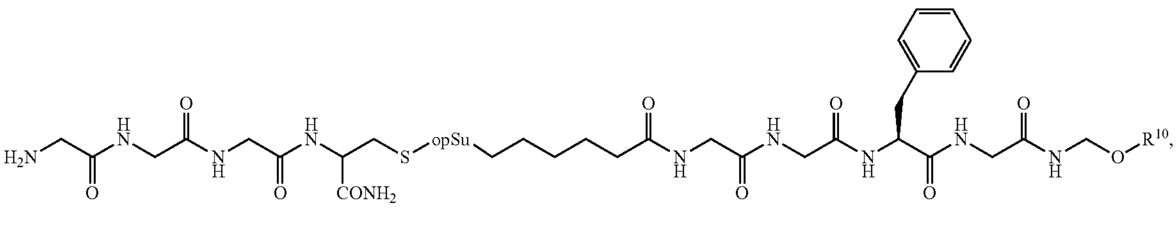

-continued
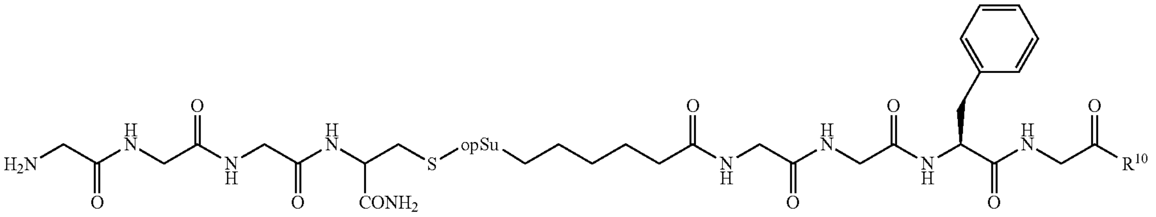
or
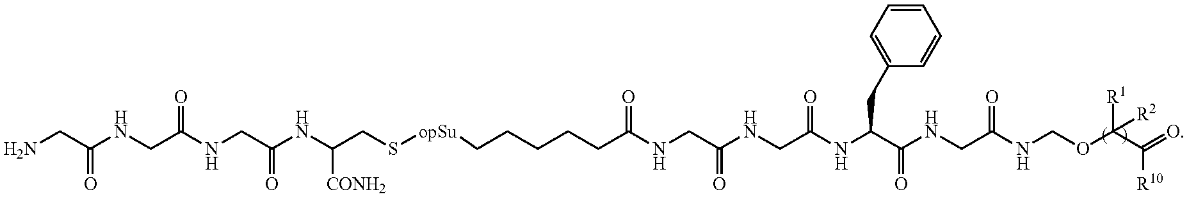
In one embodiment, I-a-0-2 has the structure of:

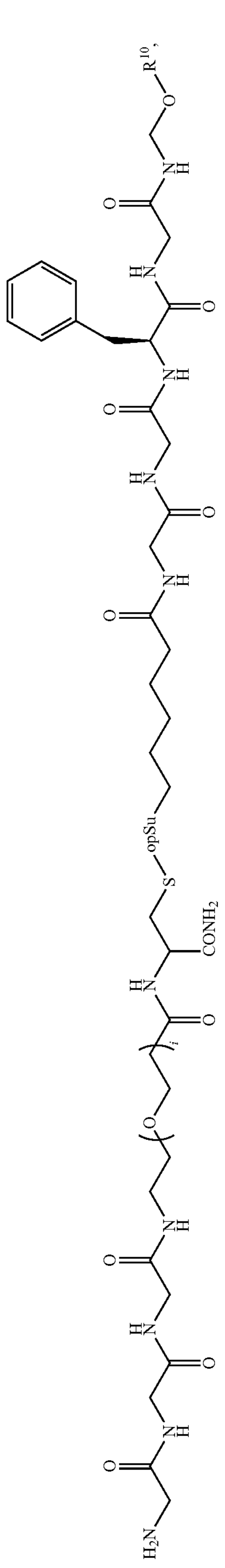
,
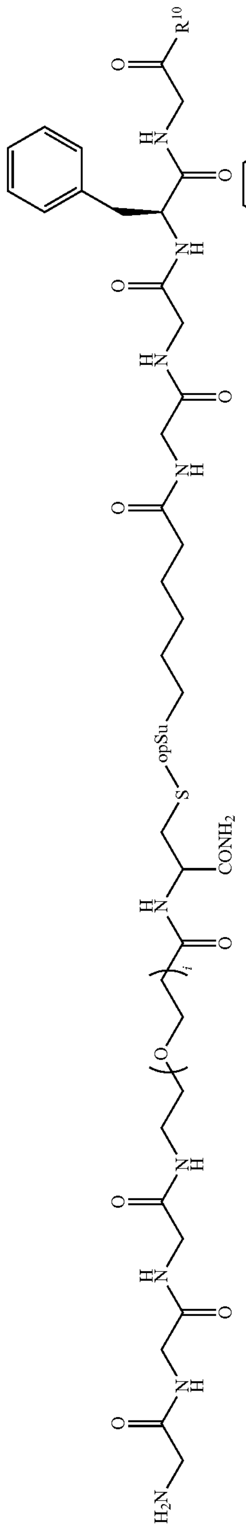
or
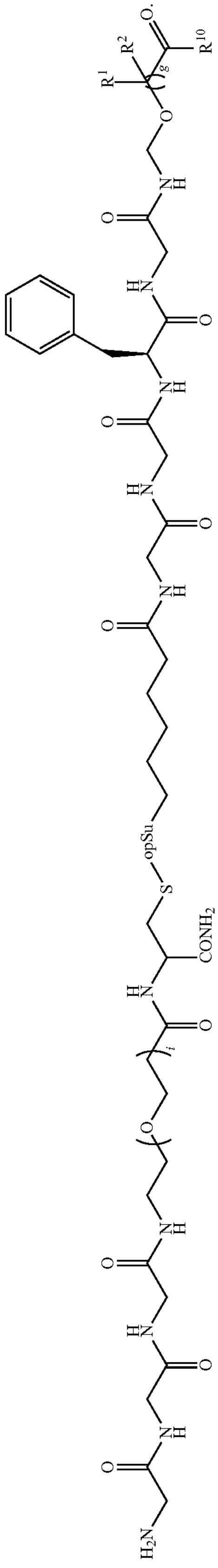
.

In one embodiment, I-a-0-3 has the structure of:

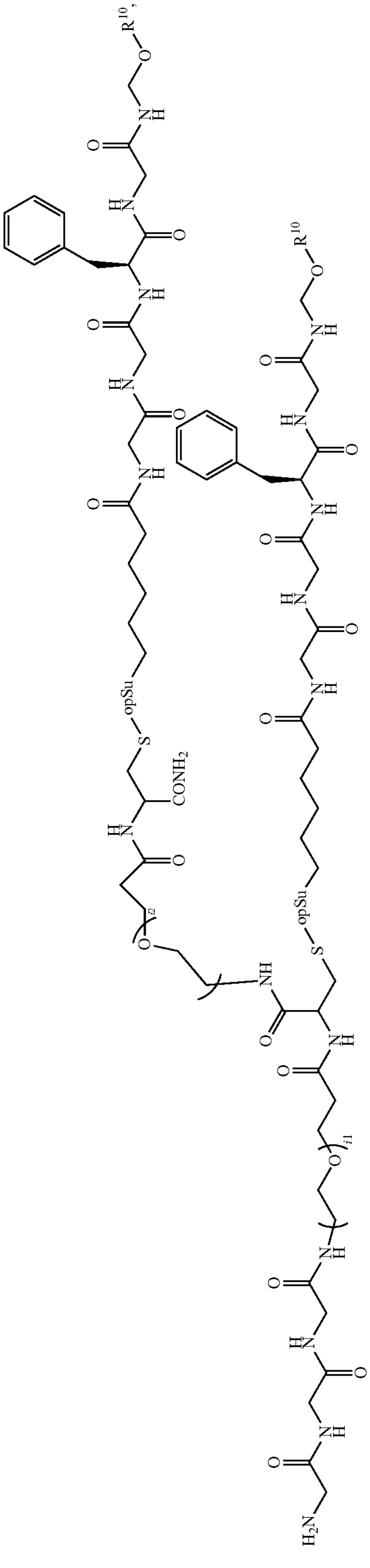
,
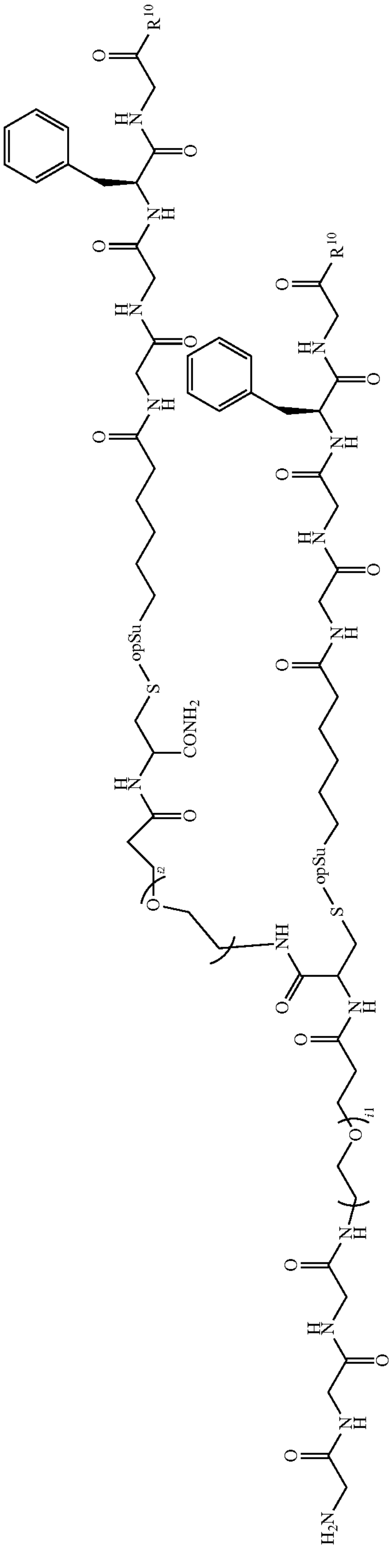
or

-continued
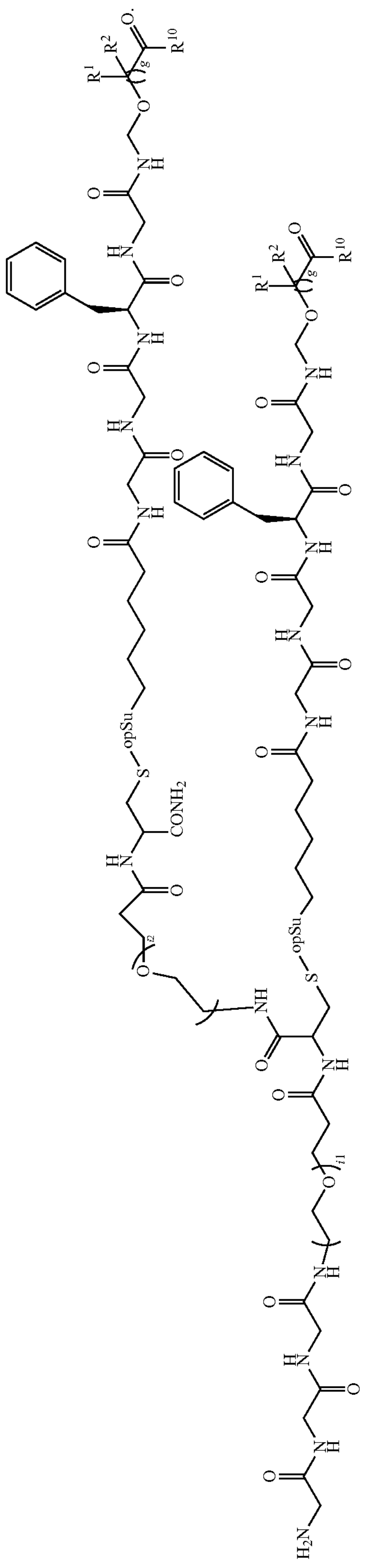

In one embodiment, I-a-0-4 has the structure of:
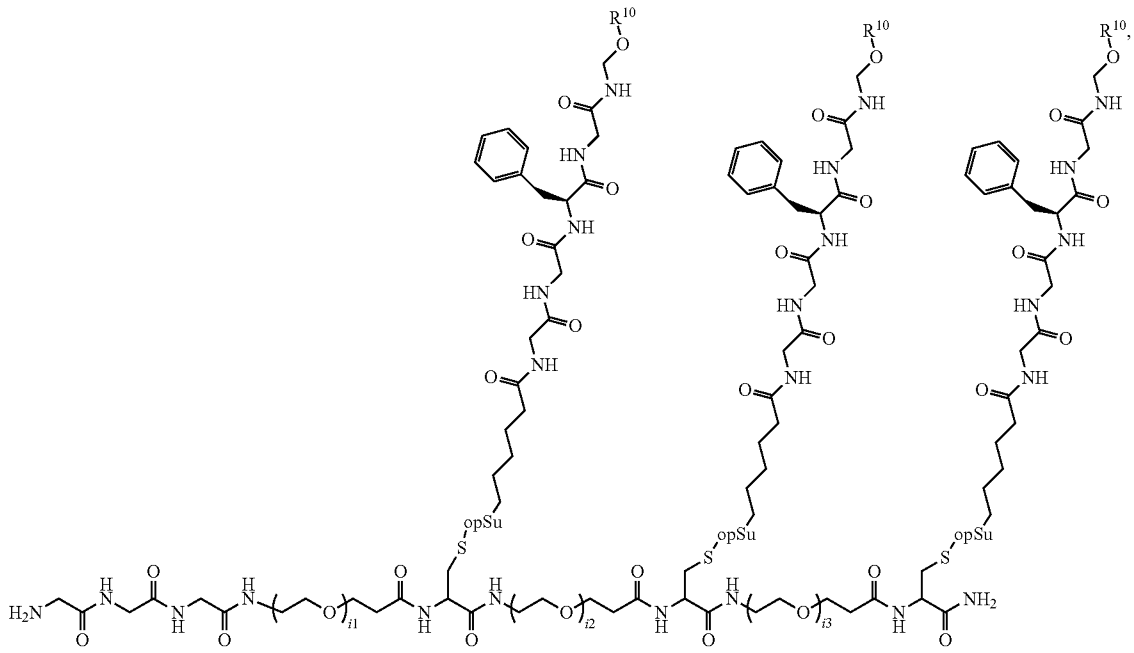
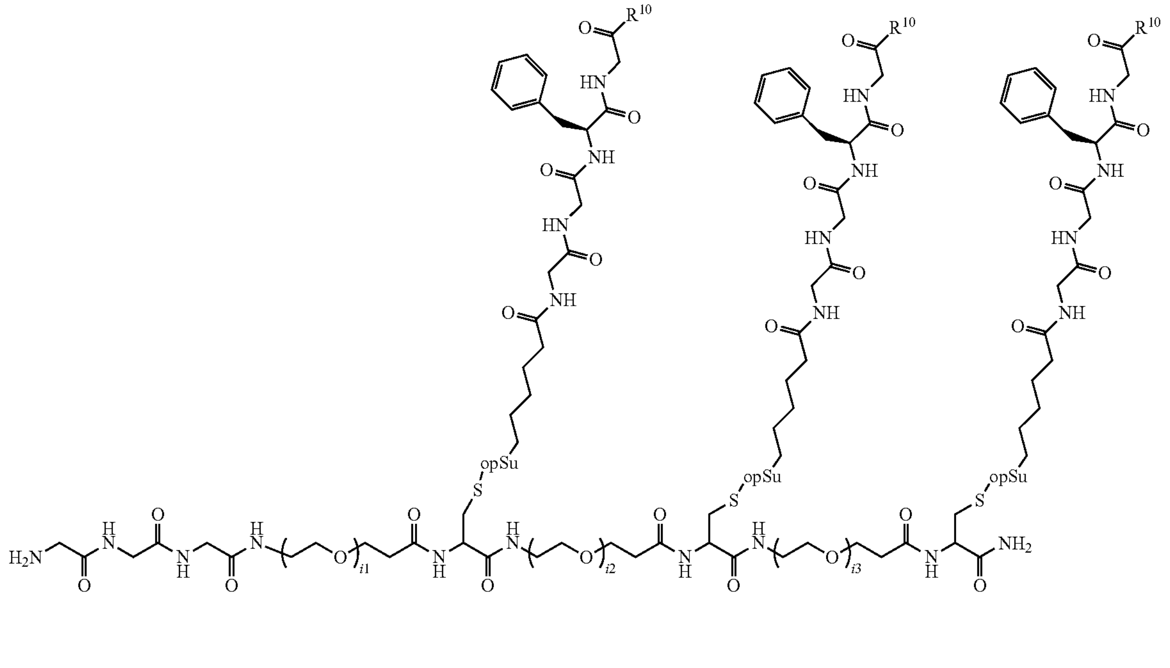
or

-continued
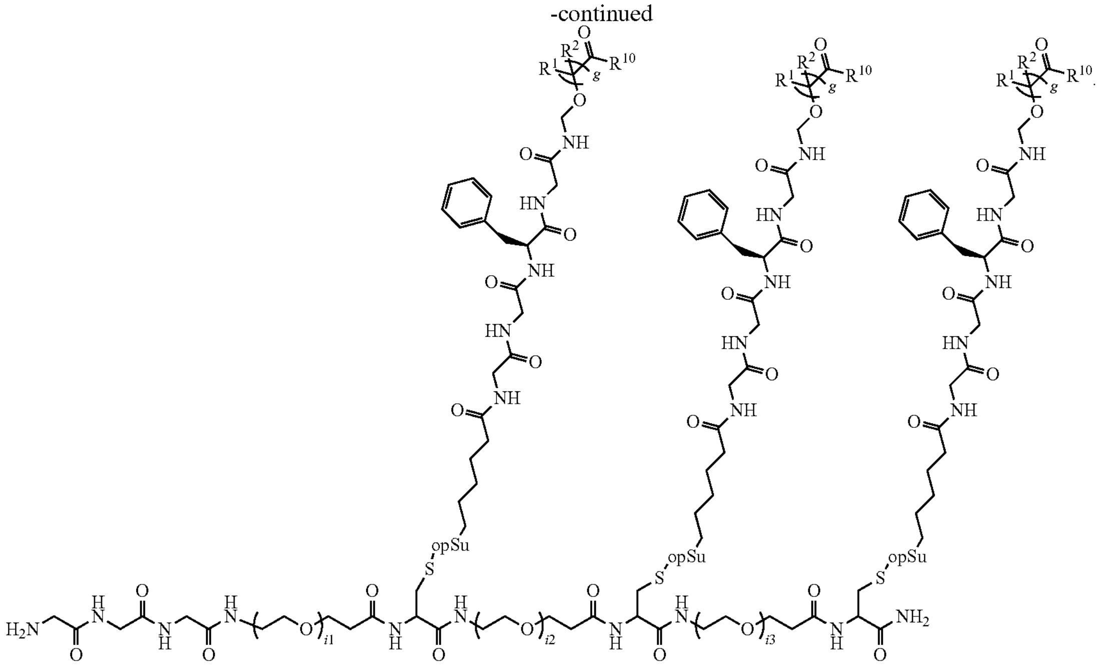
In one embodiment, I-a-0-5 has the structure of:

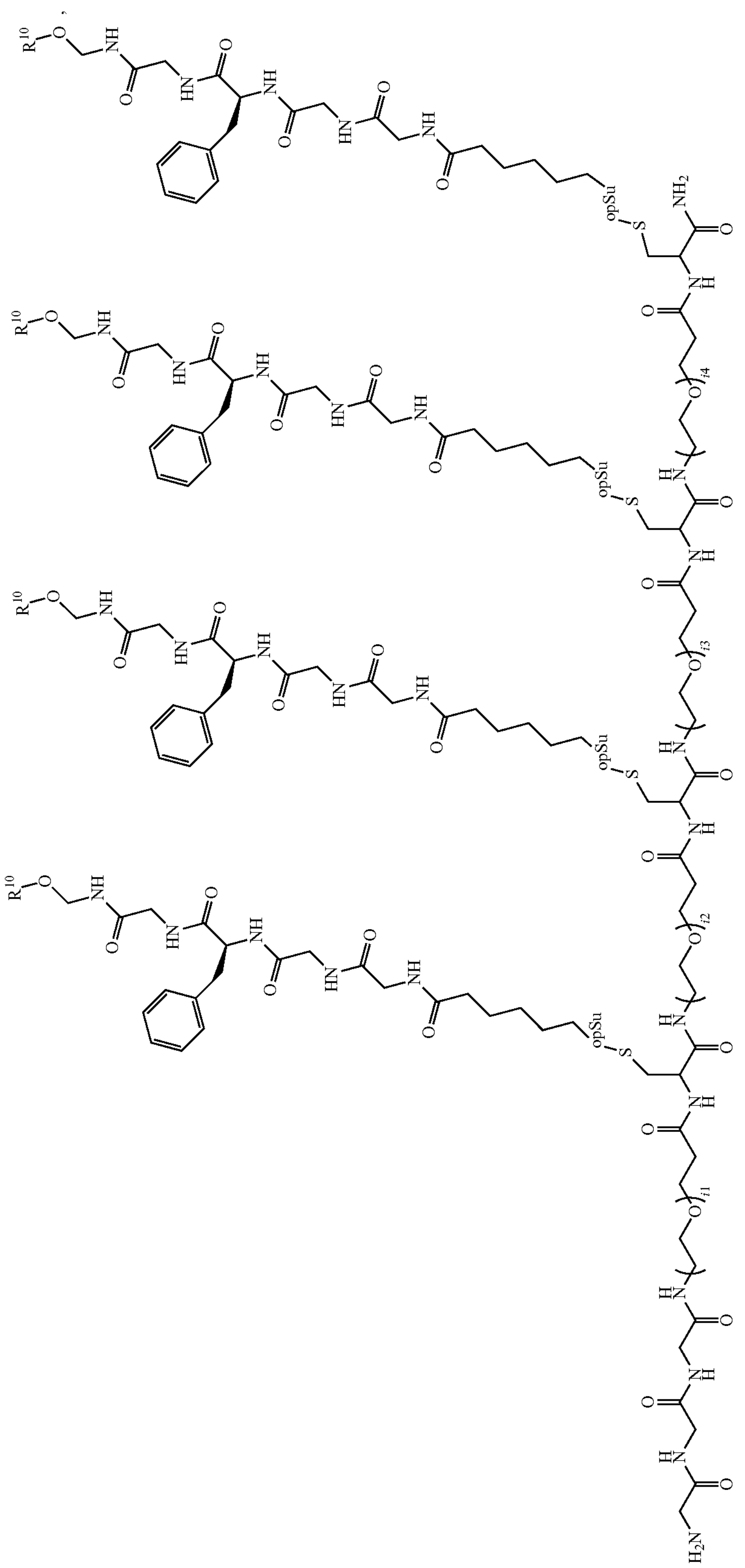

-continued
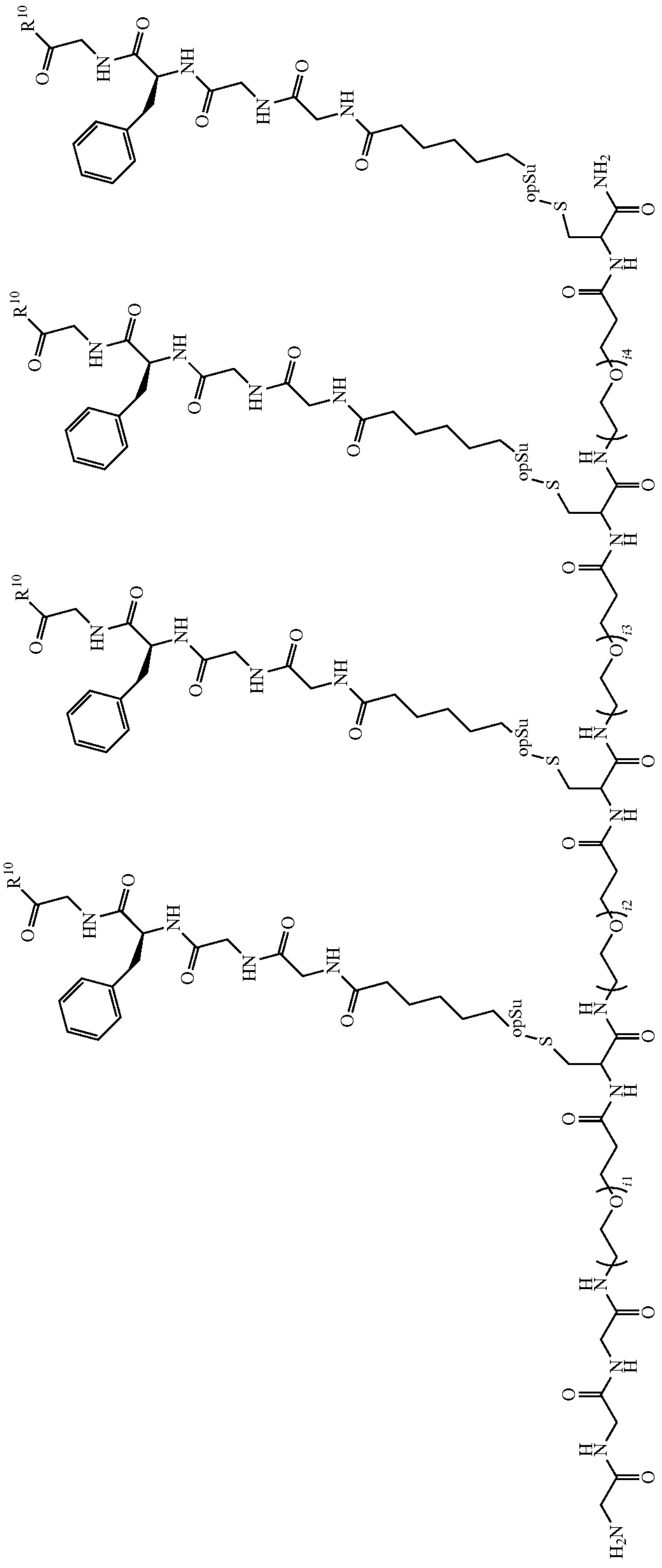
or

-continued
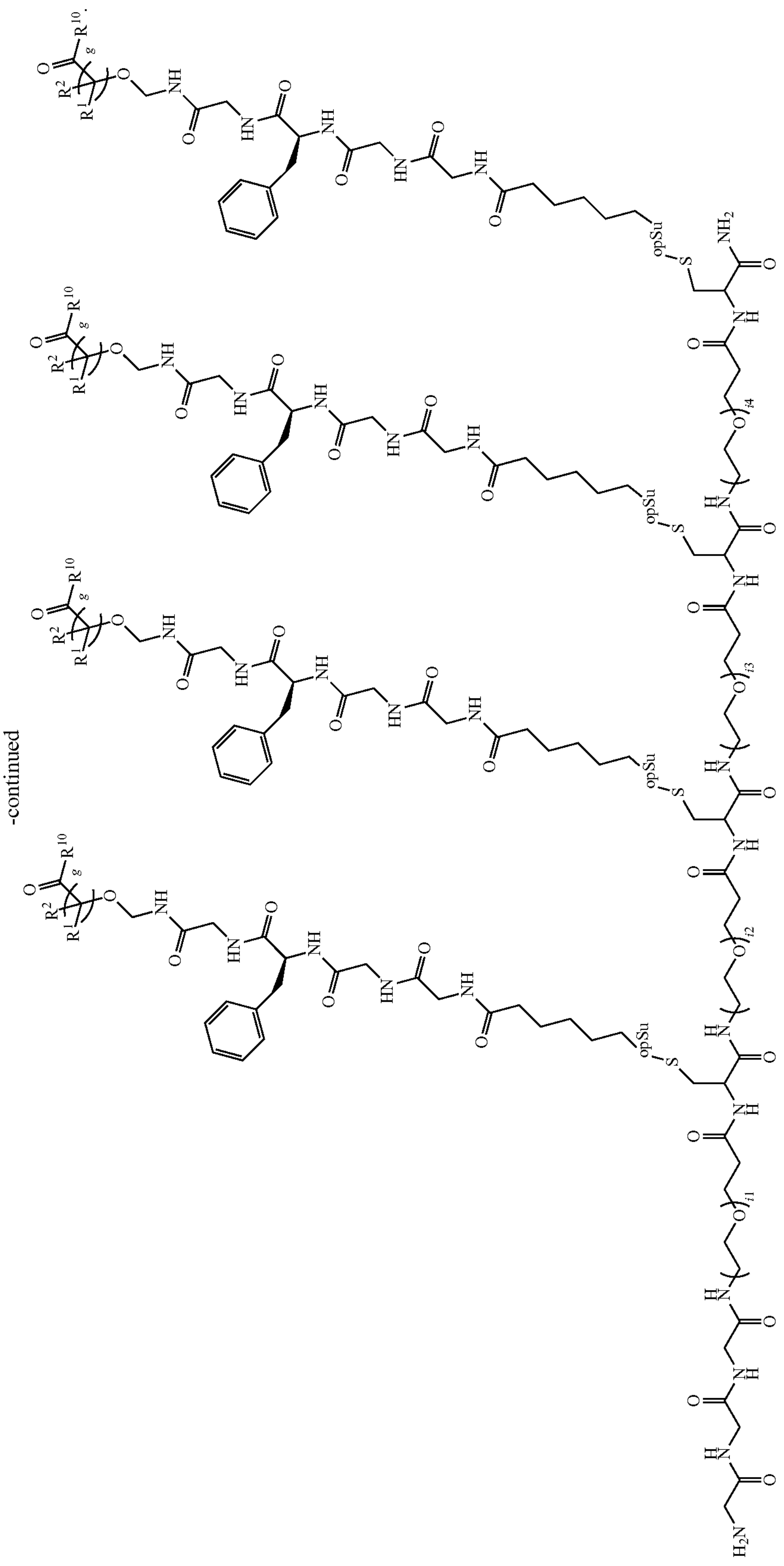

In one embodiment, I-a-1-1 has the structure of:
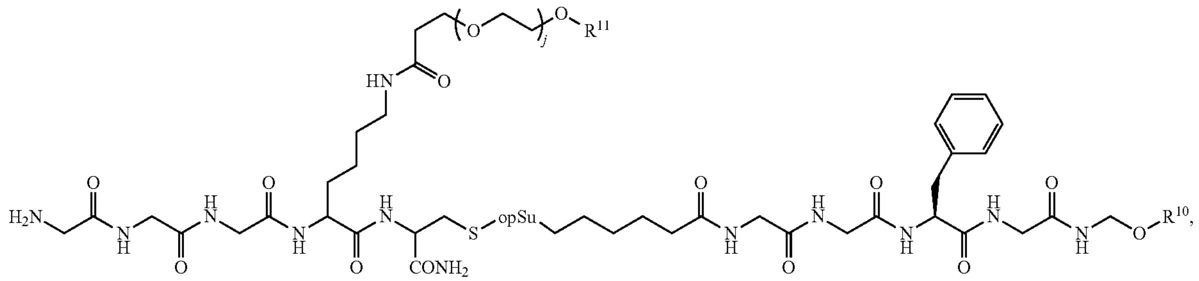
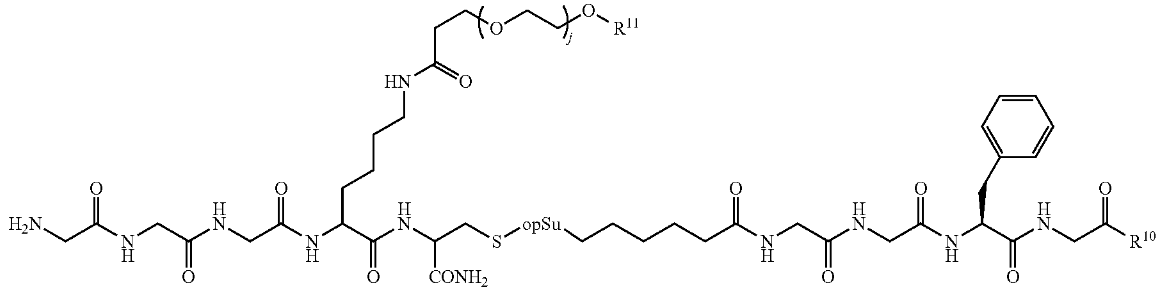
or
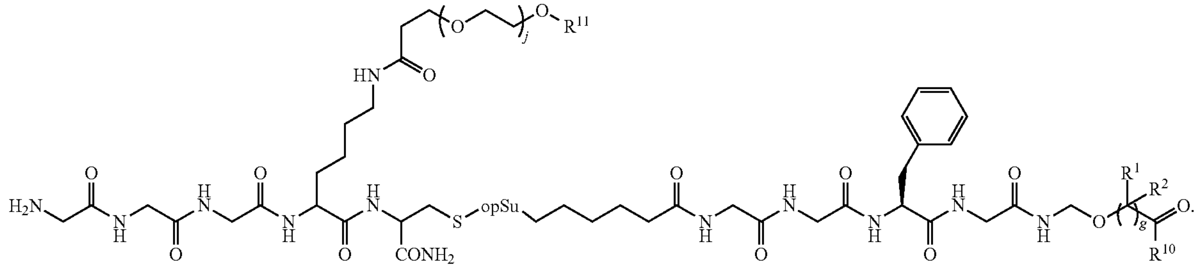
In one embodiment I-a-1-2 has the structure of:

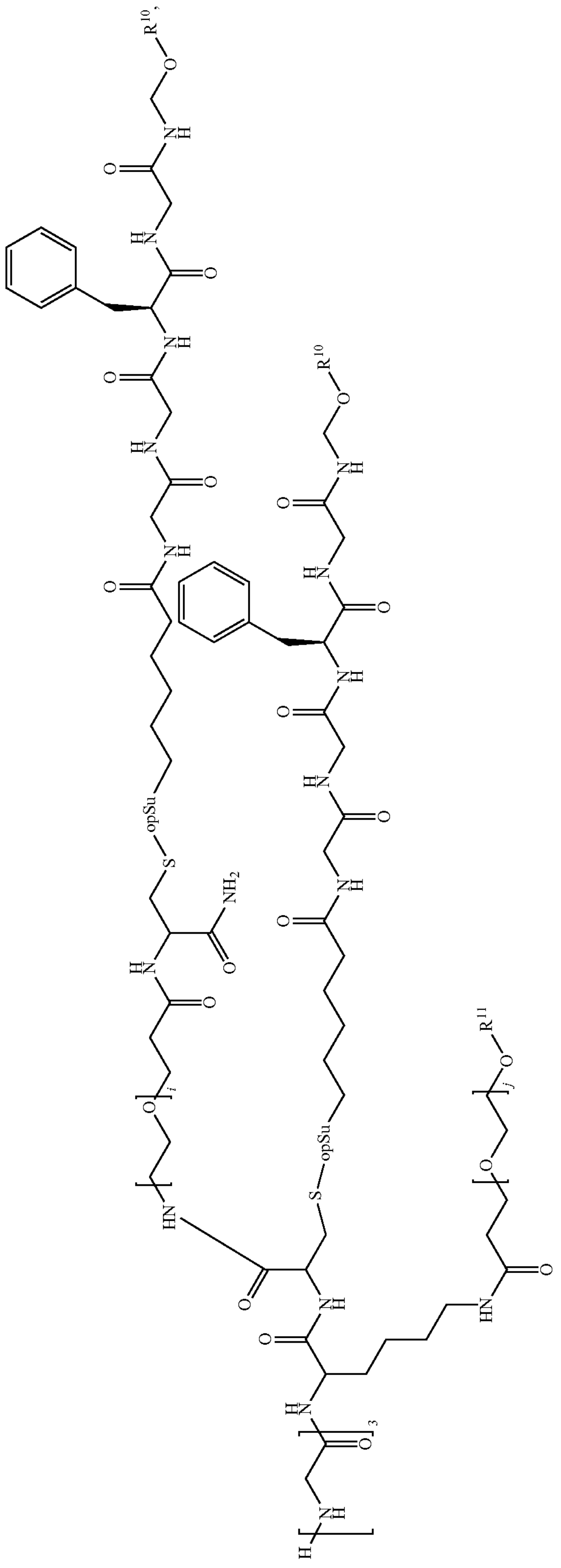

-continued
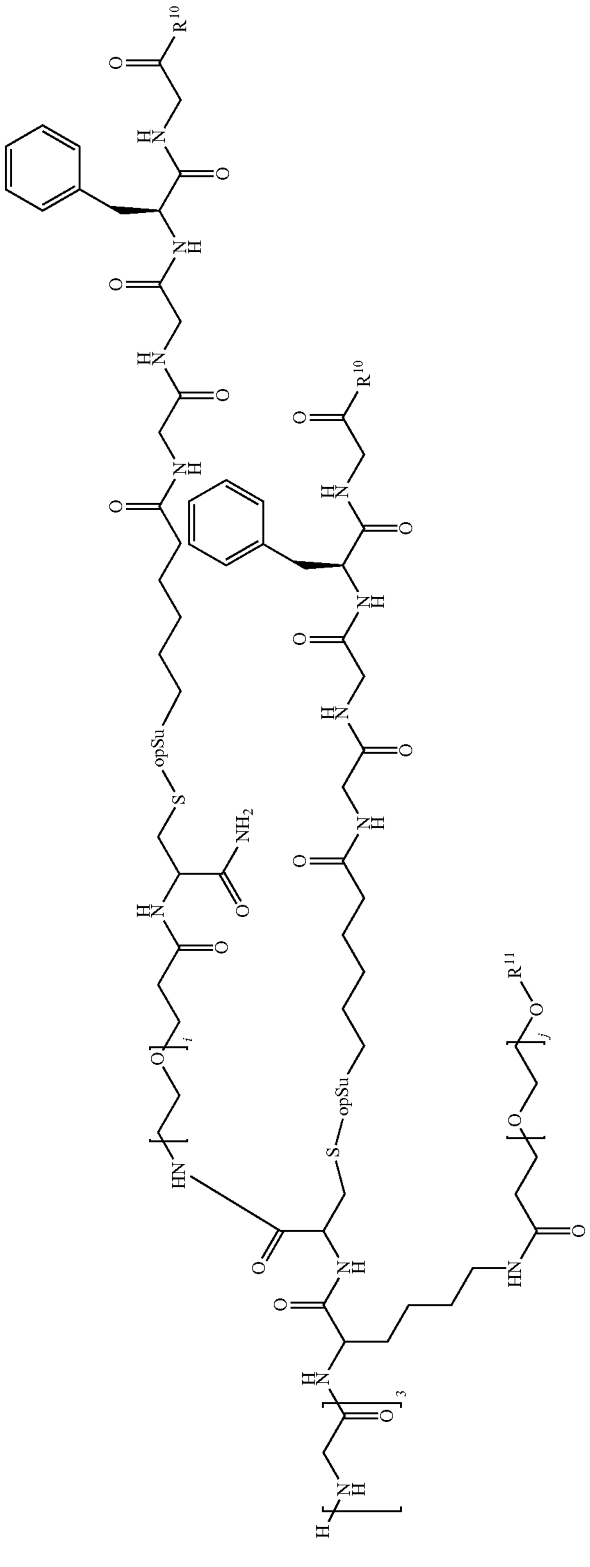
or

-continued
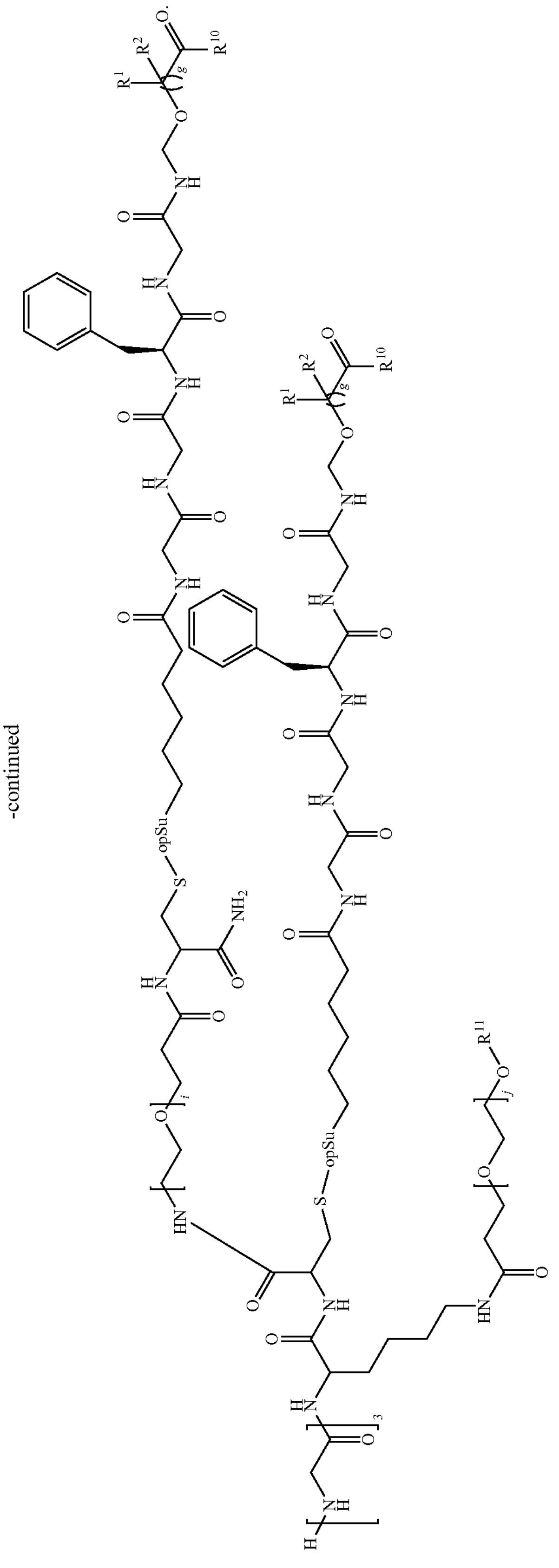

In one embodiment, I-a-1-3 has the structure of:
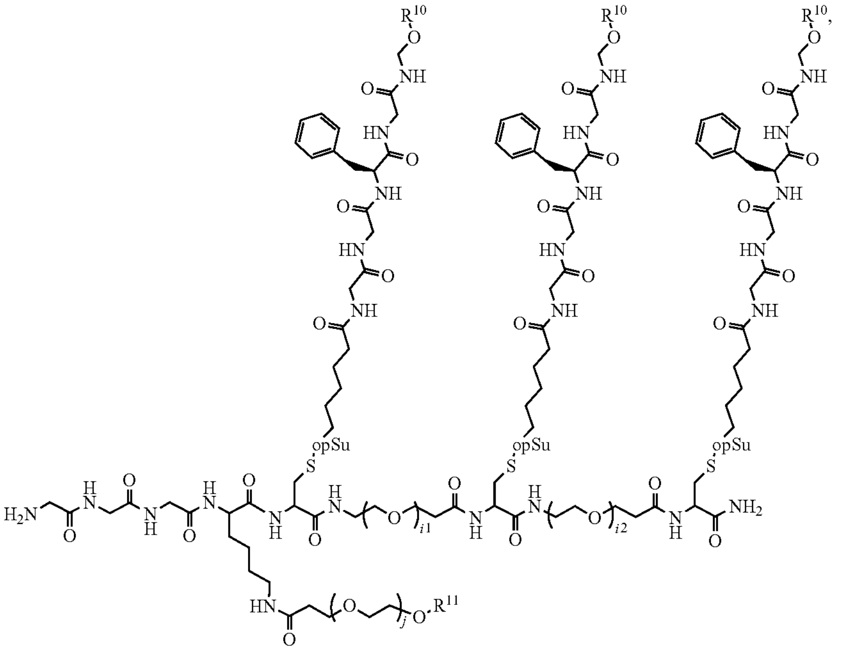
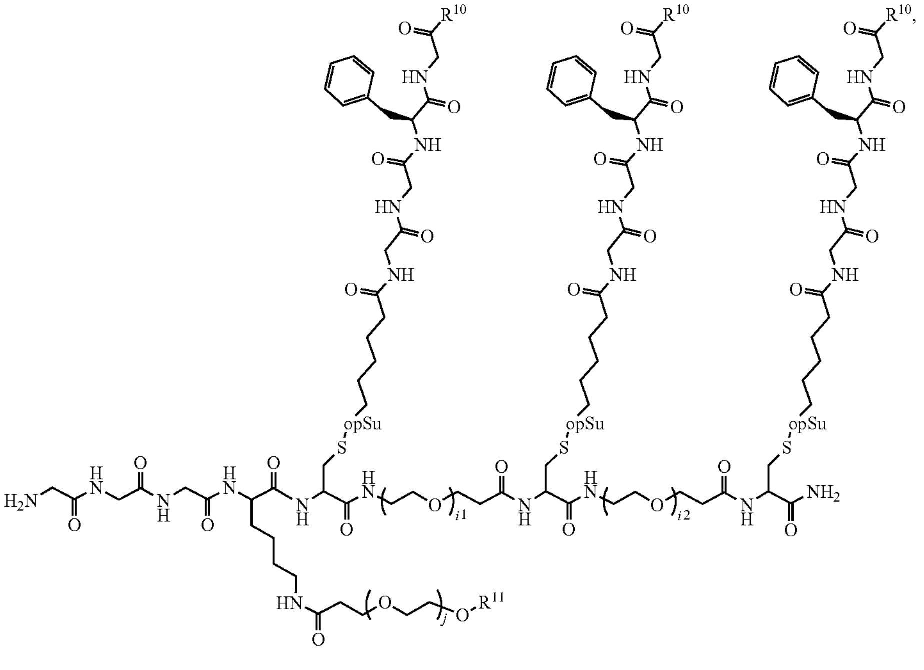
or

-continued
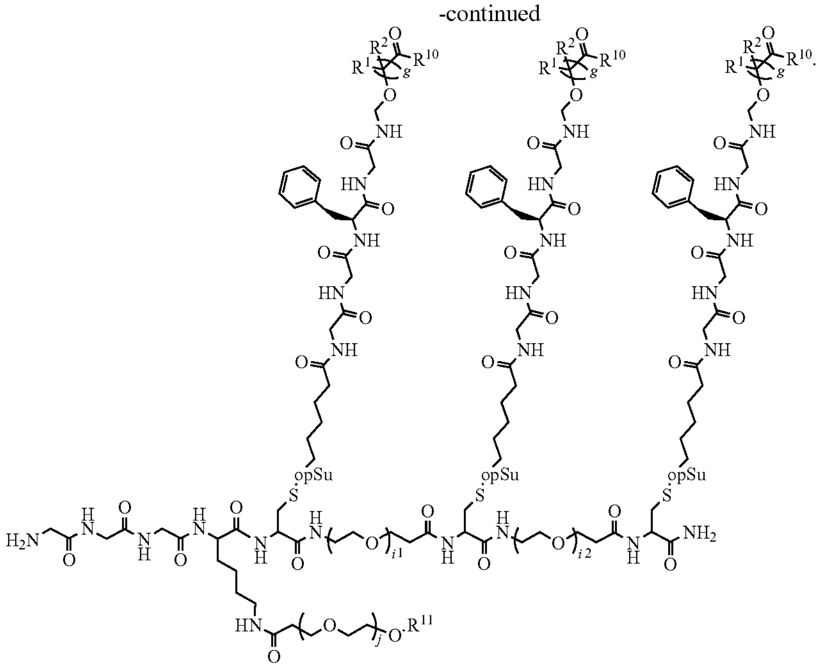
In one embodiment, I-a-1-4 has the structure of:

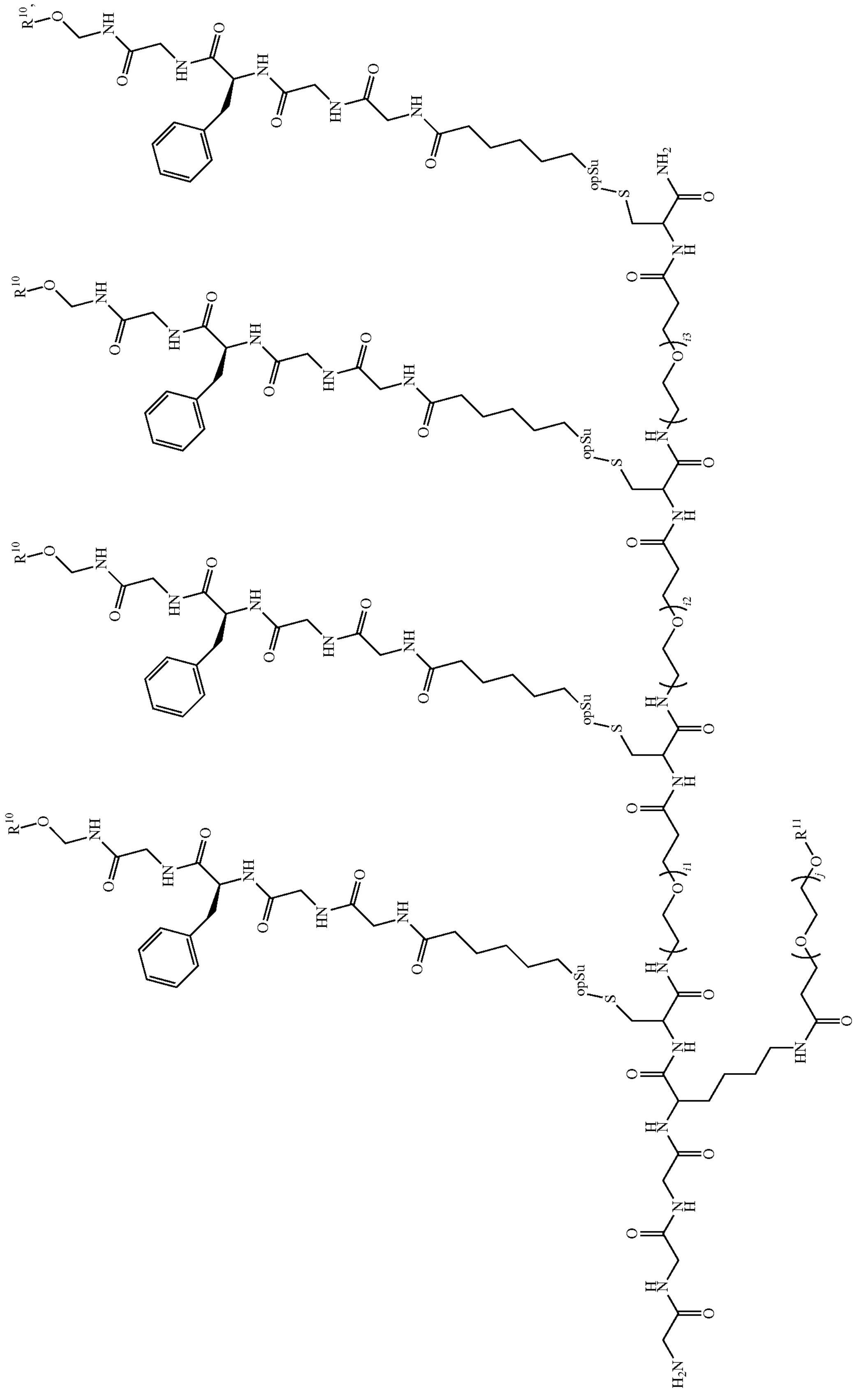

-continued
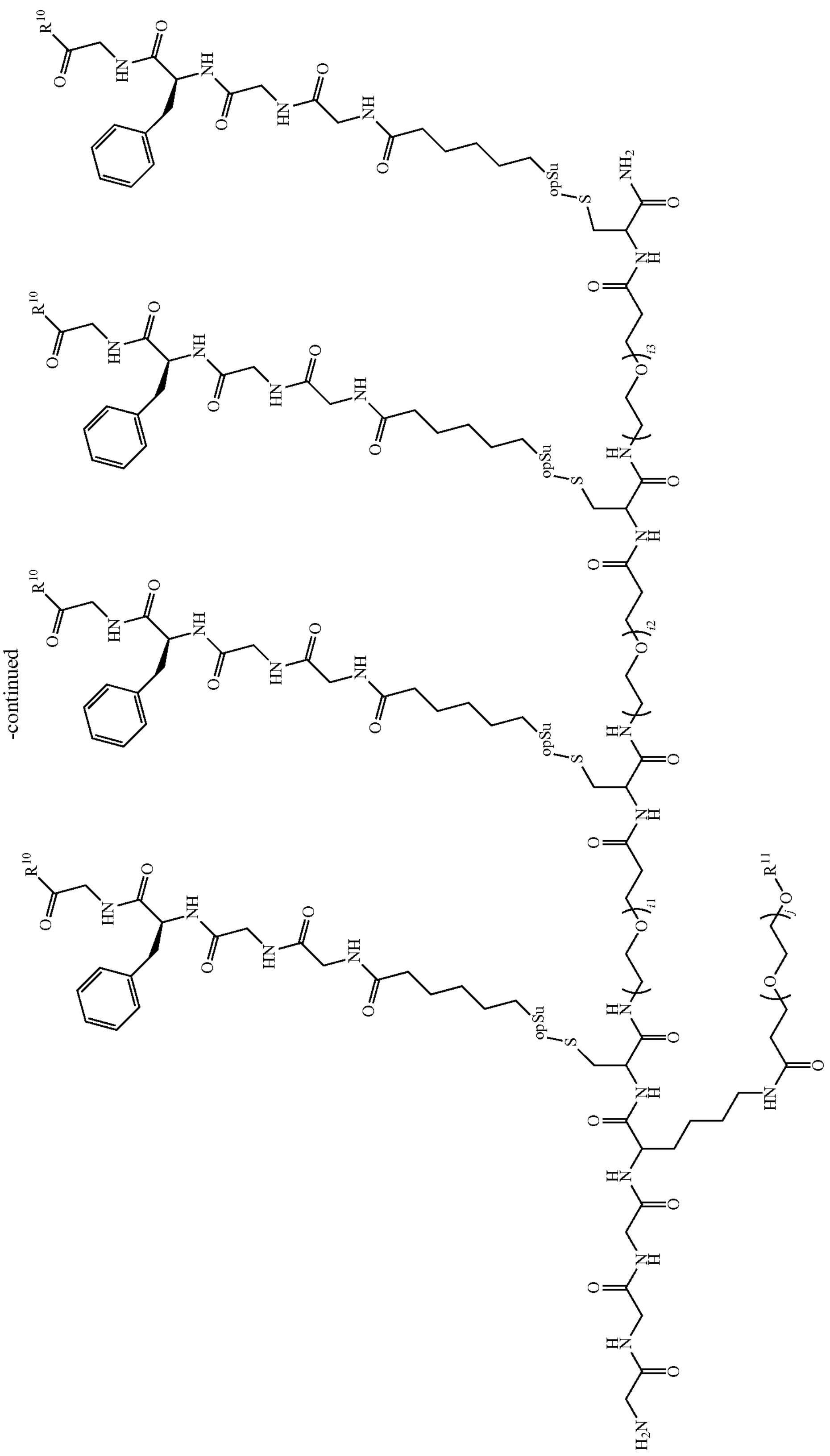
or

-continued
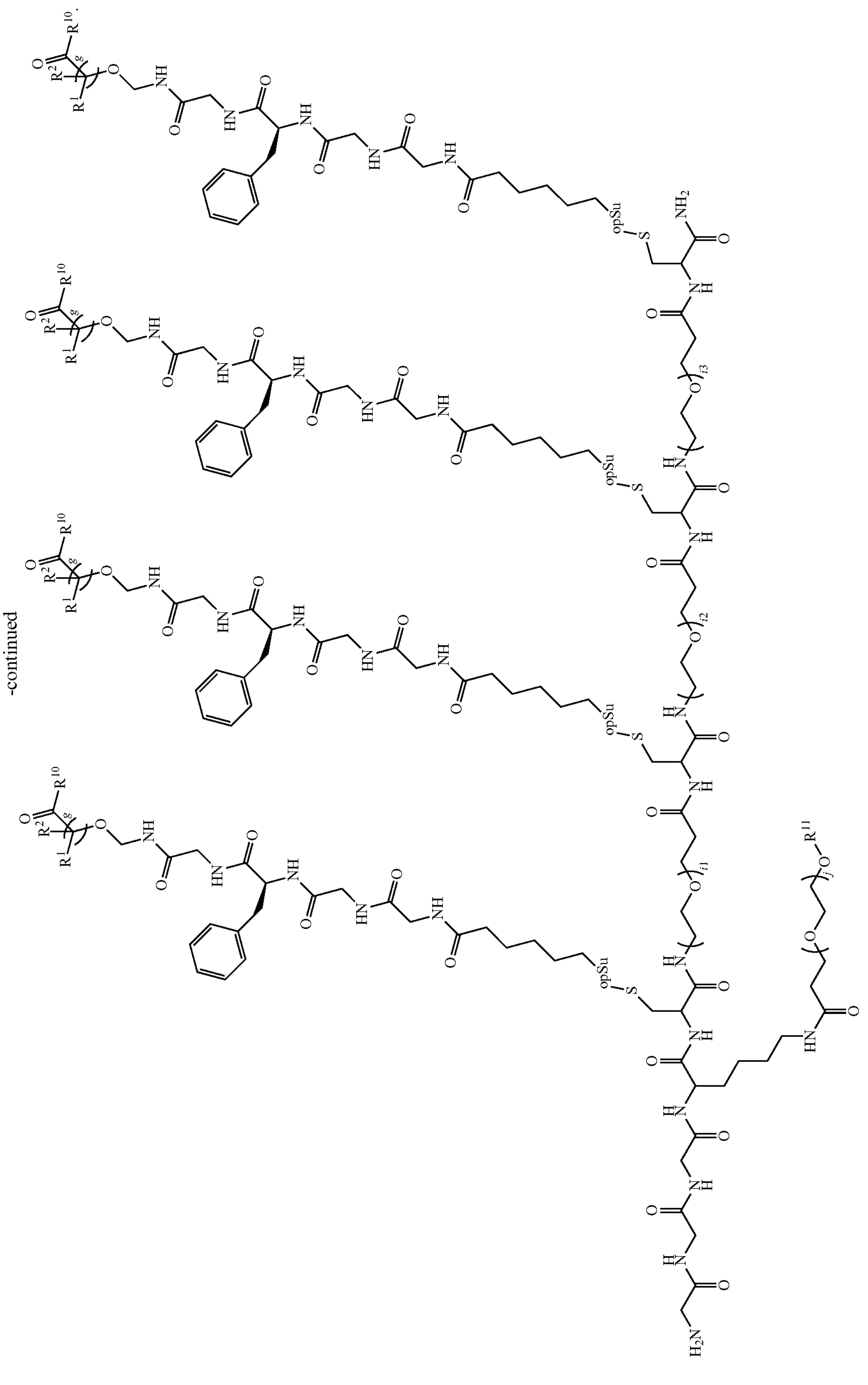

In one embodiment, n is 3, $L^2$ is $-(C_2H_4-O)_p-(CH_2)_2(CO)-$, p is 2, $L^1$ is GGFG, B is $-NH-CH_2-U-R^{10}$ or $-R^{10}$ or $-NH-CH_2-U-(CR^1R^2)_g-(CO)-R^{10}$, U is O, g is 1. In one embodiment, I-b-1 has the structure of:

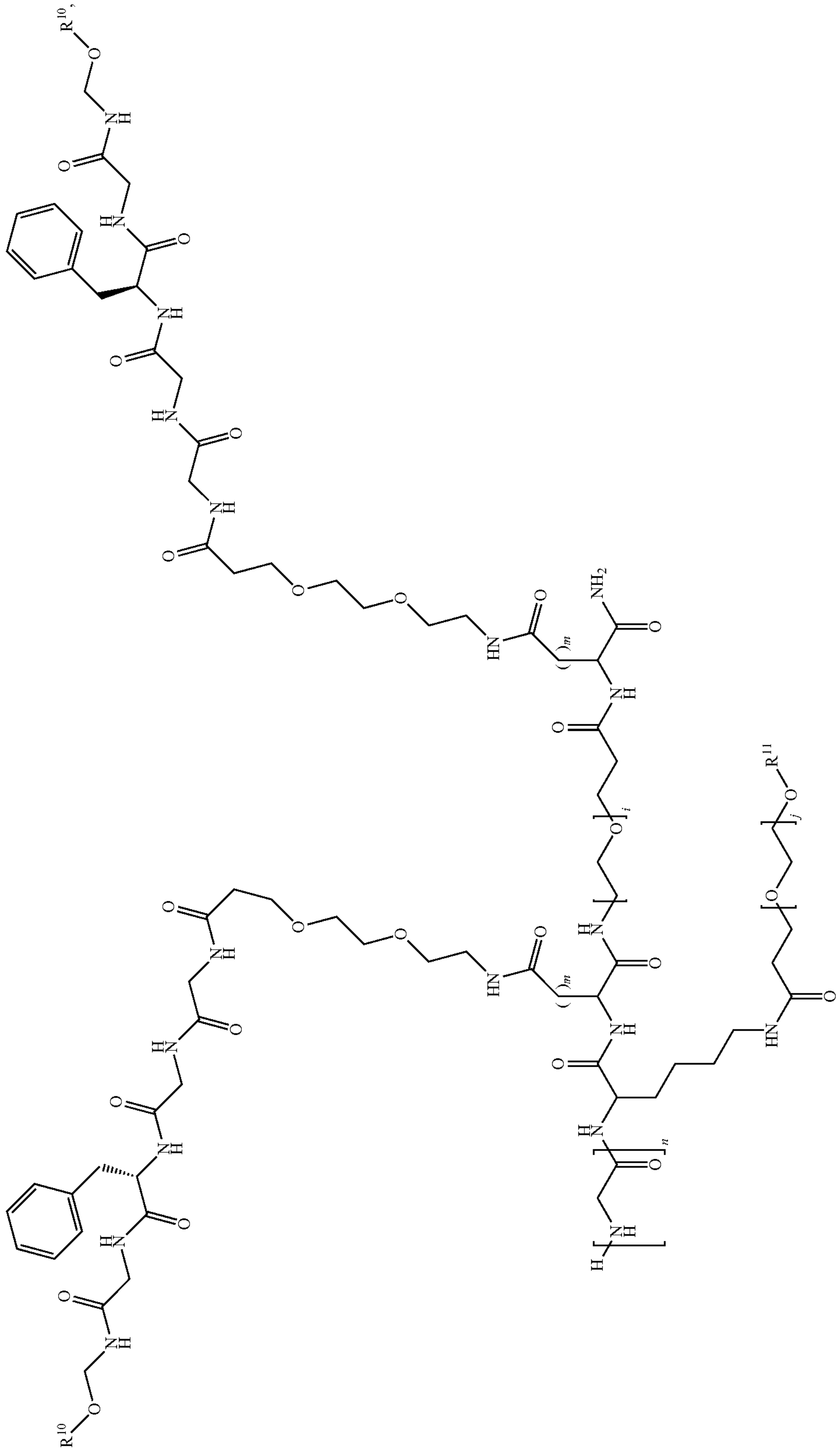

-continued
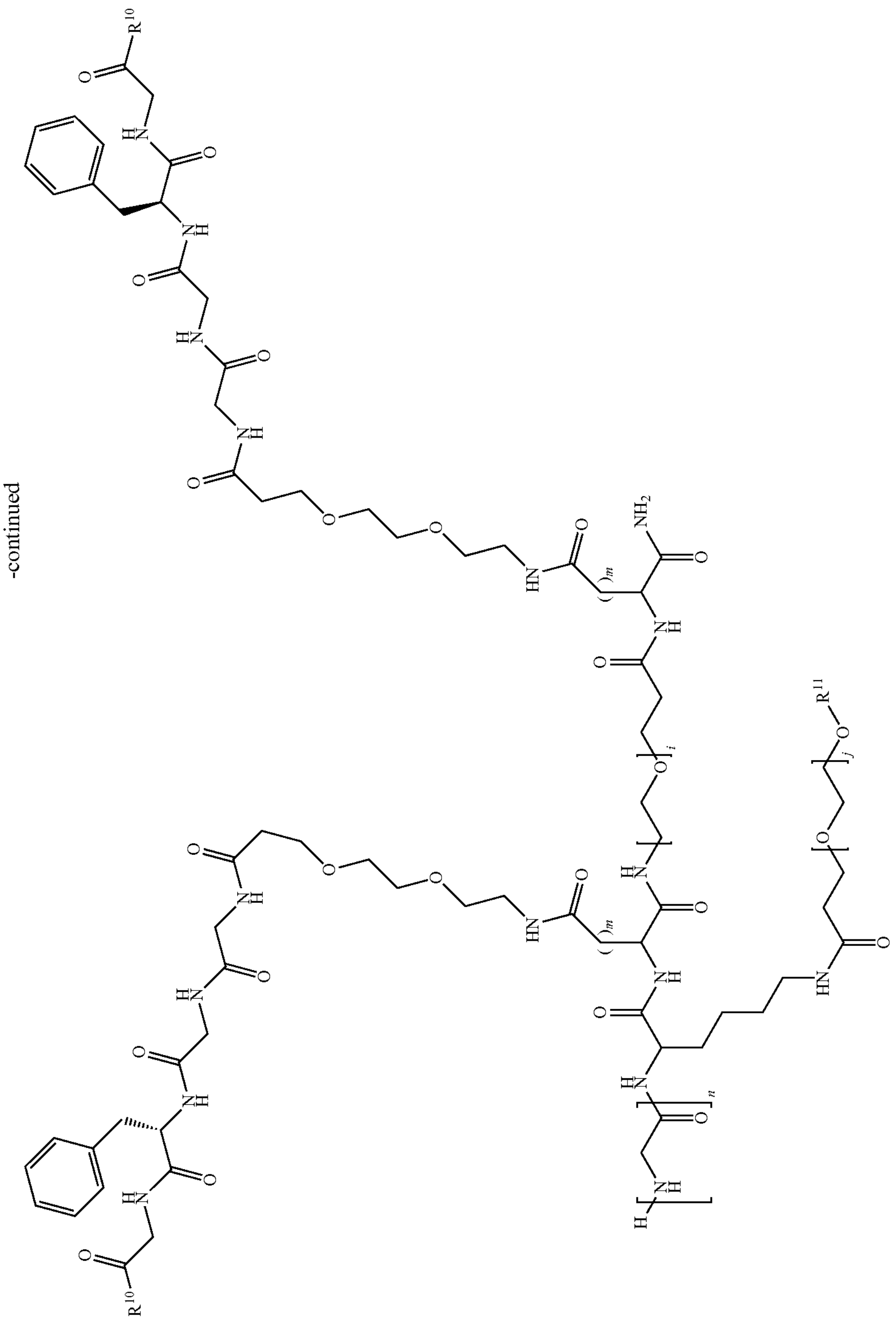
or

-continued
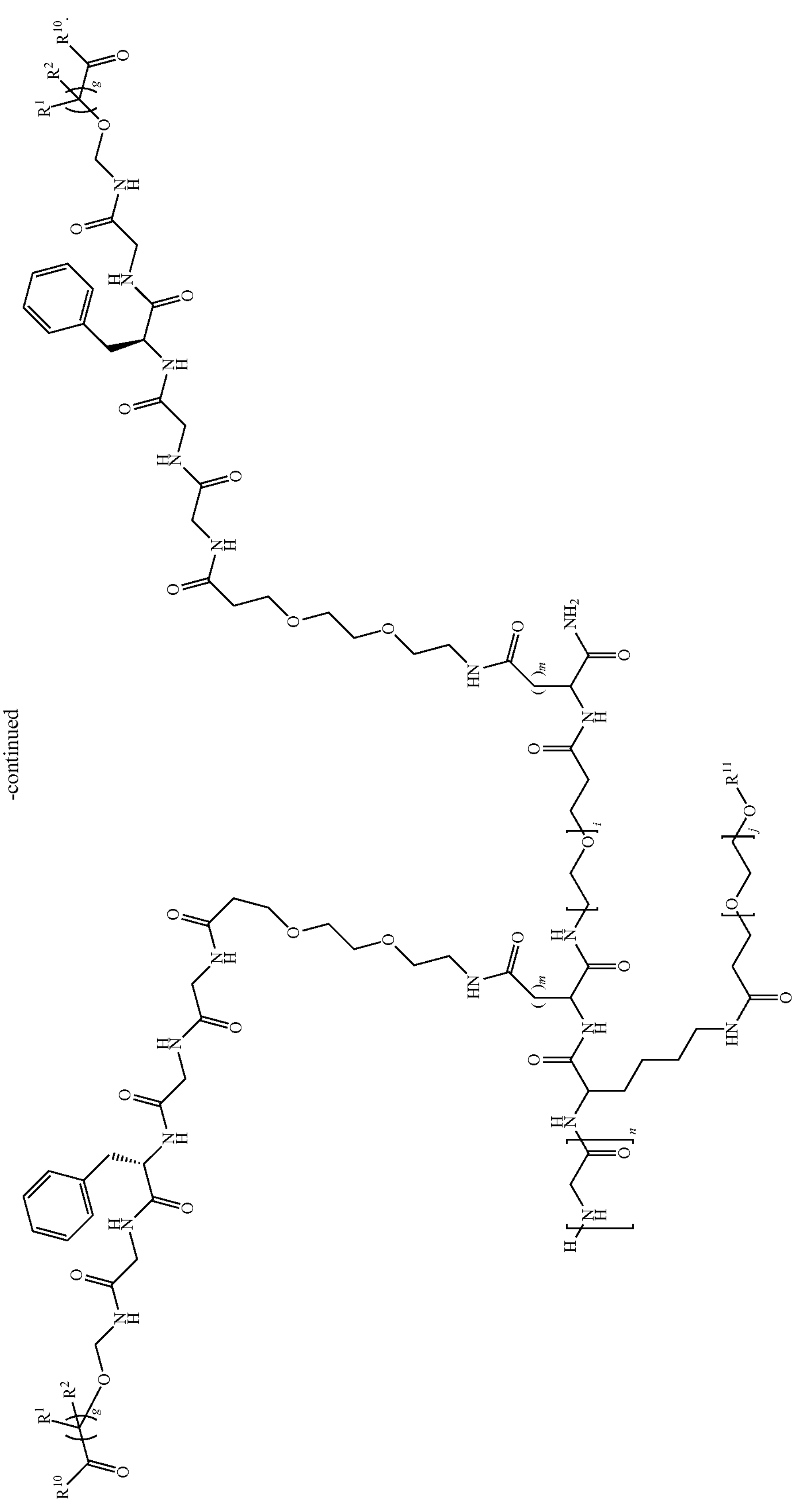

In one embodiment, n is 3, $L^2$ is —$(C_2H_4$—$O)_p$—$(CH_2)_2$(CO)—, p is 2, $L^1$ is GGFG, B is —NH—$CH_2$—U—$R^{10}$ or —$R^{10}$ or —NH—$CH_2$—U—$(CR^1R^2)_g$—(CO)—$R^{10}$, U is O, g is 1. In one embodiment, I-b-O has the structure of:
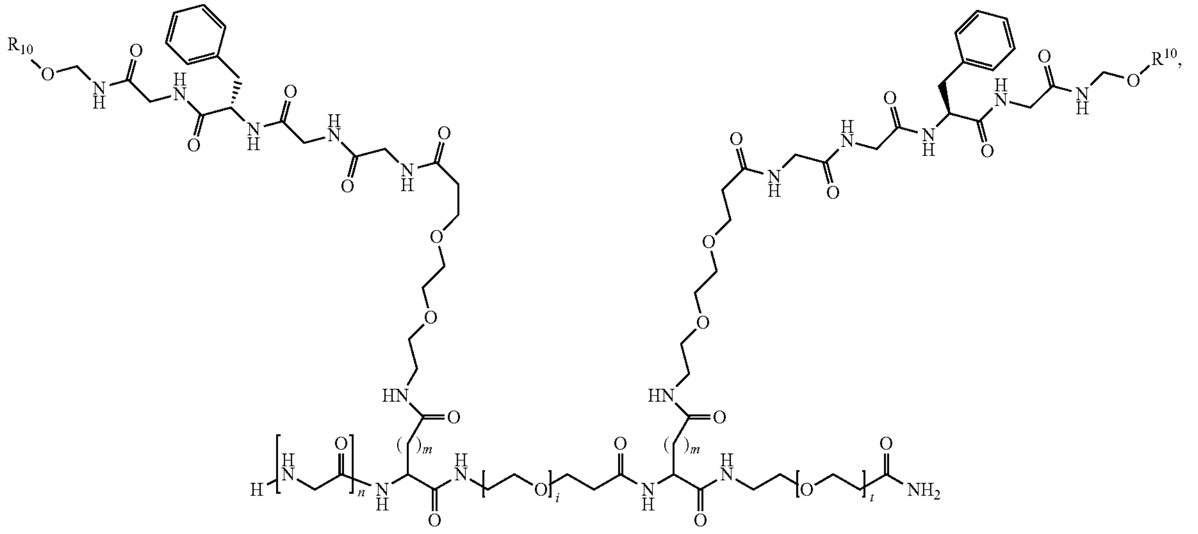
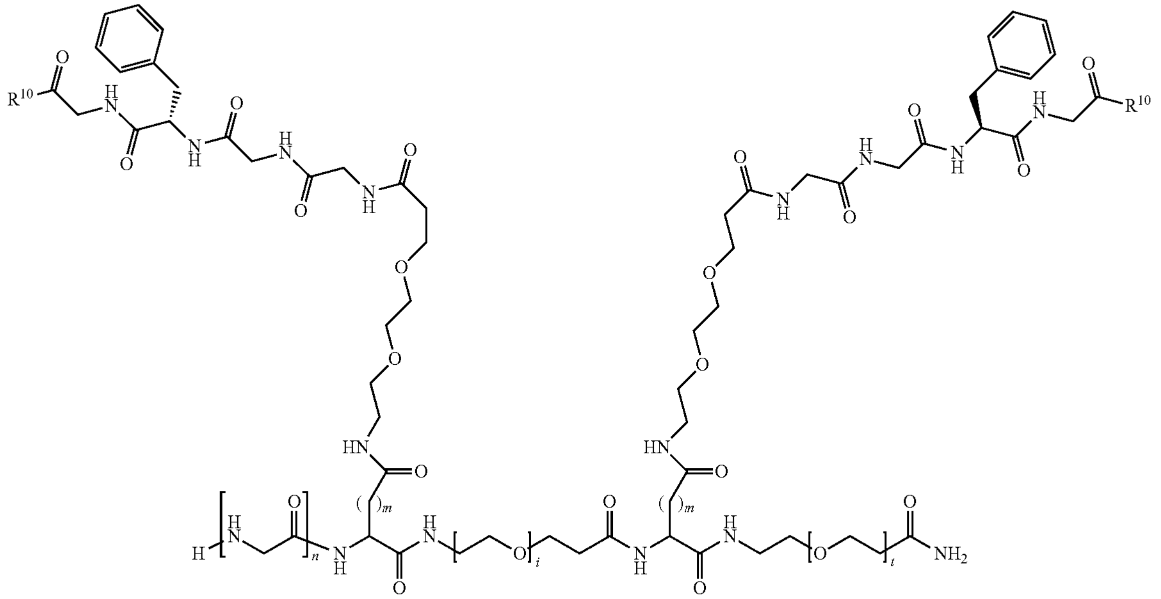
or
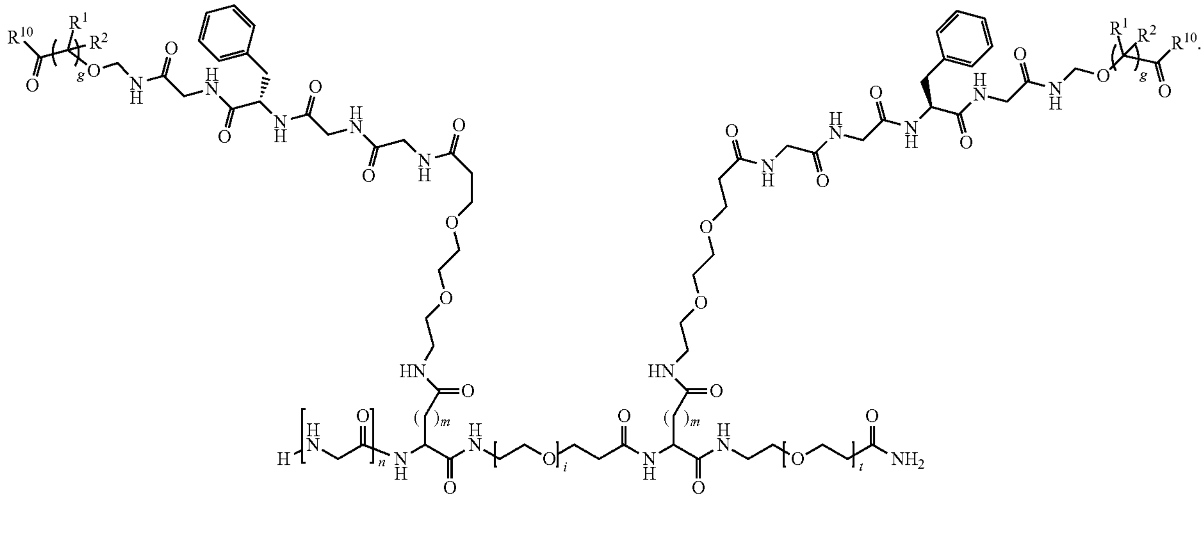

In one embodiment, 1 is 4, g is 1, $R^{11}$ is methyl.
In one embodiment, i is 2, g is 1, $R^{11}$ is methyl.
In one embodiment, I-a-0-2 is as follows (I-a-0-2-1 to I-a-0-2-3):
(I-a-0-2-1)
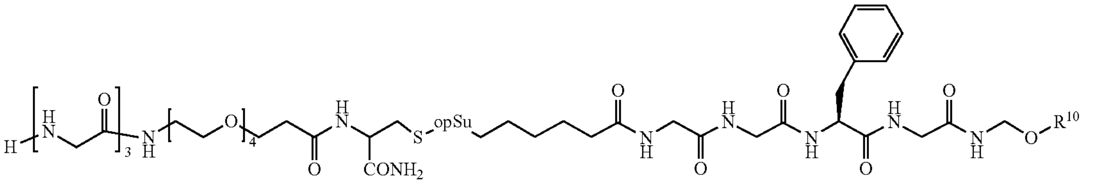
(I-a-0-2-2)
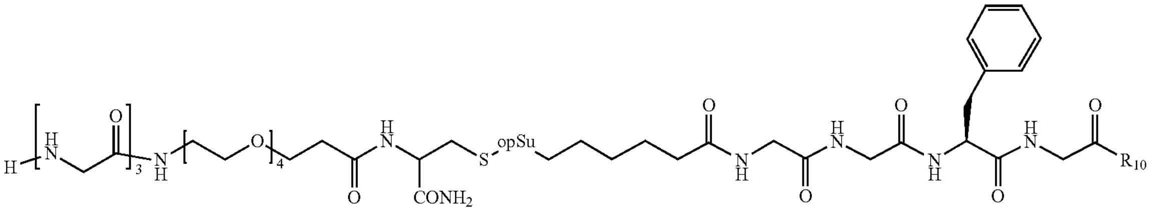
(I-a-0-2-3)
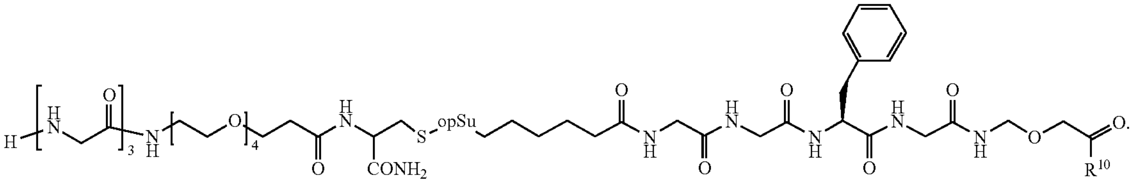
In one embodiment, 1 is 4, j is 8, g is 1, $R^{11}$ is methyl. In one embodiment, I-a-1-2 is as follows (I-a-1-2-1 to I-a-1-2-3):
(I-a-1-2-1)
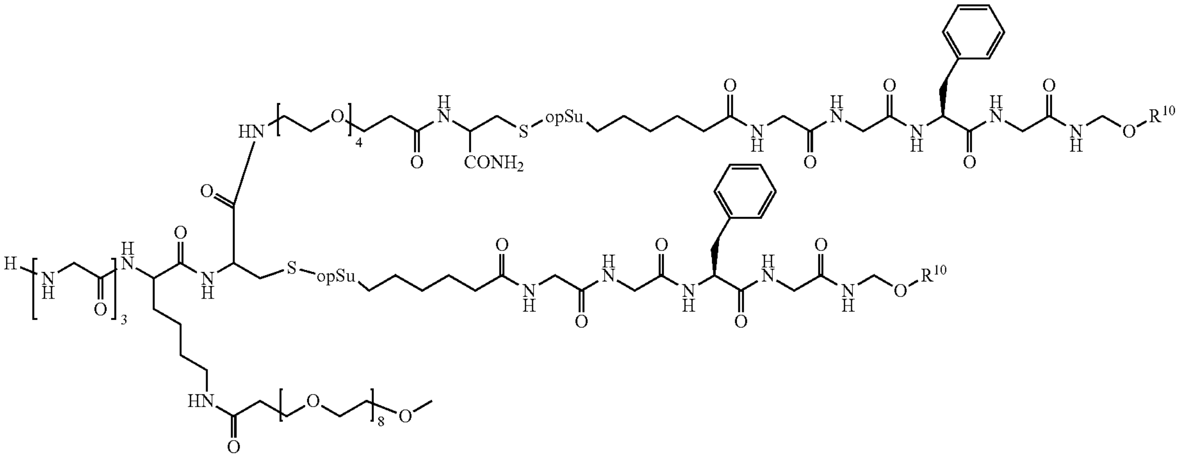

-continued
(I-a-1-2-2)
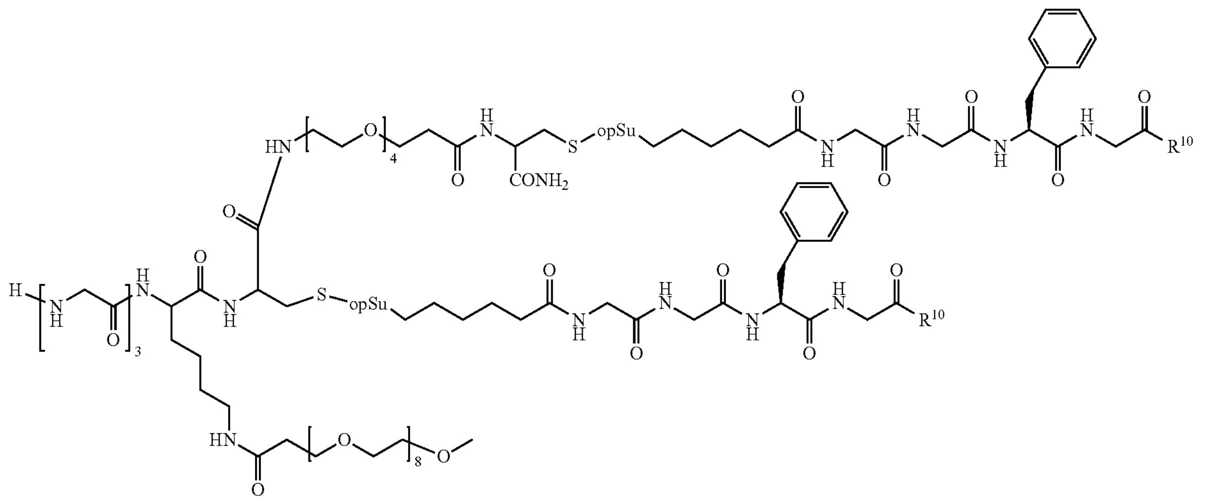
(I-a-1-2-3)
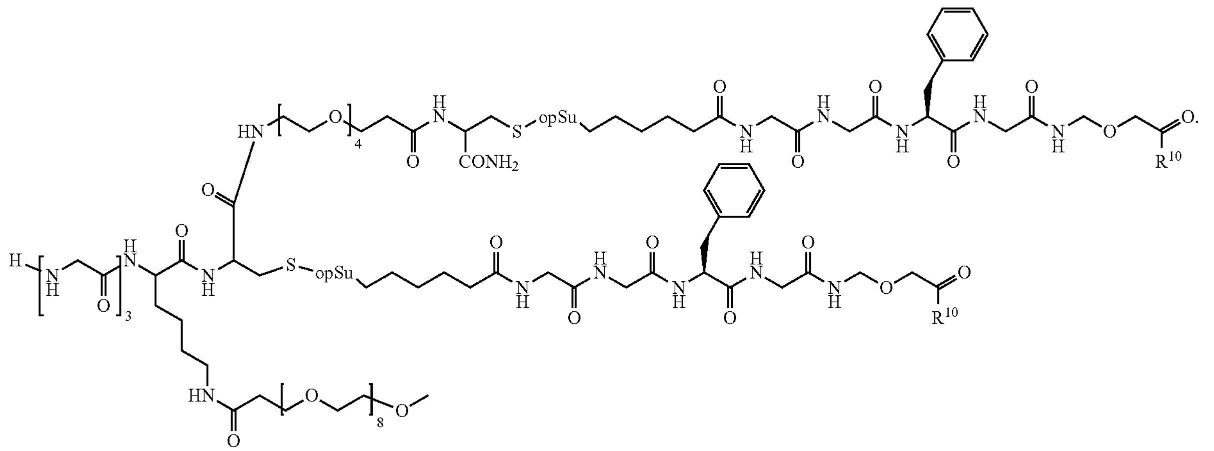
In one embodiment, n is 3, i is 4, j is 12, g is 1, $R^{11}$ is methyl. In one embodiment, I-a-1-2 is as follows (I-a-1-2-4 to I-a-1-2-6):
(I-a-1-2-4)
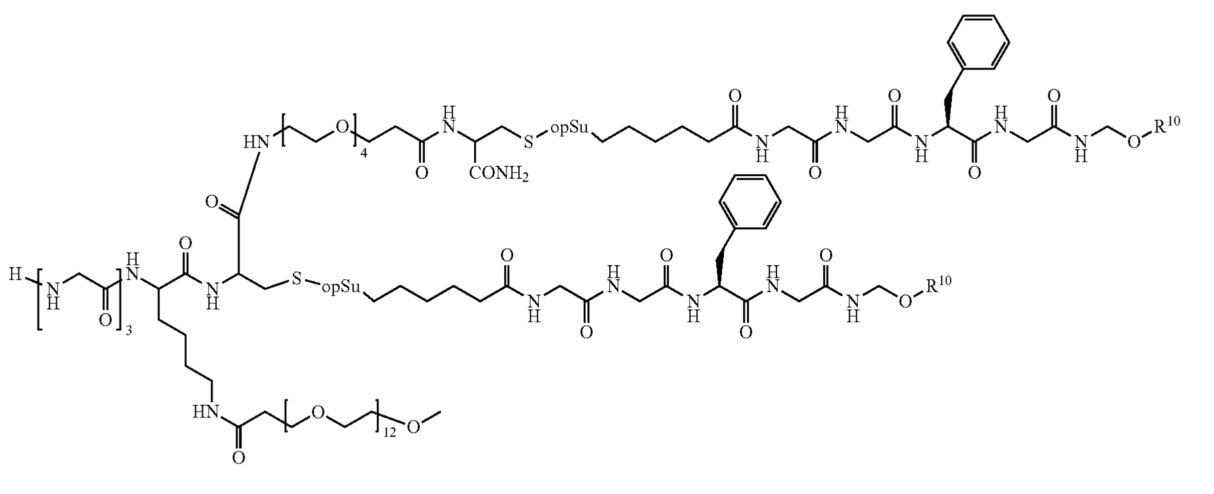

-continued
(I-a-1-2-5)
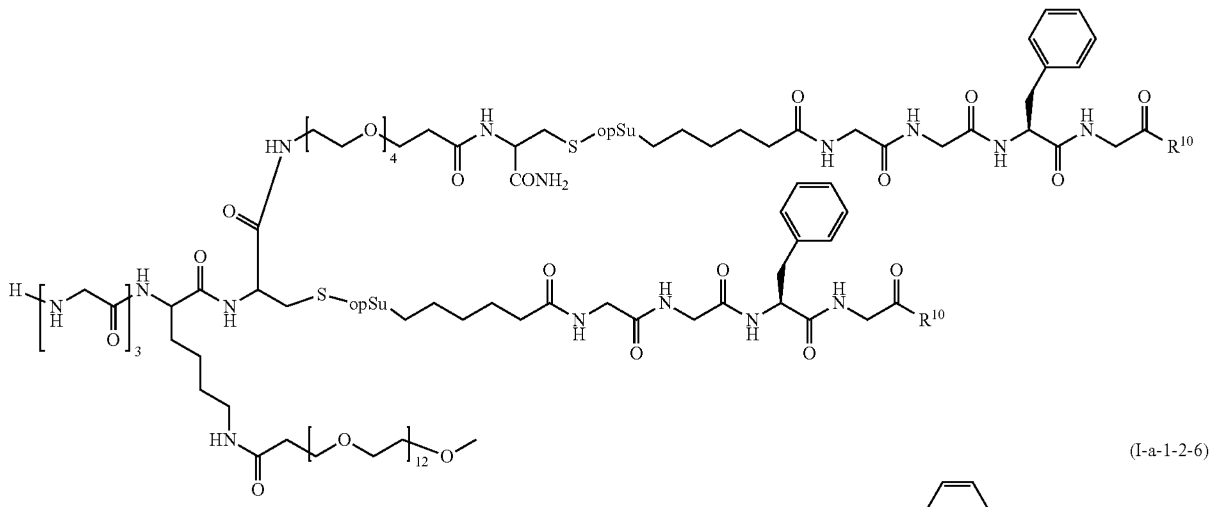
(I-a-1-2-6)
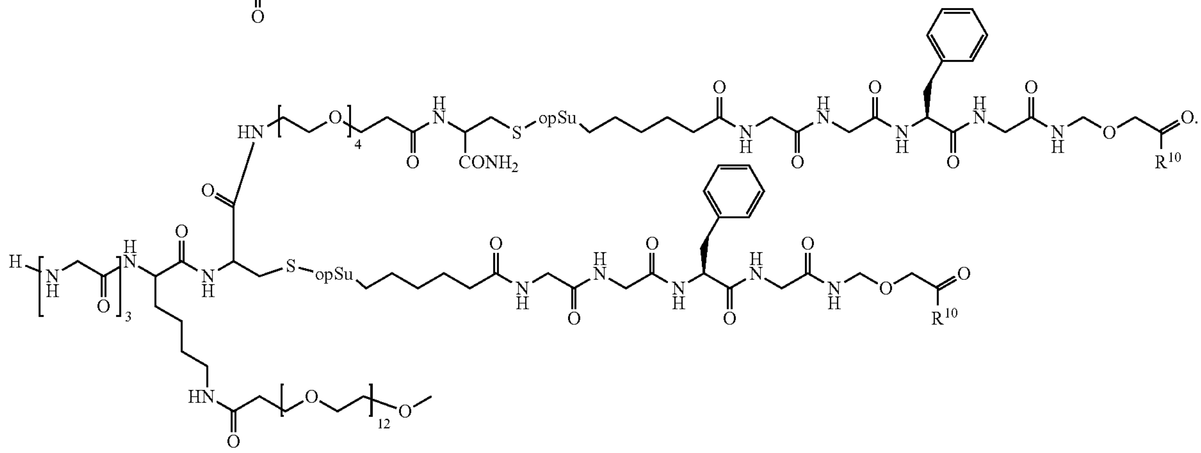
In one embodiment, i is 4, j is 8, g is 1, m is 1, n is 3, $R^{11}$ is methyl. In one embodiment, I-b-1 is as follows (I-b-1-1 to I-b-1-3):
(I-b-1-1)
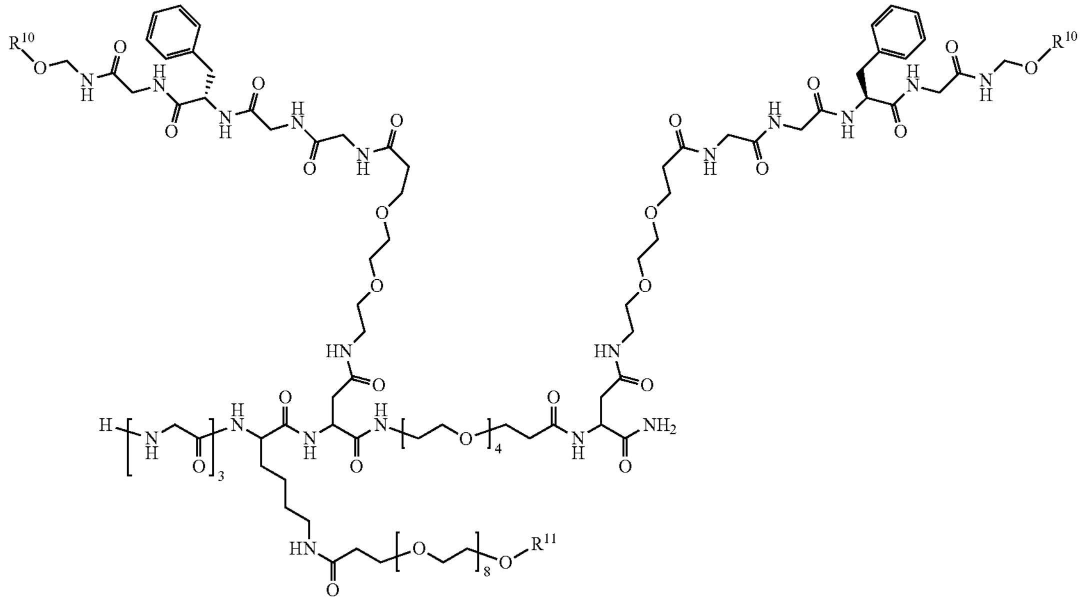

-continued
(I-b-1-2)
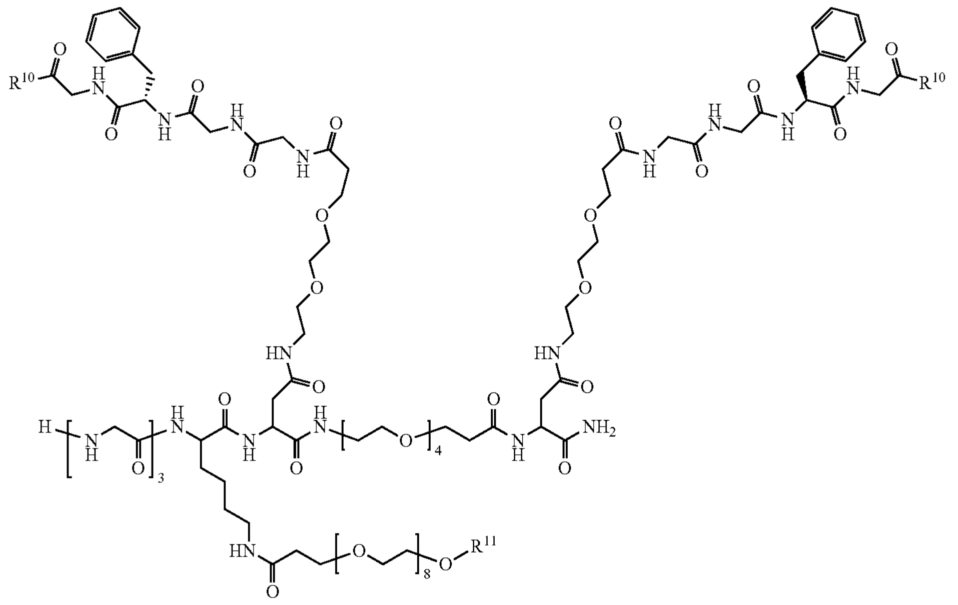
(I-b-1-3)
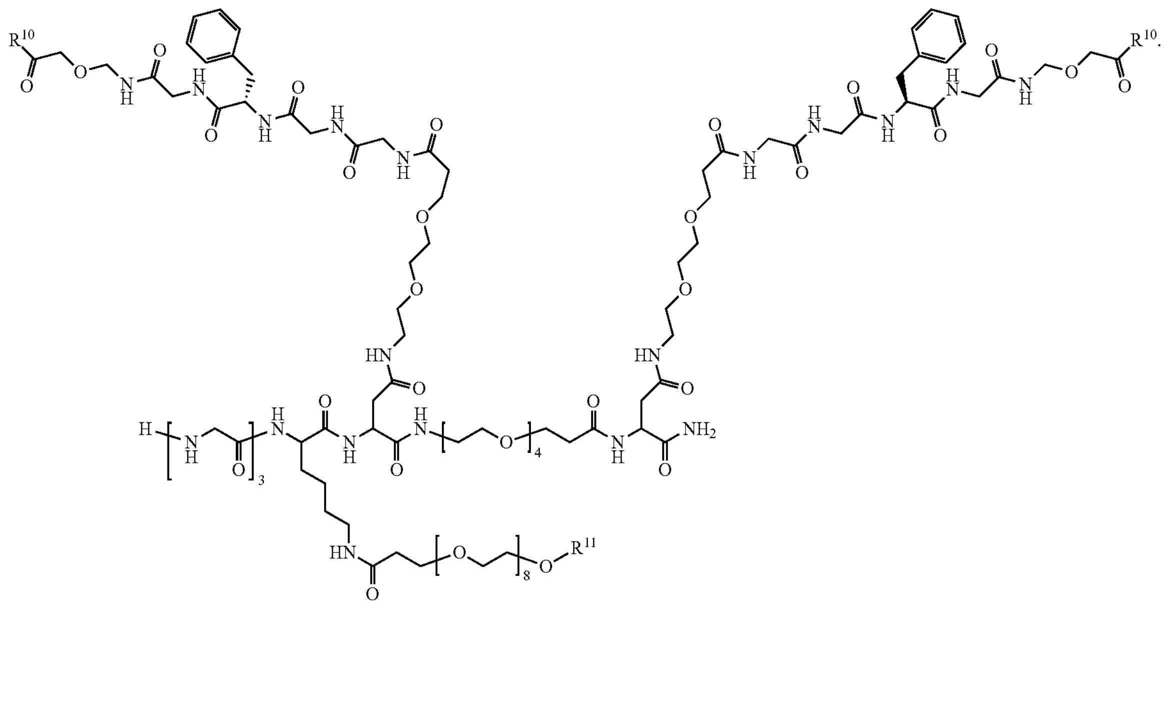

In one embodiment, i is 4, j is 12, g is 1, in is 1, n is 3, $R^{11}$ is methyl. In one embodiment, I-b-1 is as follows (I-b-1-4 to I-b-1-1-6):
(I-b-1-4)
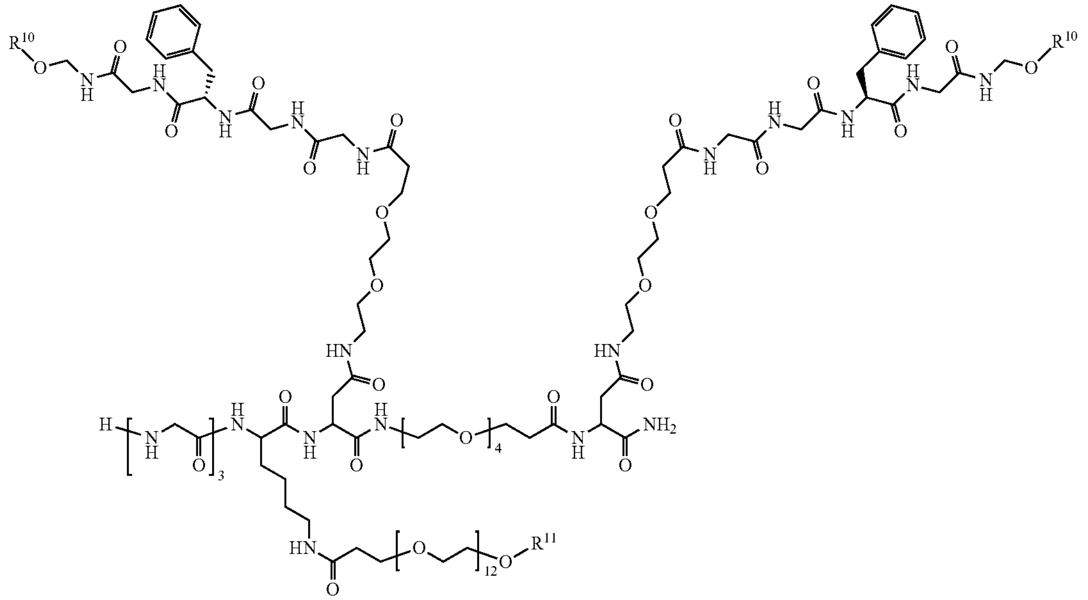
(I-b-1-5)
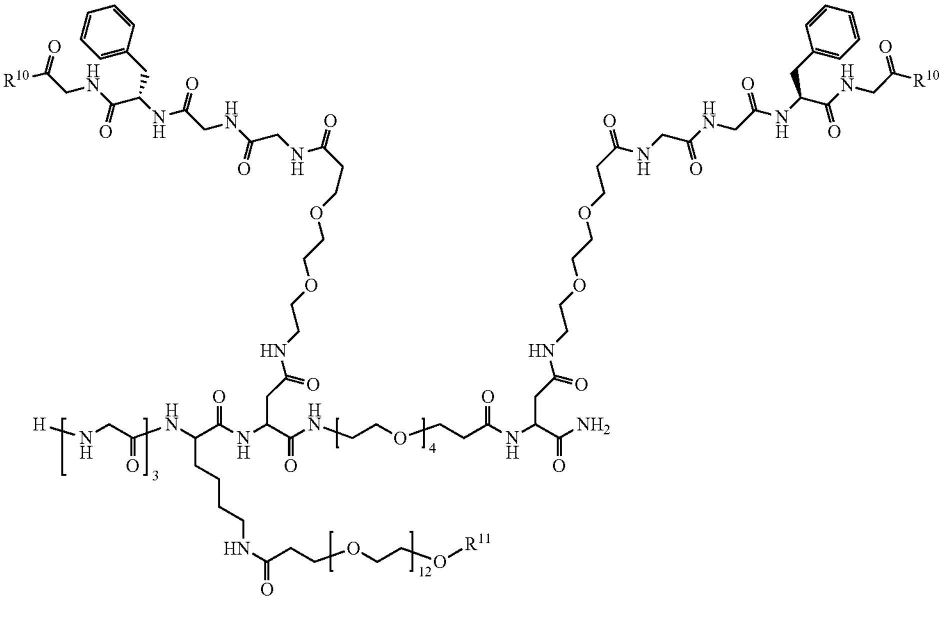

-continued
(I-b-1-6)
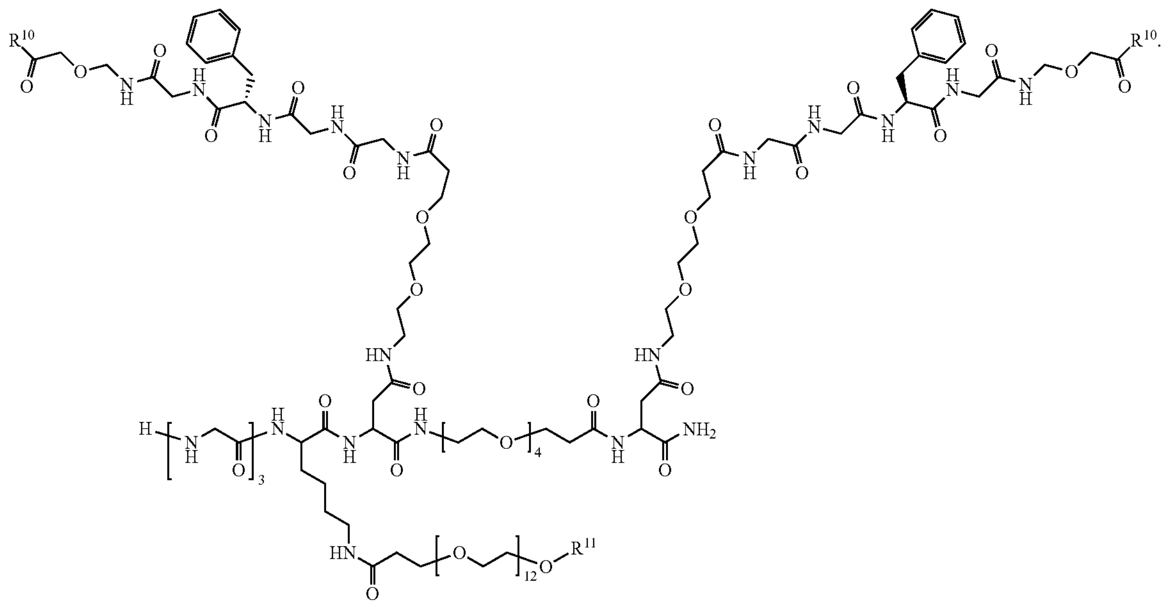
In one embodiment, i is 4, j is 8, g is 1, m is 2, n is 3, $R^{11}$ is methyl. In one embodiment, I-b-1 is as follows (I-b-1-7 to I-b-1-9):
(I-b-1-7)
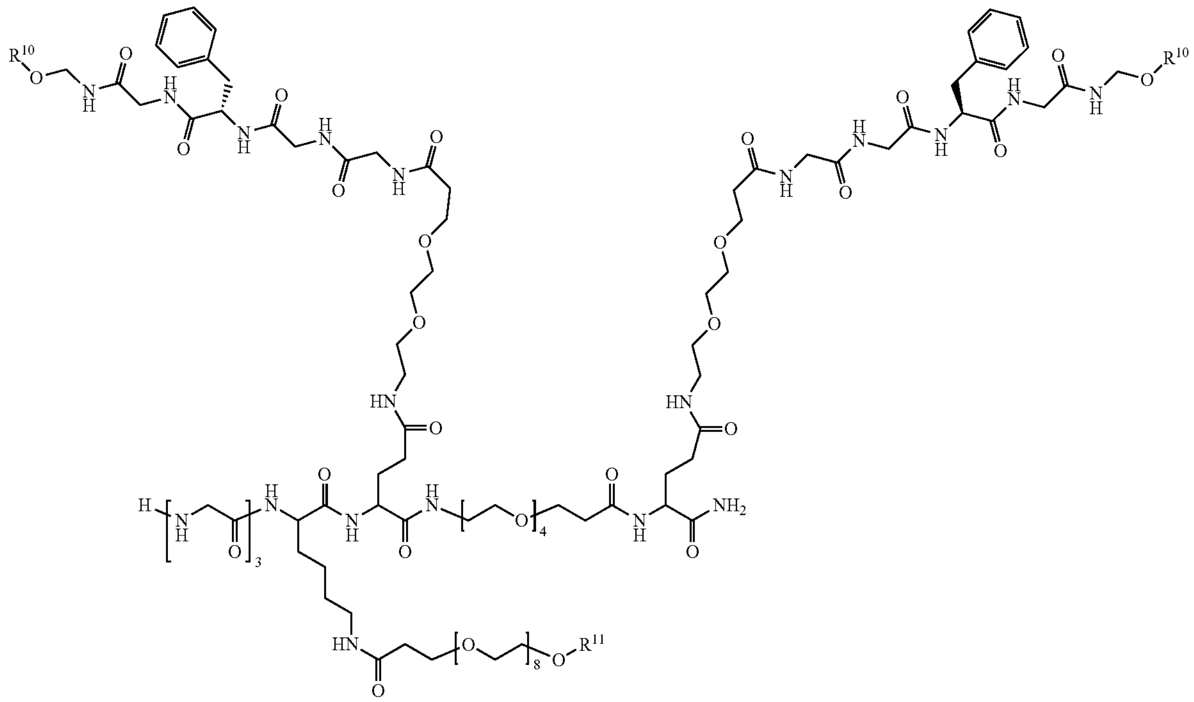

-continued
(I-b-1-8)
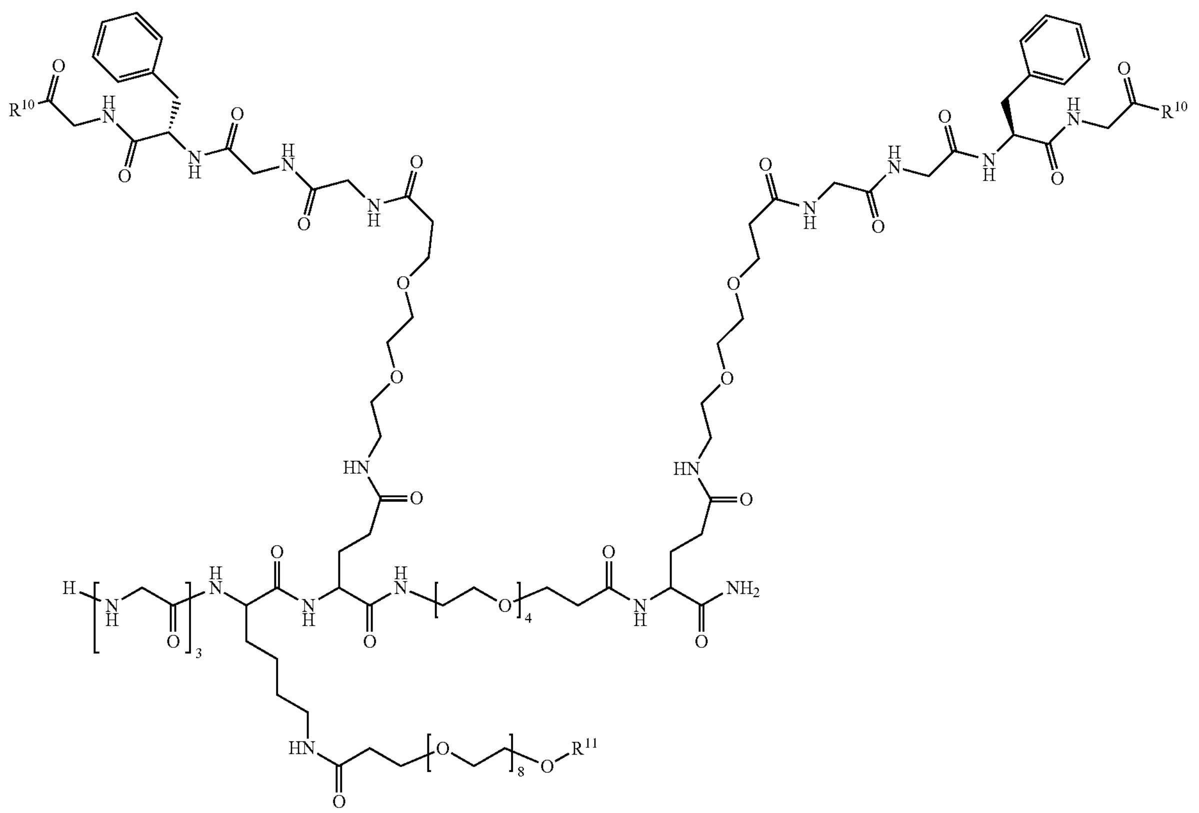
(I-b-1-9)
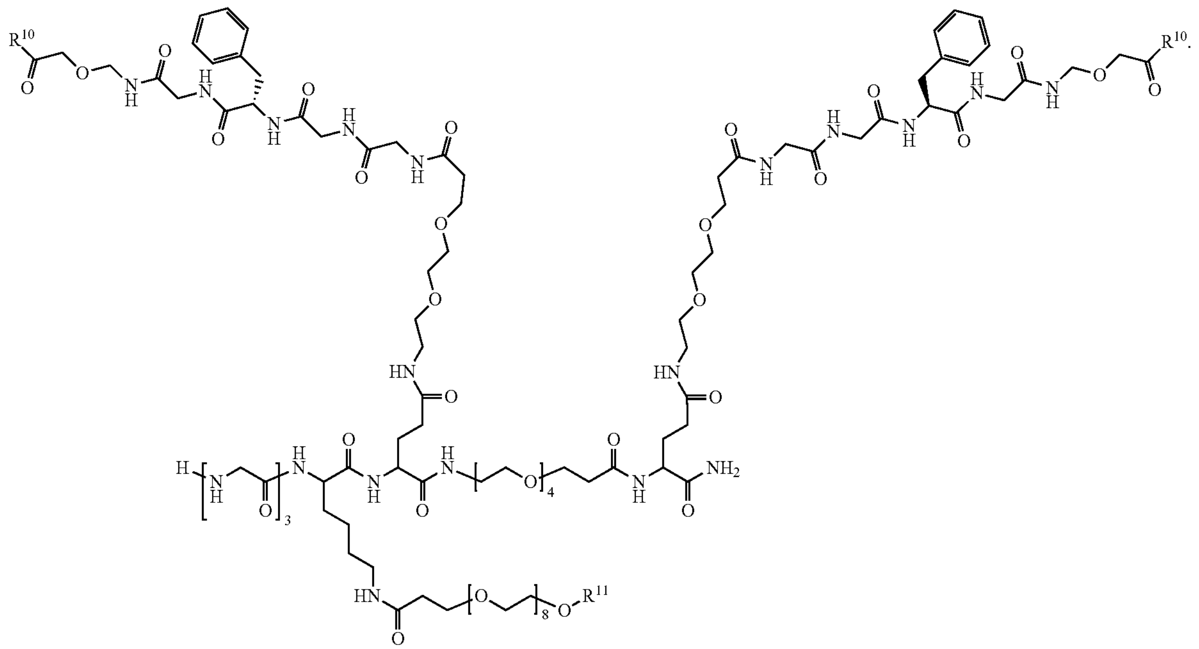
In one embodiment, i is 4, j is 12, g is 1, m is 2, n is 3, $R^{11}$ is methyl. In one embodiment, I-b-1 is as follows (I-b-1-10 to I-b-1-12):

(I-b-1-10)
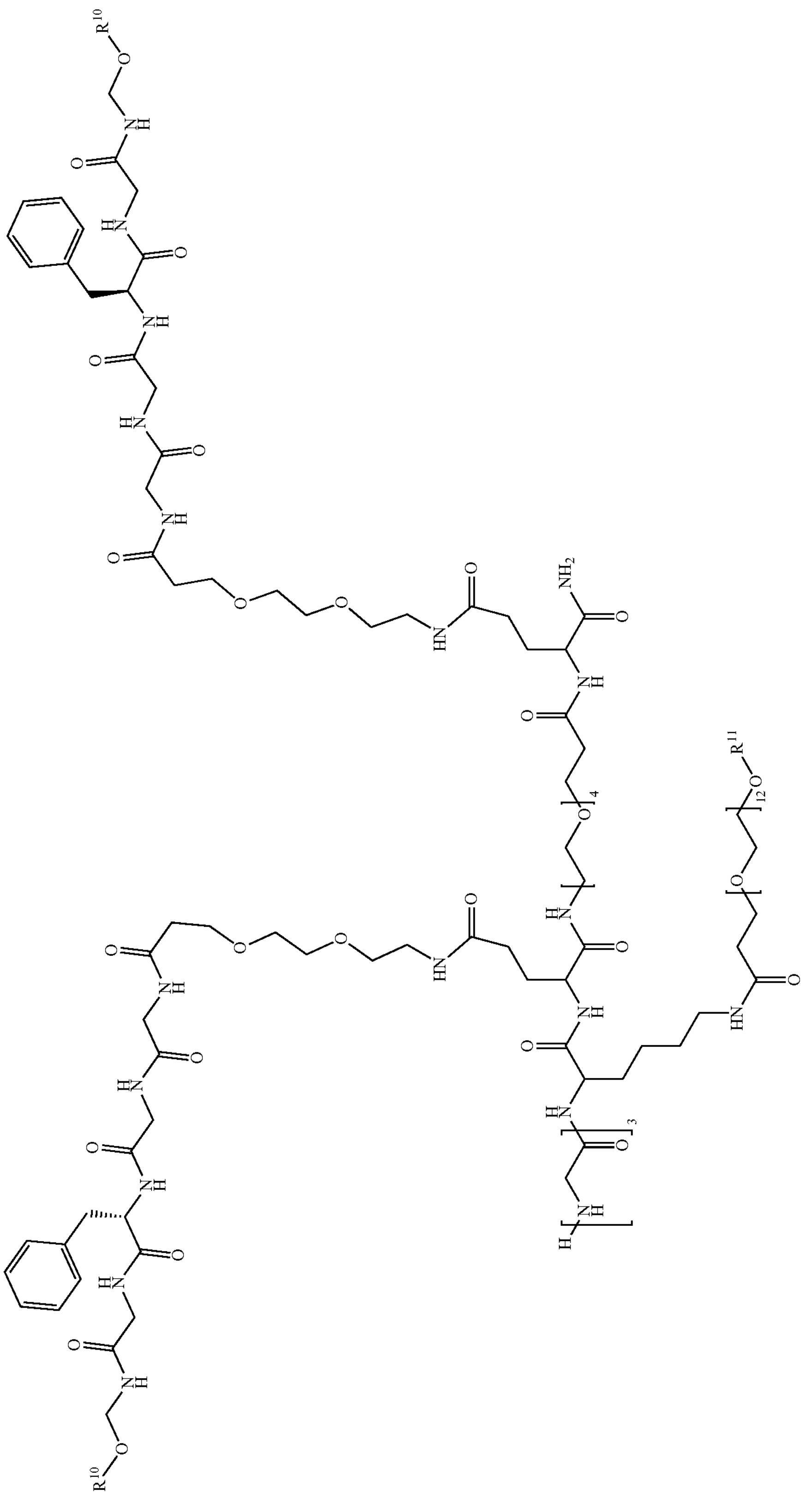

-continued
(I-b-1-11)
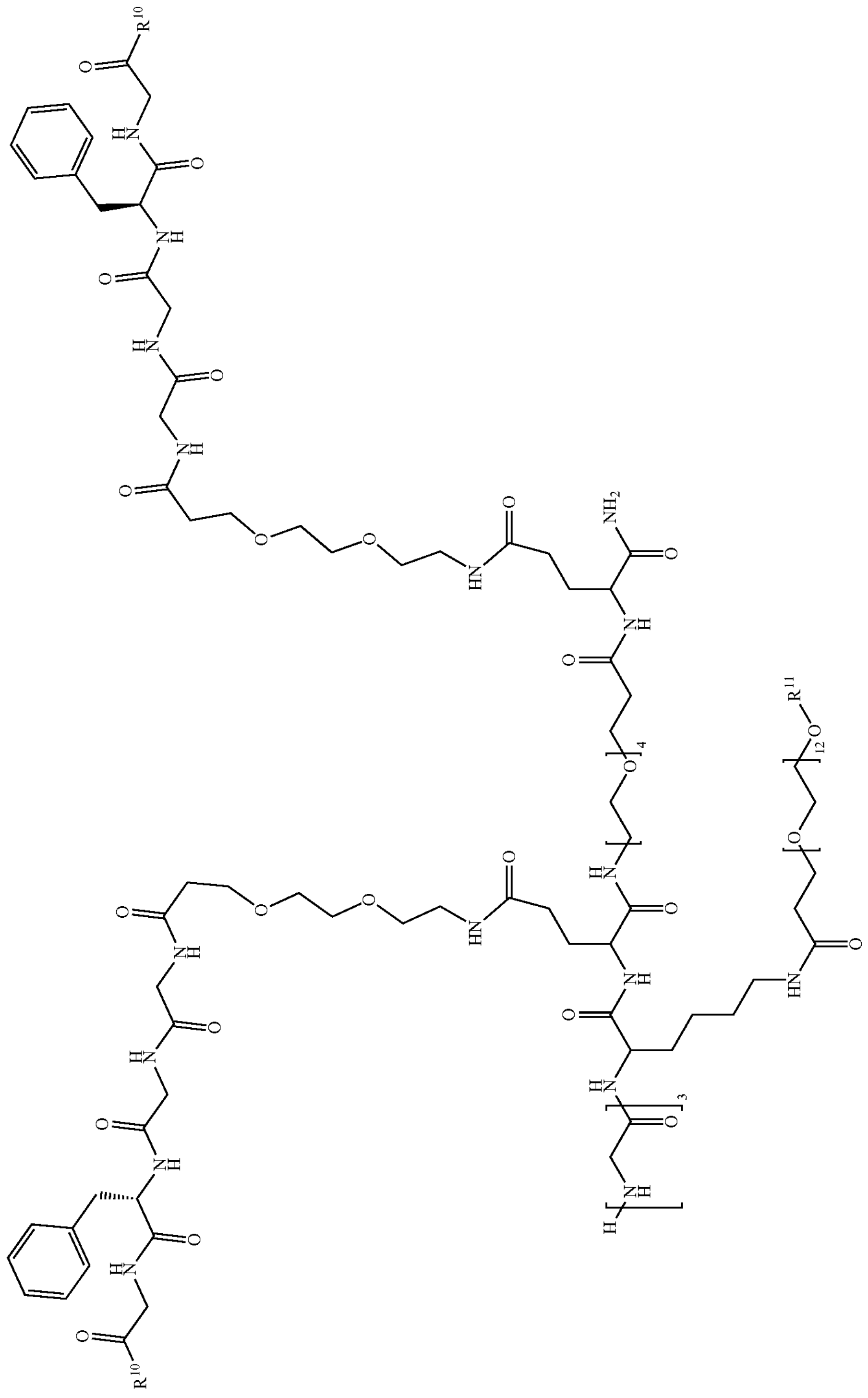

-continued
(I-b-1-12)
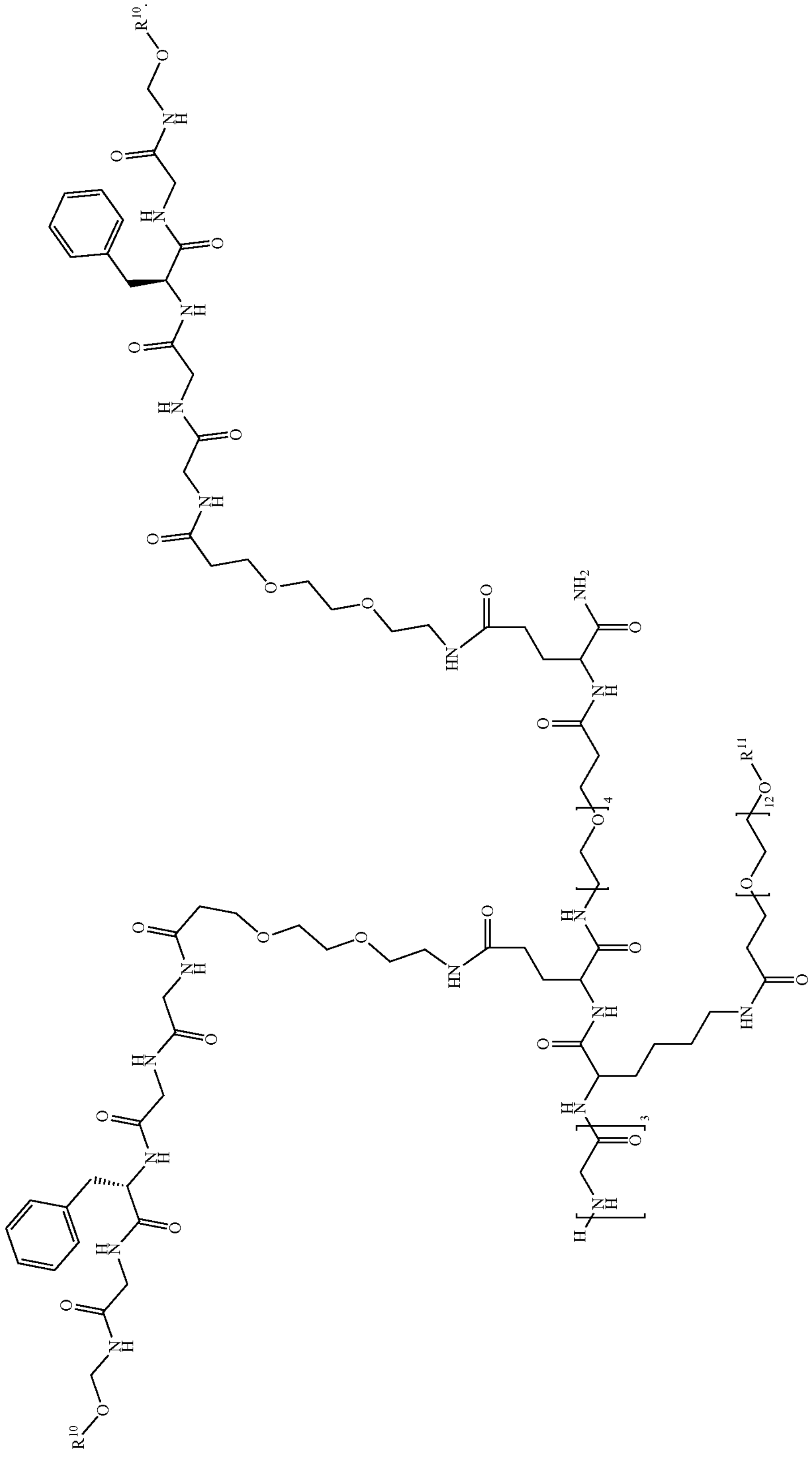

In one embodiment, i is 4, t is 8, g is 1, m is 1, n is 3, $R^{11}$ is methyl. In one embodiment, I-b-O is as follows (I-b-0-1 to I-b-0-3):
(I-b-0-1)
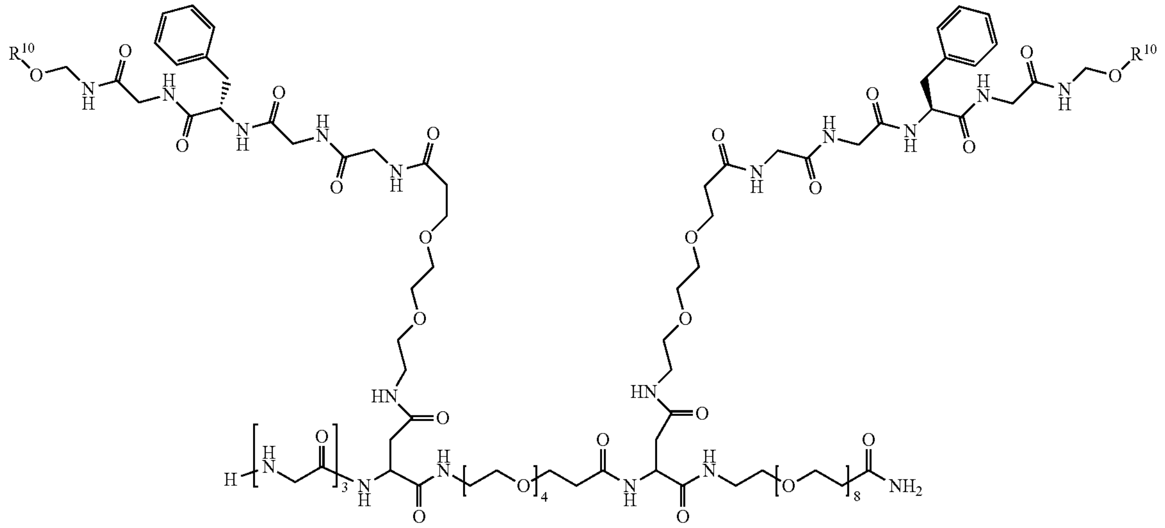
(I-b-0-2)
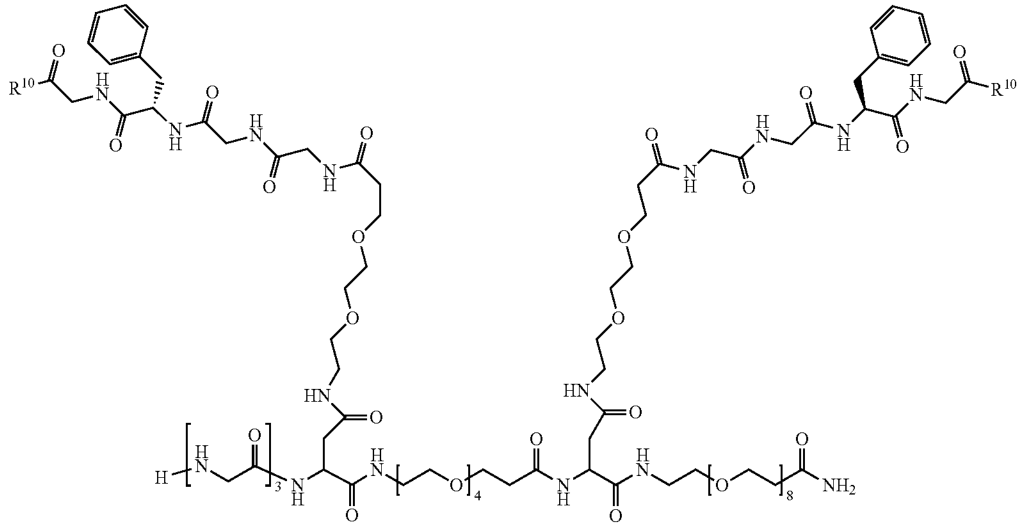

-continued
(I-b-0-3)
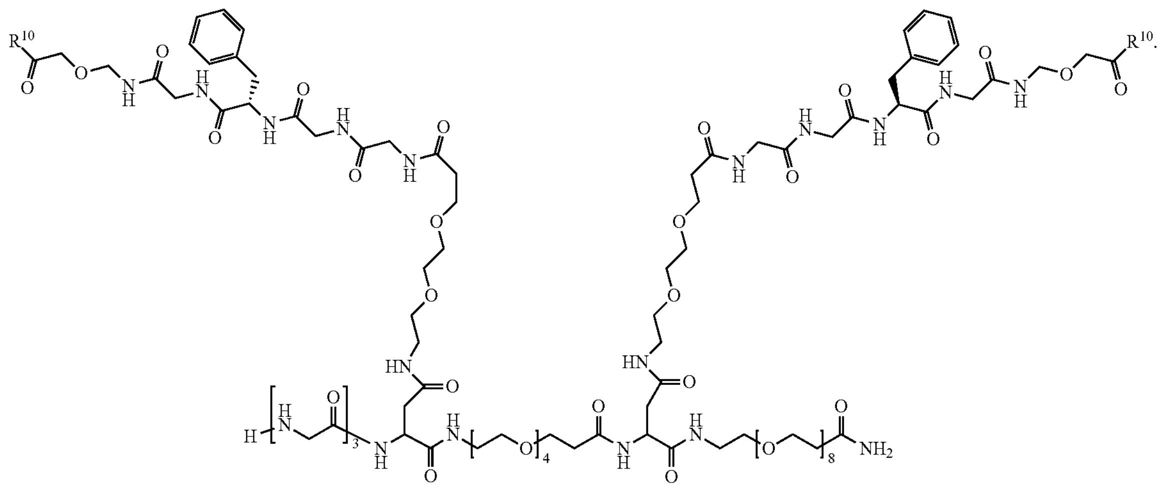
In one embodiment, i is 4, t is 12, g is 1, m is 1, n is 3, $R^{11}$ is methyl. In one embodiment, I-b-O is as follows (I-b-0-4 to I-b-0-6):
(I-b-0-4)
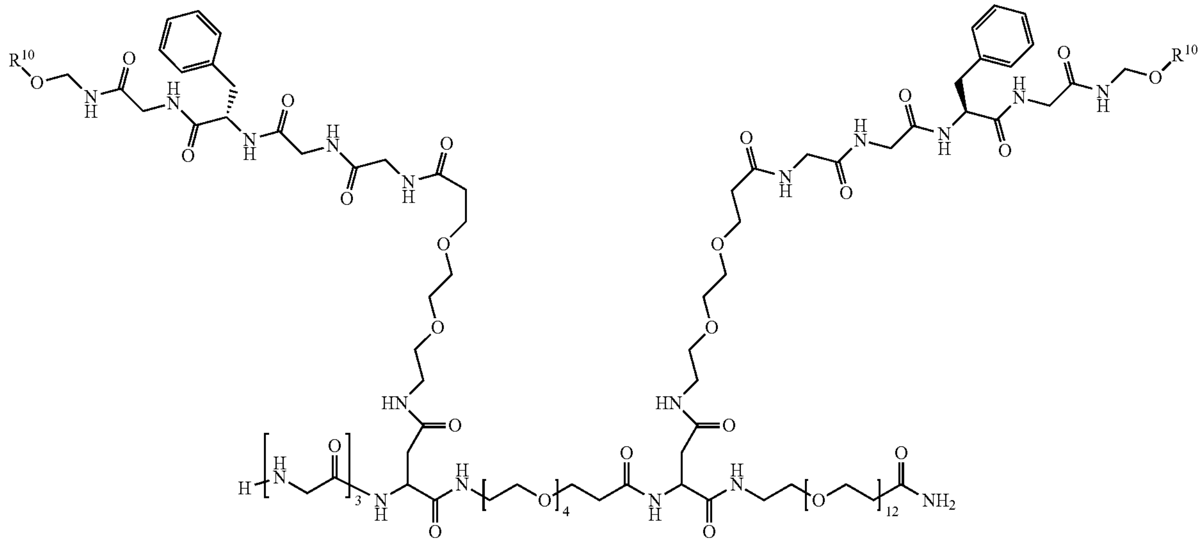

-continued
(I-b-0-5)
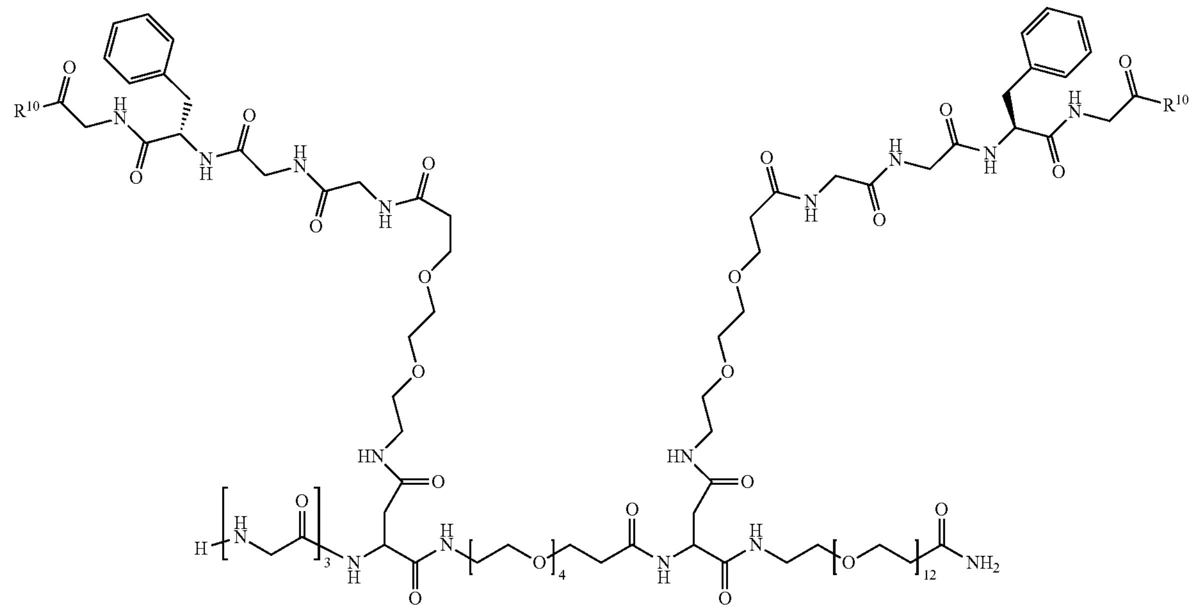
(I-b-0-6)
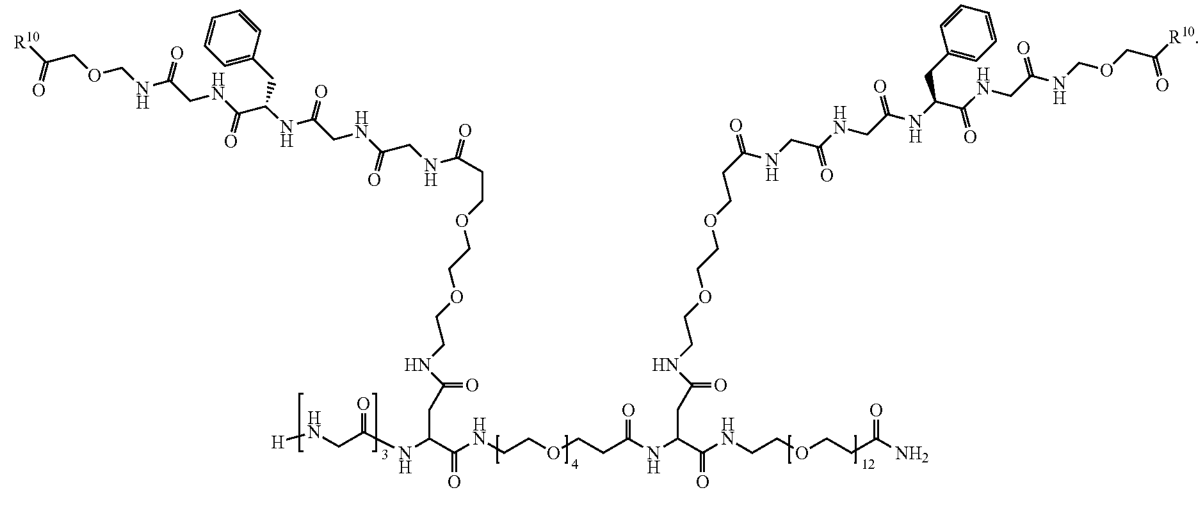

In one embodiment, i is 4, t is 8, g is 1, m is 2, n is 3, $R^{11}$ is methyl. In one embodiment, I-b-O is as follows (I-b-0-7 to I-b-0-9):
(I-b-0-7)
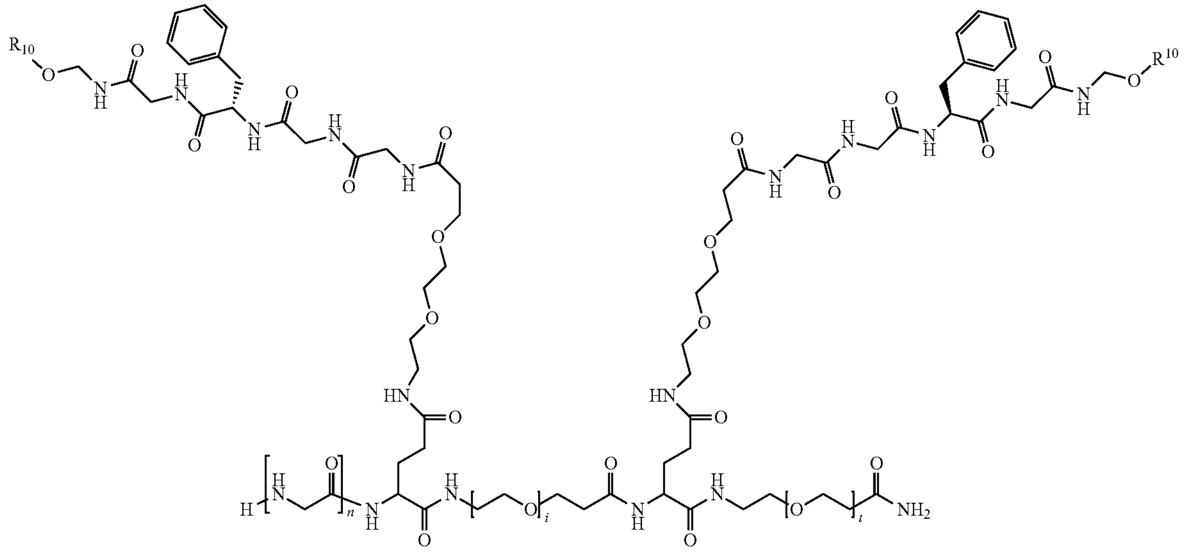
(I-b-0-8)
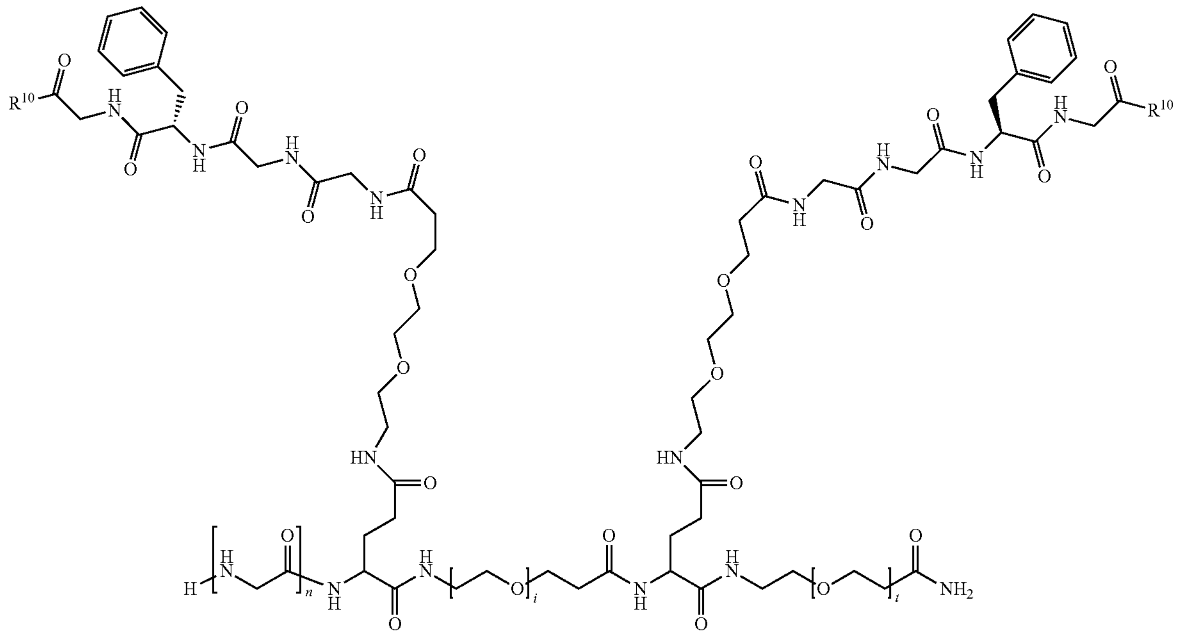

-continued
(I-b-0-9)
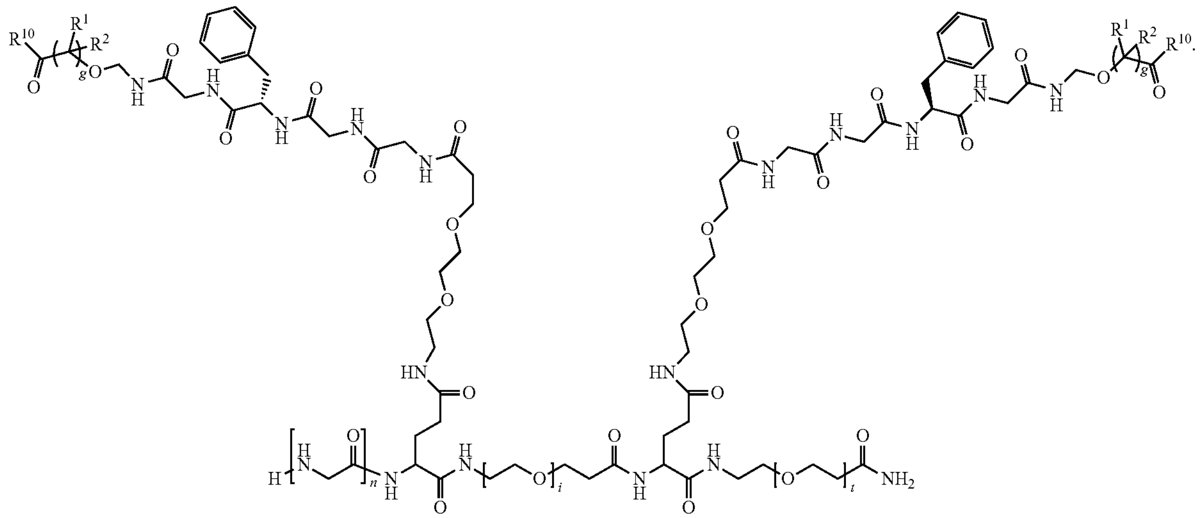
In one embodiment, i is 4, t is 12, g is 1, m is 2, n is 3, $R^{11}$ is methyl. In one embodiment, I-b-O is as follows (I-b-0-10 to I-b-0-12):
(I-b-0-10)
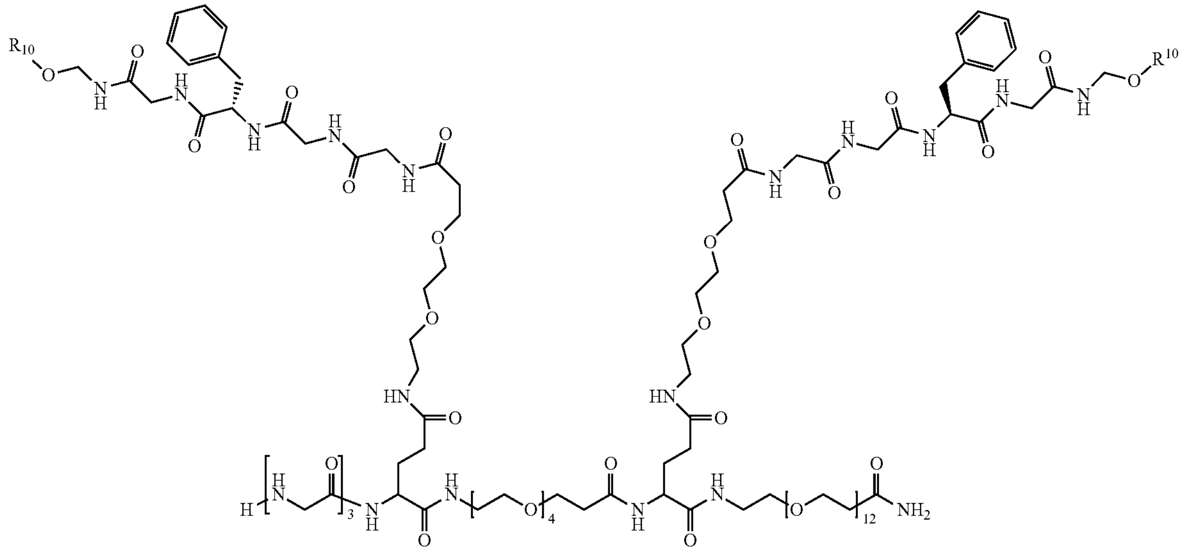

-continued (I-b-0-11)

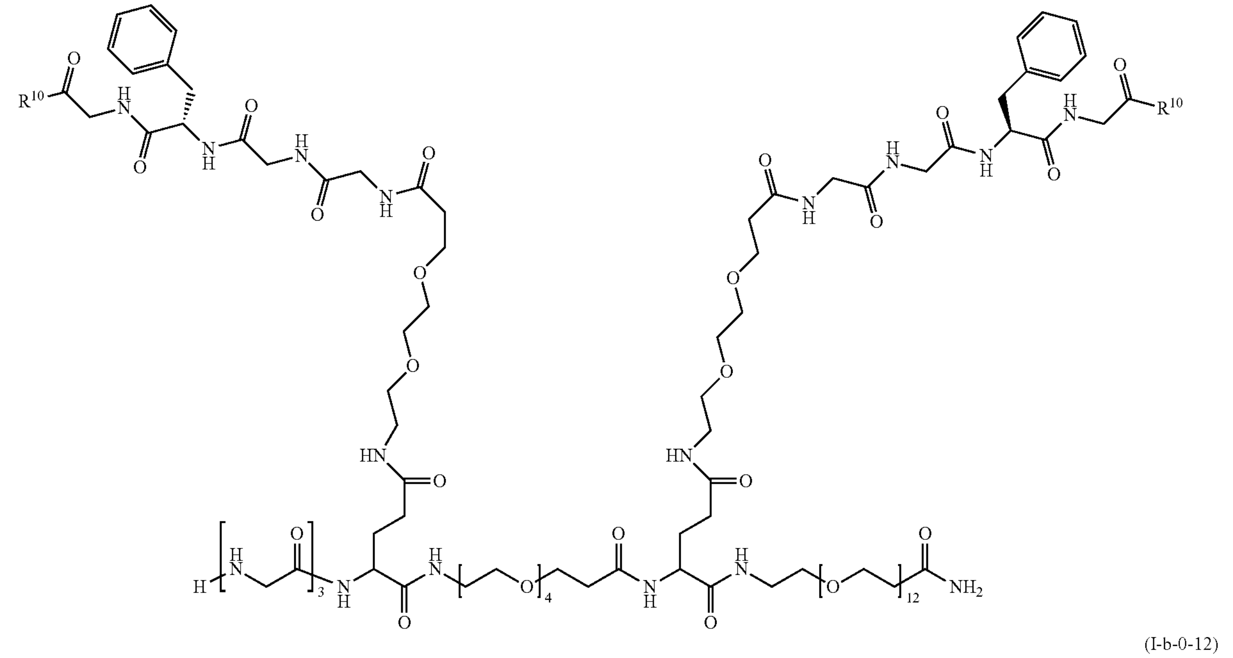

(I-b-0-12)

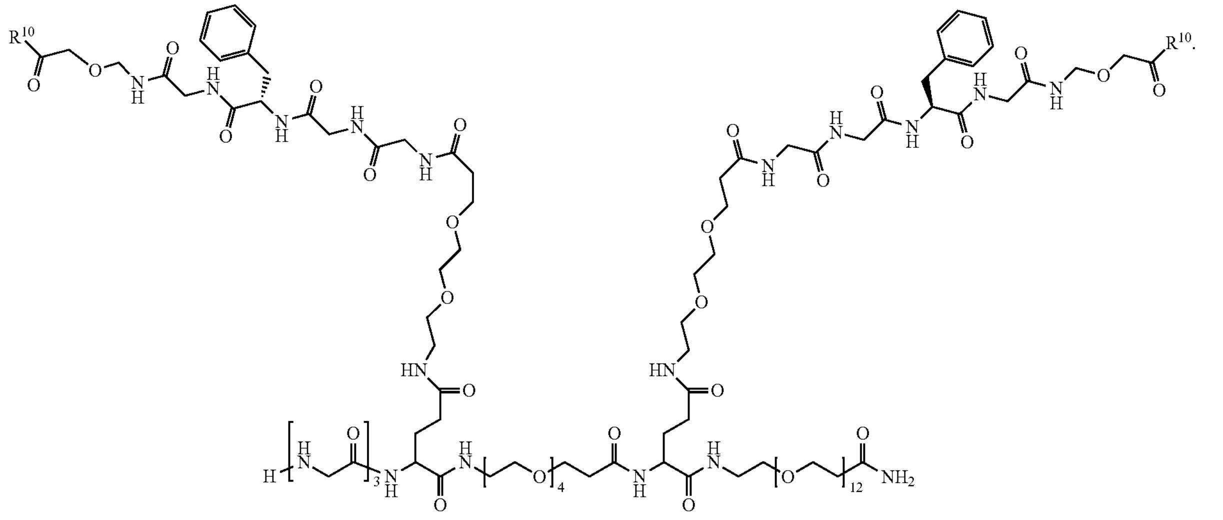

Payload-Bearing Formula (I) Compound

The reactive group comprised by B is covalently conjugated with a payload containing another reactive group to give a payload-bearing formula (I) compound.

In yet another aspect, provided is a compound having the structure of formula (II)

formula (II)

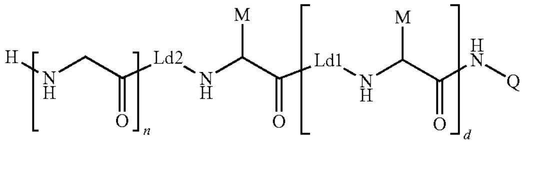

wherein

Q is hydrogen, —$C_2H_4$-$(PEG)_t$-(CO)$NH_2$ or LKb-P;

M is hydrogen or LKa-LKb-P;

provided that Q and M are not simultaneously hydrogen;

P is a payload which is linked to the B moiety or $L^1$ moiety of the compound of formula (I);

n, d, Ld1, Ld2, t, LKa and LKb are as defined in formula (I).

As defined herein above, in the compound of formula (I), each LKb is independently $L^2$-$L^1$-B; each B is independently a terminal group $R^{10}$, or a combination of the following 1), 2) and 3): 1) a self-immolative spacer Sp1; 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—; and 3) a terminal group $R^{10}$; $R^{10}$ is hydrogen, or a group which can leave when reacting with a group in the payload. In one embodiment, $R^{10}$ represents the part of structure which would not appear in the product molecule resulting from the reaction of B with the payload.

In one embodiment, P is linked to the B moiety of the compound of formula (I) to form the compound of formula (II). As defined above, $R^{10}$ would not appear in the B—P structure of the compound of formula (II).

It should be understood that, when B in the compound of formula (I) is a terminal group $R^{10}$, $R^{10}$ would not appear in the compound of formula (II). Therefore, as a result, B is absent in the B—P structure of the compound of formula (II).

In one embodiment, M is hydrogen or LKa-$L^2$-$L^1$-B—P; wherein P is a payload which is linked to the B moiety or $L^1$ moiety of the compound of formula (I); each B is independently a terminal group $R^{10}$, or a combination of the following 1), 2) and 3): 1) a self-immolative spacer Sp1; 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—; and 3) a terminal group $R^{10}$; $R^{10}$ is hydrogen, or a group which can leave when reacting with a group in the payload; $R^{10}$ represents the part of structure which would not appear in the product molecule resulting from the reaction of B with the payload.

In one embodiment, M is hydrogen or LKa-$L^2$-$L^1$-B—P; wherein each B is independently absent, or is a combination of the following 1) and 2): 1) a self-immolative spacer Sp1; and 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—. In a preferred embodiment, M is hydrogen or LKa-$L^2$-$L^1$-B—P; wherein each B is independently absent, or is —NH—$CH_2$—U— or is —NH—$CH_2$—U—$(CR^1R^2)_g$(CO)—. In another embodiment, M is hydrogen or LKa-$L^2$-$L^1$-B—P. In one embodiment, in LKa-$L^2$-$L^1$-B—P, B is absent. In one embodiment, in LKa-$L^2$-L-B—P, B is a combination of the following 1) and 2): 1) a self-immolative spacer Sp1; and 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—. In one embodiment, in LKa-$L^2$-$L^1$-B—P, B is —NH—$CH_2$—U— or is —NH—$CH_2$—U—$(CR^1R^2)_g$—(CO)—; U is absent, or is O, S or NH, preferably O or S. In one embodiment, B in the compound of formula (I) is connected to the payload through an amide bond or an ester bond or an ether bond.

As defined herein above, when B in the compound of formula (I) is a terminal group $R^{10}$, B is absent in the B—P structure of the compound of formula (II). In such case, it can also be understood to be that the Cleavable sequence 1 in $L^1$ is connected to the payload to form the compound of formula (II), wherein B is absent in the resulting molecule of the connection of Cleavable sequence 1 with the payload. Accordingly, in one embodiment, P is linked to the $L^1$ moiety of the compound of formula (I) to form the compound of formula (II). Accordingly, in one embodiment, M is LKa-$L^2$-$L^1$-B—P, and B is absent; and M can also be denoted as LKa-$L^2$-$L^1$-P.

Payload

In the present disclosure, the payload may be selected from the group consisting of small molecule compounds, nucleic acids and analogues, tracer molecules (including fluorescent molecules, etc.), short peptides, polypeptides, peptidomimetics, and proteins. In one embodiment, the payload is selected from the group consisting of small molecule compounds, nucleic acid molecules, and tracer molecules. In a preferred embodiment, the payload is selected from small molecule compounds. In a more preferred embodiment, the payload is selected from the group consisting of cytotoxin and fragments thereof.

In one embodiment, the cytotoxin is selected from the group consisting of drugs that target microtubule cytoskeleton. In a preferred embodiment, the cytotoxin is selected from the group consisting of taxanes, maytansinoids, auristatins, epothilones, combretastatin A-4 phosphate, combretastatin A-4 and derivatives thereof, indol-sulfonamides, vinblastines such as vinblastine, vincristine, vindesine, vinorelbine, vinflunine, vinglycinate, anhy-drovinblastine, dolastatin 10 and analogues, halichondrin B and eribulin, indole-3-oxoacetamide, podophyllotoxins, 7-diethylamino-3-(2'-benzoxazolyl)-coumarin (DBC), discodermolide, laulimalide. In another embodiment, the cytotoxin is selected from the group consisting of DNA topoisomerase inhibitors such as camptothecins and derivatives thereof, mitoxantrone, mitoguazone. In a preferred embodiment, the cytotoxin is selected from the group consisting of nitrogen mustards such as chlorambucil, chlornaphazine, cholophosphamide, estramustine, ifosfamide, mechlorethamine, mechlorethamine oxide hydrochloride, melphalan, novembichin, phenamet, phenesterine, prednimustine, trofosfamide, uracil mustard. In yet another preferred embodiment, the cytotoxin is selected from the group consisting of nitrosoureas such as carmustine, flubenzuron, formoterol, lomustine, nimustine, ramustine. In one embodiment, the cytotoxin is selected from the group consisting of aziridines. In a preferred embodiment, the cytotoxin is selected from the group consisting of benzodopa, carboquone, meturedepa, and uredepa. In one embodiment, the cytotoxin is selected from the group consisting of an anti-tumor antibiotic. In a preferred embodiment, the cytotoxin is selected from the group consisting of enediyne antibiotics. In a more preferred embodiment, the cytotoxin is selected from the group consisting of dynemicin, esperamicin, neocarzinostatin, and aclacinomycin. In another preferred embodiment, the cytotoxin is selected from the group consisting of actinomycin, antramycin, bleomycins, actinomycin C, carabicin, carminomycin, and cardinophyllin, carminomycin, actinomycin D, daunorubicin, detorubicin, adriamycin, epirubicin, esorubicin, idarubicin, marcellomycin, mitomycins, nogalamycin, olivomycin, peplomycin, porfiromycin, puromycin, ferric adriamycin, rodorubicin, rufocromomycin, streptozocin, zinostatin, zorubicin. In yet another preferred embodiment, the cytotoxin is selected from the group consisting of trichothecene. In a more preferred embodiment, the cytotoxin is selected from the group consisting of T-2 toxin, verracurin A, bacillocporin A, and anguidine. In one embodiment, the cytotoxin is selected from the group consisting of an anti-tumor amino acid derivatives. In a preferred embodiment, the cytotoxin is selected from the group consisting of ubenimex, azaserine, 6-diazo-5-oxo-L-norleucine. In another embodiment, the cytotoxin is selected from the group consisting of folic acid analogues. In a preferred embodiment, the cytotoxin is selected from the group consisting of dimethyl folic acid, methotrexate, pteropterin, trimetrexate, and edatrexate. In one embodiment, the cytotoxin is selected from the group consisting of purine analogues. In a preferred embodiment, the cytotoxin is selected from the group consisting of fludarabine, 6-mercaptopurine, tiamiprine, thioguanine. In yet another embodiment, the cytotoxin is selected from pyrimidine analogues. In a preferred embodiment, the cytotoxin is selected from the group consisting of ancitabine, gemcitabine, enocitabine, azacitidine, 6-azauridine, carmofur, cytarabine, dideoxyuridine, doxifluridine, floxuridine. In one embodiment, the cytotoxin is selected from the group consisting of androgens. In a preferred embodiment, the cytotoxin is selected from the group consisting of calusterone, dromostanolone propionate, epitiostanol, mepitiostane, testolactone. In another embodiment, the cytotoxin is selected from the group consisting of anti-adrenals. In a preferred embodiment, the cytotoxin is selected from the group consisting of aminoglutethimide, mitotane, and trilostane. In one embodiment, the cytotoxin is selected from the group consisting of anti-androgens. In a preferred embodiment, the cytotoxin is selected from the group consisting of flutamide, nilutamide, bicalutamide, leuprorelin acetate, and goserelin. In yet another embodiment, the cytotoxin is selected from the group consisting of a protein kinase inhibitor and a proteasome inhibitor. In another embodiment, the cytotoxin is selected from the group consisting of vinblastines, colchicines, taxanes, auristatins, maytansinoids, calicheamicin, doxonubicin, duocarmucin, SN-38, ciyptophycin analogue, deruxtecan, duocarmazine, calicheamicin, centanamycin, dolastansine, and pyrrolobenzodiazepine (PBD). In a particular embodiment, the cytotoxin is selected from the group consisting of vinblastines, colchicines, taxanes, auristatins, and maytansinoids.

In a particular embodiment, the cytotoxin is exatecan or a derivative thereof, such as DX8951f and the like.

In another particular embodiment, the cytotoxin is an maytansinoid, such as DM1 and the like. Note that where a cytotoxin comprising a thiol moiety is used, the thiol moiety being capable of reaction with a maleimide moiety to form a thiosuccinimide, for example a maytansinoid, e.g., DM1, the cytotoxin can link directly via the thiosuccinimide. In such case, it could be understood that in some embodiments Payload and the thiol moiety together constitutes a cytotoxin, and therefore in such case Payload represents the rest moiety of the cytotoxin molecule except for the thiol moiety.

In a particular embodiment, the cytotoxin is an auristatin, such as MMAE (monomethyl auristatin E), MMAF (monomethyl auristatin F), MMAD (monomethyl auristatin D) and the like. The synthesis and structure of auristatin compounds are described in US20060229253, the entire disclosure of which is incorporated herein by reference.

The payload contains a reactive group which can react with the reactive group in the compound of formula (I) and thus covalently conjugate the payload with the compound of formula (I). Compounds that do not contain reactive groups require appropriate derivatization to give the payload.

In one embodiment, the cytotoxin is a compound of the following formula (i)

(i)

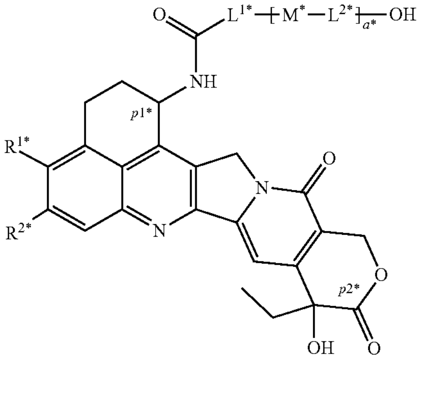

wherein, a*is 0 or 1;

the carbon atoms marked with p1* and p2* each is asymmetric center, and the asymmetric center is S configured, R configured or racemic;

$L^{1*}$ is selected from $C_{1-6}$ alkylene, which is unsubstituted or substituted with one substituent selected from halogen, —OH and —$NH_2$;

M* is —$CH_2$—, —NH— or —O—;

$L^{2*}$ is $C_{1-3}$ alkylene;

$R^{1*}$ and $R^{2*}$ are each independently selected from hydrogen, $C_{1-6}$ alkyl, halogen and $C_{1-6}$ alkoxy.

In a particular embodiment, the cytotoxin is a compound of the following formula (i')

(i')

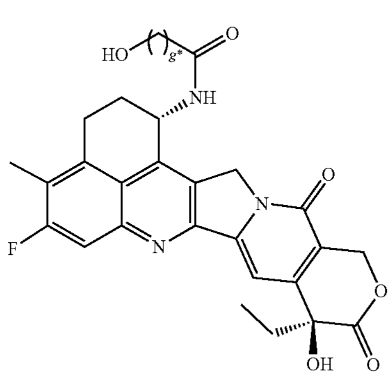

wherein, g is any integer of 1 to 6.

In one embodiment, g* is any integer of 1 to 3, preferably 1.

In one embodiment, $L^{1*}$ is selected from $C_{1-10}$ linear alkylene, $C_{1-6}$ branched alkylene, $C_{3-6}$ cyclic alkylene and $C_{3-4}$ cyclic alkyl-$C_{1-2}$ linear alkylene group, which are each independently unsubstituted or substituted with one substituent selected from halogen, —OH and —$NH_2$. In one embodiment, $L^{1*}$ is selected from $C_{1-4}$ alkylene, which is unsubstituted or substituted with one substituent selected from halogen, —OH and —$NH_2$. In a preferred embodiment, L* is selected from —$CH_2$—, —$C_2H_4$—,

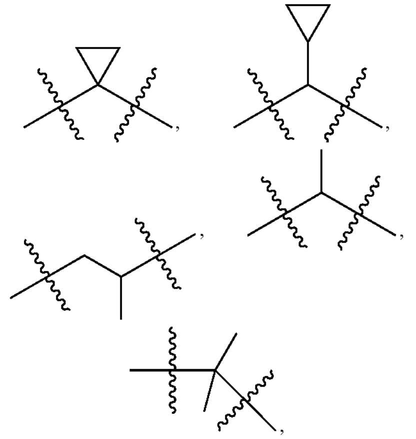

which are each independently unsubstituted or substituted with at least one substituent selected from halogen, —OH and —$NH_2$. In a preferred embodiment, $L^{1*}$ is selected from —$CH_2$—,

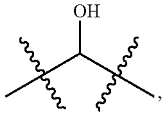
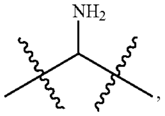
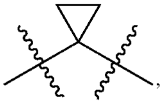 [SMILES: *C1(*)CC1]
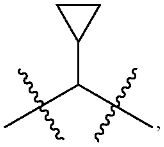
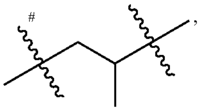
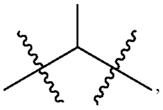
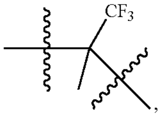
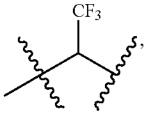

wherein "#" marks the position attached to carbonyl. In a more preferred embodiment, $L^{1*}$ is selected from —$CH_2$—,

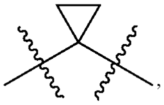
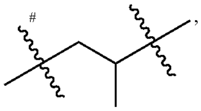
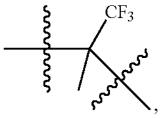
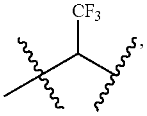

wherein "#" marks the position attached to carbonyl. In a particular embodiment, $L^{1*}$ is selected from —$CH_2$—,

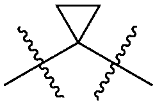
and
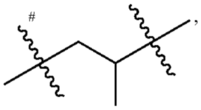

wherein "#" marks the position attached to carbonyl. In a preferred embodiment, the halogen is selected from F, Cl and Br, especially F.

In one embodiment, a* is 1, M* is —$CH_2$—, —NH— or —O—; and $L^{2*}$ is —$C_2H_4$—. In another embodiment, a* is 1, M* is —$CH_2$—, and $L^{2*}$ is —$CH_2$—. In one embodiment, a* is 0.

In one embodiment, the carbon atom marked with p1* is S configured or racemic, preferably S configured. In another embodiment, the carbon atom marked with p2* is S configured or racemic, preferably S configured.

In one embodiment, $R^{1*}$ and $R^{2*}$ are each independently selected from hydrogen, $C_{1-3}$ alkyl, halogen and $C_{1-3}$ alkoxy.

In a preferred embodiment, $R^{1*}$ and $R^{2*}$ are each independently selected from $CH_3$—, F, Cl, Br and $CH_3O$—. In one embodiment, $R^{1*}$ is selected from $CH_3$— and Cl. In another embodiment, $R^{2*}$ is F.

In one embodiment, a* is 0, $L^{1*}$ is selected from —$CH_2$—,

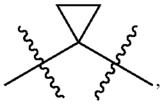
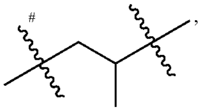
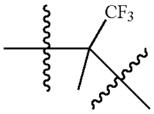
and
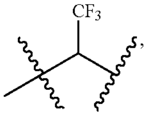

wherein "#" marks the position attached to carbonyl. In one embodiment, a* is 1, $L^{1*}$ is

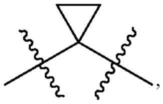 [SMILES: *C1(*)CC1]

M* is O, and $L^{2*}$ is —$C_2H_4$—.

In one embodiment, a* is 0, $R^{1*}$ is Cl, $R^{2*}$ is F, and $L^{1*}$ is selected from —$CH_2$—,

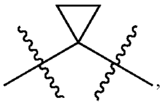
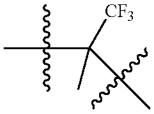
and
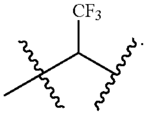

In one embodiment, a* is 0, $R^{1*}$ is $CH_3$—, $R^{2*}$ is F, and $L^{1*}$ is selected from

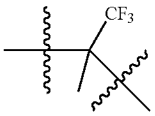
and
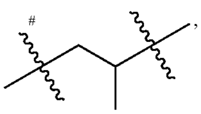

wherein "#" marks the position attached to carbonyl.

In one embodiment, a* is 1, $R^{1*}$ is $CH_3$—, $R^{2*}$ is F, $L^{1*}$ is
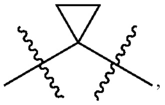
M is O, and $L^{2*}$ is —$C_2H_4$—.
In one embodiment, the cytotoxin is selected from the following compounds; wherein the wavy bond shows the connection site for connection with the compound of formula (I).
1
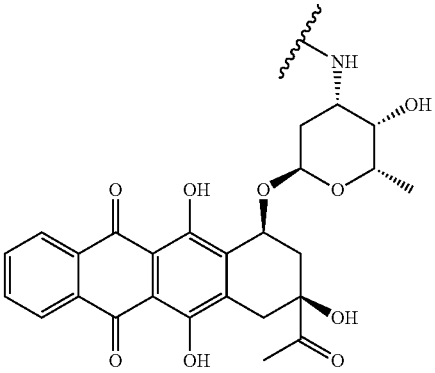
(Idarubicin)
2
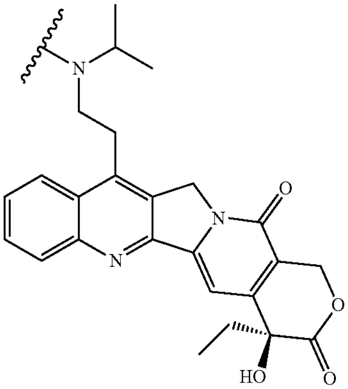
(Belotecan)
3
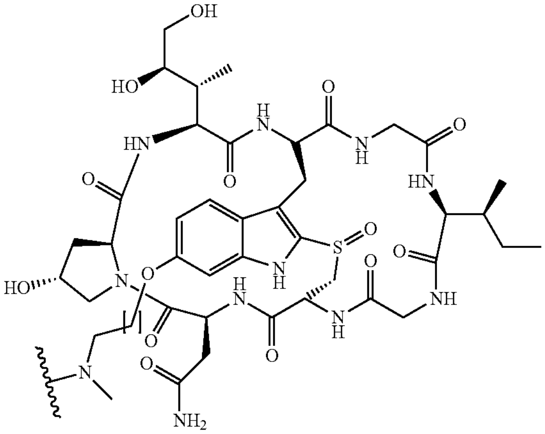
(Amanitin)
4
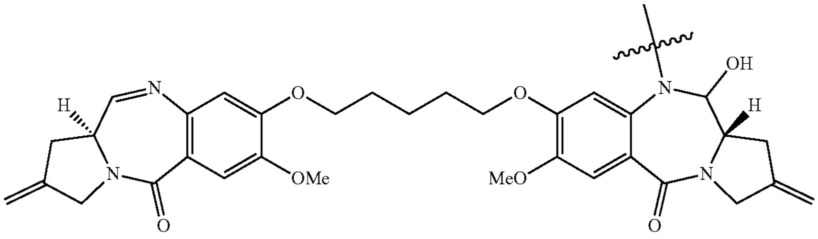
(PBD dimer)

-continued
5
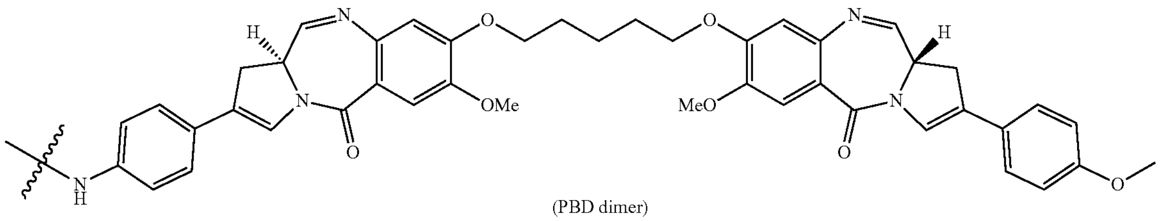
(PBD dimer)
6
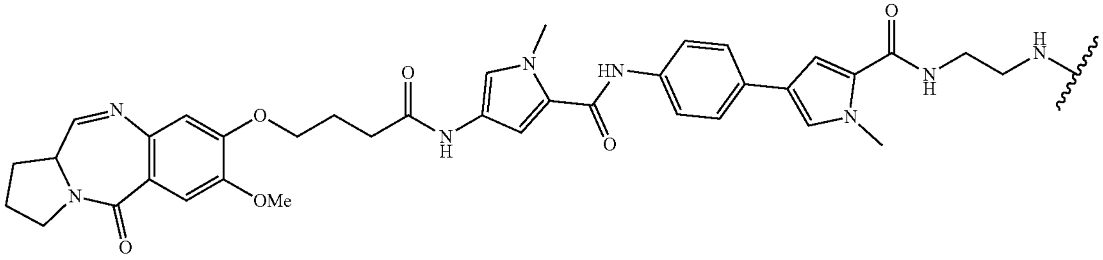
(PBD monomer)
7
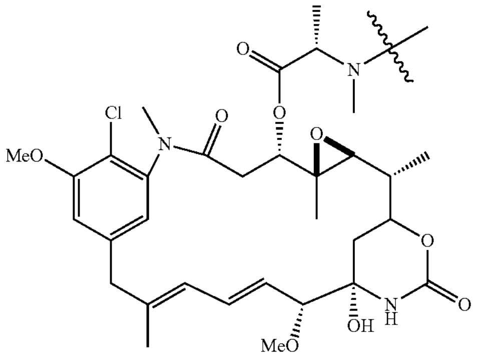
(DM)
8
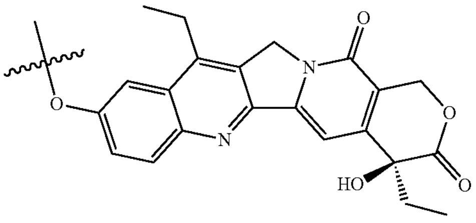
(SN-38)
9
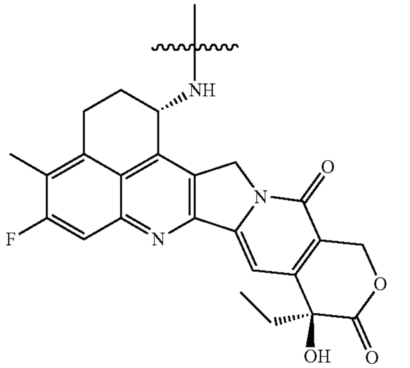
(DX8951f)
10
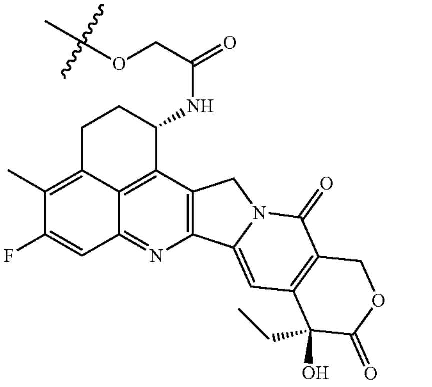
(Dxd-(1))
11
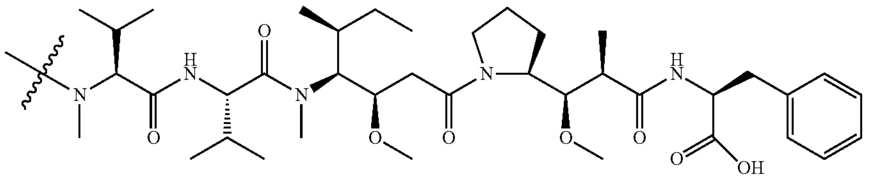
(MMAF)

-continued
12
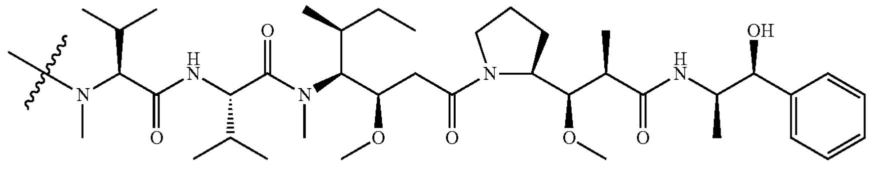
(MMAE)
13
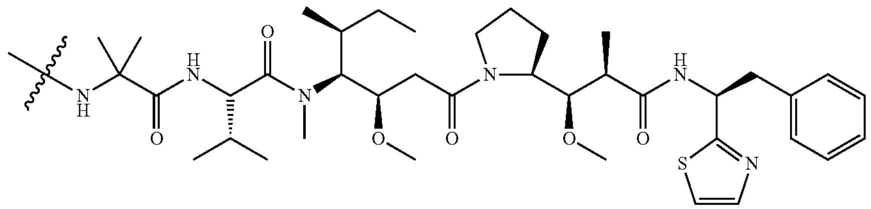
(Auristatin 0101)
14
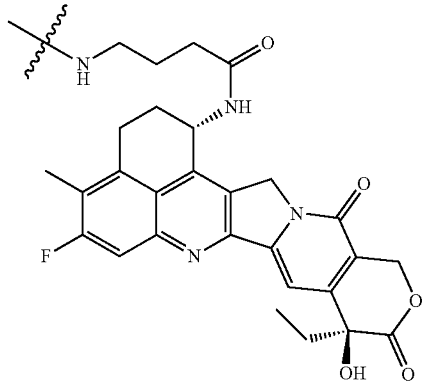
(Dxd-(2))
15
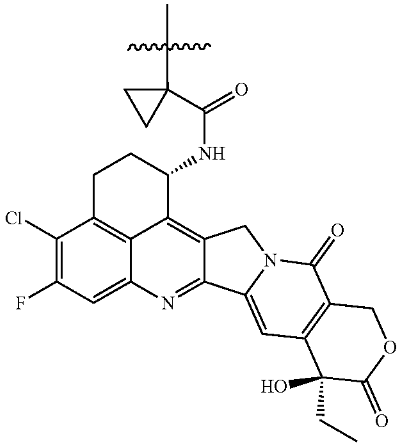
16
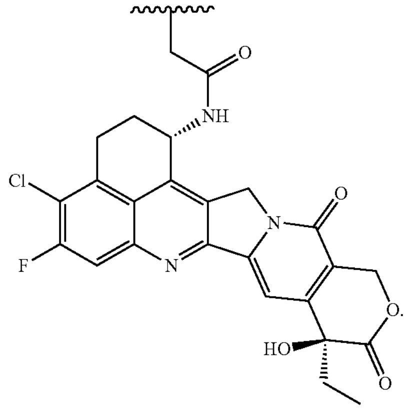

In some embodiments, the payload is selected from DX8951f (compound 9), DXd-(1) (compound 10), DXd-(2) (compound 14),
(compound 15)
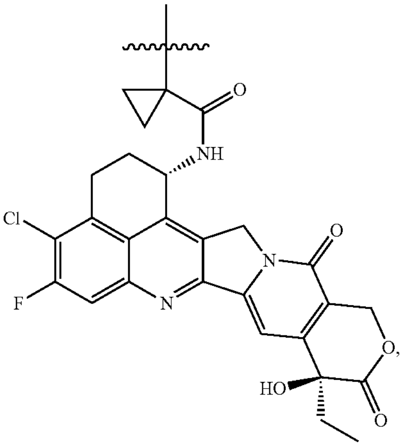
(compound 16)
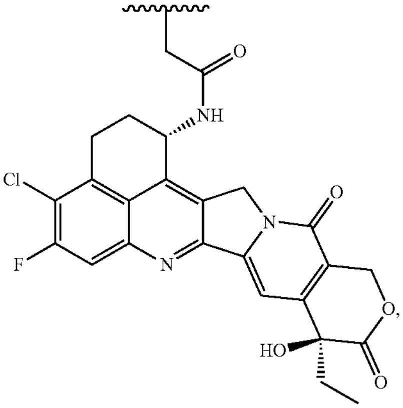
preferably DX8951f, DXd-(1)
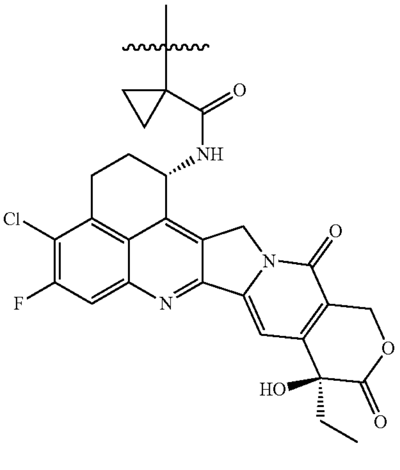
or
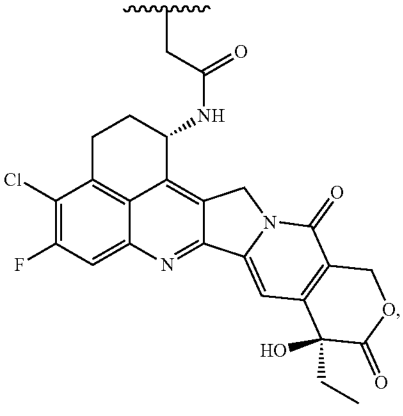
more preferably
-continued
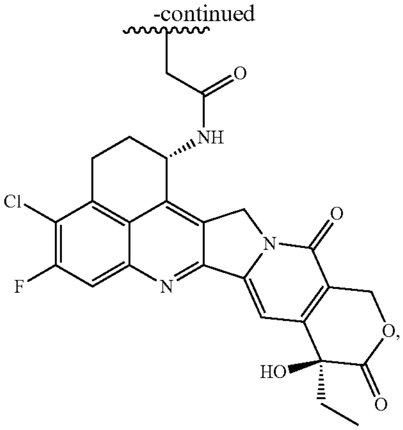
more preferably DXd-(1)
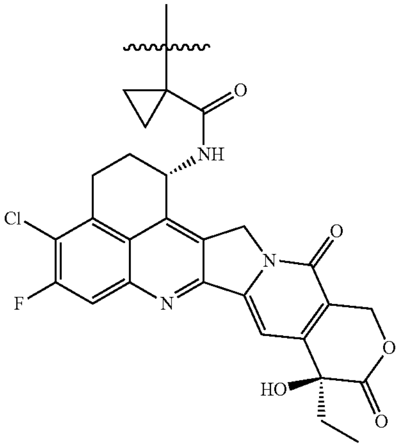
or -continued

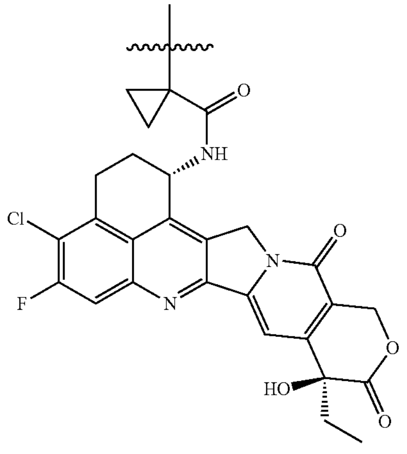

or

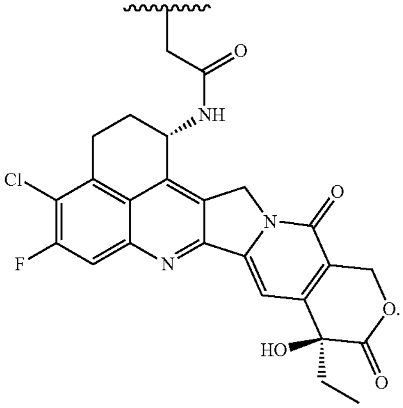

.

Preparation of the Payload-Bearing Formula (I) Compound

In one embodiment, the linking unit and the Payload are connected via reactive groups as defined above, using any reaction known in the art, including but not limit to condensation reaction, nucleophilic addition, electrophilic addition, etc.

In one embodiment, the payload is a cytotoxin. In one embodiment, the linking unit-payload intermediate (numbered as LBx) is as shown in the following table.

| Compound of formula (II) | Formula of Linker | Values of i and j (when applicable)* | Payload |
|---|---|---|---|
| II-a-0-1-1 | I-a-0-1 | — | compound 10 |
| II-a-0-2-1 | I-a-0-2 | i is 4 | compound 10 |
| II-a-0-3-1 | I-a-0-3 | i1 is 4, i2 is 4 | compound 10 |
| II-a-0-4-1 | I-a-0-4 | i1, i2, i3 are 4, respectively | compound 10 |
| II-a-0-5-1 | I-a-0-5 | i1, i2, i3 and i4 are 4, respectively | compound 10 |
| II-a-1-1-1 | I-a-1-1 | j is 8 | compound 10 |
| II-a-1-1-4 | I-a-1-1 | j is 12 | compound 10 |
| II-a-1-2-1 | I-a-1-2 | i is 4, j is 8 | compound 10 |
| II-a-1-2-4-1 | I-a-1-2 | i is 4, j is 12 | compound 10 |
| II-a-1-2-4-2 | I-a-1-2 | i is 4, j is 12 | compound 15 |
| II-a-1-2-4-3 | I-a-1-2 | i is 4, j is 12 | compound 16 |
| II-a-1-2-6 | I-a-1-2 | i is 4, j is 12, g is 1, $R^{11}$ is methyl | compound 9 |
| II-a-1-3-1 | I-a-1-3 | i1 is 4, i2 is 4, j is 8 | compound 10 |
| II-a-1-3-4 | I-a-1-3 | i1 is 4, i2 is 4, j is 12 | compound 10 |
| II-a-1-4-1 | I-a-1-4 | i1, i2, i3 are 4, respectively, j is 8 | compound 10 |

-continued

| Compound of formula (II) | Formula of Linker | Values of i and j (when applicable)* | Payload |
|---|---|---|---|
| II-a-1-4-4 | I-a-1-4 | i1, i2, i3 are 4, respectively, j is 12 | compound 10 |
| II-b-1-1-4 | I-b-1-1 | i is 4, j is 12, g is 1, m is 1, $R^{11}$ is methyl | compound 15 |

*For all the linkers listed, n is 3.

Conjugates and Preparation Thereof

Furthermore, the payload-bearing formula (I) compound which has the moiety comprising ligase recognition sequence can be conjugated with other molecules comprising a ligase recognition sequence, and can be thereby used in for example, the preparation of a targeting molecule-drug conjugate, such as an antibody-drug conjugate. Accordingly, in yet another aspect, provided is a conjugate which comprises a compound of formula (I), a targeting molecule, and a payload.

In yet another aspect, provided is a conjugate having the structure of formula (III):

formula (III)

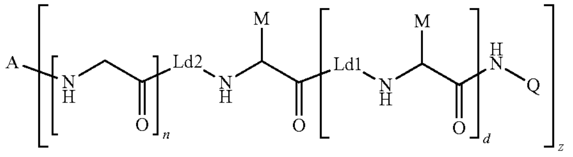

wherein, n, d, Ld1 and Ld2 are as defined in formula (I);

Q is hydrogen, —$C_2H_4$-$(PEG)_r$-(CO)$NH_2$ or LKb-P;

M is hydrogen or LKa-LKb-P;

provided that Q and M are not simultaneously hydrogen;

P is a payload which is linked to the B moiety or $L^1$ moiety of the compound of formula (I);

A is a anti-Trop2 antibody or antigen-binding fragment thereof which is linked to the $G_n$ moiety of the compound of formula (I); G is Glycine;

z is an integer of 1 to 20.

In one embodiment, LKa and LKb are as defined in formula (I).

In one embodiment, the conjugate has a drug to antibody ratio (DAR) of an integer or non-integer of 1 to 20.

As defined herein above, in one embodiment, the $G_n$ moiety of the compound of formula (I) is a recognition sequence of a ligase acceptor substrate, which facilitates enzyme-catalyzed coupling of compound of formula (I) with the targeting molecule under the catalysis of the ligase. The targeting molecule optionally modified and comprises the corresponding recognition sequence of a ligase acceptor or donor substrate.

It should be understood that, when the antibody (or antigen-binding fragment) conjugates with the G, moiety of the compound of formula (I) under the catalysis of the ligase, the recognition sequence of the ligase acceptor substrate and the recognition sequence of the ligase donor substrate react with each other and form a resulting sequence.

In one embodiment, the antibody (or antigen-binding fragment) comprises LPXTGJ as the recognition sequence of the ligase donor substrate, wherein J is as defined above. When conjugates with $G_n$, which is the corresponding recognition sequence of the ligase acceptor substrate, the upstream peptide bond of the Glycine in the LPXTGJ sequence is cleaved by Sortase A, and the resulting intermediate is linked to the free N-terminal of $G_n$ to generate a new peptide bond. The resulting sequence is $LPXTG_n$. The sequences $G_n$ and LPXTGJ are as defined above.

In one embodiment, P is linked to the B moiety or $L^1$ moiety of the compound of formula (I) and A is linked to the $G_n$ moiety of the compound of formula (I) to form the compound of formula (III).

As defined above, $R^{10}$ would not appear in the B—P structure of the compound of formula (III). As defined above, when B in the compound of formula (I) is a terminal group $R^{10}$, B is absent in the B—P structure of the compound of formula (III).

As defined above, in the A-$G_n$ structure of the compound of formula (III), A optionally comprises the corresponding sequence resulting from the reaction of the recognition sequence of the ligase acceptor substrate with the recognition sequence of the ligase donor substrate.

In one embodiment, M is hydrogen or LKa-$L^2$-$L^1$-B—P; wherein P is a payload which is linked to the B moiety or $L^1$ moiety of the compound of formula (I); each B is independently a terminal group $R^{10}$, or a combination of the following 1), 2) and 3): 1) a self-immolative spacer Sp1; 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—; and 3) a terminal group $R^{10}$; $R^{10}$ is hydrogen, or a group which can leave when reacting with a group in the payload; $R^{10}$ represents the part of structure which would not appear in the product molecule resulting from the reaction of B with the payload.

In one embodiment, M is hydrogen or LKa-$L^2$-$L^1$-B—P; wherein each B is independently absent, or is a combination of the following 1) and 2): 1) a self-immolative spacer Sp1; and 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—. In a preferred embodiment, M is hydrogen or LKa-$L^2$-$L^1$-B—P; wherein each B is independently absent, or is —NH—$CH_2$—U— or is —NH—$CH_2$—U—$(CR^1R^2)_g$—(CO)—. In another embodiment, M is hydrogen or LKa-$L^2$-$L^1$-B—P. In one embodiment, in LKa-$L^2$-$L^1$-B—P, B is absent. In one embodiment, in LKa-$L^2$-$L^1$-B—P, B is a combination of the following 1) and 2): 1) a self-immolative spacer Sp1; and 2) a bond, or one of or a combination of two or more of the bivalent groups selected from: —$CR^1R^2$—, $C_{1-10}$ alkylene, $C_{4-10}$ cycloalkylene, $C_{4-10}$ heterocyclylene and —(CO)—. In one embodiment, in LKa-$L^2$-$L^1$-B—P, B is —NH—$CH_2$—U— or is —NH—$CH_2$—U—$(CR^1R^2)_g$—(CO)—, U is absent, or is O, S or NH, preferably O or S. In one embodiment, B in the compound of formula (I) is connected to the payload through an amide bond or an ester bond or an ether bond. In one embodiment, M is LKa-$L^2$-$L^1$-B—P, and B is absent; and M can also be denoted as LKa-$L^2$-$L^1$-P.

Targeting Molecule

In one embodiment, the targeting molecule is an anti-Trop2 antibody or antigen-binding fragment thereof, comprising a heavy chain variable region ($V_H$) and a light chain variable region ($V_L$), wherein the $V_H$ comprises:

(i) HCDR1 comprising the amino acid sequence of $X_1X_2GMX_3$ (SEQ ID No:1), wherein $X_1$ is N, T or A, $X_2$ is Y or A, $X_3$ is N or Q;

(ii) HCDR2 comprising the amino acid sequence of WINT$X_4X_5$G$X_6$P$X_7$Y$X_8X_9$DFKG (SEQ ID NO: 2), wherein $X_4$ is Y, H or D, $X_5$ is T or S, $X_6$ is E or V, $X_7$ is T or K, $X_8$ is T or A, $X_9$ is D or E;

(iii) HCDR3 comprising the amino acid sequence of $X_{10}$GFGSSYWYFDV (SEQ ID NO: 3), wherein $X_{10}$ is G or S;

and/or the $V_L$ comprises:

(i) LCDR1 comprising the amino acid sequence of KASQDVSIAVA (SEQ ID NO:13) or KASQDVSTAVA (SEQ ID NO:14);

(ii) LCDR2 comprising the amino acid sequence of SASYRYT (SEQ ID NO:15); and (iii) LCDR3 comprising the amino acid sequence of QQHYITPLT (SEQ ID NO: 16).

In one embodiment, the HCDR1 comprises the amino acid sequence of NYGMN, TAGMQ, AAGMN or NAGMN.

In one embodiment, the HCDR2 comprises the amino acid of WINTYTGEPTYTDDFKG (SEQ ID NO: 8), WINTHSGVPKYAEDFKG (SEQ ID NO:9), WINTDSGEPTYTDDFKG (SEQ ID NO:10).

In one embodiment, the HCDR3 comprises the amino acid of GGFGSSYWYFDV (SEQ ID NO: 11) or SGFGSSYWYFDV (SEQ ID NO: 12).

In one embodiment, the antibody or antigen-binding fragment thereof comprises a heavy chain variable region ($V_H$) and a light chain variable region ($V_L$), wherein the $V_H$ comprises:

(i) HCDR1 comprising the amino acid sequence of $X_1$AGMN, wherein $X_1$ is N or A;

(ii) HCDR2 comprising the amino acid sequence of WINTDSGEPTYTDDFKG (SEQ ID NO: 10);

(iii) HCDR3 comprising the amino acid sequence of GGFGSSYWYFDV (SEQ ID NO:11); and/or the $V_L$ comprises:

(i) LCDR1 comprising the amino acid sequence of KASQDVSIAVA (SEQ ID NO: 13) or KASQDVSTAVA (SEQ ID No: 14);

(ii) LCDR2 comprising the amino acid sequence of SASYRYT (SEQ ID NO:15);

(iii) LCDR3 comprising the amino acid sequence of QQHYITPLT (SEQ ID NO: 16).

In one embodiment, the $V_H$ comprises:

(i) HCDR1 comprising the amino acid sequence of SEQ ID NO: 4, (ii) HCDR2 comprising the amino acid sequence of SEQ ID NO: 8, and (iii) HCDR3 comprising the amino acid sequence of SEQ ID NO: 11;

and/or the $V_L$ comprises:

(i) LCDR1 comprising the amino acid sequence of SEQ ID NO: 13, (ii) LCDR2 comprising the amino acid sequence of SEQ ID NO: 15, and (iii) LCDR3 comprising the amino acid sequence of SEQ ID NO: 16.

In one embodiment, the $V_H$ comprises:

(i) HCDR1 comprising the amino acid sequence of SEQ ID NO: 5, (ii) HCDR2 comprising the amino acid sequence of SEQ ID NO: 9, and (iii) HCDR3 comprising the amino acid sequence of SEQ ID NO: 12;

and/or the $V_L$ comprises:

(i) LCDR1 comprising the amino acid sequence of SEQ ID NO: 14, (ii) LCDR2 comprising the amino acid sequence of SEQ ID NO: 15, and (iii) LCDR3 comprising the amino acid sequence of SEQ ID NO: 16.

In one embodiment, the $V_H$ comprises:

(i) HCDR1 comprising the amino acid sequence of SEQ ID NO: 4, (ii) HCDR2 comprising the amino acid sequence of SEQ ID NO: 10, and (iii) HCDR3 comprising the amino acid sequence of SEQ ID NO: 11;

and/or the $V_L$ comprises:

(i) LCDR1 comprising the amino acid sequence of SEQ ID NO: 13, (ii) LCDR2 comprising the amino acid sequence of SEQ ID NO: 15, and (iii) LCDR3 comprising the amino acid sequence of SEQ ID NO: 16.

In one embodiment, the $V_H$ comprises:

(i) HCDR1 comprising the amino acid sequence of SEQ ID NO: 7, (ii) HCDR2 comprising the amino acid sequence of SEQ ID NO: 10, and (iii) HCDR3 comprising the amino acid sequence of SEQ ID NO: 11;

and/or the $V_L$ comprises:

(i) LCDR1 comprising the amino acid sequence of SEQ ID NO: 13, (ii) LCDR2 comprising the amino acid sequence of SEQ ID NO: 15, and (iii) LCDR3 comprising the amino acid sequence of SEQ ID NO: 16.

In one embodiment, the $V_H$ comprises:

(i) HCDR1 comprising the amino acid sequence of SEQ ID NO: 6, (ii) HCDR2 comprising the amino acid sequence of SEQ ID NO: 8, and (iii) HCDR3 comprising the amino acid sequence of SEQ ID NO: 11;

and/or the $V_L$ comprises:

(i) LCDR1 comprising the amino acid sequence of SEQ ID NO: 13, (ii) LCDR2 comprising the amino acid sequence of SEQ ID NO: 15, and (iii) LCDR3 comprising the amino acid sequence of SEQ ID NO: 16.

In one embodiment, the $V_H$ comprises structure: FR1-HCDR1-FR2-HCDR2-FR3-HCDR3-FR4, the FR1 comprises amino acid of SEQ ID NO: 17, the FR2 comprises amino acid of SEQ ID NO: 18, the FR3 comprises amino acid of SEQ ID NO: 19, the FR4 comprises amino acid of SEQ ID NO: 20.

In one embodiment, the $V_H$ comprises the amino acid sequence having at least about 90% sequence identity to amino acid sequence of SEQ ID NO: 21-25. In one embodiment, the $V_H$ comprises the amino acid sequence of SEQ ID NO: 21. In one embodiment, the $V_H$ comprises the amino acid sequence of SEQ ID NO: 22. In one embodiment, the $V_H$ comprises the amino acid sequence of SEQ ID NO: 23. In one embodiment, the $V_H$ comprises the amino acid sequence of SEQ ID NO: 24. In one embodiment, the $V_H$ comprises the amino acid sequence of SEQ ID NO: 25.

In one embodiment, the $V_L$ comprises the amino acid sequence having at least about 90% sequence identity to amino acid sequence of SEQ ID NO: 26 or SEQ ID NO: 27. In one embodiment, the $V_L$ comprises the amino acid sequence of SEQ ID NO: 26. In one embodiment, the $V_L$ comprises the amino acid sequence of SEQ ID NO: 27.

In one embodiment, the $V_H$ comprises the amino acid sequence having at least about 90% sequence identity to amino acid sequence of SEQ ID NO: 23 or SEQ ID NO: 24; and/or the $V_L$ comprises the amino acid sequence having at least about 90% sequence identity to amino acid sequence of SEQ ID NO: 26 or SEQ ID NO: 27.

In one embodiment, the $V_H$ comprises the amino acid sequence of SEQ ID NO: 21, the $V_L$ comprises the amino acid sequence of SEQ ID NO: 26. In one embodiment, the $V_H$ comprises the amino acid sequence of SEQ ID NO: 22, the $V_L$ comprises the amino acid sequence of SEQ ID NO: 27. In one embodiment, the $V_H$ comprises the amino acid sequence of SEQ ID NO: 23, the $V_L$ comprises the amino acid sequence of SEQ ID NO: 26. In one embodiment, the $V_H$ comprises the amino acid sequence of SEQ ID NO: 24, the $V_L$ comprises the amino acid sequence of SEQ ID NO: 26. In one embodiment, the $V_H$ comprises the amino acid sequence of SEQ ID NO: 25, the $V_L$ comprises the amino acid sequence of SEQ ID NO: 26.

In one embodiment, the antibody or an antigen-binding fragment comprises a heavy constant domain (CH) comprising an amino acid sequence having at least about 90% sequence identity to the amino acid sequence of SEQ ID NO: 28; and/or a light constant domain comprising an amino acid sequence having at least about 90% sequence identity to the amino acid sequence of SEQ ID NO: 29.

In one embodiment, the antibody or an antigen-binding fragment comprises a heavy constant domain (CH) comprising an amino acid sequence of SEQ ID NO: 28, and a light constant domain comprising an amino acid sequence of SEQ ID NO: 29.

In one embodiment, the antibody or an antigen-binding fragment binds to TROP2 with an equilibrium dissociation constant ($K_D$) of about 0.5 nM to about 20 nM. In one embodiment, the value of $K_D$ is about 0.5 nM, about 1 nM, about 2 nM, about 3 nM, about 4 nM, about 5 nM, about 6 nM, about 7 nM, about 8 nM, about 9 nM, about 10 nM, about 11 nM, about 12 nM, about 13 nM, about 15 nM, about 18 nM, about 20 nM, or the range between any two values (including the end value). In one embodiment, the value of $K_D$ is about 7.5 nM to about 13.5 nM.

In one embodiment, the targeting molecule is an anti-human TROP2 antibody or antigen-binding fragment thereof.

In one embodiment, the antibody is a recombinant antibody selected from monoclonal antibody, chimeric antibody, humanized antibody, antibody fragment, and antibody mimic. In one embodiment, the antibody mimic is selected from scFv, minibody, diabody, nanobody.

In one embodiment, the antibody or antigen-binding fragment comprises a heavy chain comprising an amino acid sequence having at least about 90% sequence identity to the amino acid sequence of SEQ ID NO: 30-33, and/or a light chain comprising an amino acid sequence having at least about 90% sequence identity to the amino acid sequence of SEQ ID NO: 34 or SEQ ID NO: 35.

At least about 90% is about 91%, about 92%, about 93%, about 94%, about 95%, about 96%, about 97%, about 98%, about 99%, about 100%, or the range between any two values (including the end value).

In one embodiment, the antibody or antigen-binding fragment comprises a heavy chain comprising an amino acid sequence of SEQ ID NO: 30-33, and/or a light chain comprising an amino acid sequence of SEQ ID NO: 34 or SEQ ID NO: 35.

In one embodiment, the antibody or antigen-binding fragment comprises a heavy chain comprising an amino acid sequence of SEQ ID NO: 30 and a light chain comprising an amino acid sequence of SEQ ID NO: 34.

In one embodiment, the antibody or antigen-binding fragment comprises a heavy chain comprising an amino acid sequence of SEQ ID NO: 31 and a light chain comprising an amino acid sequence of SEQ ID NO: 34.

In one embodiment, the antibody or antigen-binding fragment comprises a heavy chain comprising an amino acid sequence of SEQ ID NO: 32 and a light chain comprising an amino acid sequence of SEQ ID NO: 34.

In one embodiment, the antibody or antigen-binding fragment comprises a heavy chain comprising an amino acid sequence of SEQ ID NO: 33 and a light chain comprising an amino acid sequence of SEQ ID NO: 35.

Examples of anti-human TROP2 antibodies include but are not limited to Trodelvy's antibody (hRS7) and DS1062's antibody (Datopotamab). The sequences of antibodies are shown in the table 1.

In one embodiment, the pharmaceutical composition comprises antibody or antigen-binding fragment.

TABLE 1

Sequence of antibodies

| name | Amino acid | SEQ ID NO | name | Amino acid | SEQ ID NO |
|---|---|---|---|---|---|
| HCDR1 | NYGMN | 4 | LCDR1 | KASQDVSIAVA | 13 |
| | TAGMQ | 5 | | | |
| | AAGMN | 6 | | KASQDVSTAV A | 14 |
| | NAGMN | 7 | | | |
| HCDR2 | WINTYTGEPTYTDDFKG | 8 | LCDR2 | SASYRYT | 15 |
| | WINTHSGVPKYAEDFKG | 9 | | | |
| | WINTDSGEPTYTDDFKG | 10 | | | |
| HCDR3 | GGFGSSYWYFDV | 11 | LCDR3 | QQHYITPLT | 16 |
| | SGFGSSYWYFDV | 12 | | | |

| name | Amino acid | Seq ID NO |
|---|---|---|
| VH-FR1 | QVQLQQSGSELKKPG ASVKVSCKASGYTFT | 17 |
| VH-FR2 | WVKQAPGQGLKWMG | 18 |
| VH-FR3 | RFAFSLDTSVSTAYLQ ISSLKADDTAVYFCAR | 19 |
| VH-FR4 | WGQGSLVTVSS | 20 |
| $V_H$ | QVQLQQSGSELKKPGASVKVSCKASGYTFTNYGMNWVKQAPGQGL KWMGWINTYTGEPTYTDDFKGRFAFSLDTSVSTAYLQISSLKADD TAVYFCARGGFGSSYWYFDVWGQGSLVTVSS | 21 |
| | QVQLVQSGAEVKKPGASVKVSCKASGYTFTTAGMQWVRQAPGQG LEWMGWINTHSGVPKYAEDFKGRVTISADTSTSTAYLQLSSLKS EDTAVYYCARSGFGSSYWYFDVWGQGTLVTVSS | 22 |
| | QVQLQQSGSELKKPGASVKVSCKASGYTFTNAGMNWVKQAPGQGL KWMGWINTDSGEPTYTDDFKGRFAFSLDTSVSTAYLQISSLKADD TAVYFCARGGFGSSYWYFDVWGQGSLVTVSS | 23 |
| | QVQLQQSGSELKKPGASVKVSCKASGYTFTAAGMNWVKQAPGQGL KWMGWINTYTGEPTYTDDFKGRFAFSLDTSVSTAYLQISSLKADD TAVYFCARGGFGSSYWYFDVWGQGSLVTVSS | 24 |
| | QVQLQQSGSELKKPGASVKVSCKASGYTFTNYGMNWVKQAPGQGL KWMGWINTDSGEPTYTDDFKGRFAFSLDTSVSTAYLQISSLKADD TAVYFCARGGFGSSYWYFDVWGQGSLVTVSS | 25 |

TABLE 1-continued

| | | |
|---|---|---|
| $V_L$ | DIQLTQSPSSLSASVGDRVSITCKASQDVSIAVAWYQQKPGKAPK<br>LLIYSASYRYTGVPDRFSGSGSGTDFTLTISSLQPEDFAVYYCQQ<br>HYITPLTFGAGTKVEIKRTV | 26 |
| | DIQMTQSPSSLSASVGDRVTITCKASQDVSTAVAWYQQKPGKAPKL<br>LIYSASYRYTGVPSRFSGSGSGTDFTLTISSLQPEDFAVYYCQQHY<br>ITPLTFGQGTKLEIKRTV | 27 |
| $C_H$ | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKRVEPKSCDKTHTCPPCPAPELLGGPSVFLFPPKPKDTLMISRTPE<br>VTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLP<br>PSREEMTKNQVSLTCLVKGFYPSDIAVEWESNGQPENNYKTTPPVLD<br>SDGSFFLYSKLTVDKSRWQQGNVFSCSVMHEALHNHYTQKSLSLSPG<br>K | 28 |
| $C_L$ | AAPSVFIFPPSDEQLKSGTASVVCLLNNFYPREAKVQWKVDNALQS<br>GNSQESVTEQDSKDSTYSLSSTLTLSKADYEKHKVYACEVTHQGLS<br>SPVTKSFNRGEC | 29 |
| HC | QVQLQQSGSELKKPGASVKVSCKASGYTFTNYGMNWVKQAPGQGL<br>KWMGWINTYTGEPTYTDDFKGRFAFSLDTSVSTAYLQISSLKADD<br>TAVYFCARGGFGSSYWYFDVWGQGSLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPELLGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K | 30 |
| | QVQLQQSGSELKKPGASVKVSCKASGYTFTNAGMNWVKQAPGQGL<br>KWMGWINTDSGEPTYTDDFKGRFAFSLDTSVSTAYLQISSLKADD<br>TAVYFCARGGFGSSYWYFDVWGQGSLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPELLGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K | 31 |
| | QVQLQQSGSELKKPGASVKVSCKASGYTFTAAGMNWVKQAPGQGL<br>KWMGWINTYTGEPTYTDDFKGRFAFSLDTSVSTAYLQISSLKADD<br>TAVYFCARGGFGSSYWYFDVWGQGSLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPELLGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K | 32 |
| | QVQLVQSGAEVKKPGASVKVSCKASGYTFTTAGMQWVRQAPGQGL<br>EWMGWINTHSGVPKYAEDFKGRVTISADTSTSTAYLQLSSLKSEDT<br>AVYYCARSGFGSSYWYFDVWGQGTLVTVSSASTKGPSVFPLAPSSK<br>STSGGTAALGCLVKDYFPEPVTVSWNSGALTSGVHTFPAVLQSSGL<br>YSLSSVVTVPSSSLGTQTYICNVNHKPSNTKVDKRVEPKSCDKTHT<br>CPPCPAPELLGGPSVFLFPPKPKDTLMISRTPEVTCVVVDVSHEDP<br>EVKFNWYVDGVEVHNAKTKPREEQYNSTYRVVSVLTVLHQDWLNGK<br>EYKCKVSNKALPAPIEKTISKAKGQPREPQVYTLPPSREEMTKNQV<br>SLTCLVKGFYPSDIAVEWESNGQPENNYKTTPPVLDSDGSFFLYSK<br>LTVDKSRWQQGNVFSCSVMHEALHNHYTQKSLSLSPGK | 33 |
| LC | DIQLTQSPSSLSASVGDRVSITCKASQDVSIAVAWYQQKPGKAPKL<br>LIYSASYRYTGVPDRFSGSGSGTDFTLTISSLQPEDFAVYYCQQHY<br>ITPLTFGAGTKVEIKRTVAAPSVFIFPPSDEQLKSGTASVVCLLNN<br>FYPREAKVQWKVDNALQSGNSQESVTEQDSKDSTYSLSSTLTLSKA<br>DYEKHKVYACEVTHQGLSSPVTKSFNRGEC | 34 |
| | DIQMTQSPSSLSASVGDRVTITCKASQDVSTAVAWYQQKPGKAPKLL<br>IYSASYRYTGVPSRFSGSGSGTDFTLTISSLQPEDFAVYYCQQHYIT<br>PLTFGQGTKLEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC | 35 |

Antibody Conjugated with Linker-Payload

For the conjugation with the compound of formula (I), the antibody of the present disclosure may comprise a modified moiety to connect with Gn in the compound of formula (I). The introduction position of such modified moiety is not limited, for example, its introduction position can be, but not limited to, located at the C-terminal or the N-terminal of the heavy chain or light chain of the antibody.

In one embodiment, the conjugate of the present disclosure formed by the conjugation of the anti-human TROP2 antibody and the payload can specifically bind to TROP2 on the surface of the tumor cell and selectively kill the TROP2-expressing tumor cells. In another preferred embodiment, provided is use of a conjugate of the present disclosure or a pharmaceutical composition of the present disclosure in the manufacture of a medicament for treating a disease, disorder or condition selected from a TROP2-positive tumors. In a more preferred embodiment, the disease, disorder or condition is selected from breast cancer, urothelial carcinoma, lung cancer, liver cancer, endometrial cancer, head and neck cancer, ovarian cancer, and the like.

In an alternative embodiment, a modified moiety for the conjugation with Gn in the compound of formula (I) can be introduced at a non-terminal position of the heavy chain or light chain of the antibody using, for example, chemical modification methods.

In one embodiment, the targeting molecule of the present disclosure is an antibody or antigen-binding fragment thereof, which may comprise terminal modification. A terminal modification refers to a modification at the C-terminal or N-terminal of the heavy chain or light chain of the antibody, which for example comprises a ligase recognition sequence. In another embodiment, the terminal modification may further comprise spacer Sp2 comprising 2-100 amino acids, wherein the antibody, Sp2 and the ligase recognition sequence are sequentially linked. In a preferred embodiment, Sp2 is a spacer sequence containing 2-20 amino acids. In a particular embodiment, Sp2 is a spacer sequence selected from GA, GGGGS, GGGGSGGGGS and GGGGSGGGGSGGGGS, especially GA.

In a preferred embodiment, the light chain of the antibody or antigen-binding fragment thereof includes 3 types: wild-type (LC); the C-terminus modified light chain (LCCT), which is modified by direct introduction of a ligase recognition sequence LPXTG and C-terminus modified light chain (LCCTL), which is modified by introduction of short peptide spacers plus the ligase donor substrate recognition sequence LPXTG. The heavy chain of the antibody or antigen-binding fragment thereof includes 3 types: wild-type (HC); the C-terminus modified heavy chain (HCCT), which is modified by direct introduction of a ligase recognition sequence LPXTG; and C-terminus modified heavy chain ($HCCT_L$), which is modified by introduction of short peptide spacers plus the ligase donor substrate recognition sequence LPXTG. X can be any natural or non-natural single amino acid. In one embodiment, X is Glycine. The sequences of modified antibodies are shown in the table 2.

The conjugates of the present disclosure can further comprise a payload. The payload is as described above.

In one embodiment, the pharmaceutical composition comprises antibody-drug conjugate (ADC).

TABLE 2

Sequences of modified antibodies

| Name | Amino acid | SEQ ID NO |
|---|---|---|
| HC | QVQLQQSGSELKKPGASVKVSCKASGYTFT<br>NYGMNWVKQAPGQGLKWMGWINTYTGEPTY<br>TDDFKGRFAFSLDTSVSTAYLQISSLKADD<br>TAVYFCARGGFGSSYWYFDVWGQGSLVTVS<br>SASTKGPSVFPLAPSSKSTSGGTAALGCLV<br>KDYFPEPVTVSWNSGALTSGVHTFPAVLQS<br>SGLYSLSSVVTVPSSSLGTQTYICNVNHKP<br>SNTKVDKRVEPKSCDKTHTCPPCPAPELLG<br>GPSVFLFPPKPKDTLMISRTPEVTCVVVDV<br>SHEDPEVKFNWYVDGVEVHNAKTKPREEQY<br>NSTYRVVSVLTVLHQDWLNGKEYKCKVSNK<br>ALPAPIEKTISKAKGQPREPQVYTLPPSRE<br>EMTKNQVSLTCLVKGFYPSDIAVEWESNGQ<br>PENNYKTTPPVLDSDGSFFLYSKLTVDKSR<br>WQQGNVFSCSVMHEALHNHYTQKSLSLSPG<br>ALPETGG | 36 |
| | QVQLQQSGSELKKPGASVKVSCKASGYTFT<br>NAGMNWVKQAPGQGLKWMGWINTDSGEPTY<br>TDDFKGRFAFSLDTSVSTAYLQISSLKADD<br>TAVYFCARGGFGSSYWYFDVWGQGSLVTVS<br>SASTKGPSVFPLAPSSKSTSGGTAALGCLV<br>KDYFPEPVTVSWNSGALTSGVHTFPAVLQS<br>SGLYSLSSVVTVPSSSLGTQTYICNVNHKP<br>SNTKVDKRVEPKSCDKTHTCPPCPAPELLG<br>GPSVFLFPPKPKDTLMISRTPEVTCVVVDV<br>SHEDPEVKFNWYVDGVEVHNAKTKPREEQY<br>NSTYRVVSVLTVLHQDWLNGKEYKCKVSNK<br>ALPAPIEKTISKAKGQPREPQVYTLPPSRE<br>EMTKNQVSLTCLVKGFYPSDIAVEWESNGQ<br>PENNYKTTPPVLDSDGSFFLYSKLTVDKSR<br>WQQGNVFSCSVMHEALHNHYTQKSLSLSPG<br>ALPETGG | 37 |
| | QVQLQQSGSELKKPGASVKVSCKASGYTFT<br>AAGMNWVKQAPGQGLKWMGWINTYTGEPTY<br>TDDFKGRFAFSLDTSVSTAYLQISSLKADD<br>TAVYFCARGGFGSSYWYFDVWGQGSLVTVS<br>SASTKGPSVFPLAPSSKSTSGGTAALGCLV<br>KDYFPEPVTVSWNSGALTSGVHTFPAVLQS<br>SGLYSLSSVVTVPSSSLGTQTYICNVNHKP<br>SNTKVDKRVEPKSCDKTHTCPPCPAPELLG<br>GPSVFLFPPKPKDTLMISRTPEVTCVVVDV<br>SHEDPEVKFNWYVDGVEVHNAKTKPREEQY<br>NSTYRVVSVLTVLHQDWLNGKEYKCKVSNK<br>ALPAPIEKTISKAKGQPREPQVYTLPPSRE<br>EMTKNQVSLTCLVKGFYPSDIAVEWESNGQ<br>PENNYKTTPPVLDSDGSFFLYSKLTVDKSR<br>WQQGNVFSCSVMHEALHNHYTQKSLSLSPG<br>ALPETGGQVQLVQSGAEVKKPGASVKVSCK<br>ASGYTFTTAGMQWVRQAPGQG | 38 |
| | LEWMGWINTHSGVPKYAEDFKGRVTISADT<br>STSTAYLQLSSLKSEDTAVYYCARSGFGSS<br>YWYFDVWGQGTLVTVSSASTKGPSVFPLAP<br>SSKSTSGGTAALGCLVKDYFPEPVTVSWNS<br>GALTSGVHTFPAVLQSSGLYSLSSVVTVPS<br>SSLGTQTYICNVNHKPSNTKVDKRVEPKSC<br>DKTHTCPPCPAPELLGGPSVFLFPPKPKDT<br>LMISRTPEVTCVVVDVSHEDPEVKFNWYVD<br>GVEVHNAKTKPREEQYNSTYRVVSVLTVLH<br>QDWLNGKEYKCKVSNKALPAPIEKTISKAK<br>GQPREPQVYTLPPSREEMTKNQVSLTCLVK<br>GFYPSDIAVEWESNGQPENNYKTTPPVLDS<br>DGSFFLYSKLTVDKSRWQQGNVFSCSVMHE<br>ALHNHYTQKSLSLSPGALPETGG | 39 |
| LC | DIQLTQSPSSLSASVGDRVSITCKASQDVS<br>IAVAWYQQKPGKAPKLLIYSASYRYTGVPD<br>RFSGSGSGTDFTLTISSLQPEDFAVYYCQQ<br>HYITPLTFGAGTKVEIKRTVAAPSVFIFPP<br>SDEQLKSGTASVVCLLNNFYPREAKVQWKV<br>DNALQSGNSQESVTEQDSKDSTYSLSSTLT<br>LSKADYEKHKVYACEVTHQGLSSPVTKSFN<br>RGECGALPETGG | 40 |

TABLE 2-continued

Sequences of modified antibodies

| Name | Amino acid | SEQ ID NO |
|---|---|---|
| | DIQMTQSPSSLSASVGDRVTITCKASQDVSTAVAWYQQKPGKAPKLLIYSASYRYTGVPSRFSGSGSGTDFTLTISSLQPEDFAVYYCQQHYITPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGALPETGG | 41 |

Specific Embodiments for the Conjugate

In one embodiment, Q is hydrogen, each LKa is

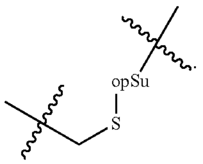

In one embodiment, Ld2 is a bond, d is 0. In one embodiment, the compound of formula (III-a) is as follows:

(conjugate III-a-0-1)

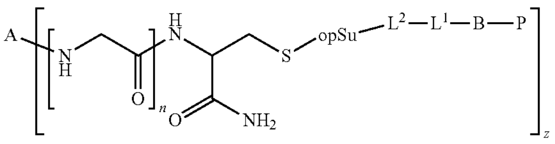

In one embodiment, d is 0, Ld2 is

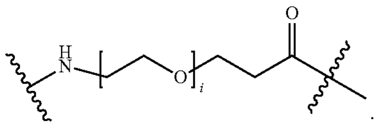

In one embodiment, the compound of formula (III-a) is as follows:

(conjugate III-a-0-2)

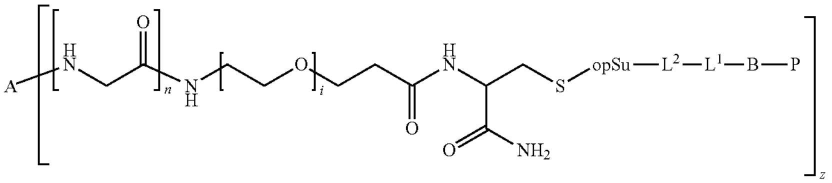

In one embodiment, formula (III) has the structure of formula (III-a):

formula (III-a)

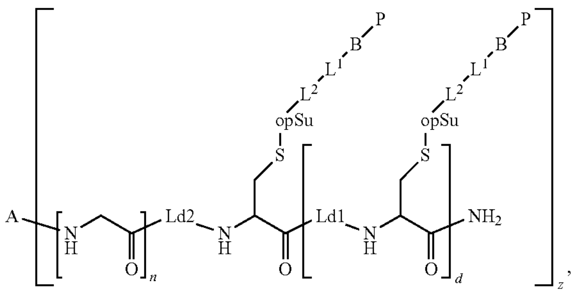

wherein A is an anti-TROP2 antibody or an antigen-binding fragment, and the antibody or antigen-binding fragment is modified to connect with the (Gly) n.

In one embodiment, d is 1, 2 or 3, Ld2 and each Ld1 are independently selected from

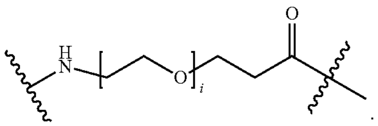

In one embodiment, the compound of formula (III-a) is as follows:
(conjugate III-a-0-3)
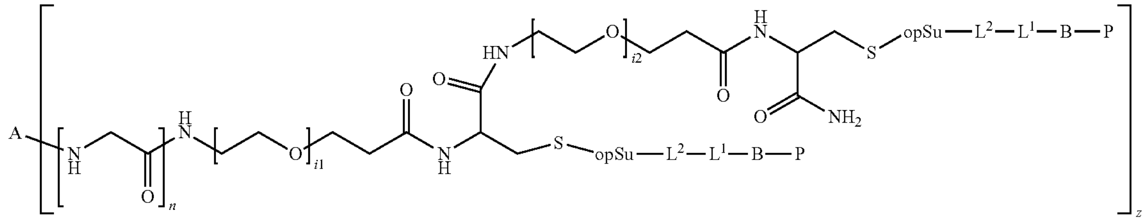
(conjugate III-a-0-4)
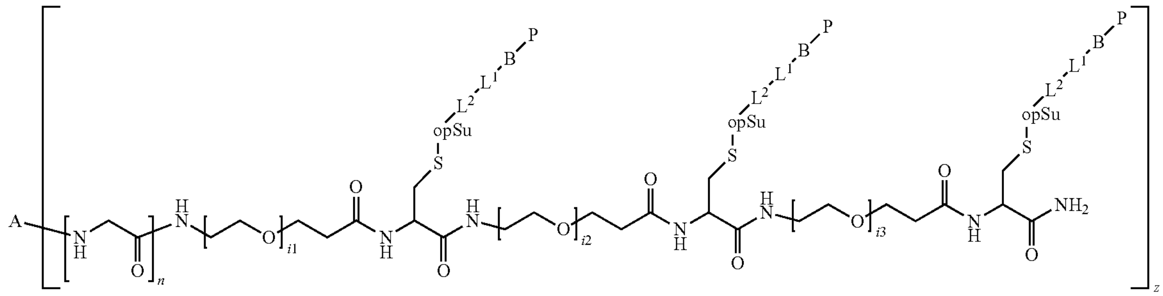
(conjugate III-a-0-5)
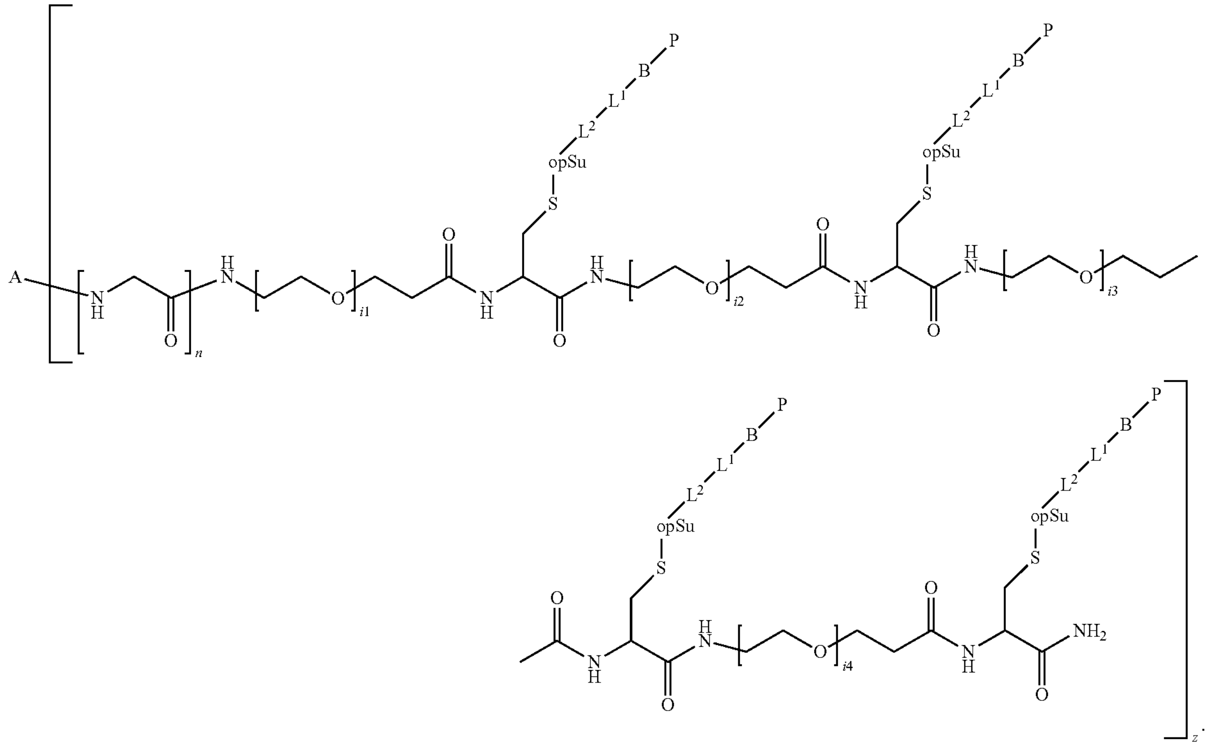

In one embodiment, Ld2 is
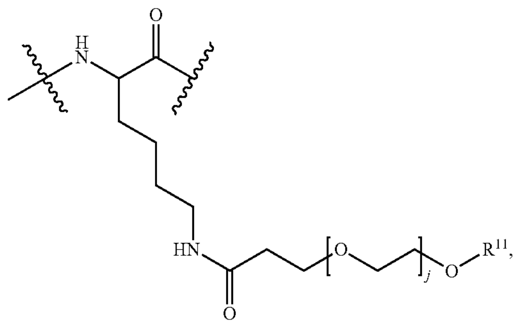
d is 0. In one embodiment, the compound of formula (III-a) is as follows:
(conjugate III-a-1-1)
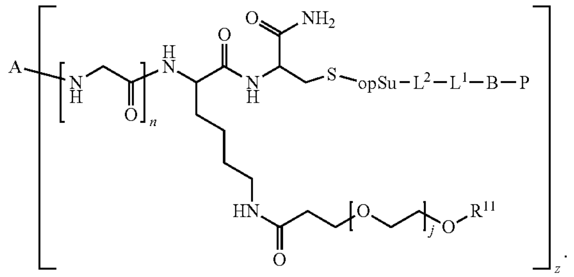
In one embodiment, d is 1, 2 or 3, Ld2 is
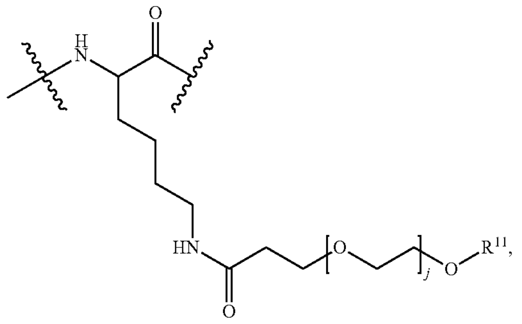
and each Ld1 is independently selected from
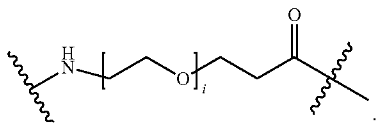
In one embodiment, the compound of formula (III-a) is as follows:
(conjugate III-a-1-2)
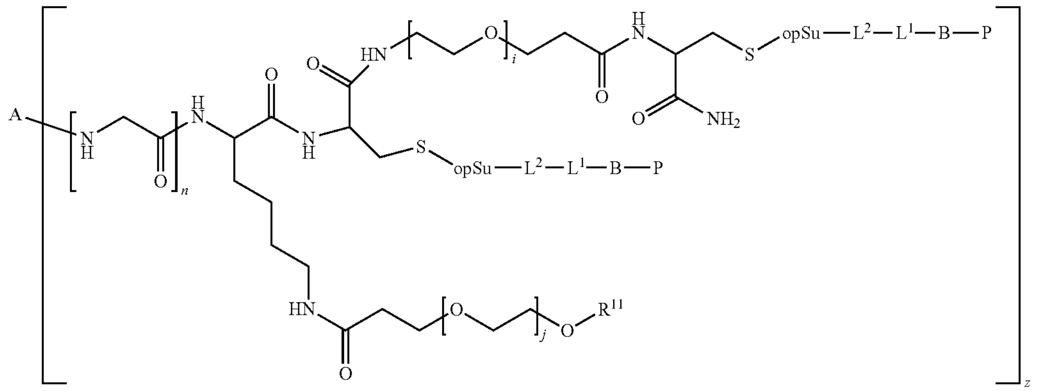

-continued (conjugate III-a-1-3)

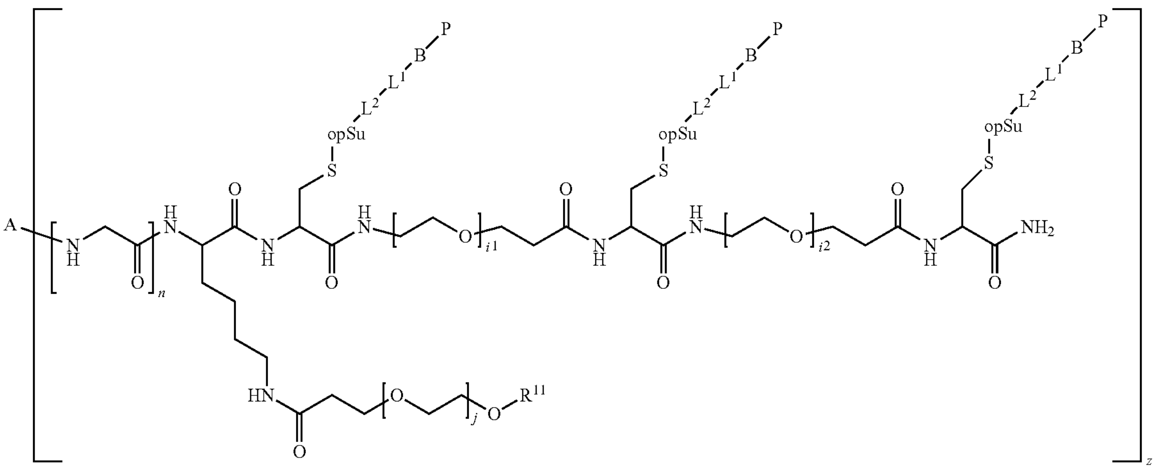

(conjugate III-a-1-4)

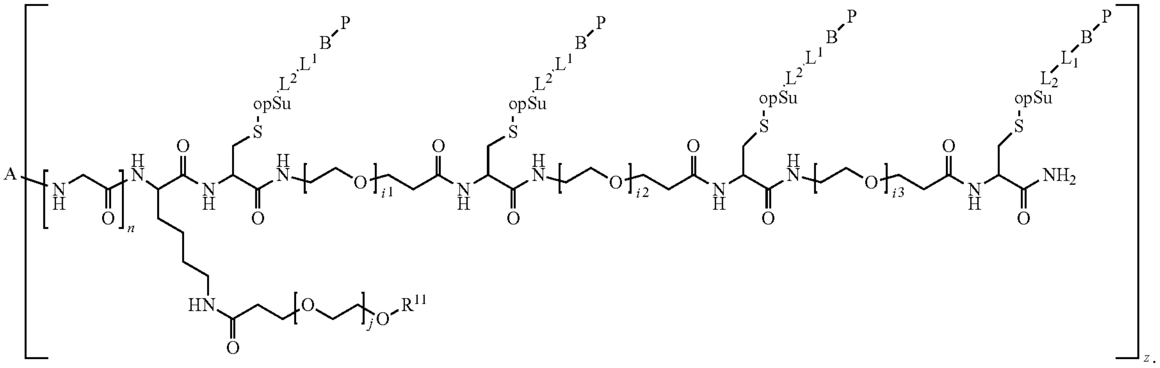

In one embodiment, z is 1 to 4. In one embodiment, z is 2 or 4. In one embodiment, z is 2. In one embodiment, in conjugate III-a-0-1, III-a-0-2, III-a-1-1, z is 2 or 4. In one embodiment, in conjugate III-a-0-3, III-a-0-4, III-a-0-5, III-a-1-3 and III-a-1-4, z is 2. In one embodiment, in conjugate III-a-1-2, z is 4.

In one embodiment, LKa is

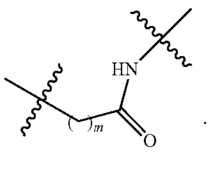

In one embodiment, formula (III) has the structure of formula (III-b):

formula (III-b)

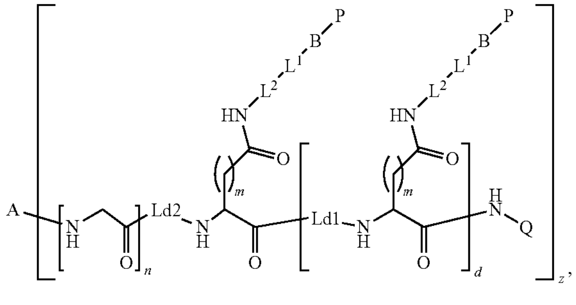

wherein A is an anti-TROP2 antibody or an antigen-binding fragment, the antibody or antigen-binding fragment is modified to connect with the $(Gly)_n$.

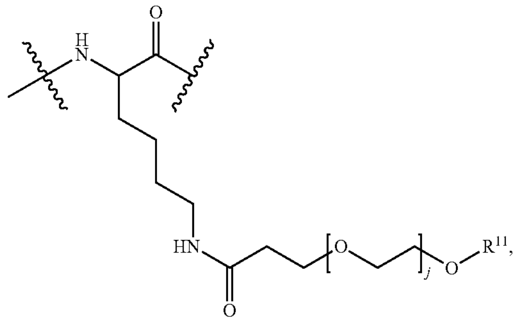
In one embodiment, Q is hydrogen, d is 1, Ld2 is
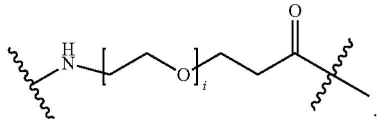
and Ld1 is selected from In one embodiment, the compound of formula (III-b) is as follows:
(conjugate III-b-1)
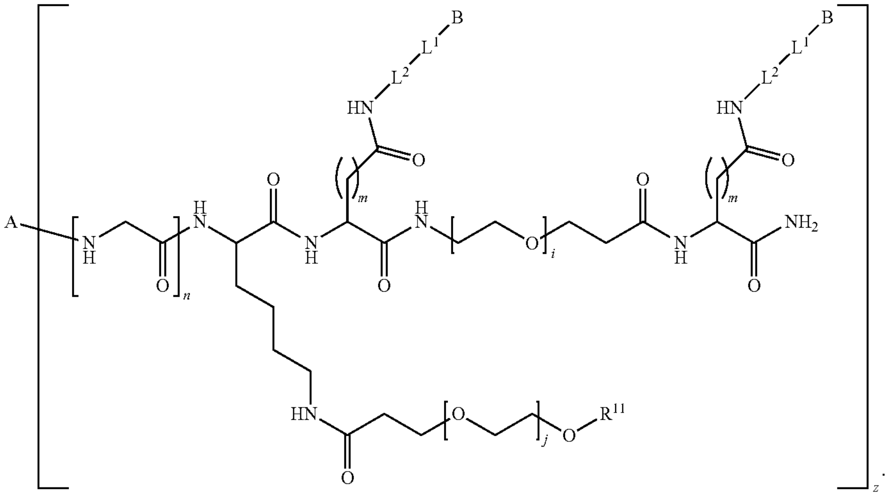
In one embodiment, Q is —$C_2H_4$-$(PEG)_t$-(CO)$NH_2$, d is 1, Ld2 is a bond, and Ld1 is selected from
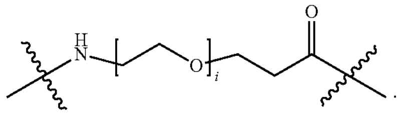
In one embodiment, the compound of formula (III-b) is as follows:
(conjugate III-b-0)
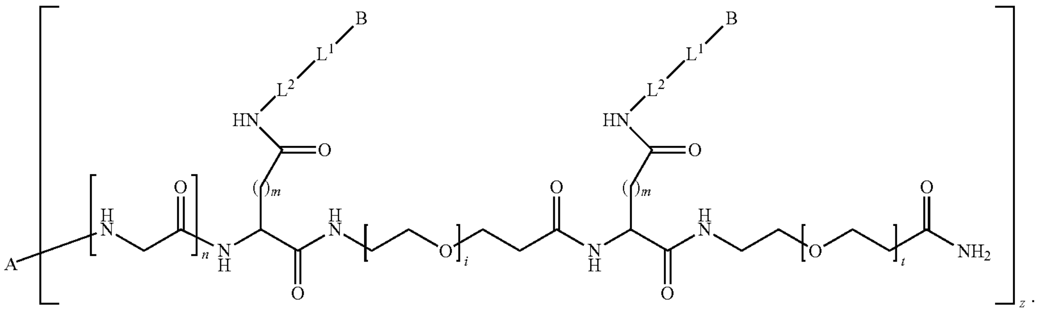

In one embodiment, z is 1 to 4. In one embodiment, z is 2 or 4. In one embodiment, z is 2. In one embodiment, in conjugate III-b-1-1 and III-b-0-1 z is 2 or 4. In one embodiment, in conjugate 11-b-1-1 and III-b-0-1, z is 4.

In one embodiment, B in compound of formula (I) is a terminal group $R^{10}$, and the Cleavable sequence 1 in $L^1$ is connected to the payload to form a compound of formula (II), wherein B is absent in the resulting molecule of the connection of Cleavable sequence 1 with the payload. In such case, M can be understood to be LKa-$L^2$-$L^1$-B—P, wherein B does not present. In such case, M can also be denoted as LKa-$L^2$-$L^1$-P. In one embodiment, n is 3, $L^2$ is —$(CH_2)_p$—$(CH_2)_2(CO)$—, p is 3, $L^1$ is GGFG, B is —NH—$CH_2$—U— or absent or —NH—$CH_2$—U—$(CR^1R^2)_g$—(CO)—, U is O, g is 1.

In one embodiment, conjugate III-a-0-1 has the structure of:

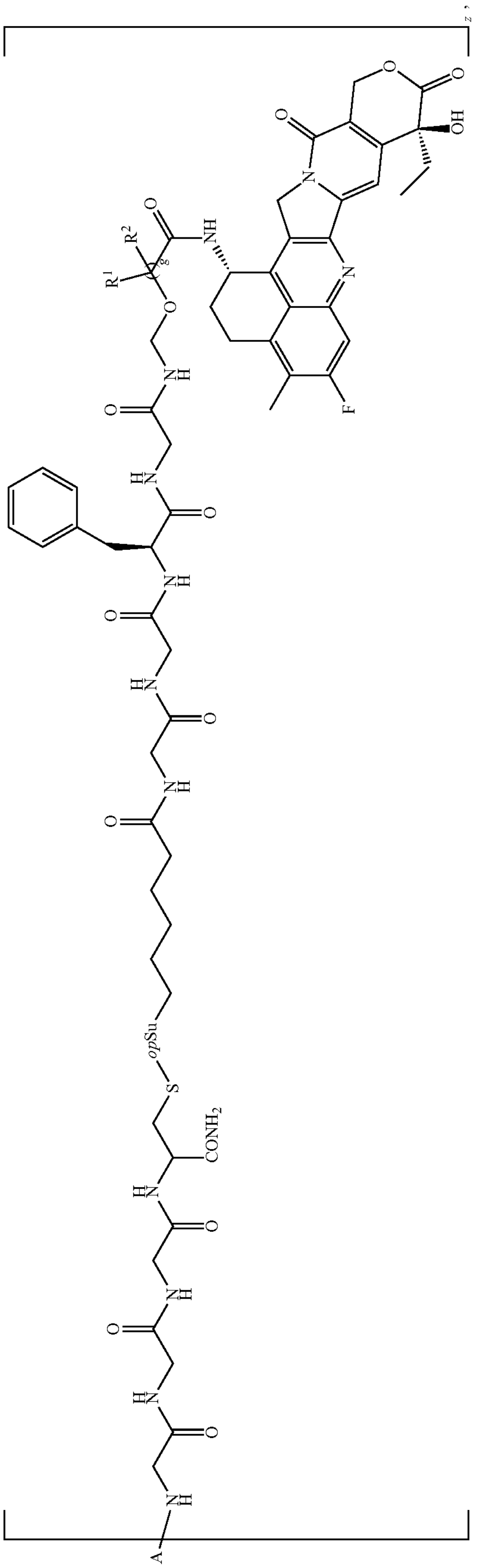

wherein A is an anti-TROP2 antibody or an antigen-binding fragment, the antibody or antigen-binding fragment is modified to connect with the $(Gly)_n$.

In one embodiment, conjugate III-a-0-2 has the structure of:

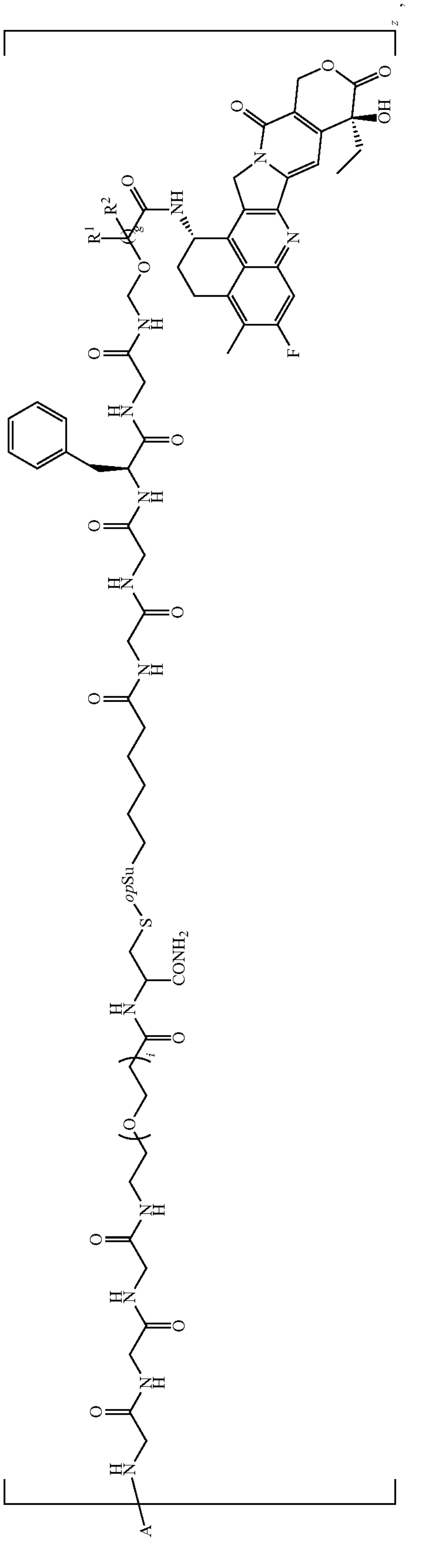
, wherein A is an anti-TROP2 antibody or an antigen-binding fragment, the antibody or antigen-binding fragment is modified to connect with the $(Gly)_n$.

In one embodiment, conjugate III-a-0-3 has the structure of:

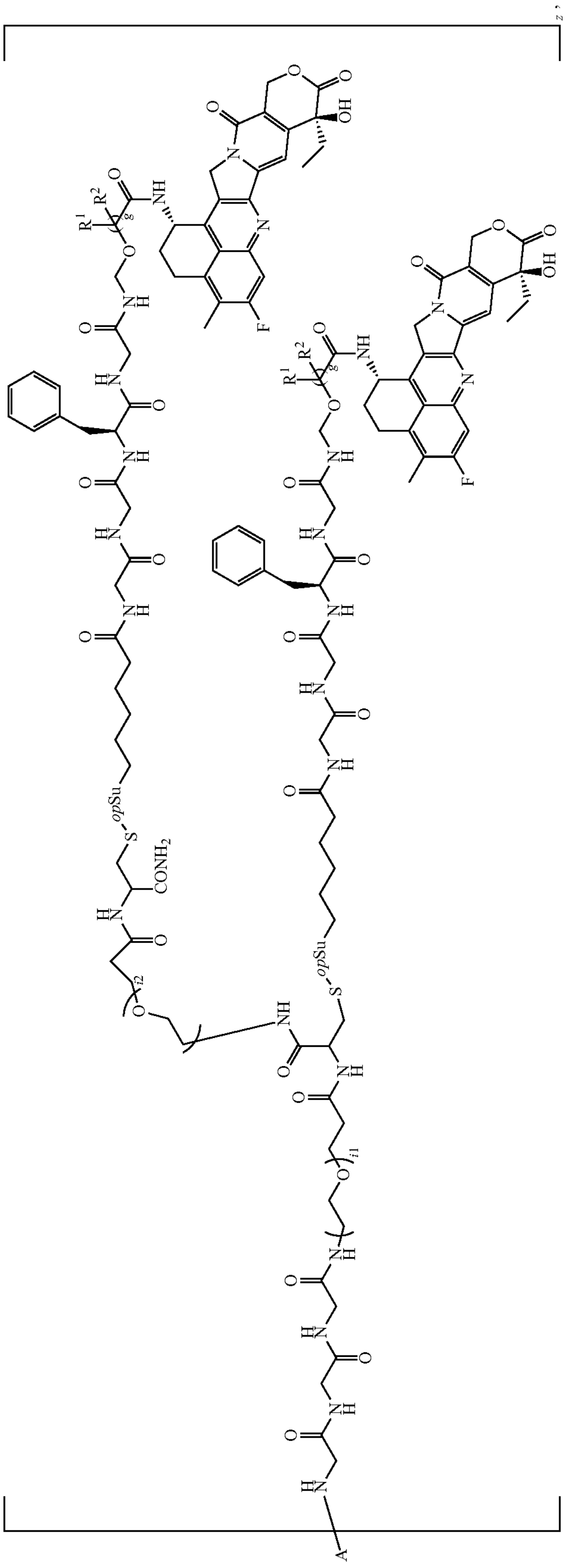

wherein A is an anti-TROP2 antibody or an antigen-binding fragment, the antibody or antigen-binding fragment is modified to connect with the $(Gly)_n$.

In one embodiment, conjugate III-a-0-4 has the structure of:

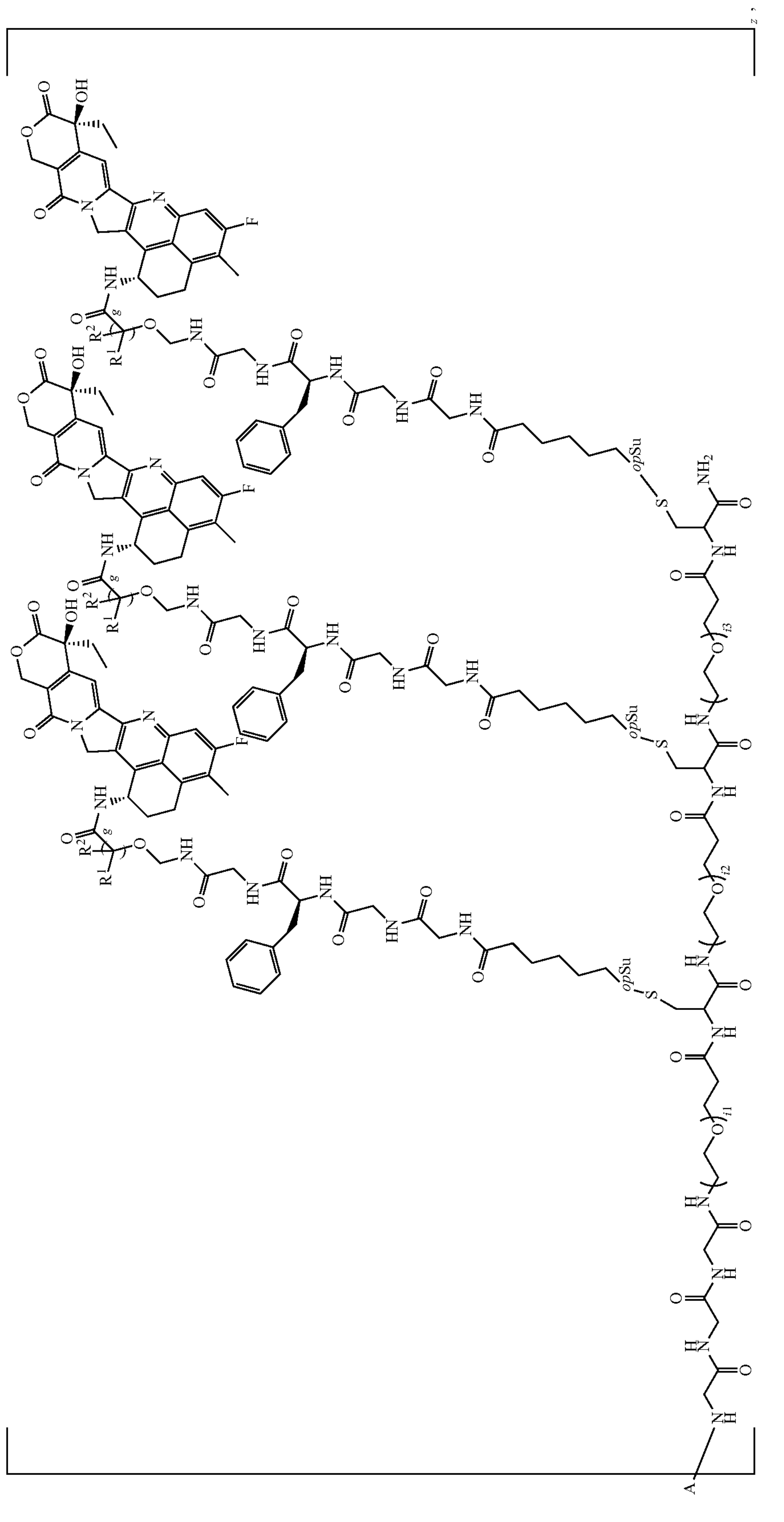

wherein A is an anti-TROP2 antibody or an antigen-binding fragment, the antibody or antigen-binding fragment is modified to connect with the $(Gly)_n$.

In one embodiment, conjugate III-a-0-5 has the structure of:

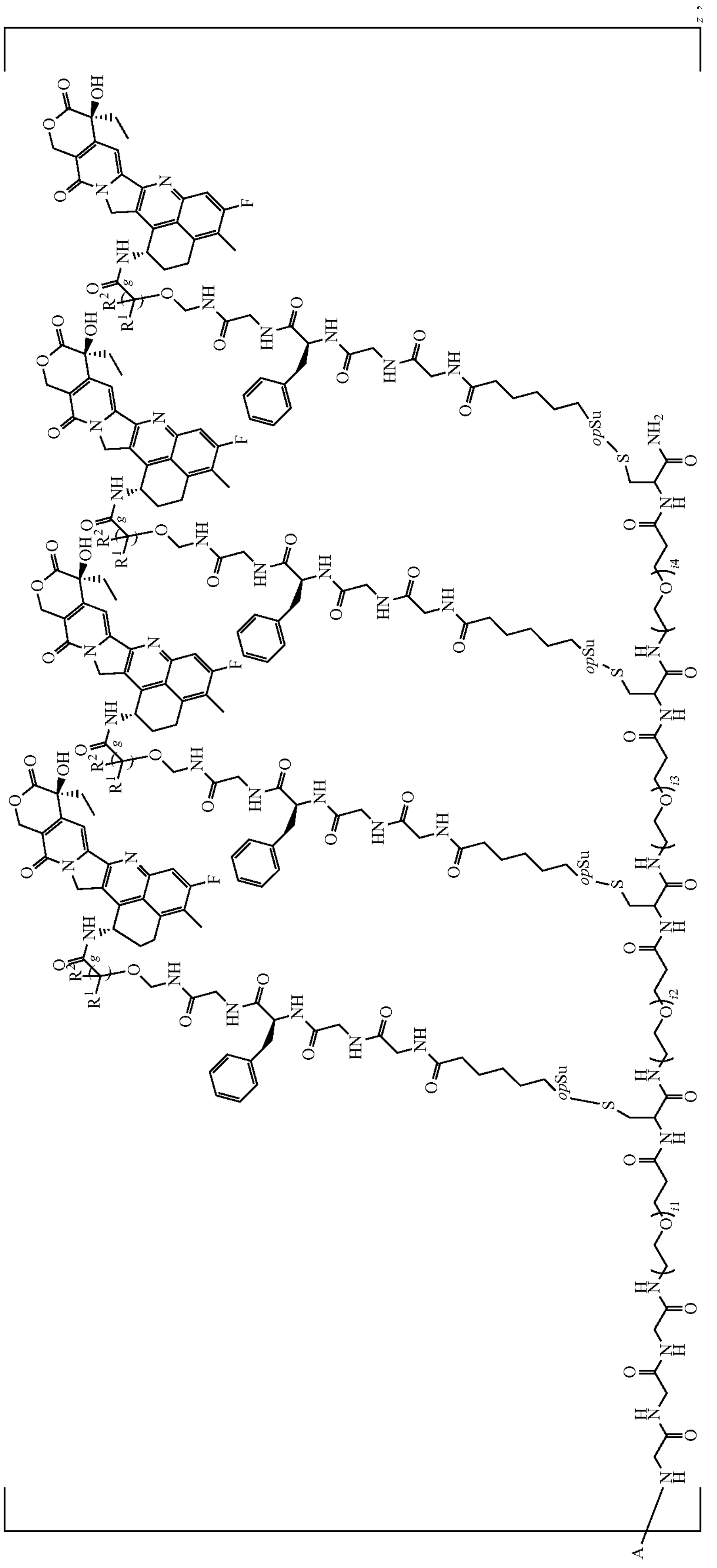

wherein A is an anti-TROP2 antibody or an antigen-binding fragment, the antibody or antigen-binding fragment is modified to connect with the $(Gly)_n$.

In one embodiment, conjugate III-a-1-1 has the structure of:

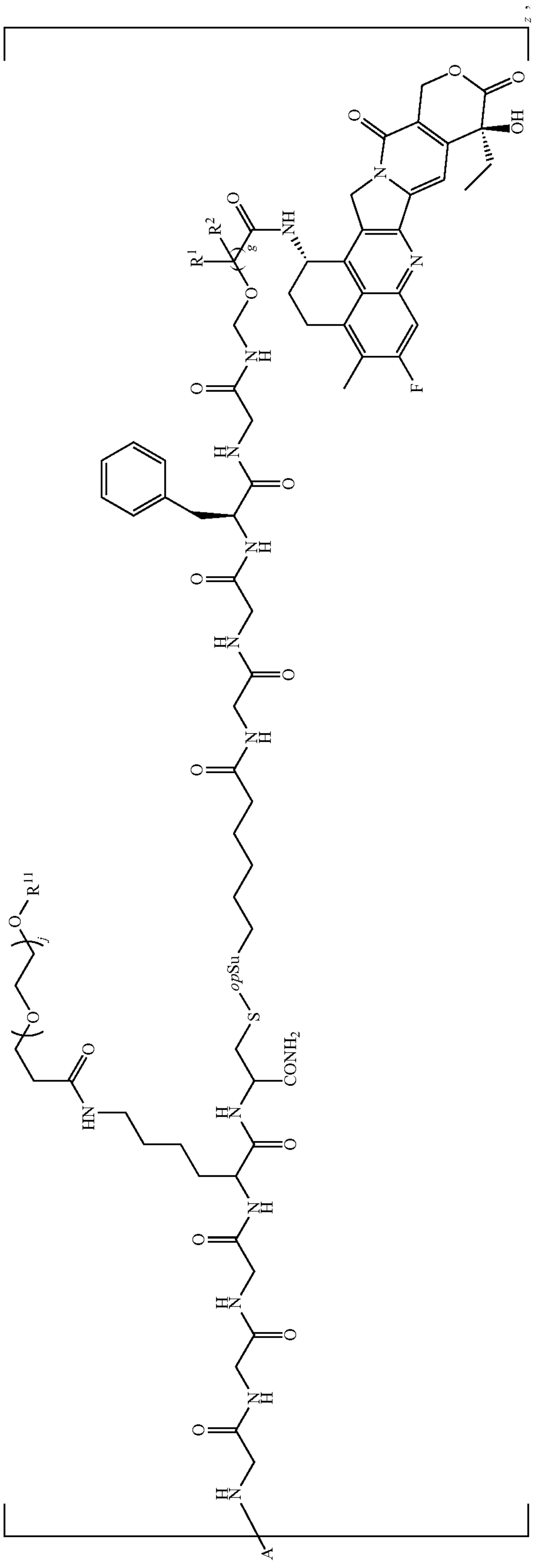

wherein A is an anti-TROP2 antibody or an antigen-binding fragment, the antibody or antigen-binding fragment is modified to connect with the $(Gly)_n$.

In one embodiment, conjugate III-a-1-2 has the structure of:

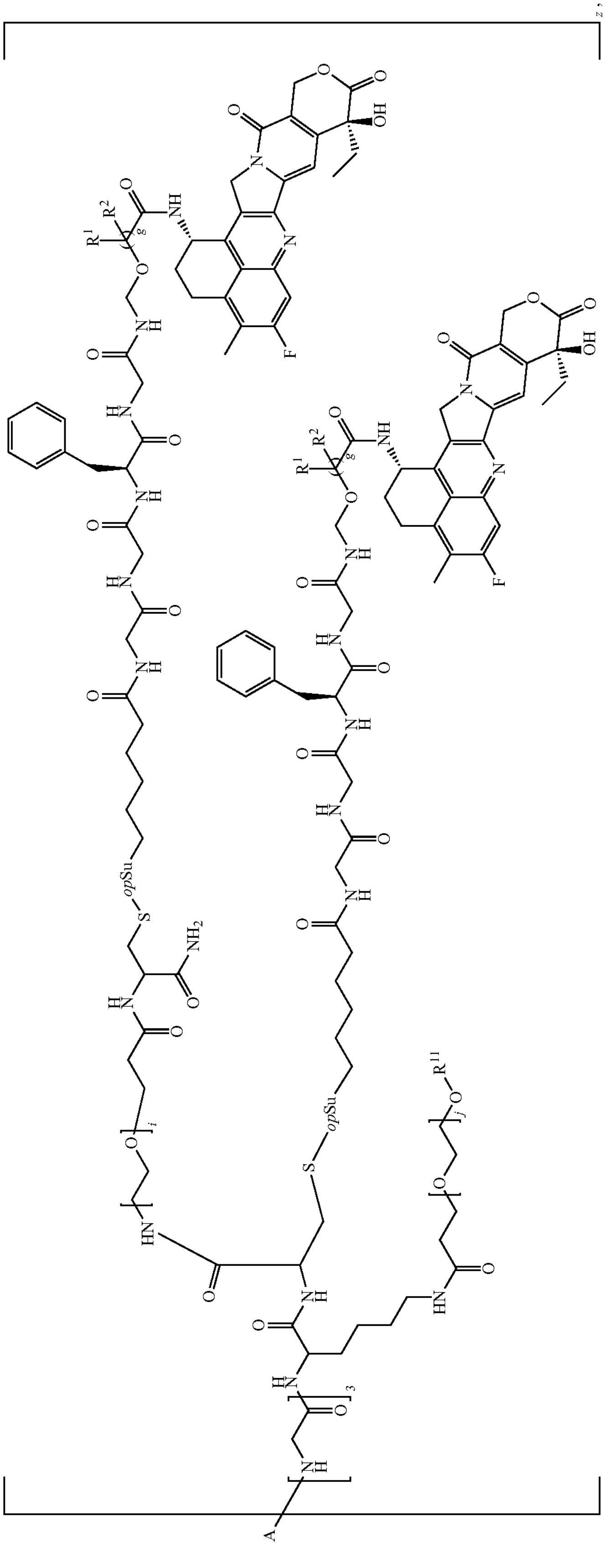

-continued
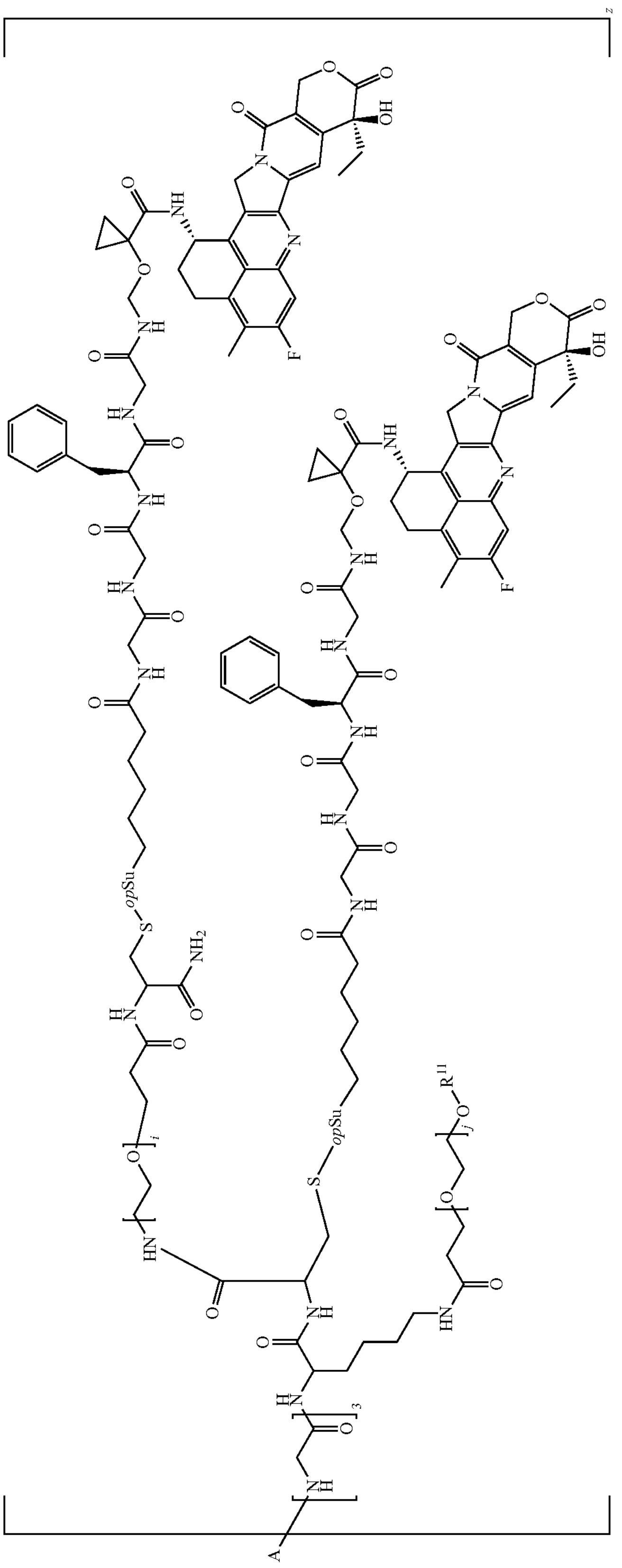
or

-continued
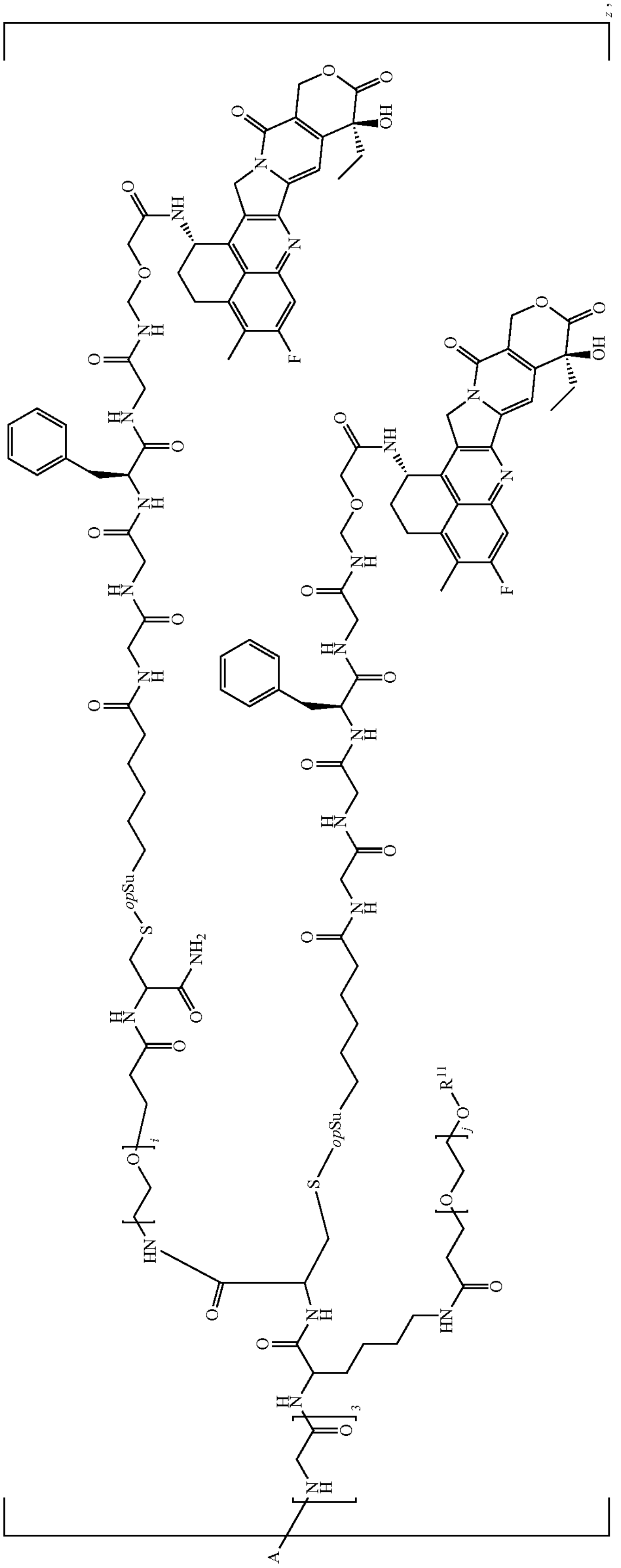

wherein A is an anti-TROP2 antibody or an antigen-binding fragment, the antibody or antigen-binding fragment is modified to connect with the $(Gly)_n$.

In one embodiment, conjugate III-a-1-3 has the structure of:

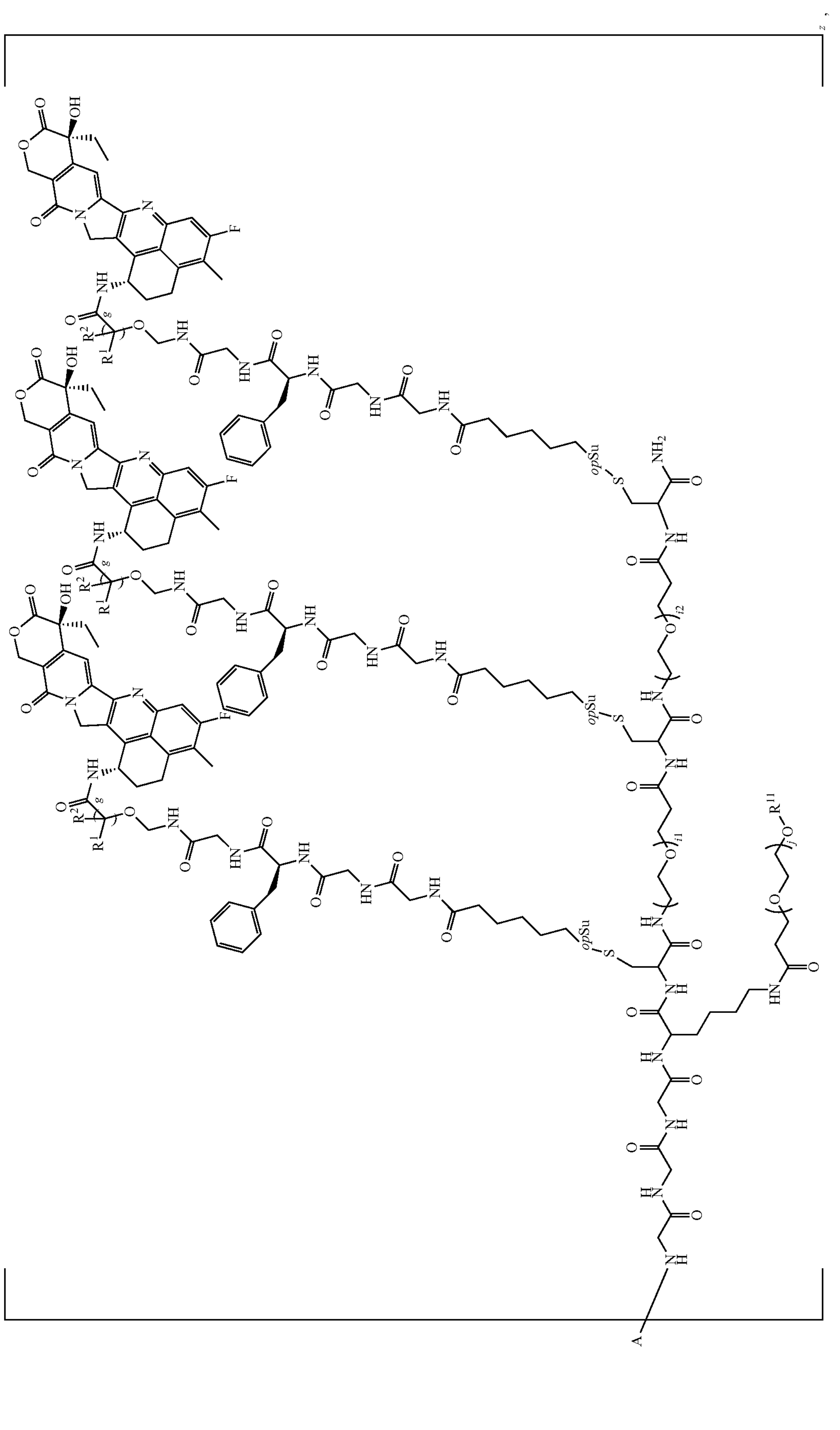

wherein A is an anti-TROP2 antibody or an antigen-binding fragment, the antibody or antigen-binding fragment is modified to connect with the $(Gly)_n$.

In one embodiment, conjugate III-a-1-4 has the structure of:

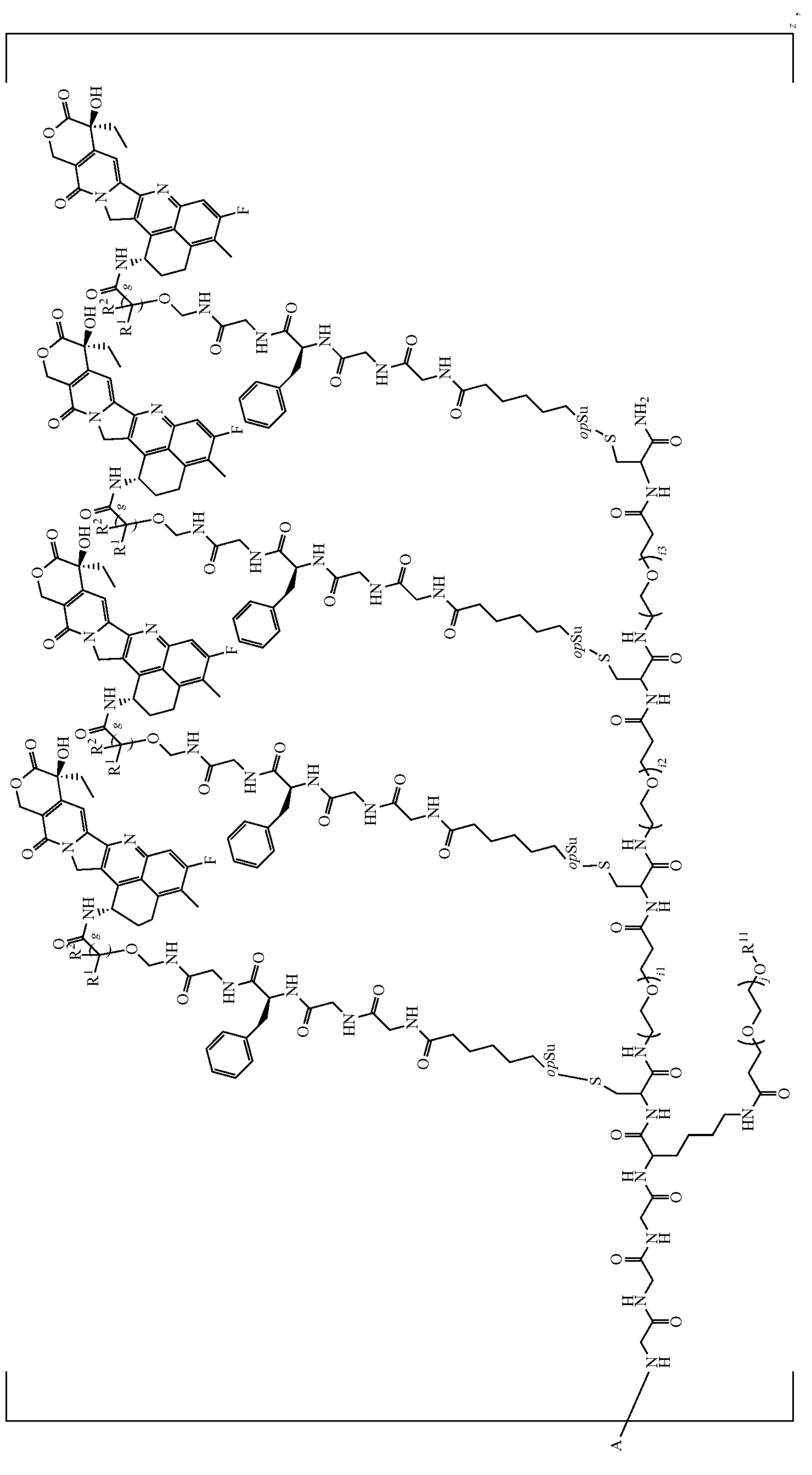

wherein A is an anti-TROP2 antibody or an antigen-binding fragment, the antibody or antigen-binding fragment is modified to connect with the $(Gly)_n$.

In one embodiment, i is 4, g is 1, $R^{11}$ is methyl.

In one embodiment, n is 3, $L^2$ is $—(C_2H_4—O)_p—(CH_2)_2(CO)—$, p is 2, $L^1$ is GGFG, B is $—NH—CH_2—U—$, U is O. In one embodiment, conjugate III-b-1-1 has the structure of:

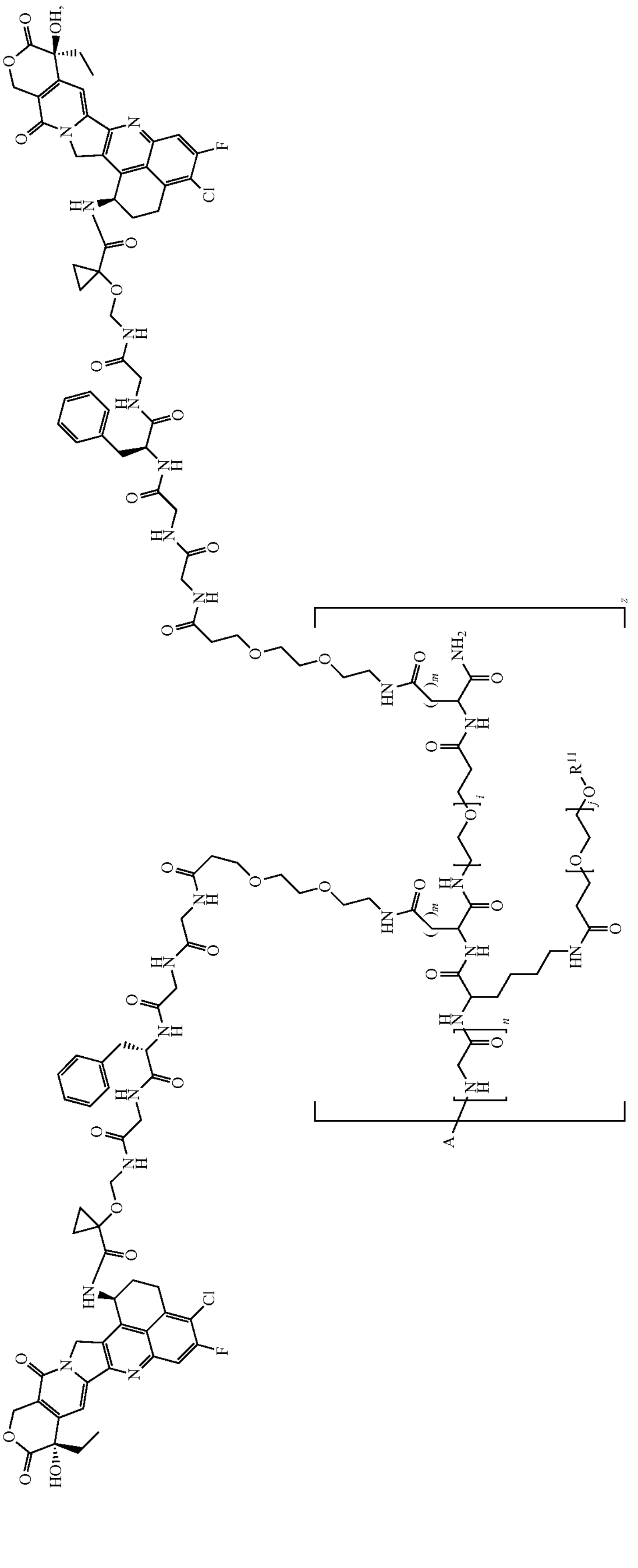

wherein A is an anti-TROP2 antibody or an antigen-binding fragment, the antibody or antigen-binding fragment is modified to connect with the $(Gly)_n$.

In one embodiment, conjugate III-a-0-2 is as follows (conjugate III-a-0-2-1):

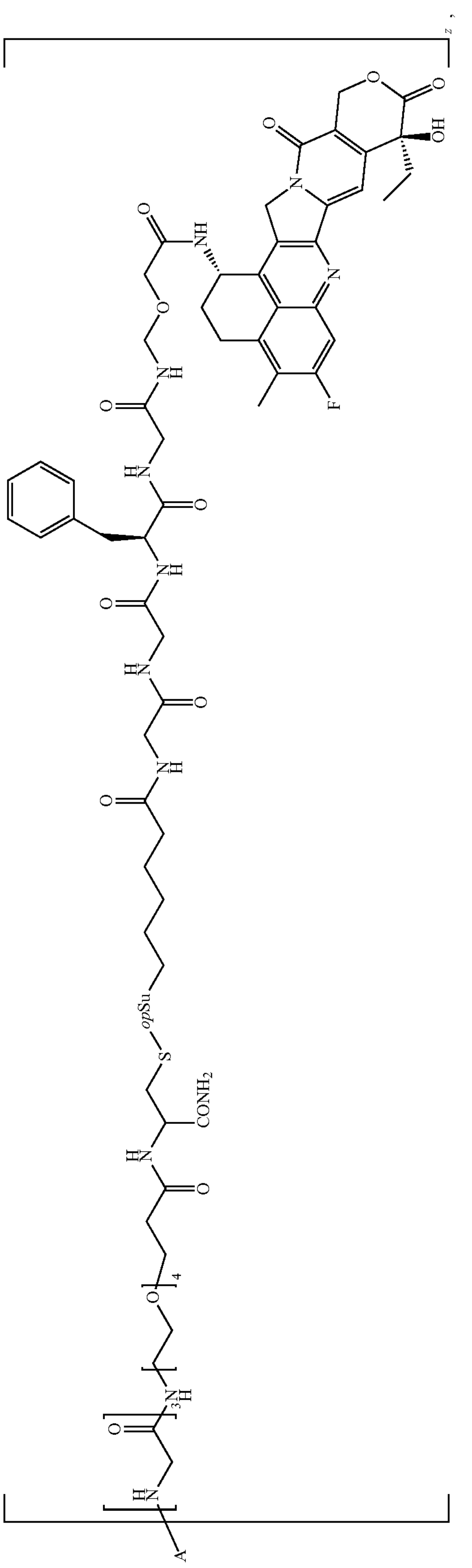
(conjugate III-a-0-2-1)

wherein A is an anti-TROP2 antibody or an antigen-binding fragment, the antibody or antigen-binding fragment is modified to connect with the $(Gly)_n$.

In one embodiment, i is 4, j is 8, g is 1, $R^{11}$ is methyl. In one embodiment, conjugate III-a-1-2 is as follows (conjugate III-a-1-2-1):

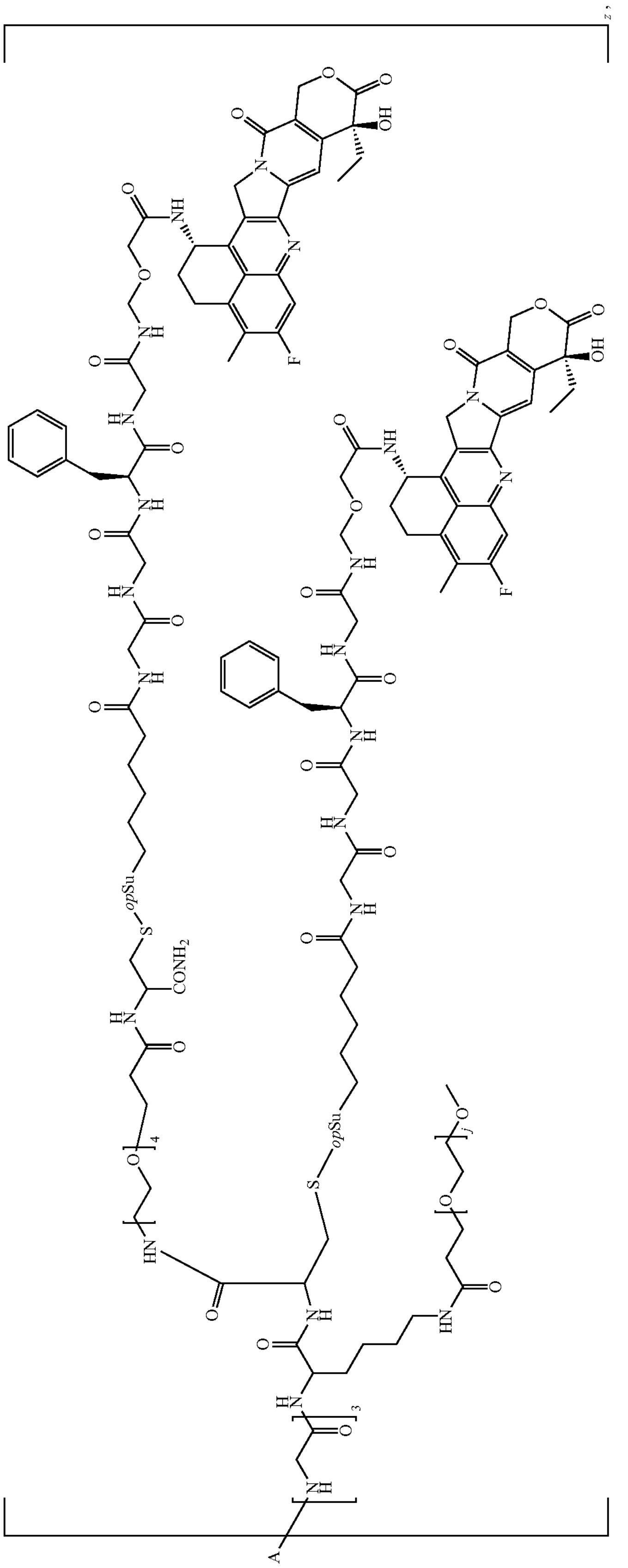
(conjugate III-a-1-2-1)

wherein A is an anti-TROP2 antibody or an antigen-binding fragment, the antibody or antigen-binding fragment is modified to connect with the $(Gly)_n$.

In one embodiment, i is 4, j is 12, g is 1, $R^{11}$ is methyl. In one embodiment, conjugate III-a-1-2 is as follows (conjugate III-a-1-2-4-1):

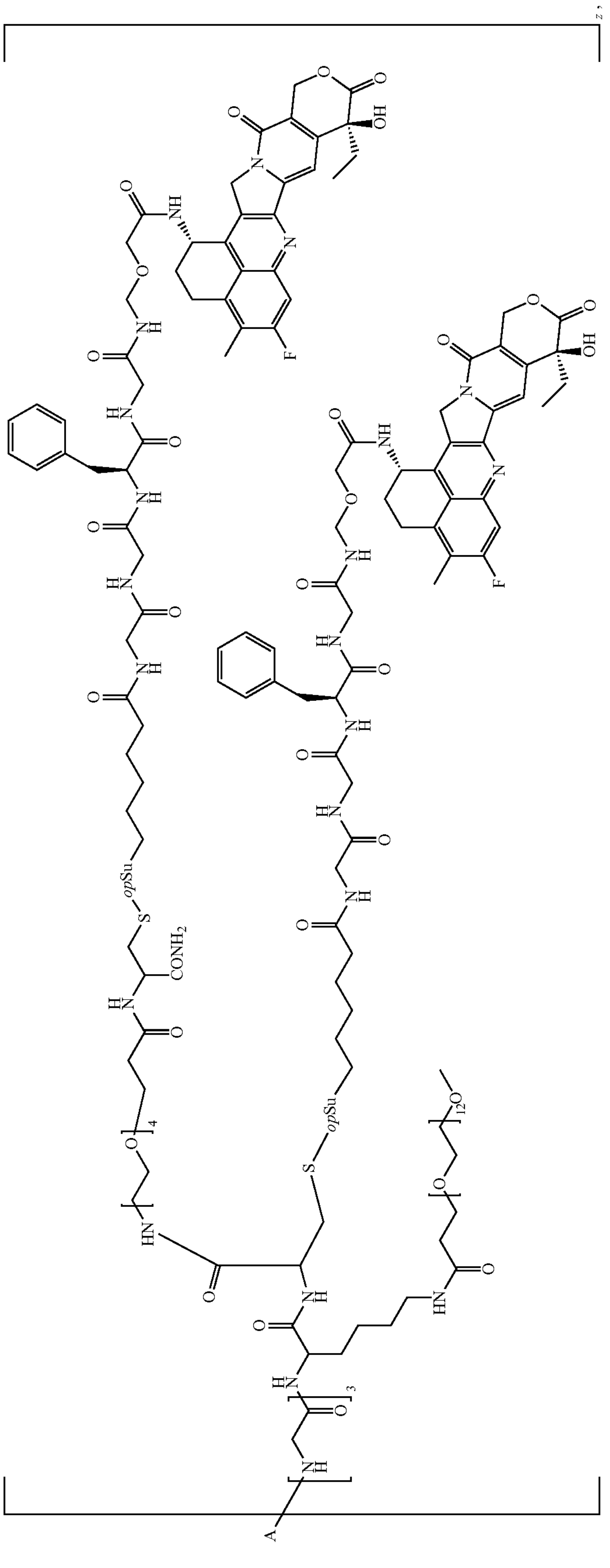
(conjugate III-a-1-2-4-1)

wherein A is an anti-TROP2 antibody or an antigen-binding fragment, the antibody or antigen-binding fragment is modified to connect with the $(Gly)_n$.

In one embodiment, i is 4, j is 12, $R^{11}$ is methyl. In one embodiment, conjugate III-a-1-2 is as follows (conjugate III-a-1-2-4-2):

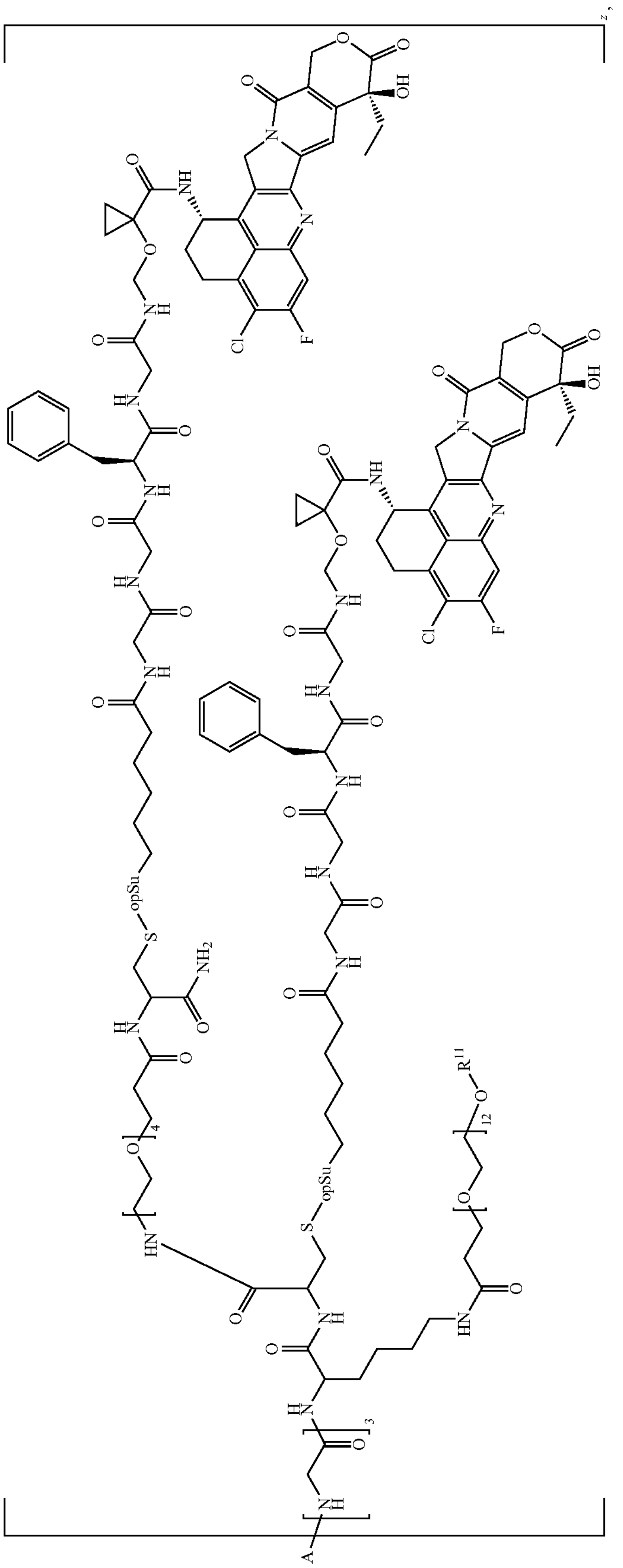

wherein A is an anti-TROP2 antibody or an antigen-binding fragment, the antibody or antigen-binding fragment is modified to connect with the $(Gly)_n$.

In one embodiment, i is 4, j is 12, $R^{11}$ is methyl. In one embodiment, conjugate III-a-1-2 is as follows (conjugate III-a-1-2-4-3):

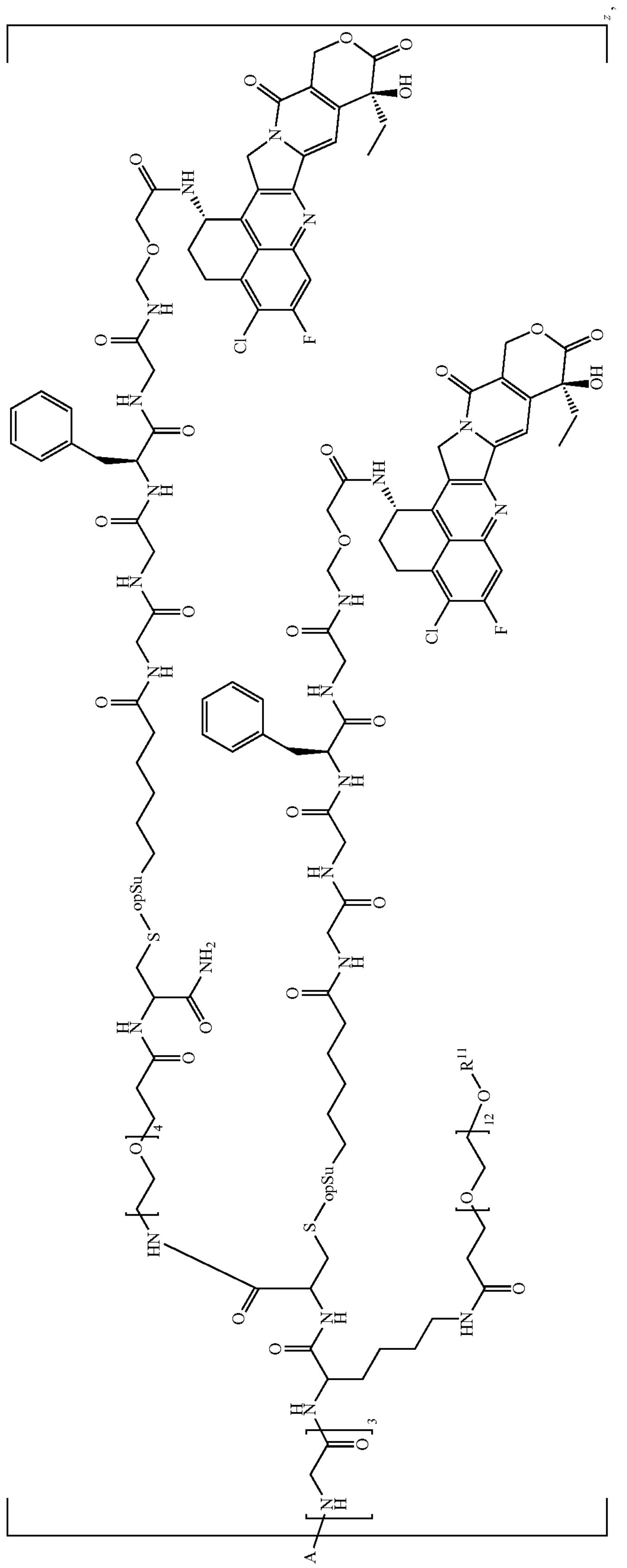

wherein A is an anti-TROP2 antibody or an antigen-binding fragment, the antibody or antigen-binding fragment is modified to connect with the (Gly) n.

In one embodiment, n is 3, i is 4, j is 12, m is 1, $R^{11}$ is methyl. In one embodiment, conjugate III-b-1-1 is as follows (conjugate III-b-1-1-4):

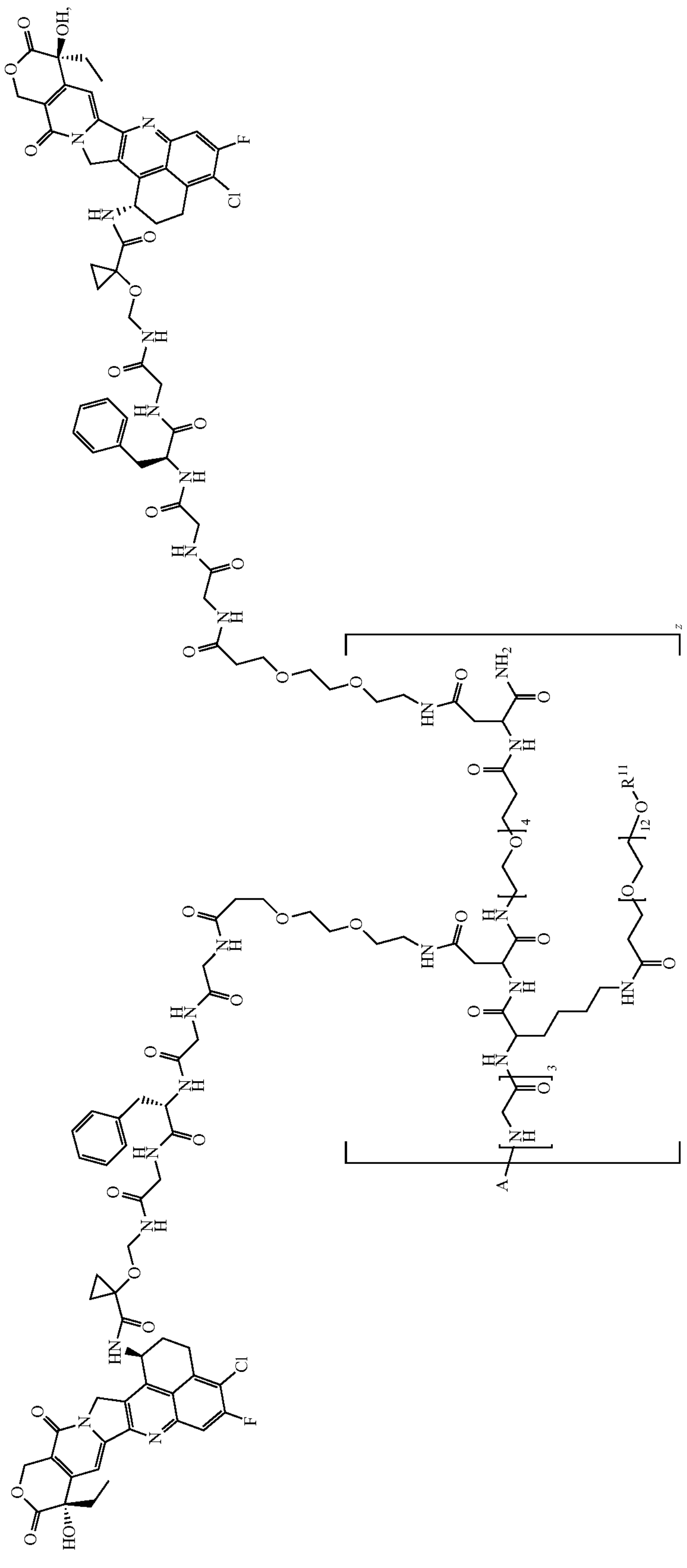

wherein A is an anti-TROP2 antibody or an antigen-binding fragment, the antibody or antigen-binding fragment is modified to connect with the (Gly) n.

Preparation of the Conjugate

The conjugates of the present disclosure can be prepared by any method known in the art. In some embodiments, the conjugate is prepared by the ligase-catalyzed site-specific conjugation of a targeting molecule and a payload-bearing formula (I) compound, wherein the targeting molecule is modified by a ligase recognition sequence. The method comprises step A and step B.

Step A. Preparation of the Linking Unit-Payload Intermediate

In a preferred embodiment, B in the compound of formula (I) is covalently linked via a reactive group to a payload containing another reactive group.

The linking unit-payload intermediate prepared using the compound of formula (I) of the present disclosure has defined structure, defined composition and high purity, so that when the conjugation reaction with an antibody is conducted, fewer impurities are introduced or no other impurities are introduced. When such an intermediate is used for the ligase-catalyzed site-specific conjugation with a modified antibody containing a ligase recognition sequence, a homogeneous ADC with highly controllable quality is obtained.

Step B. Linking the Targeting Molecule to the Payload-Bearing Formula (I) Compound The targeting molecule of the present disclosure can be conjugated with the payload-bearing formula (I) compound (i.e., the compound of formula (II)) by any method known in the art.

The targeting molecule and the payload-bearing formula (I) compound are linked to each other via the ligase-specific recognition sequences of the substrates. The recognition sequence depends on the particular ligase employed. In one embodiment, the targeting molecule is an antibody with recognition sequence-based terminal modifications introduced at the C-terminal of the light chain and/or the heavy chain, and the targeting molecule is conjugated with the compound of formula (II), under the catalysis of the wild type or optimized engineered ligase or any combination thereof, and under suitable catalytic reaction conditions.

In a specific embodiment, the ligase is Sortase A and the conjugation reaction can be represented by the following scheme:

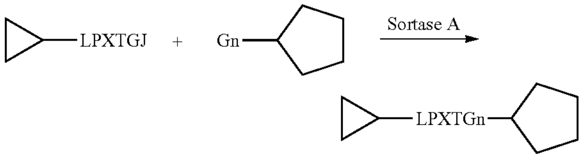

The triangle represents a portion of an antibody; and the pentagon represents a portion of a compound of formula (II). n, X and J are respectively as defined above. When conjugated with $G_n$, which is the corresponding recognition sequence of the acceptor substrate, the upstream peptide bond of the Glycine in the LPXTGJ sequence is cleaved by Sortase A, and the resulting intermediate is linked to the free N-terminal of $G_n$ to generate a new peptide bond. The resulting amino acid sequence is $LPXTG_n$. The sequences $G_n$ and LPXTGJ are as defined above.

Metabolism of the Conjugate in a Physiological Environment

When a part or whole linker is cleaved in tumor cells, the antitumor compound moiety is released to exhibit the antitumor effect of the antitumor compound. As the linker is cleaved at a connecting position to drug, the antitumor compound is released in its intrinsic structure to exhibit its intrinsic antitumor effect.

In one embodiment, Cleavable sequence 1 (such as GGFG) can be cleaved by lysosomal enzymes (such as cathepsin B and/or cathepsin L).

In one embodiment, Sp1 comprises a self-immolative spacer. In one embodiment, Sp1 comprises PABC, an acetal or a heteroacetal. In one embodiment, $L^1$ is GGFG. In one embodiment, the linker comprises -GGFG-NH—$CH_2$—O—. In one embodiment, -GGFG-NH—$CH_2$—O— represents a combination of a restriction enzyme site and a self-immolative spacer, which would cleave in the cell and release the aimed molecule (such as the drug).

Pharmaceutical Composition and Pharmaceutical Preparation

Another object of the disclosure is to provide a pharmaceutical composition comprising a prophylactically or therapeutically effective amount of a conjugate of the present disclosure, and at least one pharmaceutically acceptable carrier.

Another object of the disclosure is to provide a pharmaceutical composition comprising a prophylactically or therapeutically effective amount of anti-TROP2 antibody of the present disclosure, and at least one pharmaceutically acceptable carrier.

The pharmaceutical composition of the present disclosure may be administered in any manner as long as it achieves the effect of preventing, alleviating, preventing or curing the symptoms of a human or animal. For example, various suitable dosage forms can be prepared according to the administration route, especially injections such as lyophilized powder for injection, injection, or sterile powder for injection.

The term "pharmaceutically acceptable" means that when contacted with tissues of the patient within the scope of normal medical judgment, no undue toxicity, irritation or allergic reaction, etc. shall arise, having reasonable advantage-disadvantage ratios and effective for the intended use.

The term pharmaceutically acceptable carrier refers to those carrier materials which are pharmaceutically acceptable and which do not interfere with the bioactivities and properties of the conjugate. Examples of aqueous carriers include but are not limited to buffered saline, and the like. The pharmaceutically acceptable carrier also includes carrier materials which brings the composition close to physiological conditions, such as pH adjusting agents, buffering agents, toxicity adjusting agents and the like, and sodium acetate, sodium chloride, potassium chloride, calcium chloride, sodium lactate, and the like. In some embodiments, The term "carrier" refers to a diluent, adjuvant, excipient, or vehicle that is administered with an active ingredient for treatment. Such pharmaceutical carriers may be sterile liquids, such as water and oils, including oils originated from petroleum, animal, plant or synthesis, such as peanut oil, soybean oil, mineral oil and sesame oil. Water is a preferred carrier when the pharmaceutical composition is administered intravenously. Saline and solutions of glucose in water or glycerol can also be used as a liquid carrier, particularly for injection. Suitable pharmaceutical excipients include starch, glucose, lactose, sucrose, gelatin, malt, rice, flour, chalk, silica gel, sodium stearate, glycerol monostearate, talc, sodium chloride, skimmed milk powder, glycerol, propylene, glycol, water, ethanol and the like. If desired, the composition may also comprise a small amount of a wetting agent, an emulsifier, or a pH buffering agent such as acetates, citrates or phosphates In one embodiment, the pharmaceutical composition of the present disclosure has a drug to antibody ratio (DAR) of an integer or non-integer of about 1 to about 20, such as about 1 to about 10, about 1 to about 8, about 1 to about 6, about 1 to about 4, about 1 to about 3, about 1 to about 2.5, about 1 to about 2. In a particular embodiment, the conjugate of the present disclosure has a DAR of about 2, about 4, about 6 or about 8.

Treatment Method and Use

The conjugates or antibodies are useful for the treatment of tumors and/or autoimmune diseases. Tumors susceptible to conjugate treatment include those characterized by specific tumor-associated antigens or cell surface receptors, and those will be recognized by the targeting molecule in the conjugate and can be killed by the payload/cytotoxin in the conjugate.

Accordingly, in yet another aspect, also provided is use of a conjugate or an antibody of the present disclosure or a pharmaceutical composition of the present disclosure in the manufacture of a medicament for treating a disease, disorder or condition selected from a tumor or an autoimmune disease.

In another aspect, provided is a conjugate of the present disclosure or a pharmaceutical composition of the present disclosure for use in the treatment of a tumor or an autoimmune disease.

In another aspect, provided is an antibody of the present disclosure or a pharmaceutical composition of the present disclosure for use in the treatment of a tumor or an autoimmune disease.

In a further aspect, provided is a method of treating a tumor or an autoimmune disease, the method comprising administering to an individual in need thereof an effective amount of a conjugate or an antibody of the present disclosure or a pharmaceutical composition of the present disclosure.

In a preferred embodiment, the conjugate of the present disclosure formed by conjugation of the anti-human TROP2 antibody and the small molecule cytotoxin can specifically bind to TROP2 on the surface of the tumor cell and selectively kill the TROP2-expressing tumor cells. In another preferred embodiment, provided is use of a conjugate (or an antibody) of the present disclosure or a pharmaceutical composition of the present disclosure in the manufacture of a medicament for treating a disease, disorder or condition selected from TROP2-positive tumors. In a more preferred embodiment, the disease, disorder or condition is TROP2-positive tumor. In one embodiment, the TROP2-positive tumor is selected from the group consisting of breast cancer, gastric cancer, lung cancer, ovarian cancer, urothelial cancer, and the like.

The dosage of the conjugate (or the antibody) administered to the subject can be adjusted to a considerable extent. The dosage can vary according to the particular route of administration and the needs of the subject, and can be subjected to the judgment of the health care professional.

Beneficial Effects

The antibody-drug conjugate of the present invention uses specially designed linker-payload, and is more stable and can achieve great efficacy in lower DAR, and therefore can reduce side effects and increase the therapeutic index.

The present disclosure utilizes a linking unit with unique structure and uses a ligase to catalyze the conjugation of the targeting molecule and the payload. The conjugate of the present disclosure has good homogeneity, high activity and high selectivity. Furthermore, the toxicity of the linking unit-payload intermediate is much lower than that of the free payload, and thus the manufacture process of the drug is less detrimental, which is advantageous for industrial production.

The conjugate of the present disclosure achieves at least one of the following technical effects:

(1) High inhibitory activity against target cells, or strong killing effect on target cells.

(2) Good physicochemical properties (e.g., solubility, physical and/or chemical stability).

(3) Good pharmacokinetic properties (e.g., good stability in plasma, appropriate half-life and duration of action).

(4) Good safety (low toxicity on non-target normal cells or tissues, and/or fewer side effects, wider treatment window), etc.

(5) Highly modular design, simple assembly of multiple drugs.

EXAMPLES

Preparation Example

In order to more clearly illustrate the objects and technical solutions, the present disclosure is further described below with reference to specific examples. It is to be understood that the examples are not intended to limit the scope of the disclosure. The specific experimental methods which were not mentioned in the following examples were carried out according to conventional experimental method.

Instruments, Materials and Reagents

Unless otherwise stated, the instruments and reagents used in the examples are commercially available. The reagents can be used directly without further purification.

MS: Thermo Fisher Q Exactive Plus, Water2795-Quattro micro triple quadrupole mass spectrometer HPLC: Waters 2695, Agilent 1100, Agilent 1200

Semi-preparative HPLC: Lisure HP plus 50D

Flow Cytometry: CytoFLEX S

HIC-HPLC: Butyl-HIC; mobile phase A: 25 mM PB, 2M $(NH_4)_2SO_4$, pH 7.0; mobile phase B: 25 mM PB, pH 7.0; flow rate: 0.8 ml/min; acquisition time: 25 min; injection amount: 20 μg; column temperature: 25° C.; detection wavelength: 280 nm; sample chamber temperature: 8° C.

SEC-HPLC: column: TSK-gel G3000 SWXL, TOSOH 7.8 mm ID×300 mm, 5 μm; mobile phase: 0.2 M $KH_2PO_4$, 0.25 M KCl, pH 6.2; flow rate: 0.5 ml/min; acquisition time: 30 min; injection volume: 50 μl; column temperature: 25° C.; detection wavelength; 280 nm; sample tray temperature: 8° C.

CHO was obtained from Thermo Fisher Scientific; pcDNA 3.3 was obtained from Life Technology; HEK293F was obtained from Prejin; PEIMAX transfection reagent was obtained from Polyscience; MabSelect Sure ProA was obtained from GE; Capto S ImpAct was obtained from GE; Rink-amide-MBHA-resin and dichloro resin were obtained from Nankai synthesis; HCC1954 was obtained from ATCC CAT #CRL-2338; SK-BR-3 was obtained from ATCC CAT #HTB-30; BT-474 was obtained from ATCC CAT #HTB-20; NCI-N87 cells was obtained from ATCC CAT #CRL-5822; MCF7 was obtained from ATCC CAT #HTB-22; MDA-MB- 231 was obtained from ATCC CAT #HTB-26; MDA-MB-468 was obtained from ATCC CAT #HTB-132; CFPAC-1 was obtained from ATCC CAT #CRL-1918; NCI-H2110 was obtained from ATCC CAT #CRL-5924; JIMT-1 was obtained from Wuxi Apptech; Capan-1 was obtained from ATCC CAT #CRL-1573; optimized recombinant enzyme Sortase A derived from *Staphylococcus aureus* is prepared in *E. coli.*

Example 1 Construction of Antibody Expression Vector, Antibody Expression, Purification and Identification 1.1 Construction of Expression Vectors Encoding Anti-TROP2 Antibodies To generate expression vectors encoding the light chains of anti-TROP2 antibodies, the nucleic acid sequences of LC were individually cloned into a pCDNA 3.3 vector (Life technology); to generate the expression vectors encoding the heavy chains of anti-TROP2 antibodies, the nucleic acid sequences of HC were individually cloned into a pCDNA 3.3 vector (Life technology).

TABLE 3

Sequence of antibodies

| Name | HC or LC | SEQ ID NO |
|---|---|---|
| hRS7 (from TRODELVY) | HC | 30 |
| | LC | 34 |
| Datopotamab | HC | 33 |
| | LC | 35 |
| Ab13 | HC | 31 |
| | LC | 34 |
| Ab16 | HC | 32 |
| | LC | 34 |
| GQhRS7 | HC | 30 |
| | LC | 40 |
| GQAb13 | HC | 31 |
| | LC | 40 |
| GQAb16 | HC | 32 |
| | LC | 40 |

Note:
In preparation process of ADC, the upstream peptide bond of GG in the LPETGG sequence is cleaved by Sortase A, and the resulting intermediate is linked to the free N-terminal of $G_3$ in linker-payload to generate a new peptide bond.

1.2 Expression of Anti-TROP2 Antibodies

Plasmids encoding the light and heavy chains of anti-TROP2 antibodies were paired and mixed at a mass ratio of 2:1. The plasmid pair and the PEIMAX (Polyscience) transfection reagent were separately diluted in HEK293F basic medium and then mixed evenly. The mixture was let stand at room temperature and added to the HEK293F seed cell culture. The cell was cultured at 32 for 24 h and sampled for cell density and viability analysis and supplemented with 10% volume of HEK293F feed medium. Then the culture temperature was shifted to 32° C. for the following culture. At 72 h of incubation, the cell culture was sampled again for cell density and viability analysis. At 144 h of incubation, the cell culture was sampled for cell density and viability analysis.

1.3 Purification of Anti-TROP2 Antibodies

The antibodies were purified by affinity chromatography following the manufacturer's instruction. Briefly, the chromatography column (BestChrom, Shanghai, China) was packed with the MabSelect SureLX resin (GE Healthcare) and equilibrated with 50 mM Tris, 150 mM NaCl, pH 7.4. Then the supernatant of the cell culture was obtained and applied onto the column. The column was washed with 50 mM Tris, 150 nM NaCl, pH 7.4 to remove non-specifically bound proteins. Then the antibodies were eluted by 50 mM citrate Buffer, pH 3.5 and the antibody-containing eluate was adjusted to pH 6.5 using 1 M Tris-HCl, pH 9.0. Finally, the buffer of the antibodies was exchanged to 50 mM Tris, 150 mM NaCl, pH 7.4 by an Anicon Ultra-15 centrifugal Filter (Merk Millipore).

1.4 Binding Kinetics and Affinity Analysis

Binding kinetics and affinity analysis were performed. Surface Plasmon Resonance (SPR) analysis was performed on a Biacore T200 (GE healthcare) with a Sensor Chip Protein A (GE healthcare) following manufacturer's instructions. All measurements were performed at 25° C. in the HBS-$EP^+$ buffer (10 mM HEPES, pH 7.4, 150 mM NaCl, 3 mM EDTA, and 0.05% surfactant P20). About 110-140 RU (Resonance unit) of each of the purified antibodies was captured on flow cells 2 and 4 (i.e., the reaction surface) of the sensor chip, respectively. Flow cells 1 and 3 were treated with the HBS-$EP^+$ buffer to serve as reference surfaces.

Serial dilutions of the recombinant extracellular domain of human TROP2 (i.e., the analyte) (Acrobio system) (243, 81, 27, 9, 3, 1, 0.333, and 0.111 nM, respectively) were prepared in HBS-$EP^+$ buffer. Capturing of the antibodies was followed by a three-minute injection (association phase) of serial dilutions of TROP2 at a flow rate of 30 μL/min and ten minutes of buffer flow (dissociation phase). The chip surface was regenerated by two pulses of 30-second injection of 10 mM Glycine-HCl pH 1.5 at a flow rate of 50 μL/min. The collected data were processed on a Biacore T200 Evaluation software using methods known in the art, comprising the following steps: (1) setting the response on the y-axis and the start of the injection on the x-axis to zero, (2) performing double referencing by firstly subtracting the reference surface data from the reaction surface data to get the analyte injection curves, and then subtracting the buffer injection curves from the analyte injection curves, and (3) performing the kinetic analysis using the 1:1 binding model with a global fit. The result for each antibody was presented as Ka (on-rate), Kd (off-rate) and $K_D$ (equilibrium dissociation constant).

1.5 SEC-HPLC Detection of Anti-TROP2 Antibodies

Antibody samples were centrifuged at 12,000 rpm for 5 min, and the supernatants were applied to a SEC-HPLC column to detect the percentages of the monomer (corresponding to the intact antibody), high molecular weight (HMW, corresponding to the antibody aggregates due to aggregation) and low molecular weight (LMW, corresponding to the antibody fragments due to degradation) forms of each antibody.

| | $K_D$ | Purity (SEC-HPLC) | | | HIC retention |
|---|---|---|---|---|---|
| Antibody | (nM) | HMW(%) | Monomer (%) | LMW(%) | time |
| Datopotamab (DS1062a Ab) | 13 | 0.41 | 99 | 0 | 6.605 ± 0.056 |

-continued

| | $K_D$ | Purity (SEC-HPLC) | | | HIC retention |
|---|---|---|---|---|---|
| Antibody | (nM) | HMW(%) | Monomer (%) | LMW(%) | time |
| hRS7 | 1.28 | 1.22 | 99 | 0.1 | 9.412 ± 0.003 |
| Ab13 | 8.16 | 0.62 | 99 | 0 | 7.476 ± 0.025 |
| Ab16 | 13.1 | 0.47 | 99 | 0 | 9.358 ± 0.037 |

Trop2 is widely expressed in normal tissues, affinity of Ab13 and Ab16 is reduced. Low affinity antibodies should be able to improve safety while maintaining efficacy which has been verified in previous experiments.

1.6 Internalization Activity

MDA-MB-468 in good viability, were trypsinized, collected, suspended in cold FACS buffer (DPBS+2% FBS) and adjusted to $2\times10^6$ cells/ml. Anti-Trop2 antibodies and isotype control antibody samples were fluorescence labeled by mixing with anti-human-IgG-Fc-AF647 secondary antibody at molar ratio of 1:1 at room temperature for 20 minutes. The labeled antibody was added to the cell suspension at the final concentration of 10 μg/ml. The antibody-cell mixture was incubated on ice for one hour. After the surface binding, the antibody-cell mixture was washed twice by cold FACS buffer to remove the excess antibody. Cells were incubated at 37° C. for antibody internalization for 0 min, 10 min, 30 min, 60 min, 90 min, 120 min, 180 min and 240 min, and transferred $1\times10^5$ cells per well into V-bottom 96 well plate at each time point. The internalization was stopped by returning the cells to ice bath. Non-internalization cells (0 min) were divided into MAX and MIN groups, while antibody internalized cells were marked as I group. MIN and I groups were washed by quench buffer (150 mM NaCl+100 mM Glycine, pH=2.0 to 2.5) twice to dissociate surface binding of antibody. After the quench, all the groups were washed by FACS buffer twice and analyzed in APC channel by flow cytometry.

The MFI data was taken into the formula below, and the result was analyzed by one phase exponential association function in Prism 6.

Isotype control: $MFI_{(I)}=MFI_{(sample,I)}-MFI_{(isotype\ control\ antibody,I)}$ $MFI_{(MAX)}=MFI_{(sample,MAX)}-MFI_{(negative\ antibody,MAX)}$ $MFI_{(MIN)}=MFI_{(sample,MIN)}-MFI_{(negative\ antibody,MIN)}$ Internalization ratio: $R_{(t)}=(MFI_{(I)}-MFI_{(MIN)})/MFI_{(MAX)}\times100\%$.

Figure 1B:
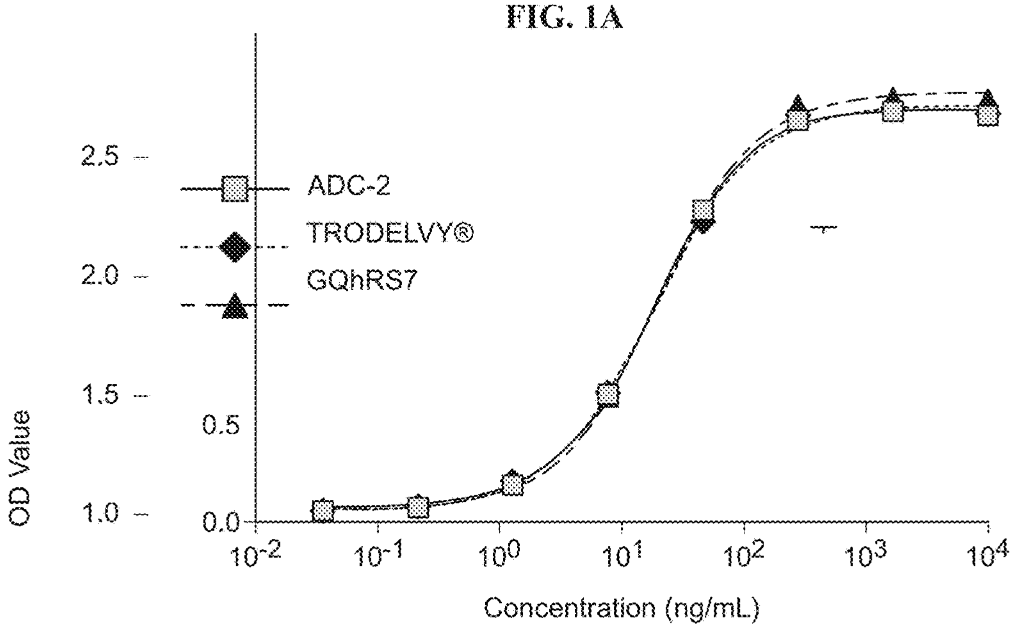
FIG. 1B shows the binding activity on Trop2 ECD.
Figure 1C:
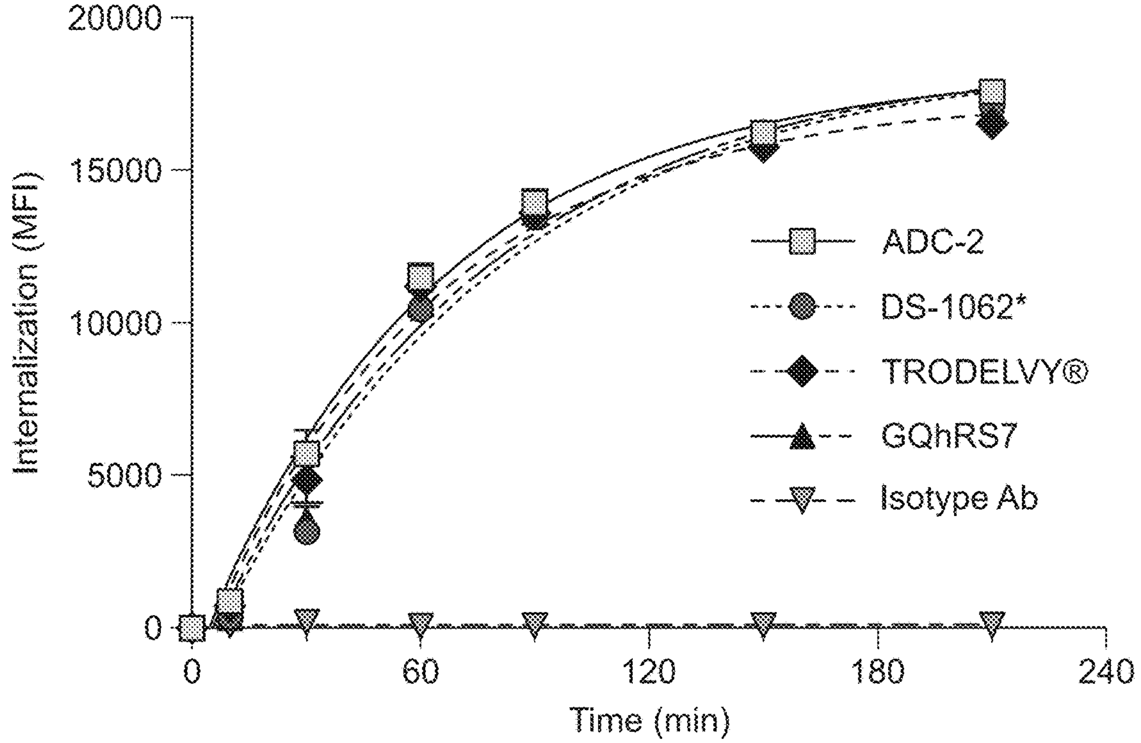
FIG. 1C shows the internalization on NCI-N87.

As showed in FIG. 1A-C, all four antibodies show comparable internalization activity on MDA-MB-468.

Example 2 Preparation of Intermediates

Example 2.1 Preparation of Linker-Payload 1 and Linker-Payload 2

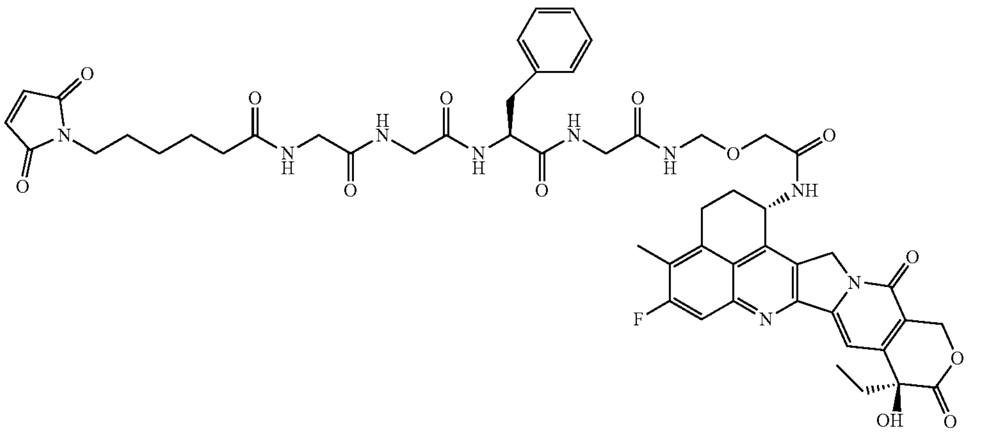

MC-GGFG-Dxd

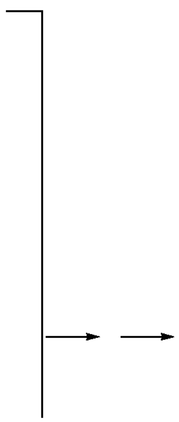

-continued
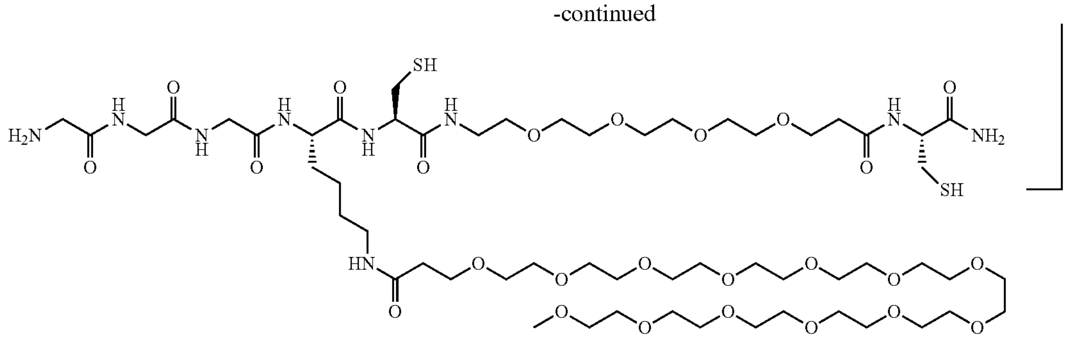
linker-payload intermediate 1
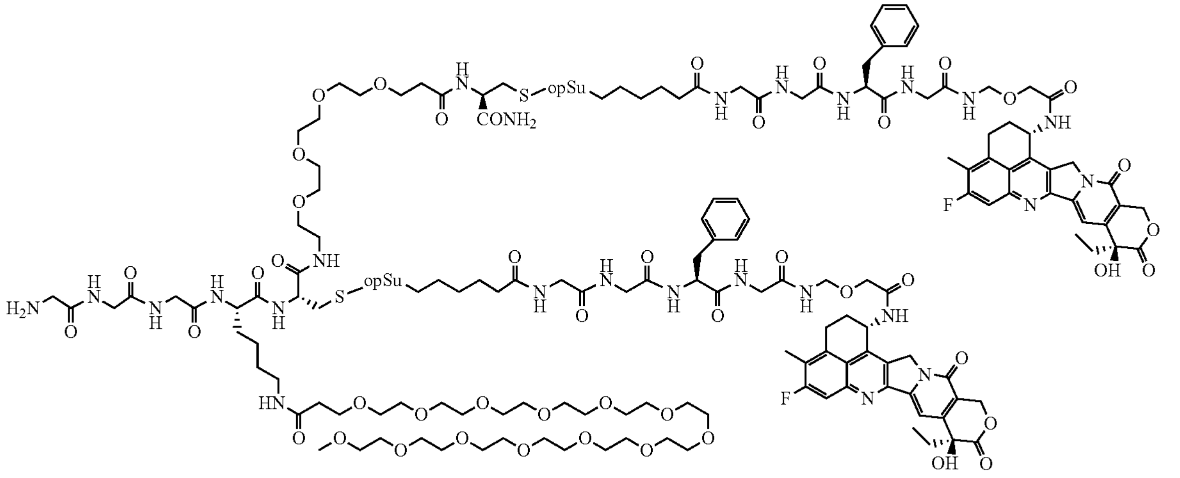
linker-payload 1
opSu is a mixture of
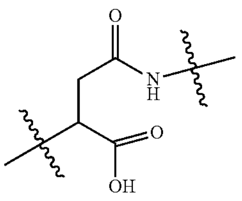
and
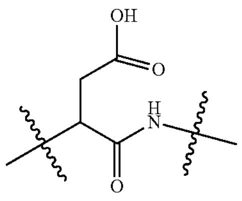
;
Preparation of Intermediate MC-GGFG-DXd
The intermediate MC-GGFG-DXd is commercial available or prepared following the procedures as described in EP2907824. This compound is used to prepare linker-payload 1.
Preparation of Linker-Payload Intermediate 1
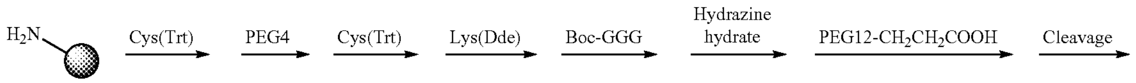

-continued

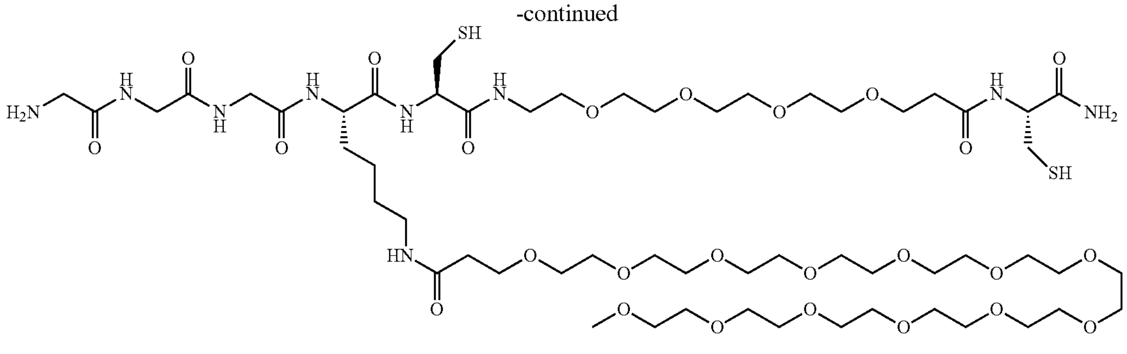

linker-payload intermediate 1

Linker-payload intermediate 1 can be synthesized by a conventional solid phase polypeptide synthesis using Rink-amide-MBHA-resin. Fmoc was used to protect the amino acid in the linking unit. The coupling reagent was selected from HOBT, HOAt/DIC, DCC, EDCI or HATU. After synthesis, the product was cleaved from resin using TFA/TIS/$H_2O$ solution. The product was purified by prep-HPLC, lyophilized and stored for use. MS m/z: $[M-H]^-=1382.6$.

Preparation of Linker-Payload 1

Linker-payload intermediate 1 and MC-GGFG-DXd (molar ratio ~1:2) were weighed and dissolved in water and DMF, respectively, and then thoroughly mixed to give a mixture, which was reacted at 0-40° C. for 0.5-30 h. Once the reaction was completed, the reaction mixture was directly added with an appropriate amount of Tris Base solution or other solution that promotes the ring-opening reaction, and the reaction was performed at 0-40° C. for another 0.2-20 h. After the reaction was completed, the product was purified by semi-preparative/preparative HPLC and lyophilized to obtain linker-payload 1. MS m/z: $[(M+3H)/3]^+=1163.3$.

Preparation of Linker-Payload 2

The following linker-payload Linker-payload 2 can be prepared using similar synthetic routes and reagents as Linker-payload 1.

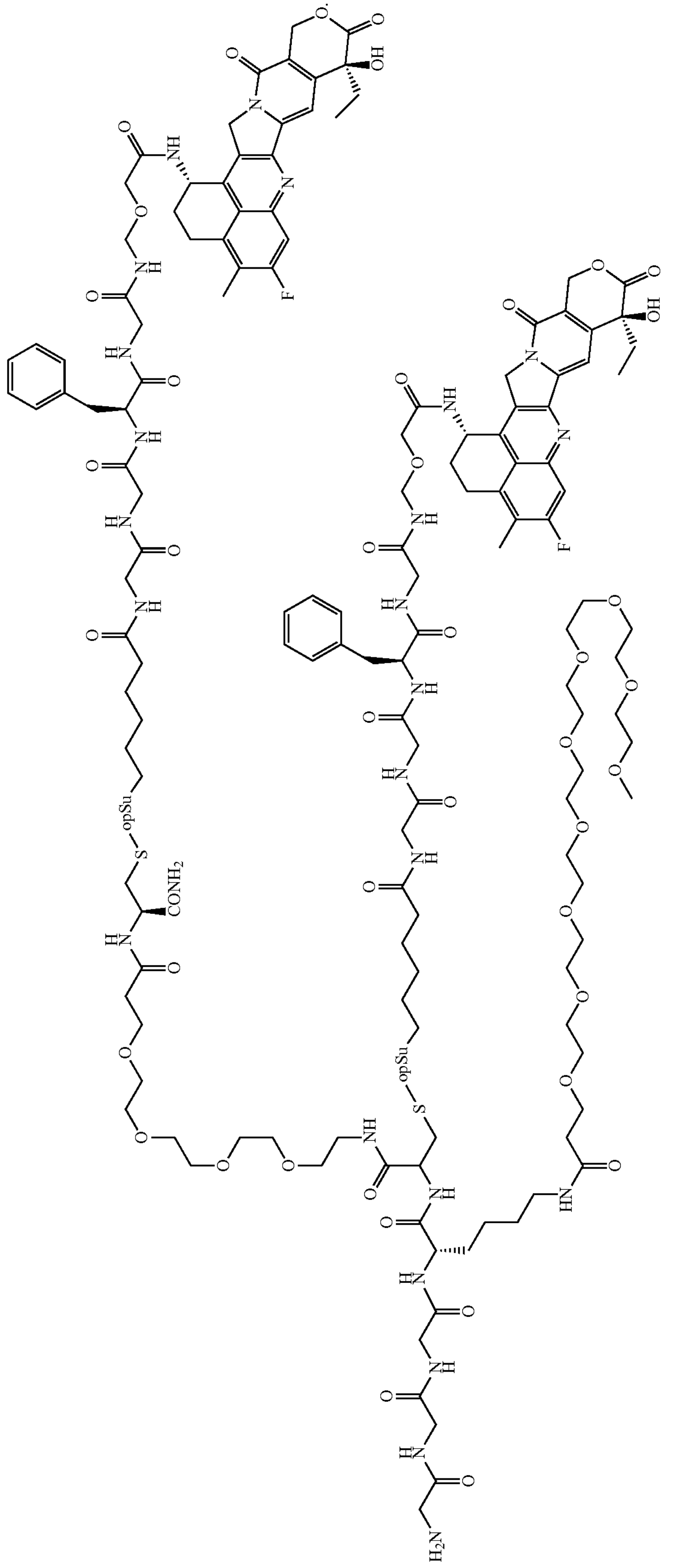
linker-payload 2 opSu is a mixture of
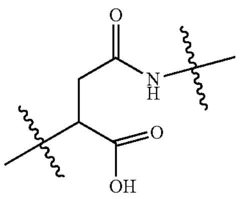
and
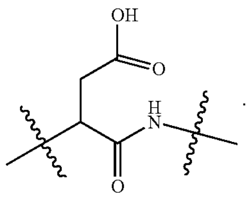
.
Example 2.2 Preparation of Linker-Payload 3 and Linker-Payload 4
Preparation of Intermediate 11
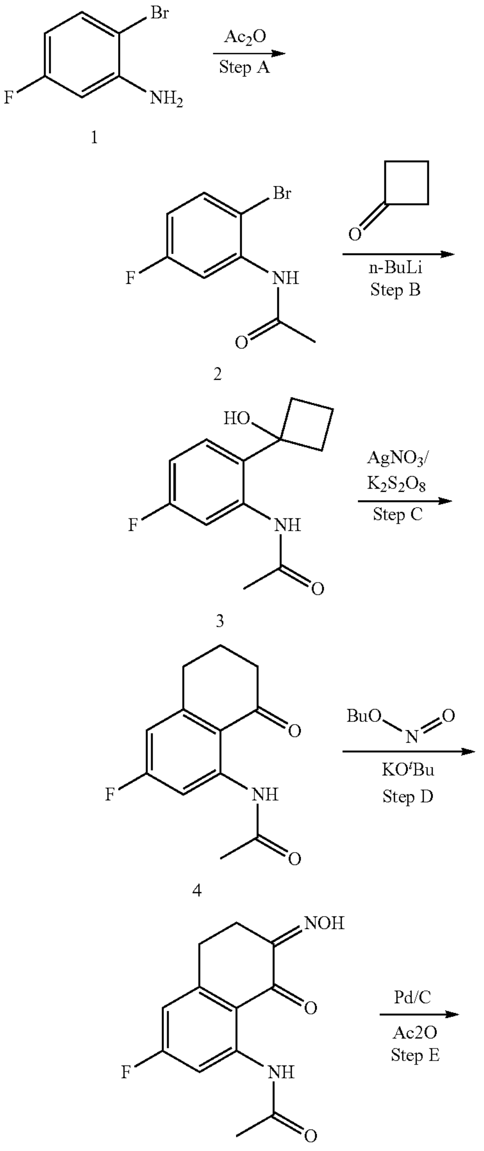
1
2
3
4
5
-continued
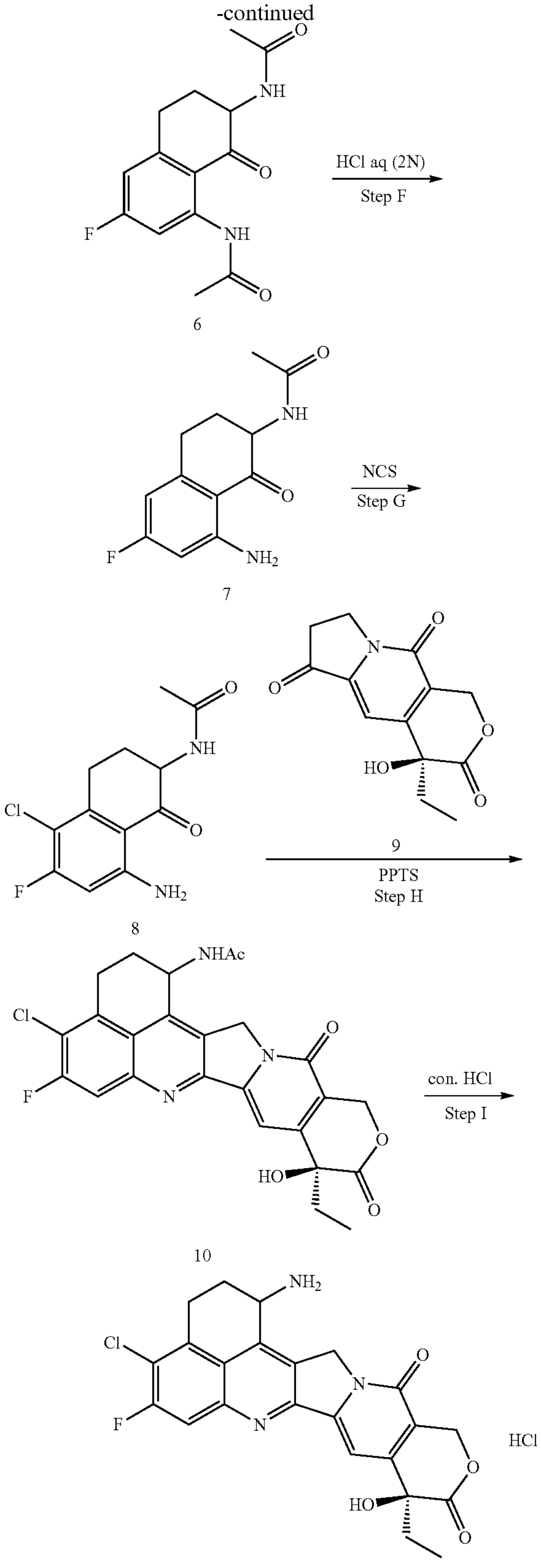
6
7
8
9
10
11
Step A: N-(2-bromo-5-fluorophenyl)acetamide: To a stirred solution of acetic anhydride (214 g, 2.10 mol) in acetic acid (500 mL) was added con. $H_2SO_4$ (3 mL), followed with 2-bromo-5-fluoroaniline (100 g, 526.27 mmol) in portions at room temperature. The mixture was stirred for 3 h, then poured into 2000 mL ice-water. A precipitate was formed, which was collected by filtration and dried in vacuo at room temperature to afford N-(2-bromo-5-fluorophenyl)acetamide (105 g) as a yellow solid. $^1$H NMR (400 MHz, DMSO-$d_6$) δ 7.68 (dd, J=8.9, 6.0 Hz, 1H), 7.61 (ddd, J=10.7, 5.3, 3.1 Hz, 1H), 7.02 (ddd, J=8.9, 8.0, 3.1 Hz, 1H), 2.11 (s, 3H). MS m/z 232.0 (M+H).

Step B: N-(5-fluoro-2-(1-hydroxycyclobutyl)phenyl)acetamide: To a stirred solution of N-(2-bromo-5-fluorophenyl) acetamide (105 g, 452.48 mmol) in THF (1000 mL) was added n-BuLi (594 mL, 1.6 M in n-hexane, 950.22 mmol) dropwise over 1 h at −78° C. After completion, the mixture was stirred for 0.5 h under $N_2$. Then a solution of cyclobutanone (38.06 g, 542.98 mmol) in THF (50 mL) was added dropwise at −78° C. over 0.5 h, the mixture was stirred at −78° C. to room temperature for 6 h. The mixture was poured into 500 mL saturated $NH_4Cl$ aq at 0° C. Extracted with ethyl acetate (500 mL×3), washed with brine (250 mL×2), dried over $Na_2SO_4$ and concentrated. The mixture was triturated with (PE/EA=1:1, 100 mL) for 10 mins, filtered and the cake was collected and dried in vacuo to afford N-(5-fluoro-2-(1-hydroxycyclobutyl)phenyl)acetamide (24 g) as a yellow solid. LCMS m/z 206.1 (M−18+H), 246.1 (M+Na).

Step C: N-(3-fluoro-8-oxo-5,6,7,8-tetrahydronaphthalen-1-yl)acetamide: To a stirred mixture of N-(5-fluoro-2-(1-hydroxycyclobutyl)phenyl)acetamide (24 g, 107.50 mmol) in $CH_2Cl_2$ (170 mL) and water (170 mL) was added silver nitrate ($AgNO_3$) (5.48 g, 32.25 mmol) and potassium persulfate ($K_2S_2O_8$) (58.12 g, 215.01 mmol), the mixture was stirred at 30° C. for 6 h. The mixture was filtered on Celite and washed with $CH_2Cl_2$ (100 mL), the filtrate was concentrated and purified by FCC (EA/PE=0-40%) to afford N-(3-fluoro-8-oxo-5,6,7,8-tetrahydronaphthalen-1-yl)acetamide (14 g) as a light yellow solid. MS m/z 222.1 (M+H).

Step D: N-(3-fluoro-7-(hydroxyimino)-8-oxo-5,6,7,8-tetrahydronaphthalen-1-yl)acetamide: To a stirring mixture of N-(3-fluoro-8-oxo-5,6,7,8-tetrahydronaphthalen-1-yl)acetamide (14 g, 63.28 mmol) in THF (500 mL) at 0° C. was added 1-butyl nitrite (8.48 g, 63.28 mmol), followed with t-BuOK (8.52 g, 75.94 mmol). The mixture was stirred at 0° C. for 2 h. After completion, the mixture was acidified by HCl (2 N) to adjust pH=3. The mixture was extracted by ethyl acetate (200 mL×3), washed by brine (100 mL×2), dried over $Na_2SO_4$ and concentrated under reduced pressure. The crude mixture was triturated with tert-butyl methyl ether (200 mL) for 10 mins, filtered and the cake was collected and dried in vacuo to afford N-(3-fluoro-7-(hydroxyimino)-8-oxo-5,6,7,8-tetrahydronaphthalen-1-yl)acetamide (12 g) as a yellow solid. MS m/z 251.1 (M+H).

Step E: N,N'-(3-fluoro-8-oxo-5,6,7,8-tetrahydronaphthalene-1,7-diyl)diacetamide: To a solution of N-(3-fluoro-7-(hydroxyimino)-8-oxo-5,6,7,8-tetrahydronaphthalen-1-yl) acetamide (12 g, 47.96 mmol) in acetic anhydride (90 mL) and THF (90 mL) was added 10% Pd/C (1 g), the mixture was stirred at 25° C. under $H_2$ atmosphere for 16 h. After cooling to 0° C., $Et_3N$ (20 mL) was added dropwise, the mixture was stirred at 0° C. for 1 h. Filtered on Celite, the filtrate was poured into ice-water (500 mL). Extracted with ethyl acetate (500 mL×3), washed with brine (250 mL×2), dried over $Na_2SO_4$ and concentrated. The residue was triturated with tert-butyl methyl ether (120 mL) for 10 mins, filtered and the cake was collected and dried in vacuo to give N,N'-(3-fluoro-8-oxo-5,6,7,8-tetrahydronaphthalene-1,7-diyl)diacetamide (7.9 g) as a yellow solid. MS m/z 279.1 (M+H).

Step F: N,N'-(3-fluoro-8-oxo-5,6,7,8-tetrahydronaphthalene-1,7-diyl)diacetamide: To a solution of N,N'-(3-fluoro-8-oxo-5,6,7,8-tetrahydronaphthalene-1,7-diyl)diacetamide (7.9 g, 28.39 mmol) in MeOH (150 mL) was added HCl aq (2 N, 150 mL), the mixture was stirred at 50° C. for 7 h. After cooling to 0° C., Sat. $NaHCO_3$ aq was added dropwise to adjust pH=8. Extracted with ethyl acetate (200 mL×3), washed with brine (200 mL×2), dried over $Na_2SO_4$ and concentrated under reduced pressure to give N,N'-(3-fluoro-8-oxo-5,6,7,8-tetrahydronaphthalene-1,7-diyl)diacetamide (6.0 g) as a yellow solid. $^1$H NMR (400 MHz, Chloroform-d) δ 6.57 (s, 3H), 6.18 (td, J=11.1, 2.4 Hz, 2H), 4.52 (dt, J=13.3, 5.0 Hz, 1H), 3.13 (ddd, J=17.5, 13.0, 4.6 Hz, 1H), 3.00-2.81 (m, 1H), 2.69 (dtd, J=9.4, 4.6, 2.5 Hz, 1H), 2.09 (s, 3H), 1.79 (qd, J=13.0, 4.3 Hz, 1H). MS m/z 237.1 (M+H).

Step G: N-(8-amino-5-chloro-6-fluoro-1-oxo-1,2,3,4-tetrahydronaphthalen-2-yl)acetamide: To a solution of N,N'-(3-fluoro-8-oxo-5,6,7,8-tetrahydronaphthalene-1,7-diyl)diacetamide (4.0 g, 16.93 mmol) in DMF (80 mL) was added NCS (2.26 g, 16.93 mmol) in portions at 0° C., the mixture was stirred at room temperature for 16 h. The mixture was poured into 200 mL ice-water. A precipitate was formed, which was collected by filtration and dried in vacuo at room temperature to afford N-(8-amino-5-chloro-6-fluoro-1-oxo-1,2,3,4-tetrahydronaphthalen-2-yl)acetamide (4.0 g) as a yellow solid. 1H NMR (400 MHz, DMSO-$d_6$) δ 8.11 (d, J=8.0 Hz, 1H), 7.71 (s, 2H), 6.62 (d, J=11.9 Hz, 1H), 4.53 (ddd, J=13.0, 8.0, 4.7 Hz, 1H), 3.18-3.04 (m, 1H), 2.91 (ddd, J=17.5, 12.4, 4.8 Hz, 1H), 2.21-2.08 (m, 1H), 1.99-1.83 (m, 4H). MS m/z 271.0 (M+H).

Step H: N-((9S)-4-chloro-9-ethyl-5-fluoro-9-hydroxy-10,13-dioxo-2,3,9,10,13,15-hexahydro-1H,12H-benzo[de]pyrano[3',4':6,7]indolizino[1,2-b]quinolin-1-yl)acetamide: To a mixture of N-(8-amino-5-chloro-6-fluoro-1-oxo-1,2,3,4-tetrahydronaphthalen-2-yl)acetamide (4.0 g, 14.78 mmol) in toluene (400 mL) was added (S)-4-ethyl-4-hydroxy-7,8-dihydro-1H-pyrano[3,4-f]indolizine-3,6,10(4H)-trione (4.28 g, 16.25 mmol), pyridinium p-Toluenesulfonate (1.11 g, 4.43 mmol) and o-cresol (10 mL), the mixture was heated to reflux under $N_2$ for 24 h. The solvent was removed by reduced pressure and the mixture was purified by FCC ($THF/CH_2Cl_2$=0-60%) to afford N-((9S)-4-chloro-9-ethyl-5-fluoro-9-hydroxy-10,13-dioxo-2,3,9,10,13,15-hexahydro-1H,12H-benzo[de]pyrano[3',4':6,7]indolizino[1,2-b]quinolin-1-yl)acetamide (4.1 g) as a brown solid. MS m/z 498.1 (M+H).

Step I: (9S)-1-amino-4-chloro-9-ethyl-5-fluoro-9-hydroxy-1,2,3,9,12,15-hexahydro-10H,13H-benzo[de]pyrano[3',4':6,7]indolizino[1,2-b]quinoline-10,13-dione: A mixture of N-((9S)-4-chloro-9-ethyl-5-fluoro-9-hydroxy-10,13-dioxo-2,3,9,10,13,15-hexahydro-1H,12H-benzo[de]pyrano[3',4':6,7]indolizino[1,2-b]quinolin-1-yl)acetamide (2.0 g, 4.02 mmol) in 20 mL con. HCl aq was stirred at 70° C. under $N_2$ for 36 h. The mixture was concentrated under reduced pressure to give crude (9S)-1-amino-4-chloro-9-ethyl-5-fluoro-9-hydroxy-1,2,3,9,12,15-hexahydro-10H,13H-benzo[de]pyrano[3',4':6,7]indolizino[1,2-b]quinoline-10,13-dione hydrochloride (2 g) as a brown solid. MS (ESI) m/z 456.1 (M+H).

Preparation of Intermediate 12 (12-1, 12-2)

12-1

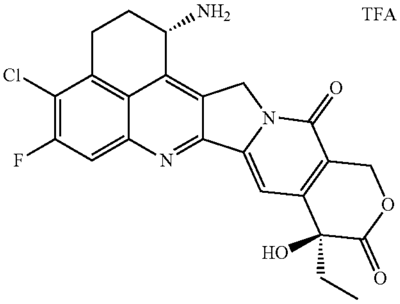

TFA

+

-continued 12-2

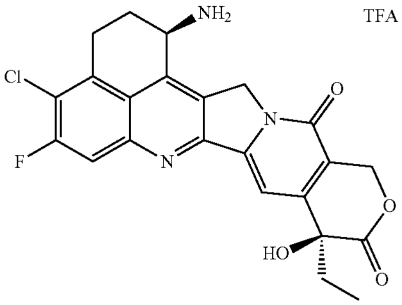

TFA 12-1 and 12-2 were prepared by prep-HPLC from (9S)-1-amino-4-chloro-9-ethyl-5-fluoro-9-hydroxy-1,2,3,9,12,15-hexahydro-10H,13H-benzo[de]pyrano[3',4':6,7]indolizino[1,2-b]quinoline-10,13-dione hydrochloride (intermediate 11) as TFA salt.

| Number | Structure | $^1$HNMR | MS (M + H) | Retention time on HPLC (min) |
|---|---|---|---|---|
| 12-1 | 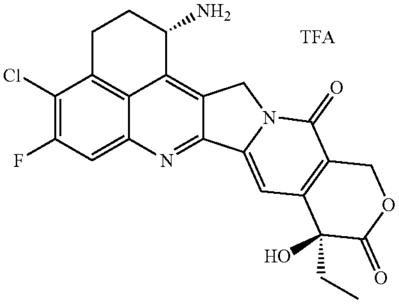 TFA | $^1$H NMR (400 MHz, DMSO-d6) δ 8.51 (d, J = 4.8 Hz, 3H), 8.17 (d, J = 10.2 Hz, 1H), 7.38 (s, 1H), 6.56 (s, 1H), 5.74 (d, J = 19.4 Hz, 1H), 5.52-5.40 (m, 3H), 5.16 (s, 1H), 3.44 (dd, J = 16.3, 4.1 Hz, 1H), 3.19 (t, J = 13.9 Hz, 1H), 2.57 (d, J = 14.0 Hz, 1H), 2.26 (t, J = 14.3 Hz, 1H), 1.89 (hept, J = 7.0 Hz, 2H), 0.89 (t, J = 7.3 Hz, 3H). | 456.0 | 1.395 |
| 12-2 | 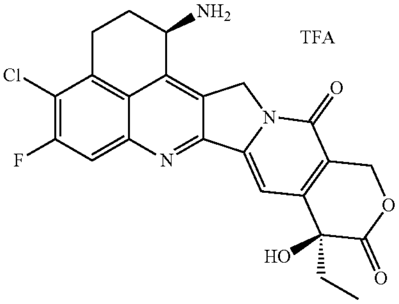 TFA | $^1$H NMR (400 MHz, DMSO-d6) δ 8.56 (s, 2H), 8.17 (d, J = 10.1 Hz, 1H), 7.38 (s, 1H), 6.57 (s, 1H), 5.74 (d, J = 19.4 Hz, 1H), 5.53-5.28 (m, 3H), 5.16 (s, 1H), 3.59-3.01 (m, 2H), 2.35-2.19 (m, 2H), 2.00-1.78 (m, 2H), 0.88 (t, J = 7.3 Hz, 3H). | 456.0 | 1.541 |

Conditions of HPLC above: Equipment: Agilent 1200; Chromatographic column: Waters XBridge C18 4.6*50 mm, 3.5 um; Flow: 2.0 mL/min; Gradient elute: 5.0%-95.0%-95.0%-5.0%-5.0%, 0.00 min-1.50 min-2.50 min-2.52 min-3.00 min; Temperature: 40° C.; Phase: A: Acetonitrile, B: $H_2O$ (0.05% TFA); Wavelength: 214 nm/254 nm.

Preparation of Linker-Payload 3
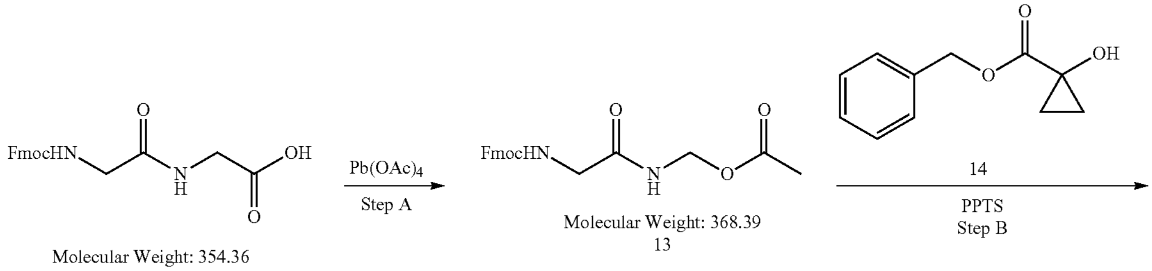
Molecular Weight: 354.36
Molecular Weight: 368.39
13
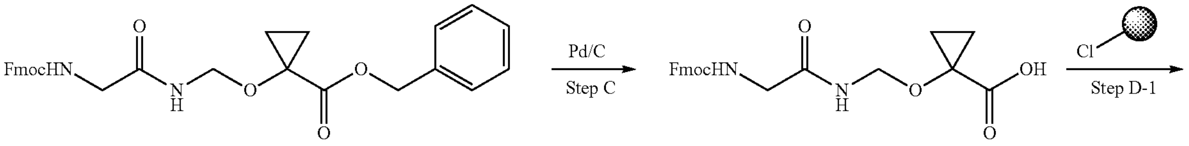
Molecular Weight: 500.55
15
Molecular Weight: 410.43
16
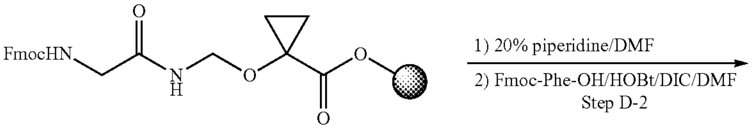
17
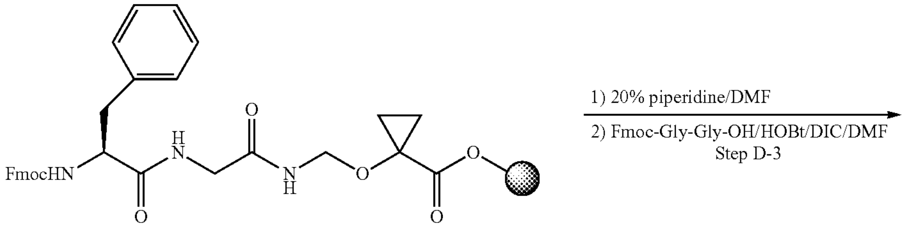
18
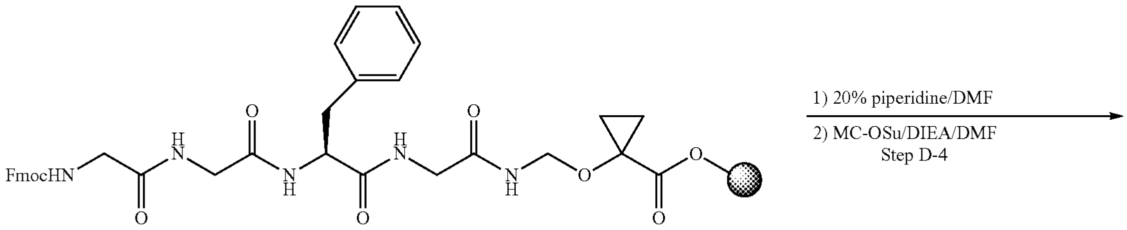
19
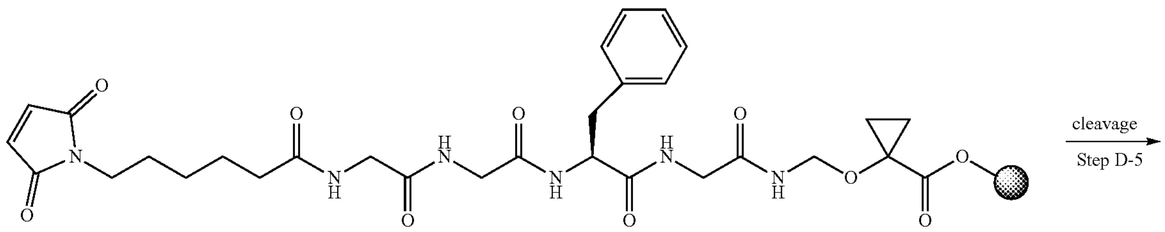
20

-continued
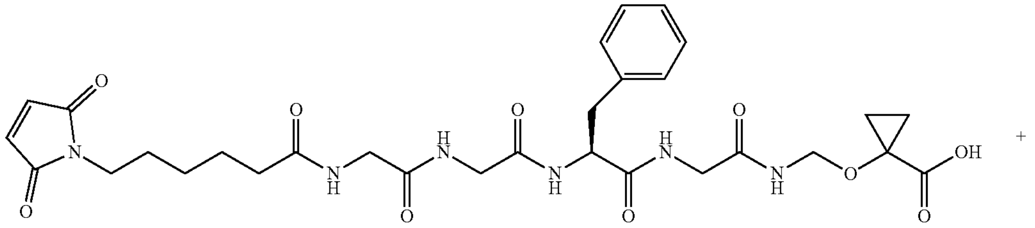
Molecular Weight: 642.67
21
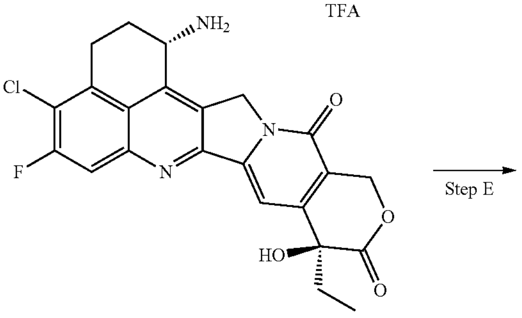
Molecular Weight: 455.87
12-1
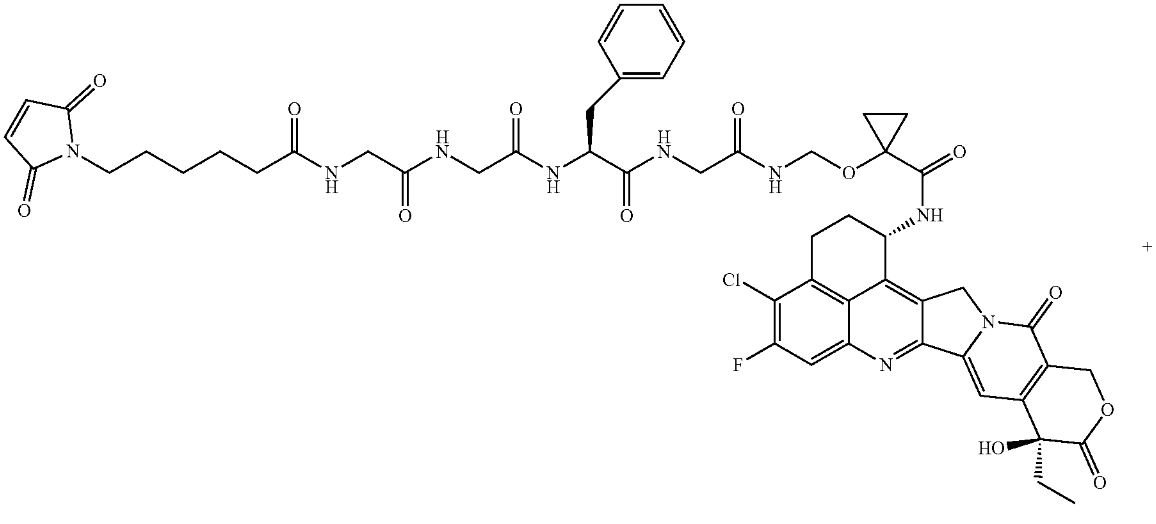
Molecular Weight: 1080.52
22
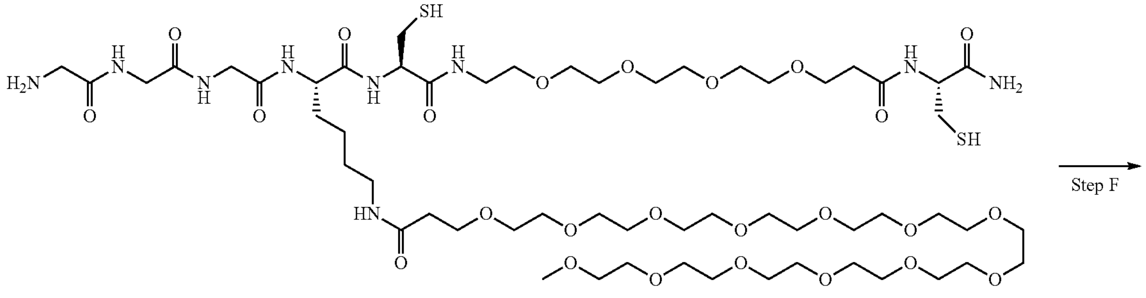
Molecular Weight: 1384.66
Linker-payload intermediate 1

-continued

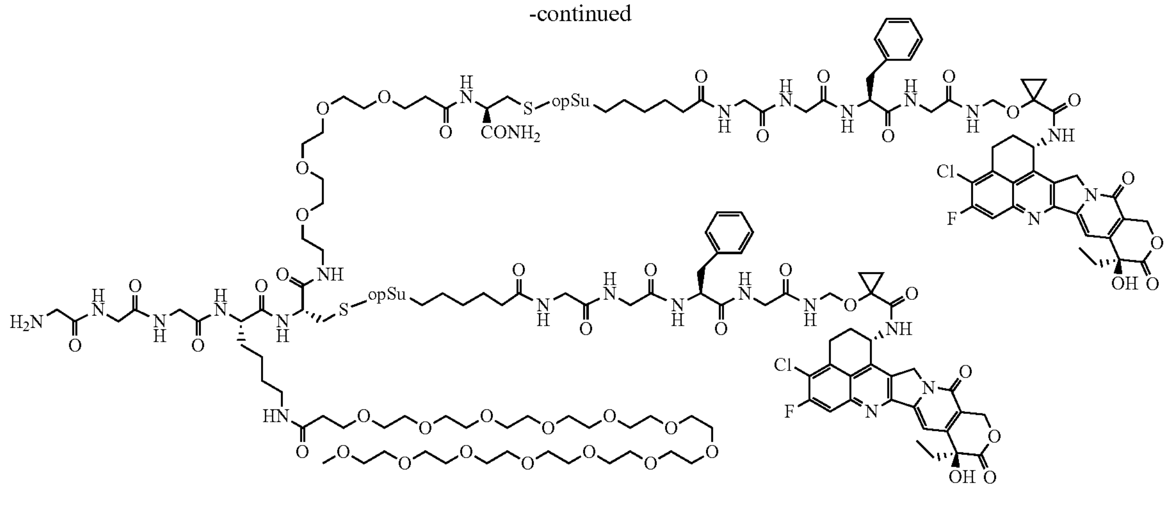

Molecular Weight: 3581.70
linker-payload 3 opSu is a mixture of

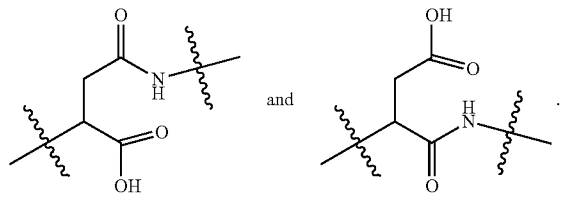 [SMILES: *NC(=O)CC(*)C(=O)O ; *NC(=O)C(*)CC(=O)O]

Preparation of Compound 13 (Step A)

4.33 g Fmoc-Gly-Gly-OH and 6.84 g $Pb(OAc)_4$ were weighed and added into a 500 ml single-neck round bottom flask. Anhydrous THF/Toluene (120/40 ml) was added under nitrogen atmosphere and stirred for dissolving. Then 1.16 mL of pyridine was added to the reaction system. The reaction system was heated to 80° C. and refluxed for 5 hr under nitrogen atmosphere. Samples were taken and detected by HPLC to monitor the reaction.

The reaction system was cooled to room temperature, filtered, and the filter cake was washed with EA for 3 times. The filtrates were combined and concentrated to dryness. Column chromatography was performed (PE:EA=100: 0-50:100) to give about 2000 mg of the target product in white solid with a yield of 44%.

Preparation of Compound 15 (Step B)

200 mg Compound 13 was weighed and added into a 100 ml single-neck round bottom flask. Then 15 ml THF was added and stirred for dissolving. Then Compound 14 (312 mg, 3.0 e.q.) and TsOH $H_2O$ (15 mg, 0.15 e.q.) were added to the reaction system. The reaction system was reacted overnight at room temperature. Samples were taken and detected by TLC (PE/EA=1:1) to monitor the reaction. The raw material basically disappeared, and a new point was detected.

Saturated sodium bicarbonate solution was added to quench reaction. Extraction was conducted with EA for 3 times. The organic phase was combined and washed with saline, dried with anhydrous magnesium sulfate and concentrated. The crude product was purified by column chromatography (PE:EA=5: 1-1:1) to give about 80 mg of the target product in colorless oil with a yield of 29%. MS m/z: $[M+H]^+$=501.1

Preparation of Compound 16 (Step C)

200 mg of Compound 15 was weighed and added into a 100 ml single-neck round bottom flask. Then 10 ml of EtOH and 5 ml of EA were added with complete dissolution. Then 40 mg of palladium carbon was added to the reaction system under nitrogen atmosphere, and the reaction system was purged with hydrogen gas for three times. The reaction system was kept under hydrogen atmosphere and stirred for 0.5 hour at room temperature. Samples were taken and detected by TLC (DCM/MeOH=10:1) to monitor the reaction. The raw material basically disappeared, and a new point was detected.

The reaction system was filtered, and the filter cake was washed with EA for 3 times. The filtrates were combined and concentrated to dryness to give 200 mg product in white solid with 100% yield. The product can be directly used in the next reaction without purification. MS m/z: $[M-H]^-$= 409.4.

Preparation of Compound 21 (Step D)

Step D-1

2.0 g of dichlororesin was weighed and placed in a polypeptide synthesis tube. DCM (10 ml) was added and swelled at room temperature for 30 minutes. The solvent was removed by vacuum suction. The resin was washed twice with DCM, with a volume of 7 mL and a time length of 1 minute for each wash. The solvent was removed by vacuum suction. Then Compound 16 (200 mg) was weighed and added into a 50 ml centrifuge tube. DCM (about 10 ml) was added. the solid was dissolved by shaking. Added to the above resin. Stirring was conducted to soak all the resin in the solution (if there was resin attached to the tube wall, a small amount of DCM was used to wash the tube wall).

Stirring was conducted for 4-5 hours. After the reaction was complete, an appropriate amount of methanol was added. Stirring was conducted for 30 min. The solvent was removed by vacuum suction. The resin was washed with DMF once, methanol once, DMF once, methanol once and DMF twice in sequence, with a volume of 10 mL and a time length of 1 minute for each wash. The solvent was removed by vacuum suction. A small amount of dry resin was taken for ninhydrin detection. The resin was colorless and transparent, and the solution was yellowish, indicating qualified for the next coupling step.

Step D-2

The deprotection was conducted twice by adding 10 mL readymade 20% piperidine/DMF solution and reacting for 10 minutes for each time. After the reaction was complete, the solution was removed by vacuum suction. The resin was washed with DMF twice, methanol once, DMF once, methanol once and DMF twice in sequence, with a volume of 10 mL and a time length of 1 minute for each wash. The solvent was removed by vacuum suction. A small amount of dry resin was taken for ninhydrin detection. Both the resin and solution were dark blue.

To a 50 mL centrifuge tube was added 563 mg Fmoc-Phe-OH, 197 mg HOBt. Then about 7 mL DMF was added. The solid was dissolved by shaking. Then 0.24 mL DIC was added. Activated for 10-30 minutes to give the activated reaction solution.

3 molar equivalent of activated reaction solution added to the resin. Stirring was conducted to soak the resin completely in the solution (if there was resin attached to the tube wall, a small amount of DCM was used to wash the tube wall). Stirring was conducted for 2-3 hours. After the reaction was complete, the solvent was removed by vacuum suction. The resin was washed with DMF twice, methanol once, DMF once, methanol once and DMF twice in sequence, with a volume of 10 mL and a time length of 1 minute for each wash. The solvent was removed by vacuum suction. A small amount of dry resin was taken for ninhydrin detection. The resin was colorless and transparent, and the solution was yellowish, indicating qualified for the next coupling step.

Step D-3

The deprotection was conducted twice by adding 10 mL readymade 20% piperidine/DMF solution and reacting for 10 minutes for each time. After the reaction was complete, the solution was removed by vacuum suction. The resin was washed with DMF twice, methanol once, DMF once, methanol once and DMF twice in sequence, with a volume of 10 mL and a time length of 1 minute for each wash. The solvent was removed by vacuum suction. A small amount of dry resin was taken for ninhydrin detection. Both the resin and solution were dark blue.

To a 50 mL centrifuge tube was added 531 mg Fmoc-GG-OH, 197 mg HOBt. Then about 10 mL DMF was added. The solid was dissolved by shaking. Then 0.24 mL DIC was added. Activated for 10-30 minutes to give the activated reaction solution.

3 molar equivalent of activated reaction solution was added to the resin. Stirring was conducted to soak the resin completely in the solution (if there was resin attached to the tube wall, a small amount of DCM was used to wash the tube wall). Stirring was conducted for 2-3 hours. After the reaction was complete, the reaction solution was removed by vacuum suction. The resin was washed with DMF twice, methanol once, DMF once, methanol once and DMF twice in sequence, with a volume of 10 mL and a time length of 1 minute for each wash. The solvent was removed by vacuum suction. A small amount of dry resin was taken for ninhydrin detection. The resin was colorless and transparent, and the solution was yellowish, indicating qualified for the next coupling step.

Step D-4

The deprotection was conducted twice by adding 10 mL readymade 20% piperidine/DMF solution and reacting for 10 minutes for each time. After the reaction was complete, the solution was removed by vacuum suction. The resin was washed with DMF twice, methanol once, DMF once, methanol once and DMF twice in sequence, with a volume of 10 mL and a time length of 1 minute for each wash. The solvent was removed by vacuum suction. A small amount of dry resin was taken for ninhydrin detection. Both the resin and solution were dark blue. Then, 462 mg MC-OSu was placed in a 50 mL centrifuge tube, about 10 mL DMF was added. The solid was dissolved by shaking. Then 0.24 mL DIEA was added to the resin. Stirring was conducted to soak the resin completely in the solution (if there was resin attached to the tube wall, a small amount of DCM was used to wash the tube wall). Stirring was conducted for 2-3 hours. After the reaction was complete, the reaction solution was removed by vacuum suction. The resin was washed with DMF twice, methanol once, DMF once, methanol once and DMF twice in sequence, with a volume of 10 mL and a time length of 1 minute for each wash. The solvent was removed by vacuum suction. A small amount of dry resin was taken for ninhydrin detection. The resin was colorless and transparent, and the solution was yellowish, indicating qualified for the next coupling step.

Step D-5

The resin was washed twice with 10 mL of methanol. Then the solvent was removed thoroughly by vacuum suction. The resin was poured out and weighed. The lysis buffer was prepared in a 250 mL conical flask, wherein: the ratio of TFE/DCM was 80%/20%, and the volume was 7-8 times of the weight of peptide resin. The lysis buffer was added into the peptide resin, shaken well. The resin was fully soaked in the lysis buffer, and lysis was carried out at room temperature for 2-3 hours. The lysis buffer was then filtered out using a simple filter made of a syringe, and the resin was washed with 1-2 ml DCM and discarded. Then 150 mL precooled anhydrous ether was added to the lysis buffer, shaken well and then stood for 20-30 minutes. Using a 50 mL centrifuge tube, the above system was centrifuged in a centrifuge at 3500 rpm for 3 minutes, and the supernatant was poured out and discarded. The solid was shaken with precooled anhydrous ether, washed once under ultrasound, centrifuged at 3500 rpm for 3 minutes, and the supernatant was poured out and discarded. The solid was placed in a centrifuge tube and allowed to air dry overnight, and then subjected to preparative purification to give 125 mg of product in white solid with a yield of 40%. MS m/z: $[M-H]^-$=641.5.

Preparation of Compound 22 (Step E)

150 mg of raw material Compound 21 and 55 mg of TSTU were weighed and added into a 10 mL single-neck round bottom flask, and anhydrous DMF (3 mL) was added under nitrogen atmosphere and stirred for 20 min. Then 18 mg Compound 12-1 and 20 μl DIEA were added in sequence to the reaction system. Stirring was conducted at room temperature for 2-8 hours under nitrogen atmosphere. Samples were taken and detected by HPLC to monitor the reaction. The raw material peak completely disappeared, and new peaks were detected.

The reaction system was subjected to preparative purification, and the target product was collected and lyophilized to give about 22 mg of product in yellowish solid. MS m/z: $[M+H]^+=1081.0$.

Preparation of linker-payload 3 (Step F)

Compound 22 (30 mg) was weighed and added into a 10 ml single-neck round bottom flask, purified water (2 ml) was added. Stirring was conducted for dissolving. DMF solution (2 ml) containing Linker-payload intermediate 1 (19.5 mg) was added to the reaction system and stirred. After reacting overnight, HPLC was used to monitor the reaction until all of the raw material had converted into intermediates. The reaction mixture was directly added with an appropriate amount of Tris Base solution or other solution that promotes the ring-opening reaction, and the reaction was performed at 0-40° C. for another 0.2-20 h. The reaction was monitored by HPLC until all the intermediates were consumed and then quenched by acetic acid solution.

The reaction system was subjected to preparative purification, and the target product was collected and lyophilized to give about 25 mg of linker-payload 3 with yellowish solid. MS m/z: $[(M+3H)/3]^+=1194.4$.

Preparation of Linker-Payload 4

The following linker-payload 4 can be prepared using similar synthetic routes and reagents as linker-payload 3. The structure of linker-payload 4 is as follow:

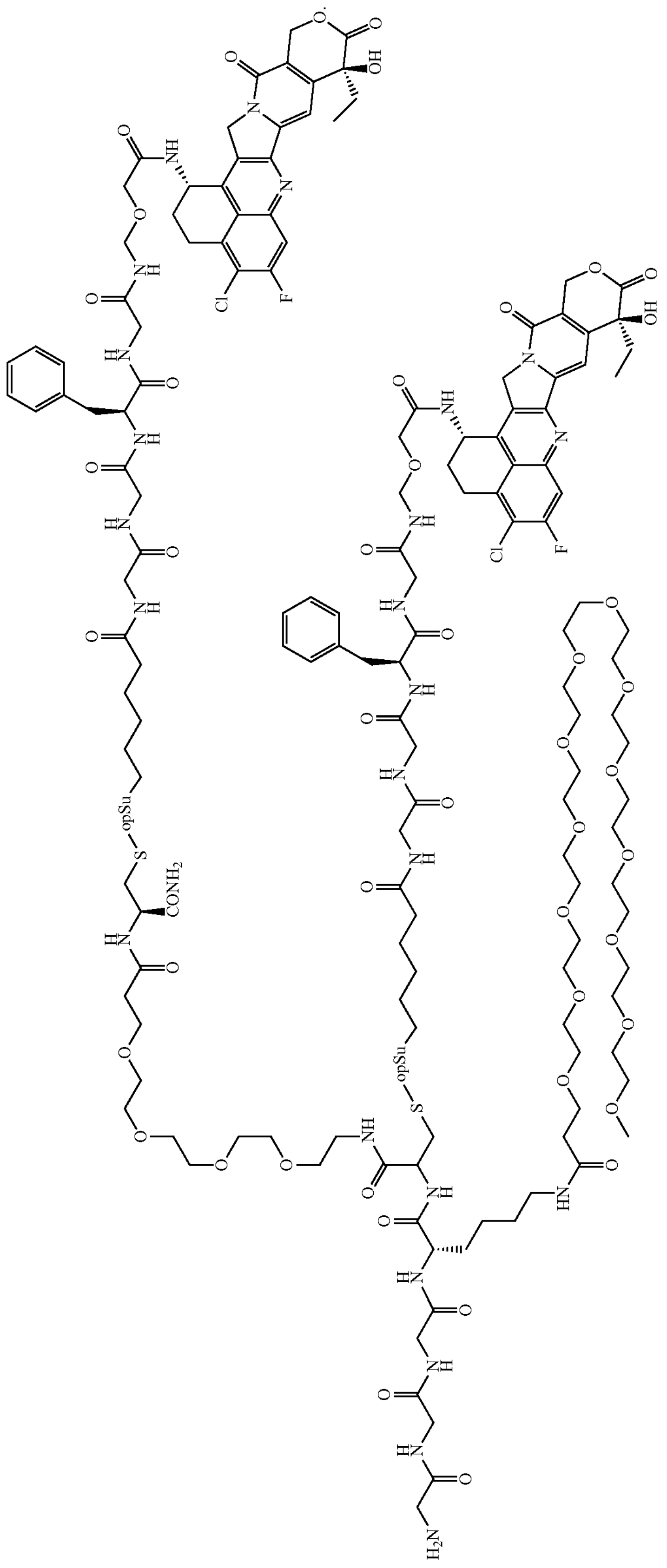
linker-payload 4 opSu is a mixture of
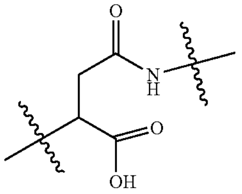
and
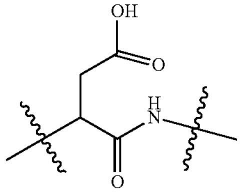
.
Example 2.3 Preparation of Linker-Payload 5
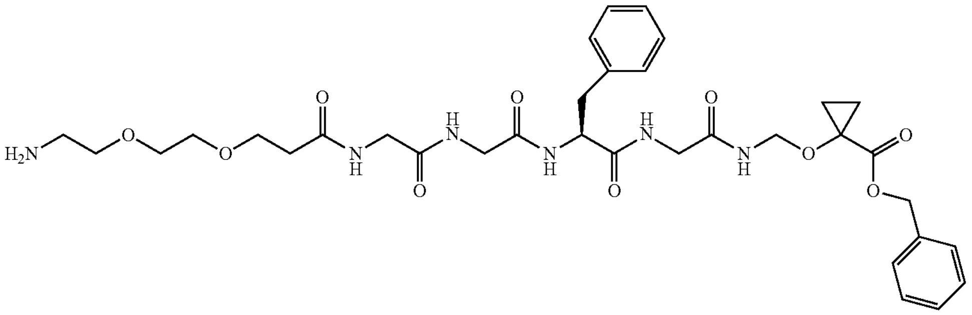
Compound a
coupling
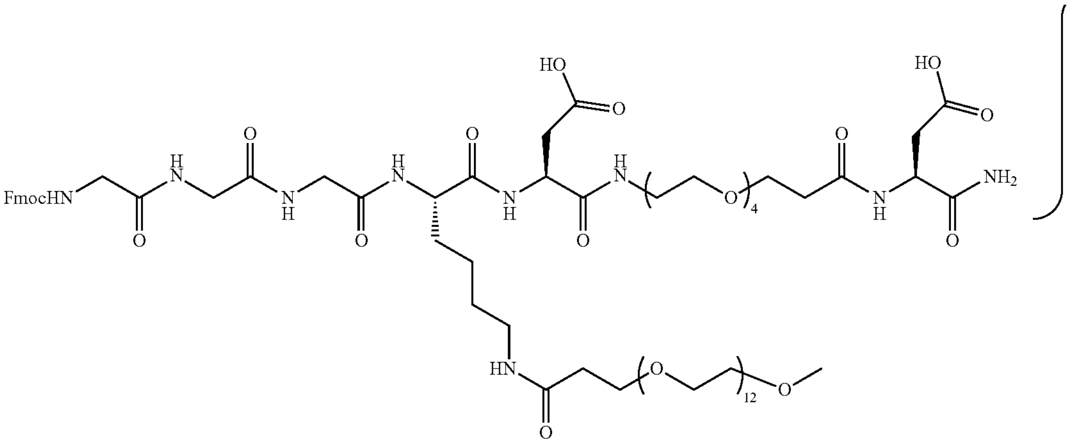
Compound b -continued
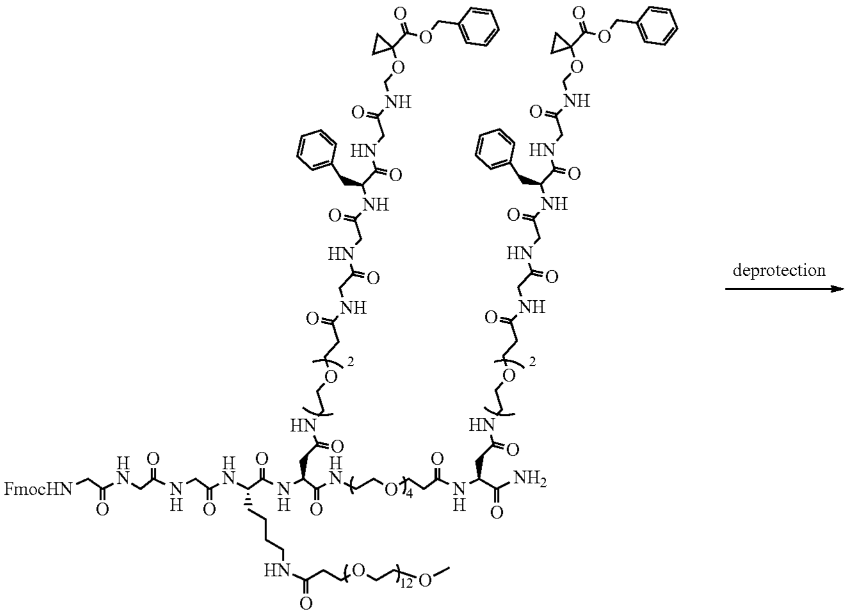
Compound c
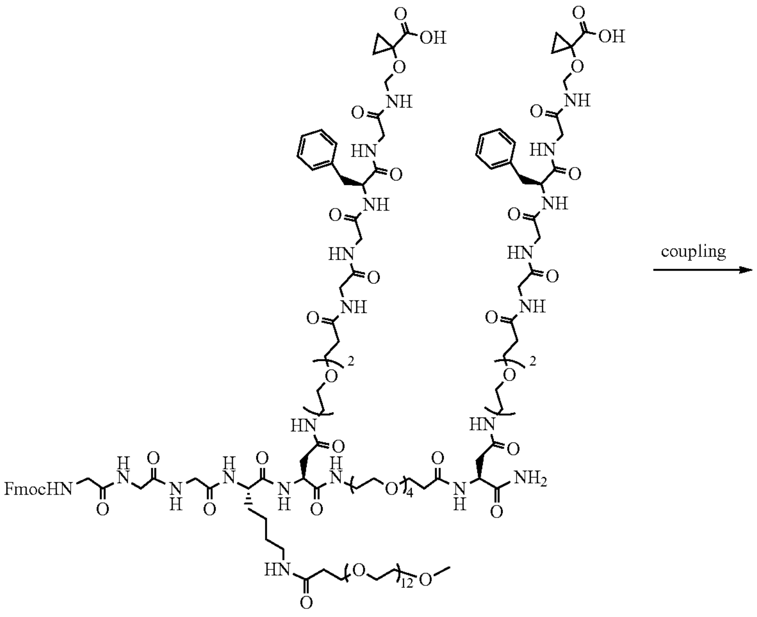
Compound d -continued

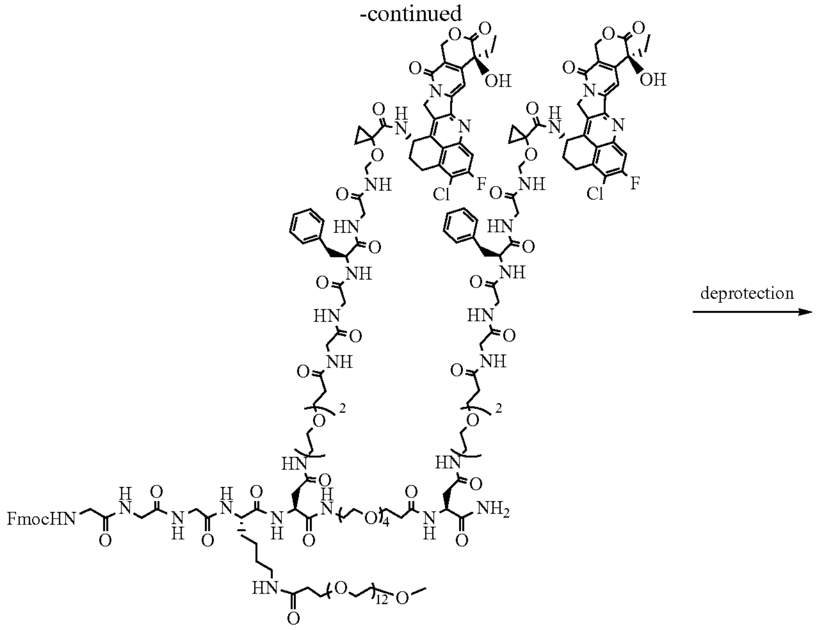

Compound e

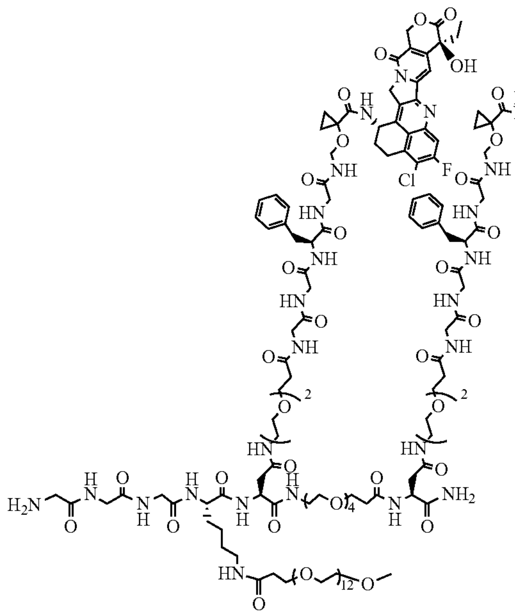

Linker-payload 5

Step 1: Preparation of Intermediate Compound b

Step 1.1 Preparation of $NH_2$-Asp(OtBu)-Rink Amide Resin 400 g of Rink amide resin was weighed and fully swelled by 2400 mL of DCM. 2400 mL of deprotection reagent was added to remove Fmoc completely and then washed several times with DMF and DCM in room temperature. In the subsequent ninhydrin test, the resin showed blue color.

88.87 g Fmoc-Asp(OtBu)-OH and 29.19 g HOBT were weighed and dissolved in 2000 mL DMF and 80 mL DIC solution. After being placed in an ice bath at −10° C. for 0.5 h, it was slowly added into the reaction kettle with resin, and the reaction was stirred at room temperature for 2-5 h with nitrogen, and then filtered. The resin was washed with DMF and DCM successively and showed colorless or light yellow in the subsequent ninhydrin test.

2400 mL of deprotection reagent was added to remove Fmoc completely and then washed several times with DMF and DCM in room temperature. In the subsequent ninhydrin test, the resin showed blue color.

Step 1.2 Preparation of $NH_2$-PEG4-Asp(OtBu)-Rink Amide Resin 131.64 g Fmoc-PEG4-OH and 48.64 g HOBT were weighed and dissolved in 2000 mL DMF and 80.0 mL DIC solution. After being placed in an ice bath at −10° C. for 0.5 h, it was slowly added to the reaction kettle with resin, and the reaction was stirred at room temperature for 2-4 h with nitrogen, and then filtered. The resin was washed with DMF and DCM successively and showed colorless or light yellow in the subsequent ninhydrin test.

2400 mL of deprotection reagent was added to remove Fmoc completely and then washed several times with DMF and DCM in room temperature. In the subsequent ninhydrin test, the resin showed blue color.

Step 1.3 Preparation of $NH_2$-Asp(OtBu)-PEG4-Asp(OtBu)-Rink Amide Resin 222.18 g Fmoc-Asp(OtBu)-OH and 72.96 g HOBT were weighed and dissolved in 2000 mL DMF and 80 mL DIC solution. After being placed in an ice bath at −10° C. for 0.5 h, it was slowly added to the reaction kettle with resin, and the reaction was stirred at room temperature for 2-4 h with nitrogen, and then filtered. The resin was washed with DMF and DCM successively and showed colorless or light yellow in the subsequent ninhydrin test.

2400 mL of deprotection reagent was added to remove Fmoc completely and then washed several times with DMF and DCM in room temperature. In the subsequent ninhydrin test, the resin showed blue color.

Step 1.4 Preparation of Dde-Lys($NH_2$)-Asp(OtBu)-PEG4-Asp(OtBu)-Rink Amide Resin 191.75 g Dde-Lys(Fmoc)-OH and 48.64 g HOBT were weighed and dissolved in 2000 mL DMF and 80.0 mL DIC solution. After being placed in an ice bath at −10° C. for 0.5 h, it was slowly added to the reaction kettle with resin, and the reaction was stirred at room temperature for 2-4 h with nitrogen, and then filtered. The resin was washed with DMF and DCM successively and showed colorless or light yellow in the subsequent ninhydrin test.

2400 mL of deprotection reagent was added to remove Fmoc completely and then washed several times with DMF and DCM in room temperature. In the subsequent ninhydrin test, the resin showed blue color.

Step 1.5 Preparation of Dde-Lys(mPEG12)-Asp(OtBu)-PEG4-Asp(OtBu)-Rink Amide Resin 170.84 g m-PEG12-$CH_2CH_2COOH$ and 48.64 g HOBT were weighed and dissolved in 2000 mL DMF and 80.0 mL DIC solution. After being placed in an ice bath at −10° C. for 0.5 h, it was slowly added to the reaction kettle with resin, and the reaction was stirred at room temperature for 2-4 h with nitrogen, and then filtered. The resin was washed with DMF and DCM successively and showed colorless or light yellow in the subsequent ninhydrin test.

Step 1.6 Preparation of $NH_2$-Lys(PEG12)-Asp(OtBu)-PEG4-Asp(OtBu)-Rink Amide Resin 2400 mL of de-Dde reagent was added, and the reaction was stirred at room temperature under nitrogen for 0.5 h, and then filtered. After repeating the operation 3 times, the resin was washed with DMF and DCM successively and showed blue color in the subsequent ninhydrin test.

Step 1.7 Preparation of Fmoc-Gly-Gly-Gly-Lys(PEG12)-Asp(OtBu)-PEG4-Asp(OtBu)-Rink Amide Resin 111.08 g Fmoc-Gly-Gly-Gly-OH and 48.64 g HOBT were weighed and dissolved in 2000 mL DMF and 80.0 mL DIC solution. After being placed in an ice bath at −10° C. for 0.5 h, it was slowly added to the reaction kettle with resin, and the reaction was stirred at room temperature for 2-4 h with nitrogen, and then filtered. The resin was washed with DMF and DCM successively and showed colorless or light yellow in the subsequent ninhydrin test. The resin peptide was washed three times with anhydrous ethanol, filtered and waited for cleavage.

Step 1.8 Preparation of Intermediate Compound b 10000 mL cleavage reagent (TFA:TIS:$H_2O$=95:2.5:2.5) was added to the 10 L reactor and cooled to −10±2° C. The dried and weighed resin was added. The reaction was warmed to room temperature and stirred under nitrogen for 2-3 h. After that, the resin was filtered and washed once with 100 mL of TFA. The filtrate and washing solution were combined.

40 L of pre-cooled (below −10° C.) cold ether was added into product solution. The mixture was stirred for 10 minutes, and then the precipitate was centrifuged. The supernatant was discarded after centrifugation, and the precipitate was collected and washed with cold ether, and the precipitate was centrifuged again (Each time the centrifugation speed was set to 3600 rpm, the centrifugation time was 5 minutes, and the temperature of the centrifuge cavity was −5° C.).

The precipitate was collected as crude Compound b. The crude product was purified by Prep-HPLC and lyophilized to obtain pure Compound b Step 2: Preparation of Intermediate Compound a

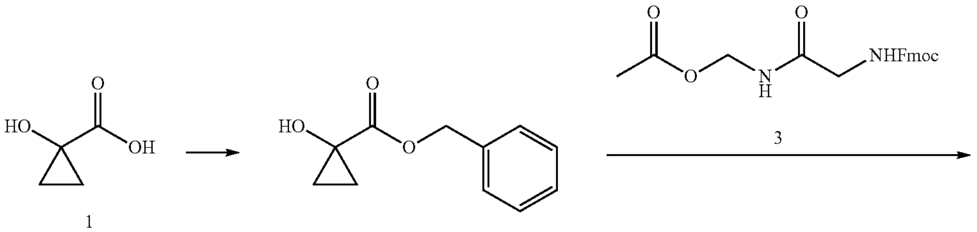

1

2

-continued
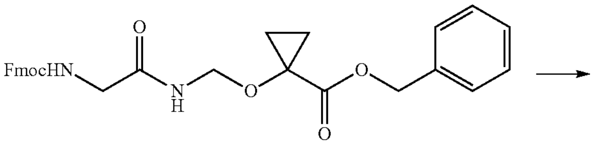
4
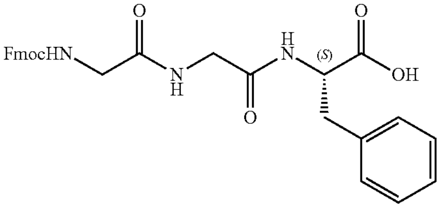
6
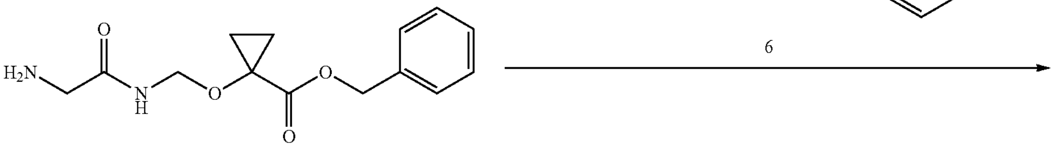
5
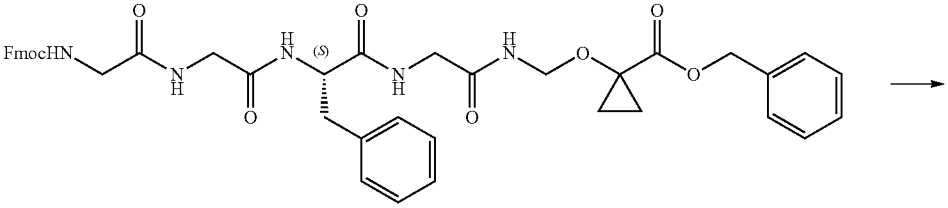
7
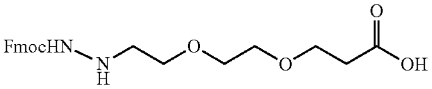
9
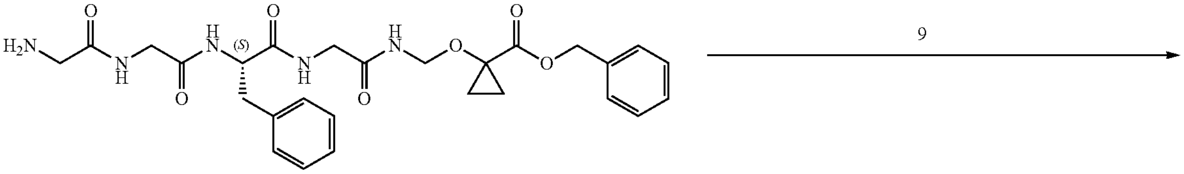
8
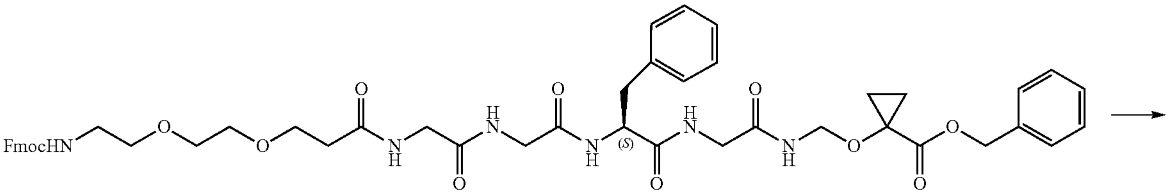
10
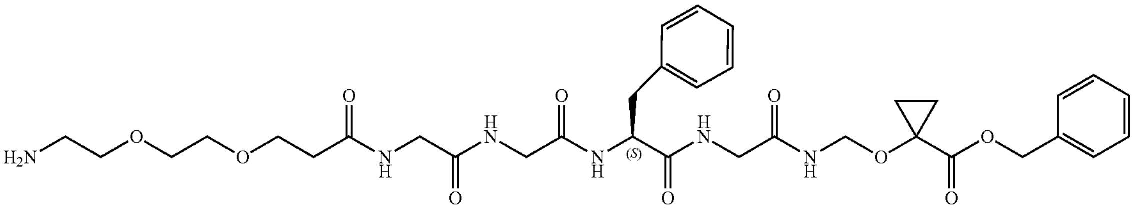
compound a Step 2.1 Preparation of Compound 2

Compound 1 (1 e.q.) and DMF (5 v/v) were added to the reaction flask, and the mixture was stirred and dissolved under nitrogen protection. After the ice bath was cooled to 0-5° C., DIEA (3 e.q.) was added dropwise, and the mixture was stirred at 5° C. for 10 min after the dropwise addition. Then benzyl bromide (1.3 e.q.) was added dropwise, and after the dropwise addition was completed, it was allowed to naturally rise to room temperature of about 20° C. and stirred for 16 hours.

The reaction solution was slowly poured into ice water, MTBE was added and stirred, and the solution was allowed to stand for separation. The aqueous phase was extracted 4 times with MTBE, the combined organic phases were washed with saturated brine, and then the organic phase was dried over anhydrous sodium sulfate, and the concentrated under vacuum to obtain a crude yellow oil, which was applied to the column by wet method. The light yellow oil was obtained by the elution of PE/EA=6:1, and the yield is 100%.

Step 2.2 Preparation of Compound 4

Under nitrogen protection, intermediate 2 (2.0 e.q.), compound 3 (1 e.q.) and THF (10 v/v) were added to the reaction flask and stirred to dissolve, TsOH (0.1 e.q.) was weighed and added to the reaction, and the reaction was kept at 20-22° C. for 4 h. The reaction solution was slowly poured into ice water, extracted 3 times with EA, the combined organic phase was washed with saturated aqueous sodium bicarbonate solution, water and saturated brine successively, the organic phase was dried with anhydrous sodium sulfate, filtered and concentrated under vacuum to obtain the crude product. The product was collected by mixing silica gel sample through column by the elution of PE/EA=1:1, and concentrated to obtain a white solid with a yield of 40%.

Step 2.3 Preparation of Compound 7

Under nitrogen protection, compound 4 and DMAc (10 v/v) were added to the reaction flask and stirred to dissolve. The reaction was cooled down to 14-18° C., DBU (0.5 e.q.) was added dropwise, and the reaction was stirred at this temperature for 1.5 h, the completion of reaction of the raw materials was monitored by TLC. The reaction was cooled down to 0-5° C., PPTS (0.5 e.q.), EDCI (1 e.q.), HOBT (1 e.q.) and compound 6 (0.85 eq) were added and reacted at 0-10° C. for 3-4 h, and the reaction was monitored by LCMS.

The reaction solution was added to ice water, 2-methyltetrahydrofuran was added to extract once, and the aqueous phase was extracted twice with 2-methyltetrahydrofuran. The organic phases were combined, washed with 0.5 M hydrochloric acid, washed with saturated aqueous $NaHCO_3$, water, and saturated brine, dried over anhydrous sodium sulfate, filtered, concentrated, evaporated to dryness, mixed with silica gel, and purified by column. The product was collected by the elution of DCM/MeOH and concentrated under vacuum to obtain a white solid with a yield of 78%.

Step 2.4 Preparation of Compound 10

Under nitrogen protection, intermediate 7 and DMAc (10 v/v) were added to the reaction flask and stirred to dissolve. The reaction was cooled down to 14-18° C., DBU (0.5 e.q.) was added dropwise, and the reaction was stirred at this temperature for 1.5 h, the completion of reaction was monitored by TLC. The reaction was cooled down to 0-5'C, PPTS (0.5 e.q.), EDCI (1 e.q.), HOBT (1 e.q.) and compound 9 (0.85 e.q.) were added and reacted at 0-10° C. for 3-4 h, and the reaction was monitored by LCMS.

The reaction solution was added to ice water, 2-methyltetrahydrofuran was added to extract once, and the aqueous phase was extracted twice with 2-methyltetrahydrofuran. The organic phases were combined, washed with 0.5 M hydrochloric acid, saturated aqueous $NaHCO_3$, water, and saturated brine, dried over anhydrous sodium sulfate, filtered, concentrated, evaporated to dryness, mixed with silica gel, and purified by column. The product was collected by the elution of DCM/MeOH and concentrated under vacuum to obtain a white solid with a yield of 50%.

Step 2.5 Preparation of Compound a

Under nitrogen protection, intermediate 10 was dissolved in DCM (15 v/v), DBU (0.5 e.q.) was added dropwise at 20° C., and the reaction was stirred at 18-22° C. for 5 h. The complete reaction was monitored by LCMS. The reaction solution was diluted with DCM and purified by the column by wet method, and the product was collected by the elution of DCM:MeOH to obtain a white solid with a yield of 82%.

Step 3: Preparation of Intermediate Compound c

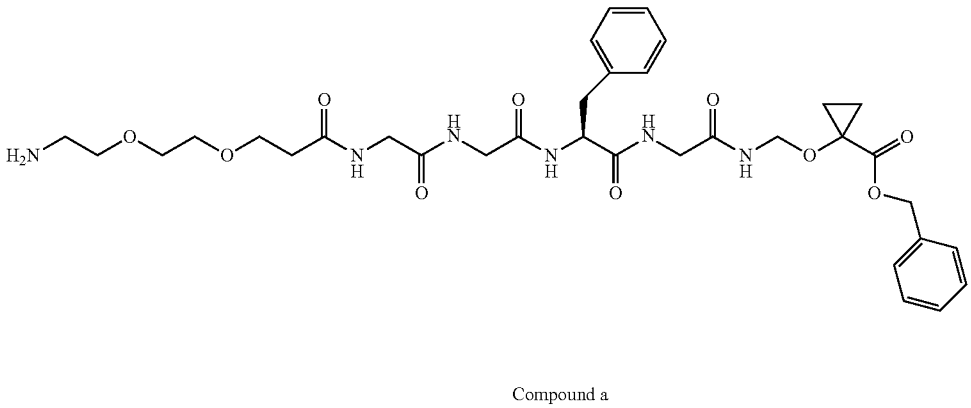

Compound a

+

-continued

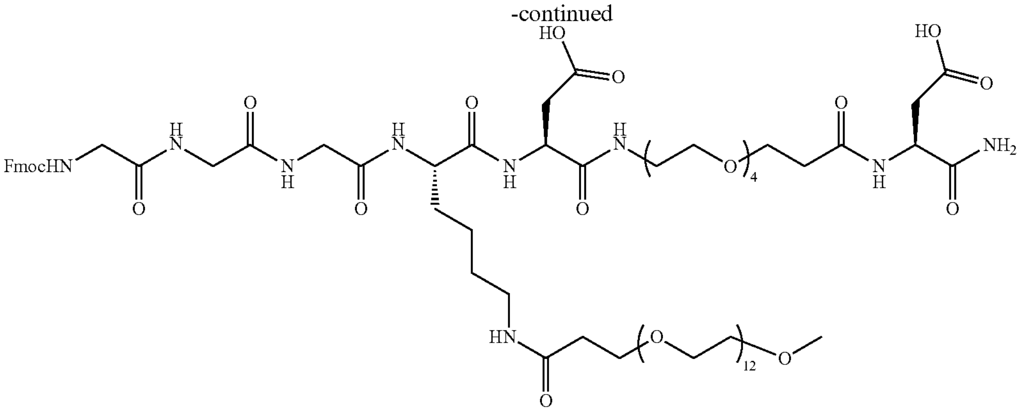

Compound b

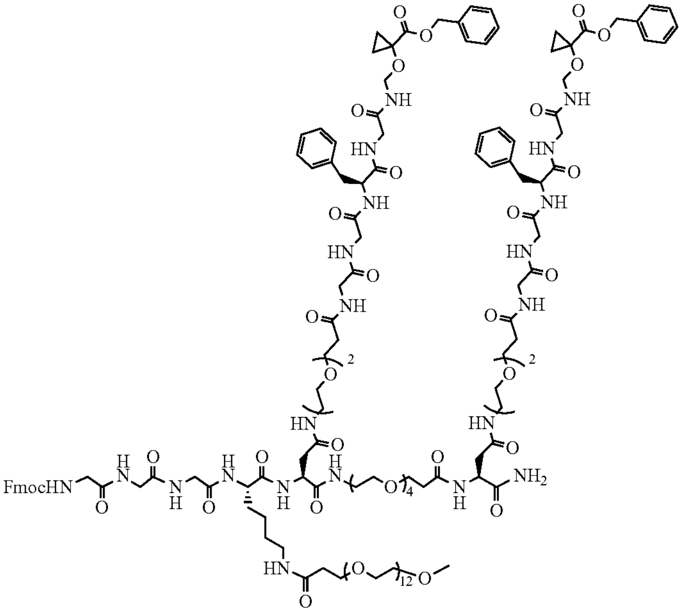

Compound c

Compound b (400 mg, 0.245 mmol) and Compound a (377 mg, 0.539 mmol) were dissolved in DMF (6 ml), then DIPEA (159 mg, 1.23 mmol) and HATU (233 mg, 0.613 mmol) were added into the reaction solution, and the reaction was stirred at room temperature for 2 h. After the disappearance of the Compound b, it was purified by prep-HPLC, and the preparation solution was lyophilized to obtain 380 mg of the product with a yield of 52%. Calcd for $C_{142}H_{207}O_{49}N_{21}$ $[(M+3H)/3]^{+}$: 997.8, found: 875.9 (fragmented mass).

Step 4: Preparation of Intermediate Compound d

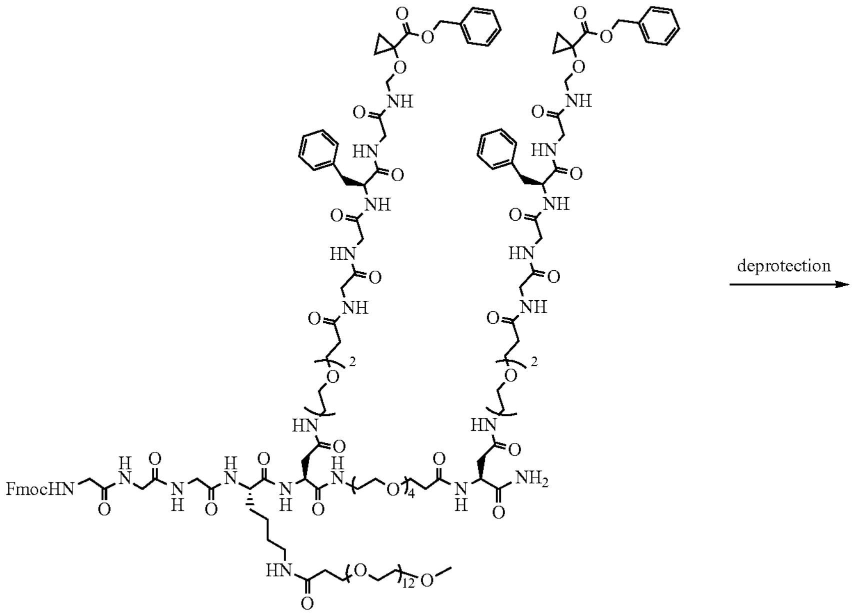

Compound c

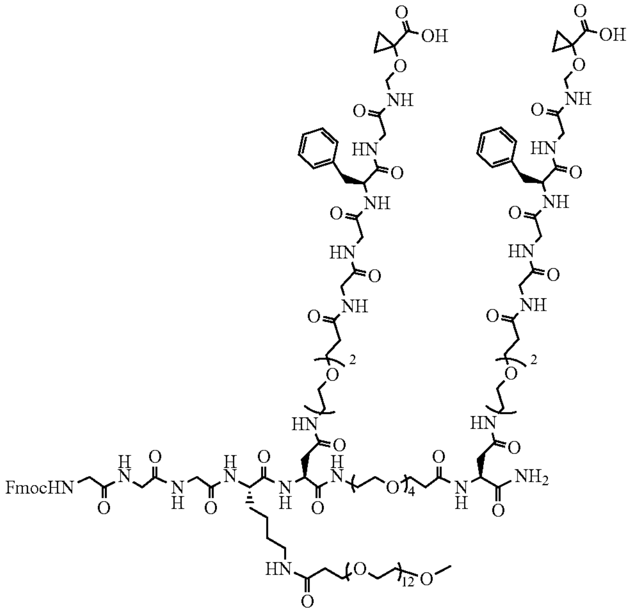

Compound d

Compound c (380 mg, 0.245 mmol) was dissolved in purified water (80 ml), and palladium hydroxide (38 mg) was added. The system replaced with hydrogen for 3 times, the reaction was stirred at room temperature for 1.5 h. The reaction progress was monitored during the period, the reaction was stopped immediately after the disappearance of the raw materials to prevent the increase of de-Fmoc products. The reaction solution was filtered and purified by prep-HPLC to obtain 270 mg of the product with a yield of 76%. Calcd for $C_{128}H_{195}O_{49}N_{21}$ $[(M+3H)/3]^+$: 937.8, found: 875.9 (fragmented mass).

Step 5: Preparation of Intermediate Compound e

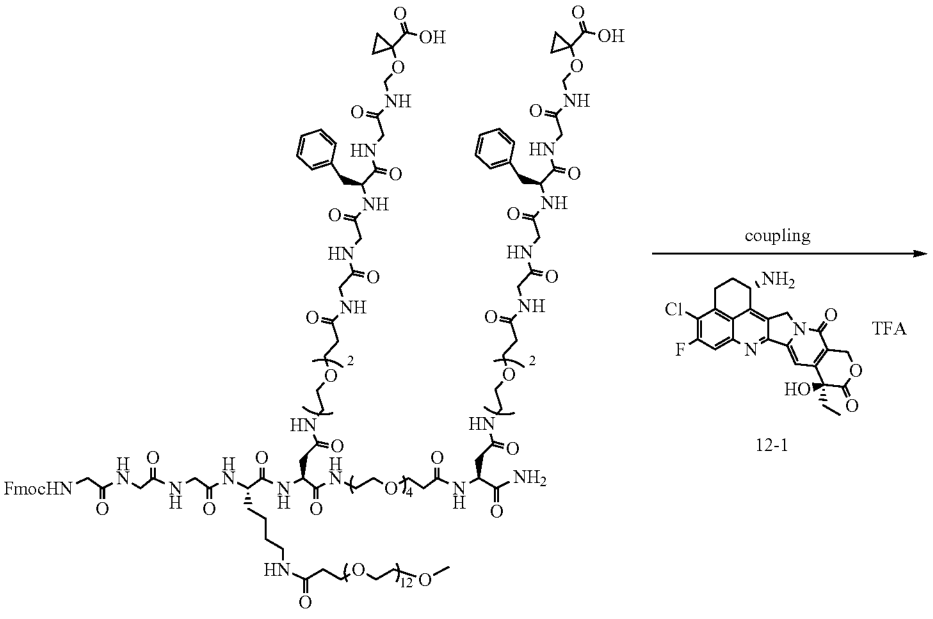

Compound d 12-1

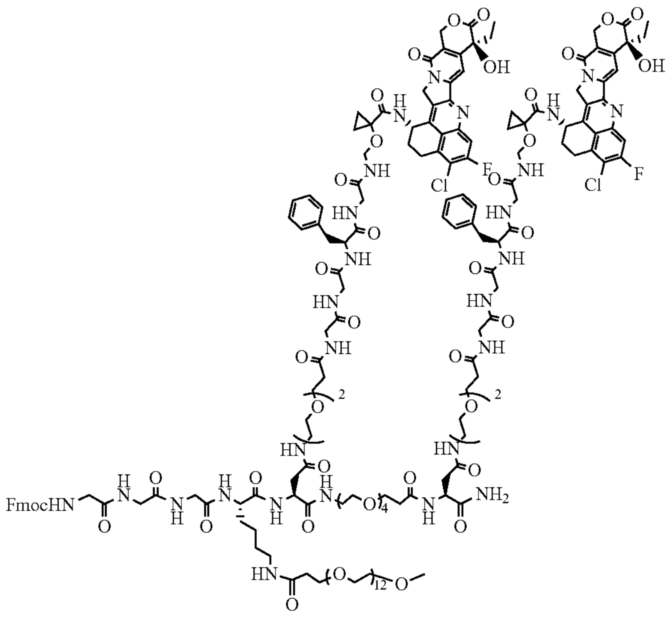

Compound e

Compound d (270 mg, 0.096 mmol) and 12-1 (120 mg, 0.211 mmol) were dissolved in DMF (5 ml), then DIPEA (62 mg, 0.48 mmol) and HATU (92 mg, 0.24 mmol) were added into the reaction solution and stirred at room temperature for 2-16 h. After the completion of reaction monitored by HPLC, the reaction mixture was directly purified by prep-HPLC, and the collected eluents were combined and lyophilized to obtain 235 mg of the product with a yield of 66%. Calcd for $C_{174}H_{229}O_{55}Cl_2F_2N_{27}$ $[(M+3H)/3]^+$: 1229.2, found: 1229.3.

Step 6: Preparation of Linker-Payload 5

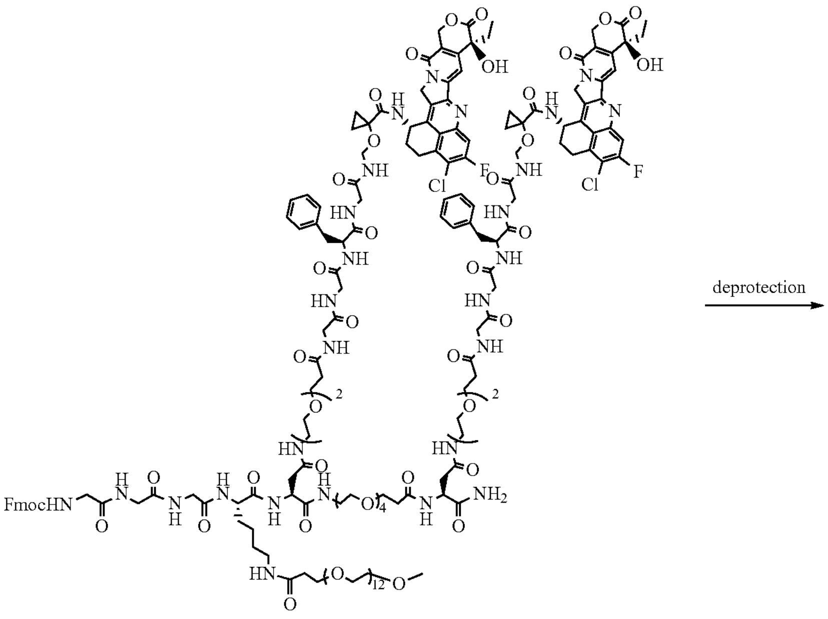

Compound e

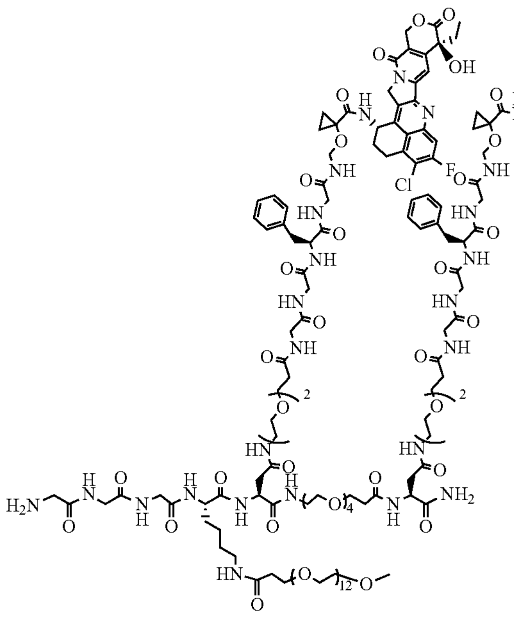

Linker-payload 5

Compound e (210 mg, 0.057 mmol) was dissolved in DMF (5 ml), then diethylamine (0.5 ml) was added and the reaction was reacted at room temperature for 15 min, the reaction end point was monitored by HPLC. After the reaction was completed, it was adjusted to neutrality with 10% TFA aqueous solution under ice bath, and the reaction was purified by prep-HPLC, and 145 mg of product was obtained after lyophilization with a yield of 73%. Calcd for $C_{159}H_{219}O_{53}Cl_2F_2N_{27}$ $[(M+3H)/3]^+$: 1155.2, found: 1155.3.

Example 3 Preparation of Targeting Molecule-Pharmaceutical Conjugates

3.1 Preparation of DS1062a Analogy and Trodelvy

DS1062a analogue (DS1062a and DS-1062*) was prepared based on the method described in patent US20160297890A, or made by WuXi Biologics.

Trodelvy was commercially available.

3.2 Preparation of ADC-1

3.2.1 Treatment of GQhRS7

GQhRS7 was treated by ultrafiltration, dialysis or desalting column. The storage solution was replaced with a ligase buffer.

3.2.2 Enzyme-Catalyzed Coupling of ADC-1

ADC-1 was prepared by coupling reaction of GQhRS7 with linker-payload 1, under the catalysis of a wild type Sortase A or a mutant ligase optimized and engineered based thereon. In the ligase buffer, the modified antibody and linker-payload were thoroughly mixed at a molar ratio of 1:1 to 1:100, and added to a solid phase coupling system. The solid phase coupling system comprised a ligase immobilized on the matrix of the solid phase coupling system. The immobilized ligase catalyzed the coupling reaction of the antibody GQhRS7 with linker-payload 1. The coupling reaction was carried out at 4-40° C. for 0.5-20 h. After the reaction was completed, the reaction mixture was subjected to ultrafiltration or dialysis to remove unreacted intermediate, giving ADC-1. ADC-1 was stored at 4° C. or −80° C. in a buffer containing 20 mM citric acid, 200 mM NaCl, pH 5.0.

3.2.3 HIC-HPLC Detection and Analysis of ADC-1

The DAR (drug-to-antibody ratio) distribution of ADC-1 was analyzed by HIC-HPLC. The antibody GQhRS7 without cytotoxin was less than 5%; and the coupled product mainly contained ADC-1 with DAR of 3.5.

3.2.4 SEC-HPLC Detection and Analysis of ADC-1

The degree of high molecular weight aggregation of ADC-1 was analyzed by SEC-HPLC. The results showed that no high molecular weight polymer was detected in ADC-1, indicating that the coupling reaction conditions were mild and did not cause damage to the antibody structure.

3.3 The Linker-payload intermediates were respectively conjugated to an antibody in a site-specific manner by a ligase to form an ADC. The method for conjugation reaction can be found in WO2015165413A1. The resulting ADCs are as listed in the following table:

| Name of ADC | Linker-Payload | Antibody |
|---|---|---|
| ADC-1 | Linker-Payload 1 | GQhRS7 |
| ADC-2 | Linker-Payload 3 | GQhRS7 |
| ADC-3 | Linker-Payload 4 | GQhRS7 |
| ADC-4 | Linker-Payload 5 | GQhRS7 |
| ADC-5 | Linker-Payload 5 | GQAb13 |
| ADC-6 | Linker-Payload 5 | GQAb16 |
| ADC-7 | Linker-Payload 2 | GQhRS7 |

3.4 Binding Activity

Human Trop 2 ECD at concentration of 0.5 μg/mL was coated on 96-well plates at 4° C. for overnight. The plates were then blocked with 3% BSA-PBST for 1 h at room temperature. After washing with PBST (0.05% Tween), a series samples of the testing articles including ADC-2 (namely ADC2), Trodelvy and GQhRS7 at different concentrations were add into 96-well plates, respectively, and then incubated at room temperature for 60 min. After incubation goat anti-human FC secondary antibody (HRP) (Sinobiological, SSA001) was added at a ratio of 1:100000 and incubated at room temperature for 60 min again. Following the wash, the plate was treated with TMB solution (Sigma, T0440) as an HRP substrate, and the reaction was stopped with 1 M $H_2SO_4$. The absorbance for each well was detected at 450 nm wavelength.

The results of this analysis are shown in FIG. 1B. The results demonstrate that ADC-2 has similar binding affinity with GQhRS7 and Trodelvy.

3.5 Internalization Activity

NCI-N87 in good viability, were trypsinized, collected, suspended in cold FACS buffer (DPBS+2% FBS). Cells were incubated with tested drugs solution with the final concentration of 50 μg/ml for one hour on ice. The antibody-cell mixture was washed twice by cold FACS buffer to remove the excess antibody. The antibody bonded cells were fluorescence labeled by mixing with 500 times diluted ice cold anti-human-IgG-Fc-AF647 secondary antibody solution for 30 minutes. After the fluorescence labelling, the antibody-cell mixture was washed twice again. Cells were incubated at 37° C. for tested drugs internalization for 10 min, 30 min, 60 min, 90 min, 150 min and 210 min. The cells were suspended by quench buffer (150 mM NaCl+100 mM Glycine, pH=2.0 to 2.5) to dissociate antibody bound on the cell surface. After the acidification, the cells were washed by cold FACS buffer twice and analyzed in APC channel by flow cytometry.

The MFI data was taken into the formula below, and the result was analyzed by one phase exponential association function in Prism8. Internalization amount: A=MFI(I)−MFI(MIN). Internalization ratio: R=[MFI(I)−MFI(MIN)]/[MFI(MAX)−MFI(Blank)]×100%

As shown in FIG. 1C, ADC2 shows comparable internalization activity with DS1062, Trodelvy and GQhRS7 on NCI-N87.

Effect Example 1 Bystander Killing Effect of Conjugates in BxPC-3/HepG2

Effect Example 1.1 Bystander Killing Effect of ADC-1 Against HepG2 in BxPC-3/HepG2 Co-Culture Assay The cell concentration of Trop2-positive cells BxPC-3 and Trop2-negative cells HepG2 were adjusted to $1\times10^6$ cells/mL, and 200 μL per well (cell volume BxPC-3: HepG2=4:1) was seeded into six-well plates, and 2.8 mL of 45% RPMI-1640+45% DMEM+10% FBS medium was supplemented. The cells were incubated overnight in a cell incubator at 37° C., 5% $CO_2$. 3 mL of 20 nM ADC-1 and DS1062a were added to cells cultured overnight (final drug concentration of 10 nM per well) respectively. A negative control group was set: 3 mL of 45% RPMI-1640+45% DMEM+10% FBS medium was added to each well. After the treatment, the cells were moved to the incubator and incubated for 96 h. After the incubation, cells were digested, and washed once with 1×PBS, then transferred to a flow tube, and centrifuged at 2000 rpm for 3 min. The supernatant was then discarded, and the cell amount and cell viability were detected. A certain amount of cells were washed with 1×PBS, the supernatant was discarded after centrifugation, 200 μL of 100 nM anti-human Trop2 antibody was added, and the cells were mixed and incubated at 4° C. for 30 min. The cells were washed with 1×PBS, the supernatant was discarded after centrifugation, 200 μL of 5 μg/mL human IgG Fc antibody was added, and the resulting cells were continued to incubate at 4° C. for 30 min after mixing. Finally, the cells were washed with 1×PBS, the supernatant was discarded after centrifugation, and the cells were resuspended in PBS, detected by flow cytometry and analyzed by FlowJo software. The results are as shown in table 4.

TABLE 4

Bystander killing test results of ADC-1 and DS1062a

| Groups | Number of viable cells ($10^4$) | Cell proportion (%) | | Amount of cells ($10^4$) | |
|---|---|---|---|---|---|
| | | BxPC-3 | HepG2 | BxPC-3 | HepG2 |
| Control | 259.0 | 22.5 | 77.5 | 58.28 | 200.73 |
| DS1062a | 44.6 | 24.4 | 75.6 | 10.88 | 33.72 |
| ADC-1 | 59.3 | 33.4 | 66.6 | 19.81 | 39.49 |

Effect Example 1.2 Bystander Killing Effect of ADC-2 Against HepG2 in BxPC-3/HepG2 Co-Culture Assay The cell concentration of Trop2-positive cells BxPC-3 and Trop2-negative HepG2 cells were adjusted to $1\times10^6$ cells/mL, and 300 μL per well (cell volume BxPC-3: HepG2=2:1) was inoculated into six-well plates, and 2.7 mL of 45% RPMI-1640+45% DMEM+10% FBS medium was supplemented. The cells were incubated overnight in a cell incubator at 37° C., 5% $CO_2$. 3 mL of 20 nM ADC-2 and DS1062a were added to cells cultured overnight (final drug concentration of 10 nM per well) respectively. And the next process was used the same process as above to evaluate the bystander killing effect of ADC-2 and DS1062a. The results are as shown in table 5.

TABLE 5

Bystander killing test results of ADC-2 and DS1062a

| Groups | Number of viable cells ($10^4$) | Cell proportion (%) | | Amount of cells ($10^4$) | |
|---|---|---|---|---|---|
| | | BxPC-3 | HepG2 | BxPC-3 | HepG2 |
| Control | 452.0 | 22.4 | 77.6 | 101.25 | 350.75 |
| DS1062a | 157.0 | 7.8 | 92.2 | 12.25 | 144.75 |
| ADC-2 | 70.0 | 21.8 | 78.2 | 15.26 | 54.74 |

Effect Example 1.3 Bystander Killing Effect of ADC-6 Against HepG2 in BxPC-3/HepG2 Co-Culture Assay The same process as effect example 1.2 was used to evaluate the bystander killing effects of control (Datopotamab), DS1062a, ADC-1, ADC-2, ADC-4 and ADC-6. The results are as shown in table 6.

TABLE 6

Bystander killing test results of ADC-6

| Groups | Number of viable cells ($10^4$) | Cell proportion (%) | | Amount of cells ($10^4$) | |
|---|---|---|---|---|---|
| | | BxPC-3 | HepG2 | BxPC-3 | HepG2 |
| Control | 452.0 | 22.4 | 77.6 | 101.25 | 350.75 |
| DS1062a | 157.0 | 7.8 | 92.2 | 12.25 | 144.75 |
| ADC-4 | 156.0 | 9.9 | 90.2 | 15.37 | 140.63 |
| ADC-1 | 177.0 | 9.0 | 91.0 | 15.86 | 161.14 |
| ADC-2 | 70.0 | 21.8 | 78.2 | 15.26 | 54.74 |
| ADC-6 | 66.4 | 21.5 | 78.5 | 14.28 | 52.12 |

Conclusions

The experimental results of effect example 1.1 showed that both ADC-1 and DS1062a analogy had bystander killing effects, and there was no significant difference in their efficacy.

The experimental results of effect example 1.2 showed that the bystander killing effect of ADC-2 was better than that of DS1062a.

The experimental results of effect example 1.3 showed that: ADC-1, ADC-2, ADC-4, ADC-6 and DS1062a analogy all had bystander killing effects. The bystander killing effects of ADC-2 and ADC-6 were better than that of DS1062a. The bystander killing effect of ADC-6 was significantly better than that of ADC-4.

Effect Example 2: Effect of Conjugates Targeting TROP2 on Cell Proliferation

Effect Example 2.1 Inhibitory Effect of ADC-7 and ADC-1 on Tumor Cell Proliferation

Figure 2:
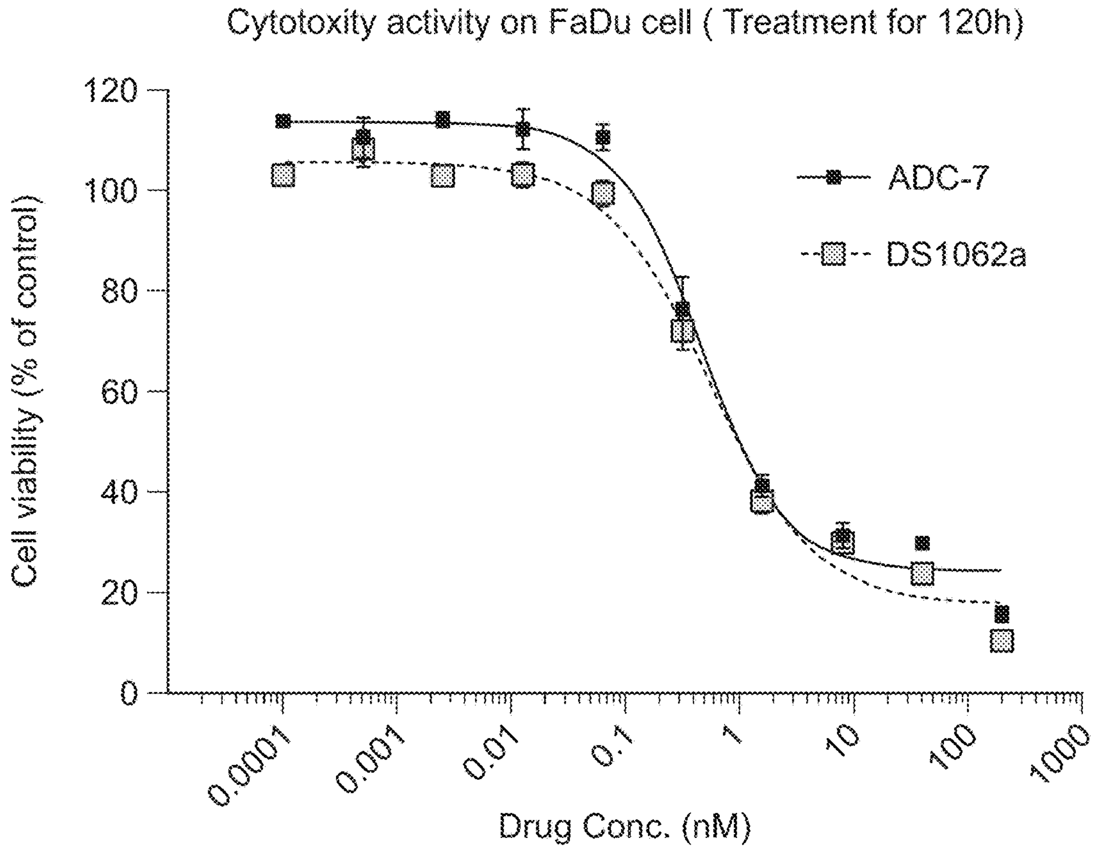
FIG. 2 shows the effect of ADC-7 and DS1062a on the viability of FaDu cells.

Effect Example 2.1.1 Inhibitory Effect of ADC-7 on the Proliferation of Human Pharyngeal Squamous Cell Carcinoma FaDu Two thousand human pharyngeal squamous cells carcinoma FaDu with high TROP2 expression were seeded into 96-well plates in 100 μL of culture medium per well, and incubated overnight in a cell incubator at 37° C. and 5% $CO_2$. 100 μL of different concentrations (200 nM, 40 nM, 8 nM, 1.6 nM, 0.32 nM, 0.064 nM, 0.0128 nM, 0.00256 nM, 0.000512 nM, and 0.0001024 nM) of ADC-7 and DS1062a were added to each well (3 replicate wells for each concentration). A positive control group was set: 100 μL Puromycin at a concentration of 10 μg/mL was added to each well. A negative control group was set: 100 μL of complete medium of FaDu cells was added to each well. After the administration was completed, the cells were moved to the incubator and incubated for 96 h. The 96-well plate was removed from the 37° C. cell incubator and equilibrated to room temperature for 30 minutes. After the medium was discarded, 100 μL of DMEM and 50 μL of CellTiter Glo reagent were added to each well, and the cells were shaken in the dark at 200 rpm for 15 minutes, and the luminescent signal reflecting cell viability was detected by a microplate reader. The inhibitory effects of the tested drugs on the proliferation of human pharyngeal squamous cell carcinoma FaDu are as shown in FIG. 2 and Table 7.

TABLE 7

| Inhibitory effects of ADC-7 and DS1062a on the proliferation of pharyngeal squamous cell carcinoma FaDu | |
|---|---|
| Drug | $IC_{50}$ (nM) |
| ADC-7 | 0.4617 |
| DS1062a | 0.5508 |

Effect Example 2.1.2 Inhibitory Effect of ADC-1 on the Proliferation of Human Pancreatic Cancer Cell BxPC-3

Figure 3:
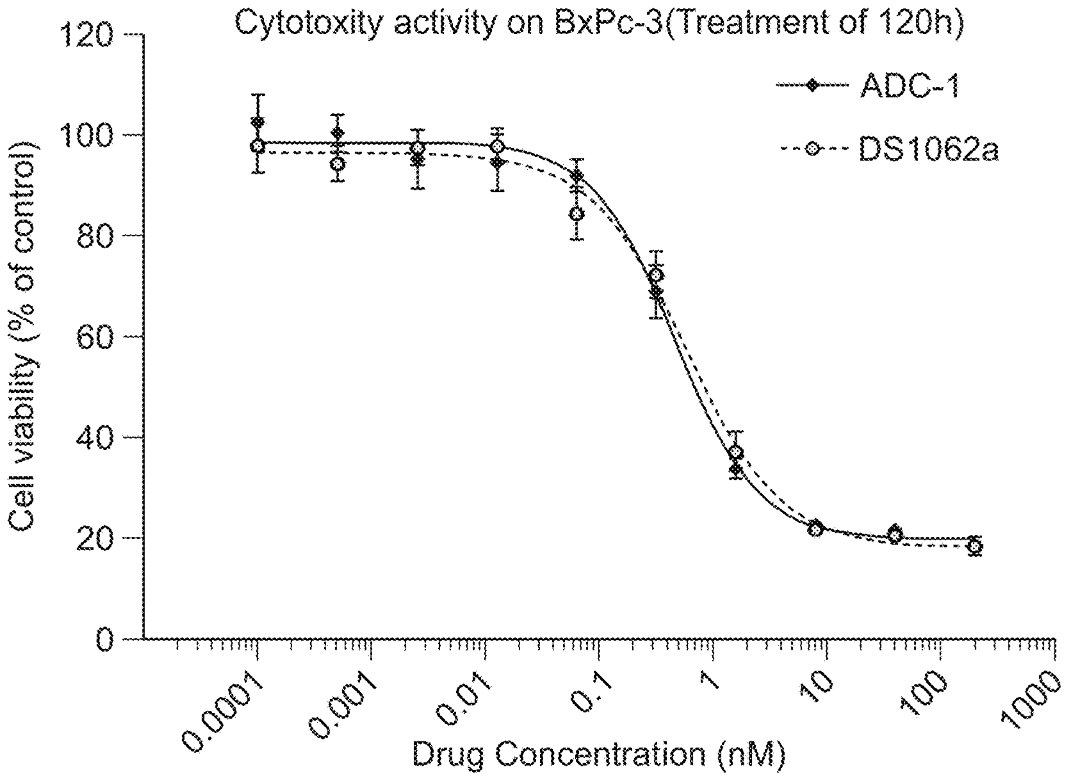
FIG. 3 shows the effect of ADC-1 and DS1062a on the viability of human pancreatic cancer cell BxPC-3.

The human pharyngeal squamous cells carcinoma FaDu in Example 2.1.1 were replaced with human pancreatic cancer cells BxPC-3 (100 μL per well containing 2000 cells), and the inhibitory effect of ADC-1 was evaluated using the same process. The inhibitory effect of the tested drugs on the proliferation of human pancreatic cancer cells BxPC-3 is as shown in FIG. 3 and Table 8.

TABLE 8

| Inhibitory effects of ADC-1 and DS1062a on the proliferation of human pancreatic cancer cell BxPC-3 | |
|---|---|
| Drug | $IC_{50}$ (nM) |
| ADC-1 | 0.4741 |
| DS1062a | 0.5835 |

Effect Example 2.1.3 Inhibitory Effect of ADC-1 on the Proliferation of Human Breast Cancer Cell MDA-MB-468

Figure 4:
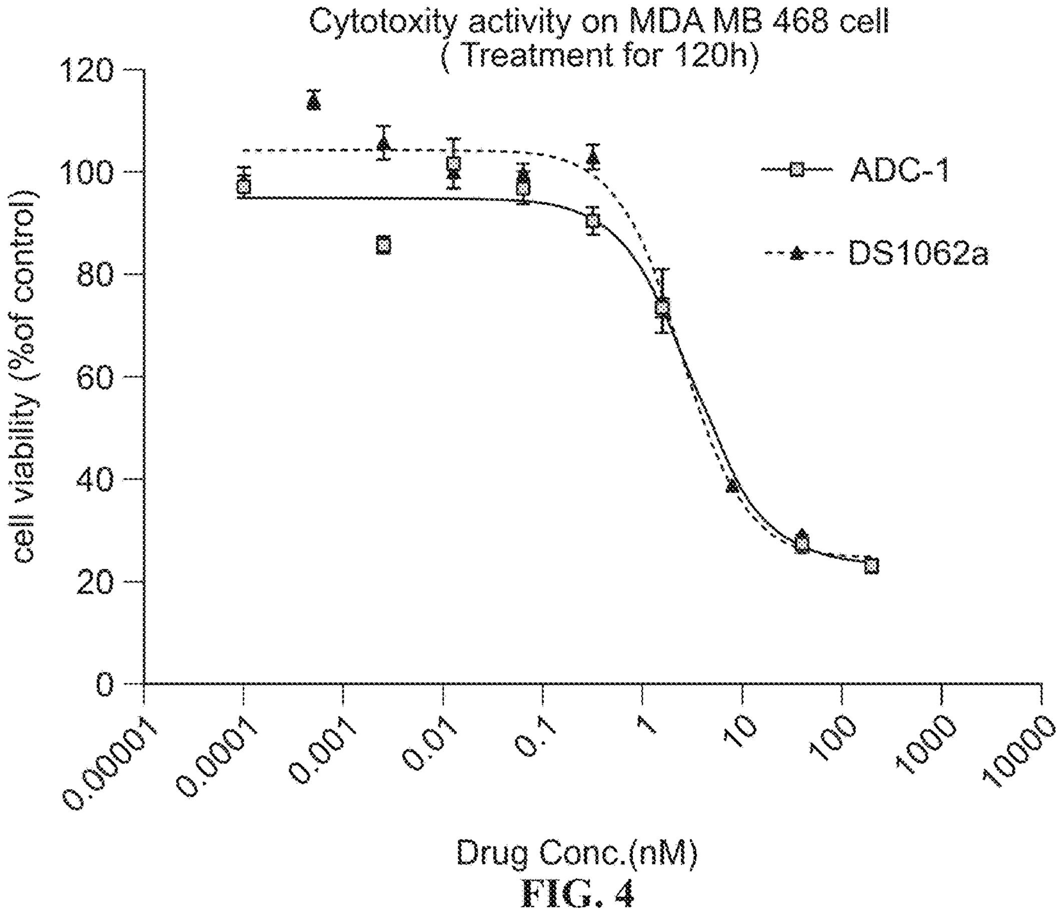
FIG. 4 shows the effect of ADC-1 and DS1062a on the viability of human breast cancer cell MDA-MB-468.

The human pharyngeal squamous cells carcinoma FaDu in Example 2.1.1 were replaced with human breast cancer cells MDA-MB-468 (100 μL per well containing 4000 cells), and the inhibitory effect of ADC-1 was evaluated using the same process. The inhibitory effect of the tested drugs on the proliferation of human breast cancer cells MDA-MB-468 is as shown in FIG. 4 and Table 9.

TABLE 9

| Inhibitory effects of ADC-1 and DS1062a on the proliferation of human breast cancer cell MDA-MB-468 | |
|---|---|
| Drug | $IC_{50}$ (nM) |
| ADC-1 | 3.347 |
| DS1062a | 2.501 |

Effect Example 2.1.4 Inhibitory Effect of ADC-7 on the Proliferation of Human Gastric Cancer Cell NCI-N87

Figure 5:
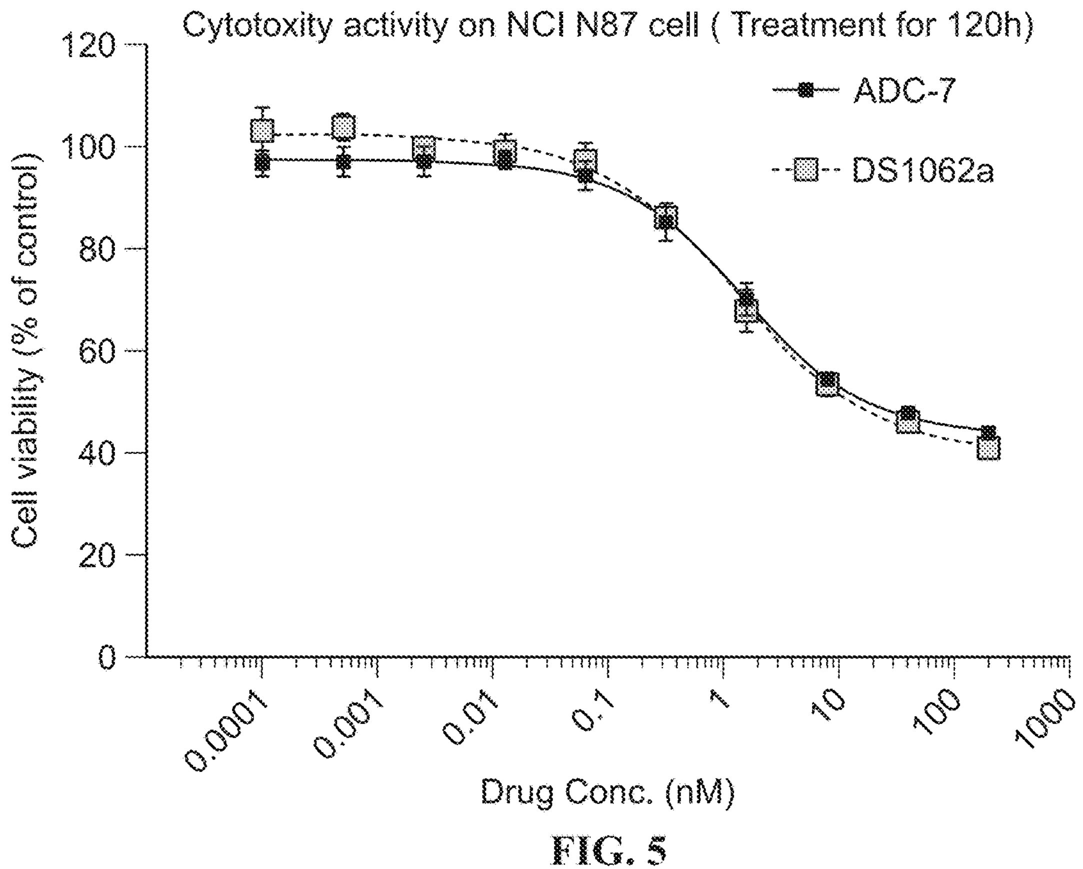
FIG. 5 shows the effect of ADC-7 and DS1062a on the viability of gastric cancer cell NCI-N87.

The human pharyngeal squamous cells carcinoma FaDu in Example 2.1.1 were replaced with human gastric cancer cells NCI-N87 (100 μL per well containing 5000 cells), and the inhibitory effect of ADC-7 was evaluated using the same process. The inhibitory effect of the tested drugs on the proliferation of human gastric cancer cell NCI-N87 is as shown in FIG. 5 and Table 10.

TABLE 10

| Inhibitory effect of ADC-7 and DS1062a on the proliferation of gastric cancer cell NCI-N87 | |
|---|---|
| Drug | $IC_{50}$ (nM) |
| ADC-7 | 1.518 |
| DS1062a | 1.262 |

Figure 6:
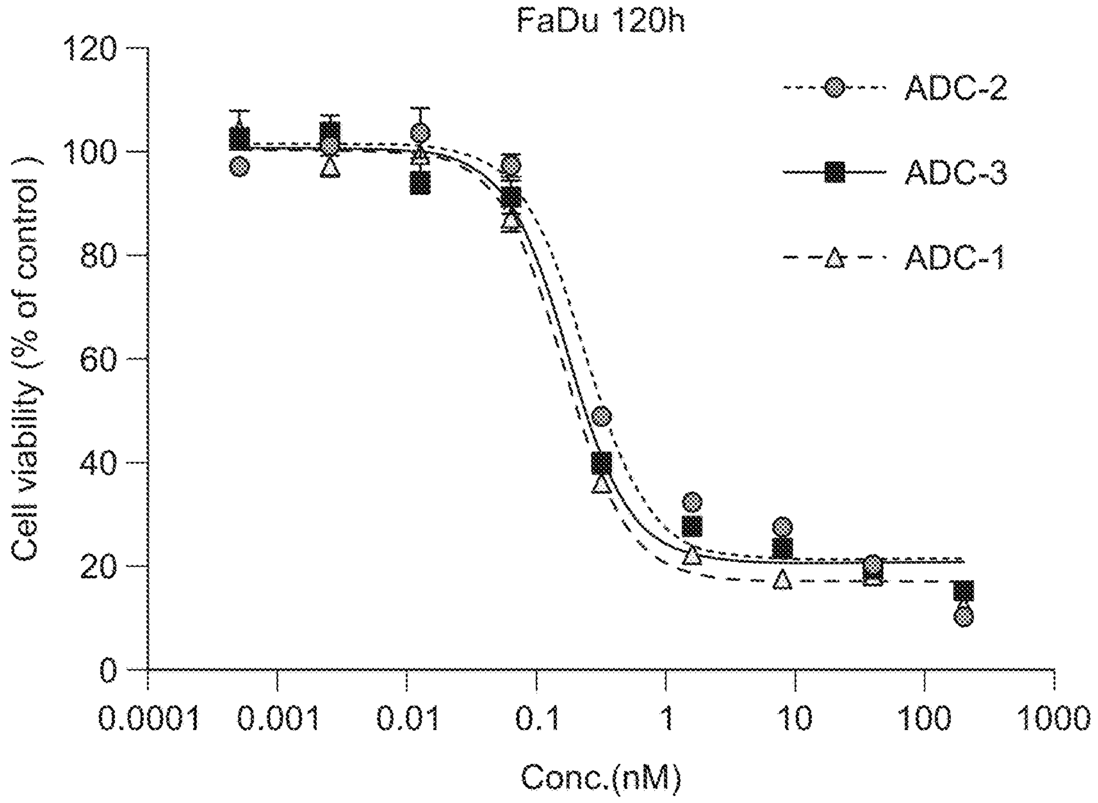
FIG. 6 shows the effect of ADC-2, ADC-3 and ADC-1 on the viability of pharyngeal squamous cells carcinoma FaDu.

Effect Example 2.2 Inhibitory Effect of ADC-2 and ADC-3 on Tumor Cell Proliferation Effect Example 2.2.1 Inhibitory Effect of ADC-2 and ADC-3 on the Proliferation of Human Pharyngeal Squamous Cells Carcinoma FaDu The tested drugs of ADC-1 and DS1062a in Example 2.1.1 were replaced with ADC-2, ADC-3 and ADC-1, and the inhibitory effects were evaluated using the same process. The inhibitory effect of the tested drugs on the proliferation of human pharyngeal squamous cell carcinoma FaDu is as shown in FIG. 6 and Table 11.

TABLE 11

| Inhibitory effect of ADC-2, ADC-3 and ADC-1 on the proliferation of pharyngeal squamous cells carcinoma FaDu | |
|---|---|
| Drug | $IC_{50}$ (nM) |
| ADC-2 | 0.2376 |
| ADC-3 | 0.1761 |
| ADC-1 | 0.1618 |

Effect Example 2.2.2 Inhibitory Effect of ADC-2 and ADC-3 on the Proliferation of Human Pancreatic Cancer Cell BxPC-3

Figure 7A:
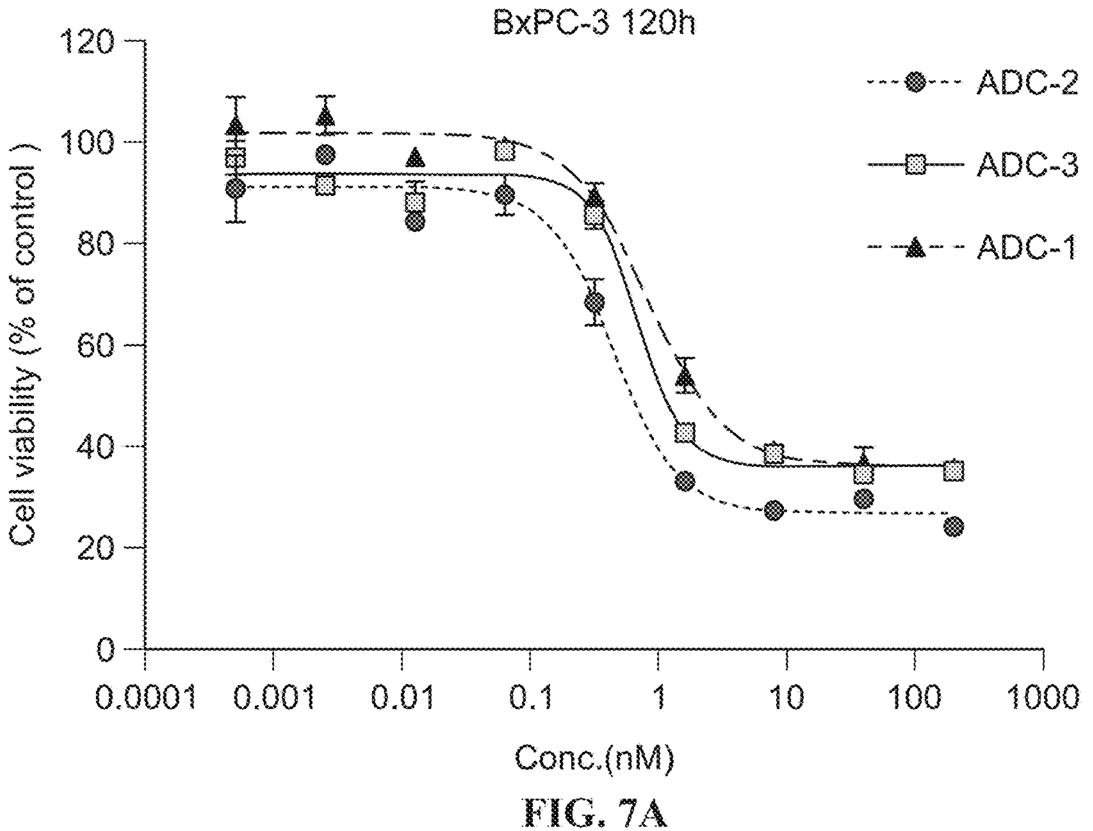
FIG. 7A shows the effect of ADC-2, ADC-3 and ADC-1 on the proliferation of human pancreatic cancer cell BxPC-3.

The human pharyngeal squamous cells carcinoma FaDu in Example 2.2.1 were replaced with human pancreatic cancer cells BxPC-3, and the inhibitory effect of ADC-2 was evaluated using the same process. The inhibitory effect of the tested drugs on the proliferation of human pancreatic cancer cells BxPC-3 is as shown in FIG. 7A and Table 12.

TABLE 12

| Inhibitory effect of ADC-2, ADC-3 and ADC-1 on the proliferation of human pancreatic cancer cell BxPC-3 | |
|---|---|
| Drug | $IC_{50}$ (nM) |
| ADC-2 | 0.4526 |
| ADC-3 | 0.6909 |
| ADC-1 | 0.8316 |

Effect Example 2.3 Inhibitory Effect of ADC-2 and DS-1062a on the Proliferation of BxPC-3, FaDu and NCI-N87

Figure 7B:
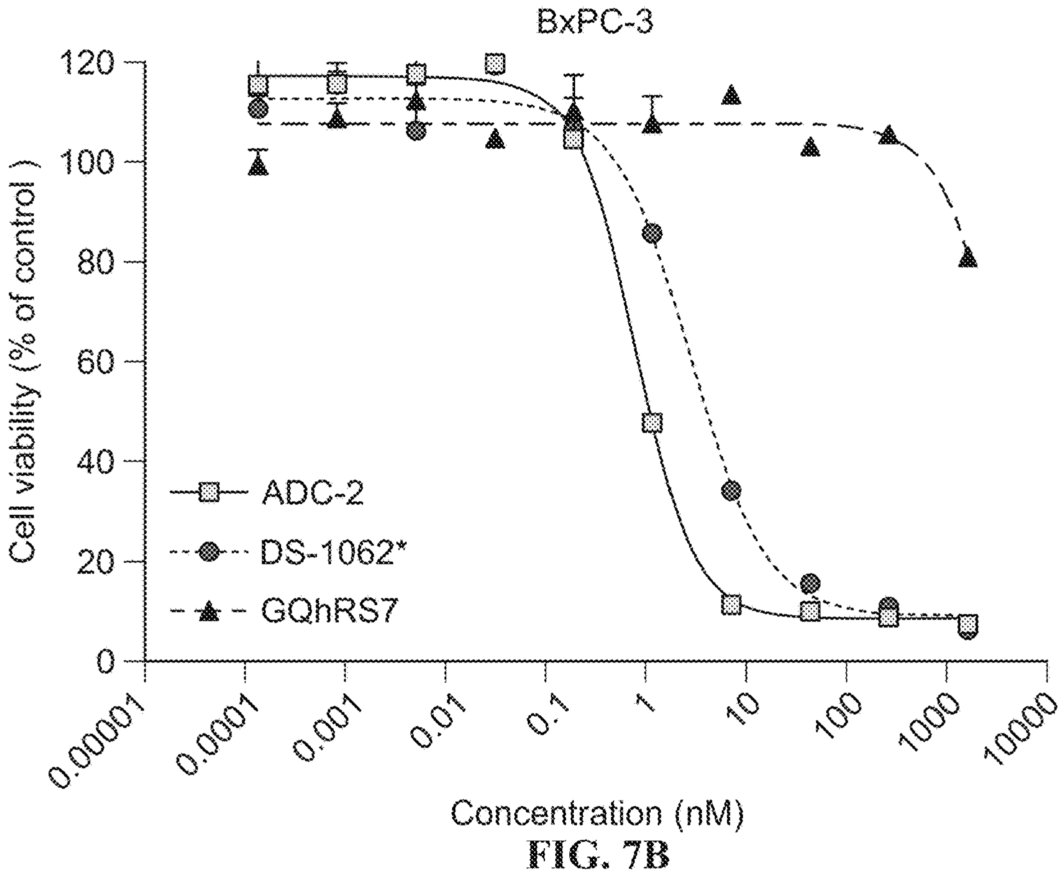
FIG. 7B shows the effect of ADC-2 on the proliferation of BxPC-3.
Figure 7C:
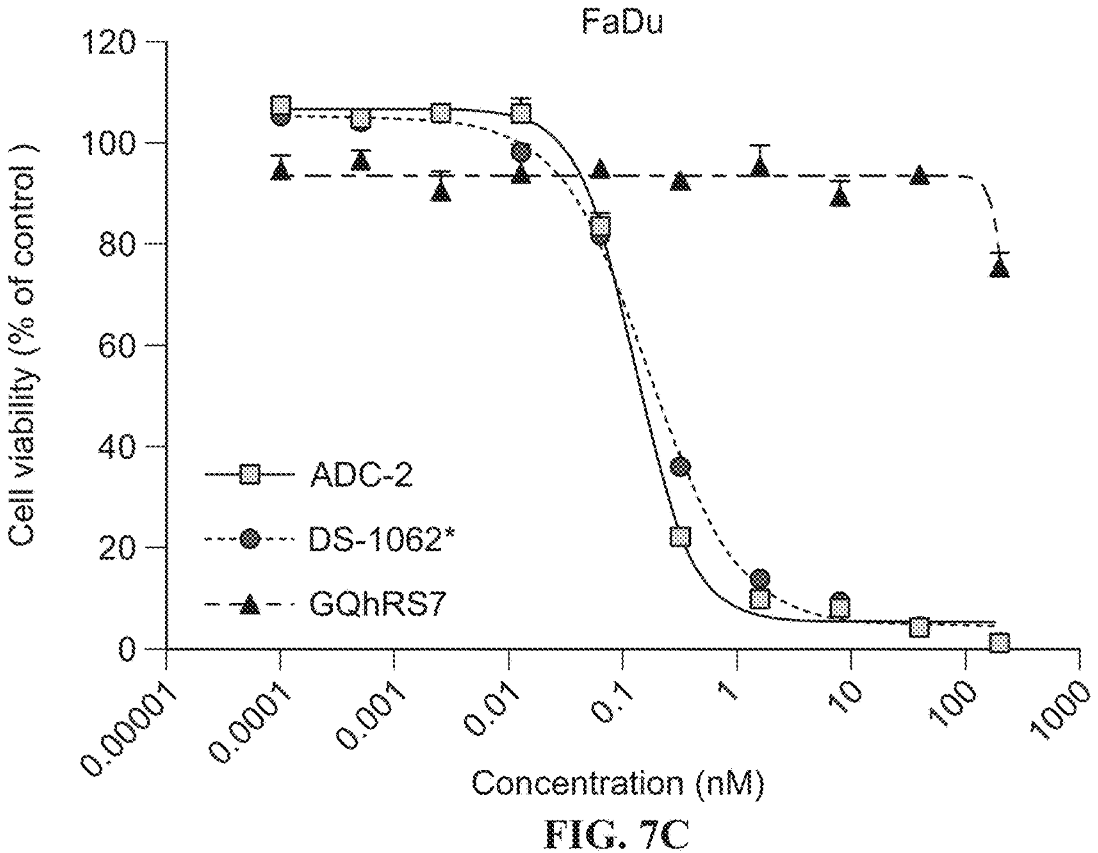
FIG. 7C shows the effect of ADC-2 on the proliferation of FaDu.
Figure 7D:
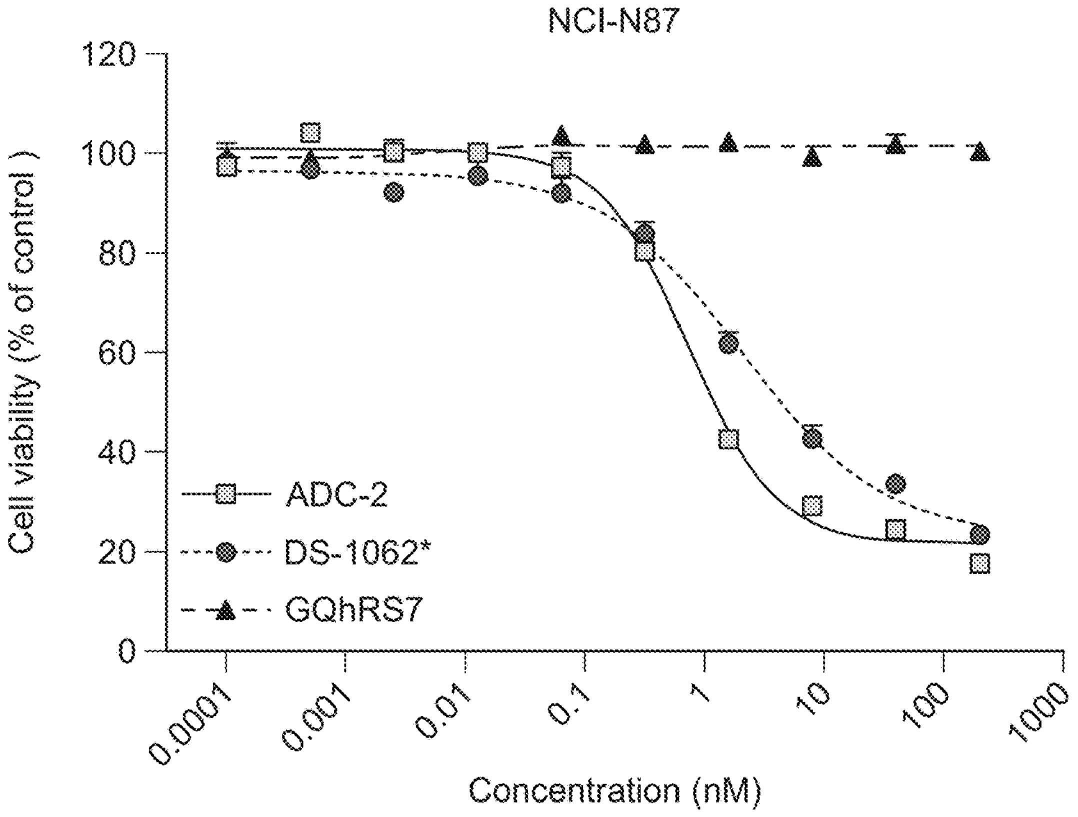
FIG. 7D shows the effect of ADC-2 on the proliferation of NCI-N87.

Cytotoxicity assays were performed using Trop2 positive cancer cells BxPC-3 (FIG. 7B), FaDu (FIG. 7C), and NCI-N87 (FIG. 7D), to analyze the effect of conjugates on tumor cell proliferation. The tested drugs included conjugates ADC2, DS1062a and the GQhRS7. In brief, 3000 to 5000 cells were plated in 96-well plates, and cells were able to attach overnight. Cells were treated with indicated drugs with various concentrations for 168 h. Cell viabilities were examined by CellTiter-Glo® Luminescent Cell Viability Assay, and percentage of cell viability was calculated.

In Trop2 positive BxPC-3, FaDu and NCI-N87, ADC2 exhibited more potent cytotoxicity than DS1062a. The $IC_{50}$ values of ADC2 are lower than DS1062a (see table below).

| | Cell lines $IC_{50}$ (nM) | | |
|---|---|---|---|
| Drugs | BxPC-3 | FaDu | NCI-N87 |
| ADC2 | 0.2260 | 0.1282 | 0.7416 |
| DS1062a | 0.6922 | 0.1701 | 2.101 |

Conclusions

The results of effect example 2.1.1 showed that both ADC-7 and DS1062a could inhibit the proliferation of FaDu cells, and the inhibitory effect of ADC-7 was slightly better.

The results of effect example 2.1.2 showed that both ADC-1 and DS1062a could inhibit the proliferation of BxPC-3 cells.

The results of effect example 2.1.3 showed that both ADC-1 and DS1062a could inhibit the proliferation of MDA-MB-468 cells.

The results of effect example 2.1.4 showed that both ADC-7 and DS1062a could inhibit the proliferation of NCI-N87 cells.

The results of effect example 2.2.1 showed that ADC-2, ADC-3 and ADC-1 could inhibit the proliferation of FaDu cells.

The results of effect example 2.2.2 showed that ADC-2, ADC-3 and ADC-1 could inhibit the proliferation of BxPC-3 cells, and the inhibitory effect of ADC-2 was slightly better than that of ADC-3 and ADC-1.

The results of effect example 2.3 showed that ADC-2 could inhibit the proliferation of BxPC-3 cells, FaDu cells and NCI-N87 cells, and the inhibitory effect of ADC-2 was better than that of DS1062a.

Effect Example 3 In Vivo Efficacy Evaluation Test

Effect Example 3.1 In Vivo Efficacy Evaluation of ADC-1

Effect Example 3.1.1 In Vivo Efficacy Evaluation of ADC-1 on BxPC-3 Cells

I. The logarithmic growth phase BxPC-3 were collected and the cell density was adjusted to $10\times10^6$ cells/mL with Matrigel buffer (PBS:Matrigel=1:1). 0.2 mL of the prepared BxPC-3 cell suspension was subcutaneously injected into the right scapula of SPF female BALB/c nude mice aged 6-8 weeks.

II. The tumor diameter was measured with a vernier caliper and the tumor volume was calculated according to the formula $V=0.5\ a\times b^2$ (where a is the longest diameter of the tumor and b is the shortest diameter of the tumor). 6 days after cell inoculation, when the average tumor volume was about 151 $mm^3$, animals were randomly divided into vehicle control group, DS1062a 3 mg/kg group and ADC-1 3 mg/kg group, with 6 animals in each group. Animals in each group were administered by tail vein injection, and the control group was given an equal volume of vehicle. The tumor volume of animals in each group was measured twice a week within 35 days after administration, and the tumor volume of animals on day 35 was compared between groups. T/C and TGI values were calculated using tumor volume. The calculation formula is as follows: T/C %=$T_{RTV}/C_{RTV}\times100\%$ ($T_{RTV}$: RTV of the treatment group; $C_{RTV}$: RTV of the vehicle control group). The relative tumor volume (RTV) was calculated based on the results of tumor measurement, and the calculation formula was $RTV=V_t/V_0$, where $V_0$ was the average tumor volume measured at the time of grouping (i.e., D0), $V_t$ was the average tumor volume at one measurement, and $T_{RTV}$ and $C_{RTV}$ took the same day of data. Calculation of TGI (%): TGI (%)=[1−(average tumor volume at the end of administration of a treatment group−average tumor volume at the beginning of administration of the treatment group)/(average tumor volume at the end of treatment of the vehicle control group−the average tumor volume at the beginning of treatment of the vehicle control group)]×100%.

Figure 8:
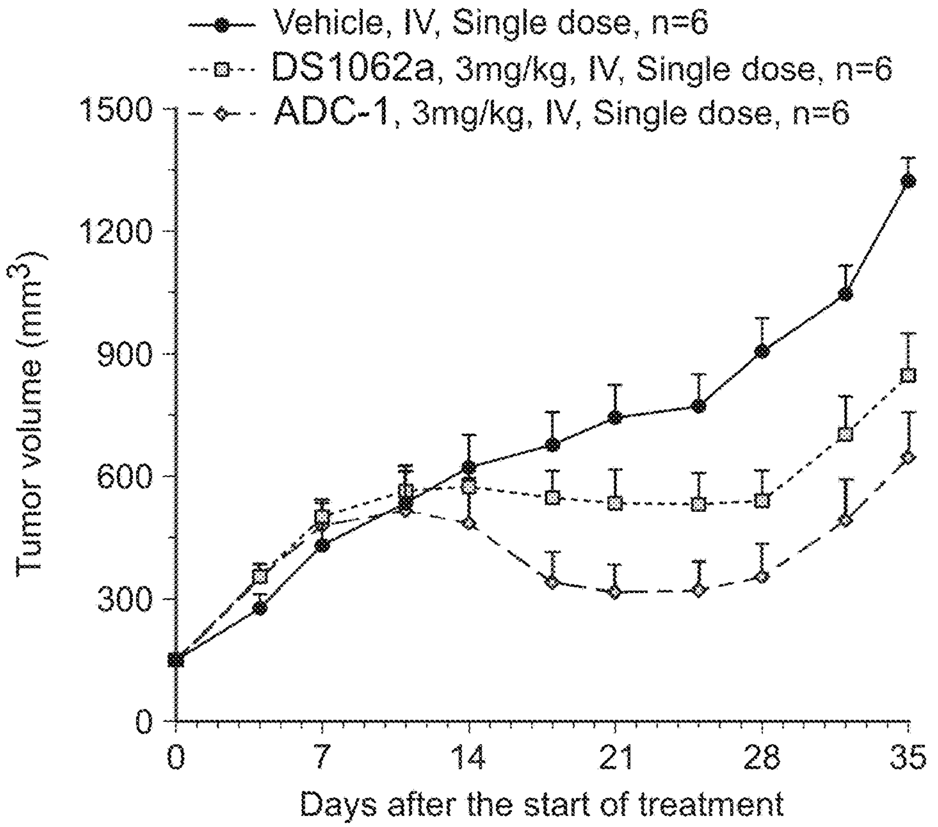
FIG. 8 shows the inhibitory effect of ADC-1 on BxPC-3 mouse xenograft tumor.

III. After 35 days of administration, ADC-1 3 mg/kg group (T/C=49.05%, TGI=57.56%, p=0.002) and DS1062a 3 mg/kg group (T/C=64.05%, TGI=40.54%, p=0.010) with a mean tumor volume of 648 $mm^3$ and 847 $mm^3$, respectively. The results were as shown in FIG. 8 and Table 13.

TABLE 13

Inhibitory effect of ADC-1 on BxPC-3 mouse xenograft tumor

| Administration group | Tumor volume ($mm^3$) Day 0 | Tumor volume ($mm^3$) Day 35 | T/C (%) | TGI (%) | p value |
|---|---|---|---|---|---|
| Vehicle | 151 ± 13 | 1,322 ± 58 | — | — | — |
| DS1062a, 3 mg/kg | 151 ± 12 | 847 ± 104 | 64.05 | 40.54 | 0.010 |
| ADC-1, 3 mg/kg | 151 ± 11 | 648 ± 109 | 49.05 | 57.56 | 0.002 |

Conclusions

According to the results of effect example 3.1.1, compared with the control group, both ADC-1 3 mg/kg group and DS1062a 3 mg/kg group could significantly inhibit tumor growth.

Figure 9:
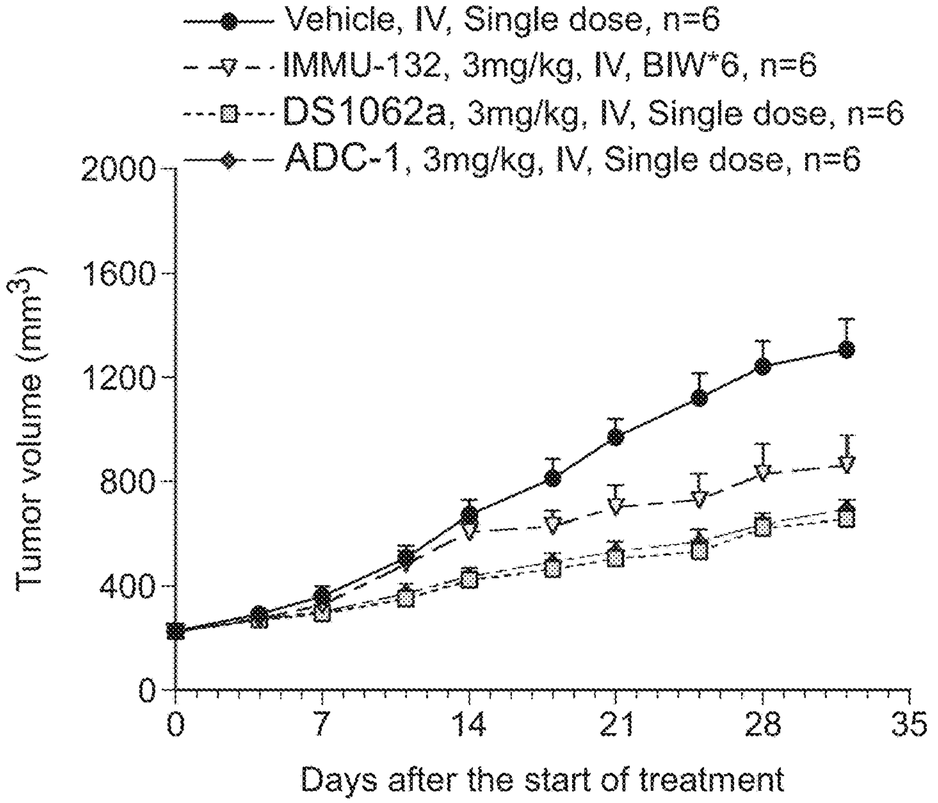
FIG. 9 shows the inhibitory effect of ADC-1 on NCI-N87 mouse xenograft tumor.

Effect Example 3.1.2 In Vivo Efficacy Evaluation of ADC-1 on NCI-N87 Gastric Cancer Cells The BxPC-3 cells in Example 3.1.1 were replaced with NCI-N87 gastric cancer cells, and 7 days after cell inoculation, when the average tumor volume was about 227 $mm^3$, animals were randomly divided into vehicle control group, IMMU-132 (Trodelvy) 3 mg/kg group, DS1062a 3 mg/kg group and ADC-1 3 mg/kg group, with 6 animals in each group. In vivo efficacy evaluation of ADC-1 was evaluated using the similar process as effect example 3.1.1, and the results are as shown in FIG. 9 and Table 14.

TABLE 14

Inhibitory effect of ADC-1 on NCI-N87 mouse xenograft tumor

| Administration group | Tumor volume ($mm^3$) Day 0 | Tumor volume ($mm^3$) Day 32 | T/C (%) | TGI (%) | p value |
|---|---|---|---|---|---|
| Vehicle | 227 ± 24 | 1,307 ± 117 | — | — | — |
| IMMU-132(BIW*6, 3 mg/kg) | 227 ± 21 | 864 ± 114 | 65.85 | 41.10 | 0.006 |

TABLE 14-continued

| Inhibitory effect of ADC-1 on NCI-N87 mouse xenograft tumor | | | | | |
|---|---|---|---|---|---|
| Administration group | Tumor volume ($mm^3$) Day 0 | Tumor volume ($mm^3$) Day 32 | T/C (%) | TGI (%) | p value |
| DS1062a(single dose, 3 mg/kg) | 228 ± 20 | 658 ± 43 | 49.98 | 60.23 | <0.001 |
| ADC-1 (single dose, 3 mg/kg) | 227 ± 24 | 697 ± 34 | 57.17 | 55.09 | <0.001 |

Conclusions

After 32 days of dosing, both of ADC-1 3 mg/kg group (T/C=57.17%, TGI=55.09%, p<0.001) and DS1062a 3 mg/kg group (T/C=49.98%, TGI=60.23%, p<0.001), with mean tumor volumes of 697 $mm^3$ and 658 $mm^3$, respectively, were able to significantly inhibit tumor growth.

Effect Example 3.1.3 In Vivo Efficacy Evaluation of ADC-1 on Human Breast Cancer BR-05-0028

Figure 10:
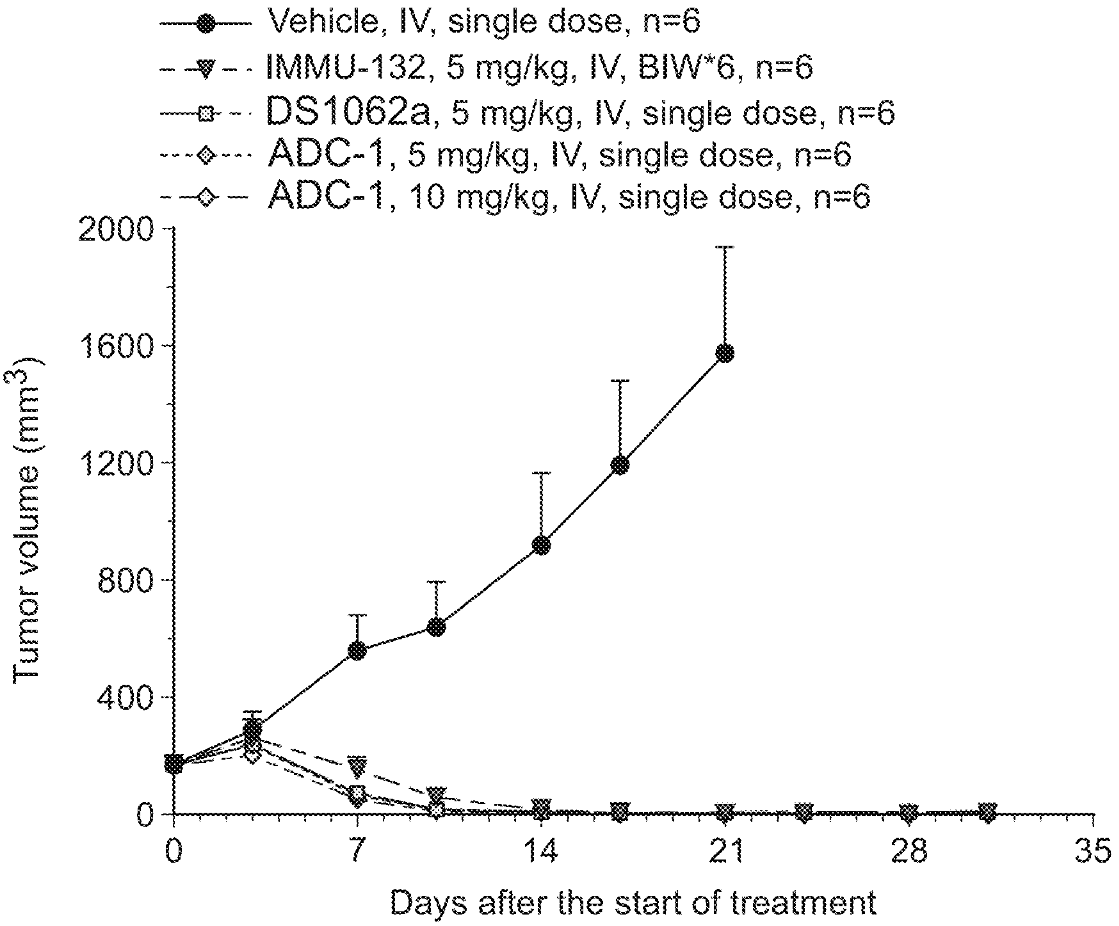
FIG. 10 shows the inhibitory effect of ADC-1 on BR-05-0028 mouse xenograft tumor.

The human breast cancer BR-05-0028 model (IHC 3+) was derived from tumor samples resected in clinical surgery. The tumor samples were inoculated into nude mice at the P0 generation, and the tumor tissue used in this example was the P5 generation. Tumor tissue with a volume of about 30 $mm^3$ was subcutaneously inoculated into the right back dorsum of SPF female BALB/c nude mice aged 6-8 weeks. 28 days after tumor tissue inoculation, when the average tumor volume was about 171 $mm^3$, animals were randomly divided into vehicle control group, IMMU-132 5 mg/kg group, DS1062a 5 mg/kg group, ADC-1 5 mg/kg group, with 6 animals in each group. In vivo efficacy evaluation of ADC-1 was evaluated using the similar process as effect example 3.1.1, and the results are as shown in FIG. 10 and Table 15.

TABLE 15

| Inhibitory effect of ADC-1 on BR-05-0028 mouse xenograft tumor | | | | | |
|---|---|---|---|---|---|
| Administration group | Tumor volume ($mm^3$) Day 0 | Tumor volume ($mm^3$) Day 21 | T/C (%) | TGI (%) | p value |
| Vehicle | 171 ± 26 | 1,576 ± 362 | — | — | — |
| IMMU-132 (BIW*6, 5 mg/kg) | 171 ± 29 | 5 ± 2 | 0.35 | 111.76 | 0.037 |
| DS1062a (single dose, 5 mg/kg) | 171 ± 23 | 8 ± 1 | 0.48 | 111.60 | 0.037 |
| ADC-1 (single dose, 5 mg/kg) | 171 ± 25 | 4 ± 2 | 0.23 | 111.88 | 0.037 |
| ADC-1 (single dose, 10 mg/kg) | 171 ± 22 | 4 ± 1 | 0.23 | 111.88 | 0.037 |

Conclusions

After 21 days of administration, IMMU-132 5 mg/kg group (T/C=0.35%, TGI=111.76%, p=0.037), DS1062a 5 mg/kg group (T/C=0.48%, TGI=111.60%, p=0.037), ADC-1 5 mg/kg group (T/C=0.23%, TGI=111.88%, p=0.037) and ADC-1 10 mg/kg group (T/C=0.23%, TGI=111.88%, p=0.037) were able to significantly inhibit tumor growth.

Effect Example 3.2 In Vivo Efficacy Evaluation of ADC-2 and ADC-3

Figure 11:
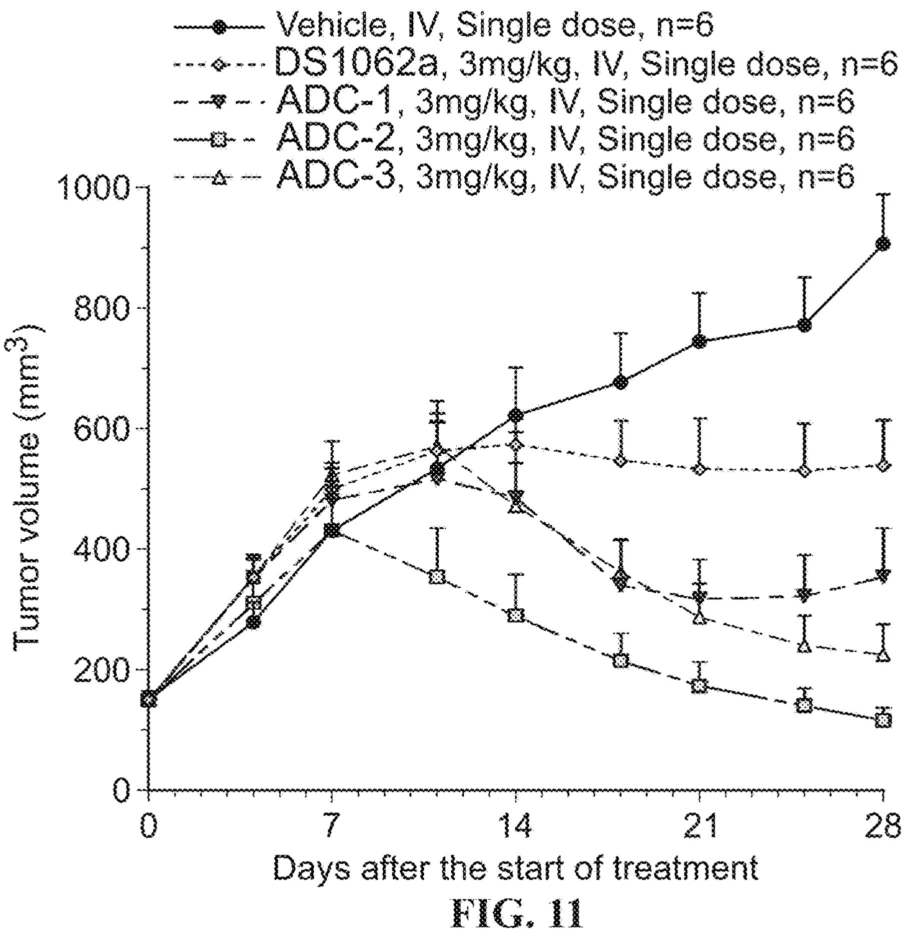
FIG. 11 shows the inhibitory effect of ADC-2 and ADC-3 on BxPC-3 mouse xenograft tumor.

Effect Example 3.2.1 In Vivo Efficacy Evaluation of ADC-2 and ADC-3 on BxPC-3 Cells 6 days after cell inoculation, when the average tumor volume was about 151 $mm^3$, animals were randomly divided into vehicle control group, DS1062a 3 mg/kg group, ADC-1 3 mg/kg group, ADC-2 3 mg/kg group and ADC-3 3 mg/kg group, with 6 animals in each group. In vivo efficacy evaluation of ADC-2 and ADC-3 was evaluated using the similar process as effect example 3.1.1, and the results are as shown in FIG. 11 and table 16.

TABLE 16

| Inhibitory effect of ADC-2 and ADC-3 on BxPC-3 mouse xenograft tumor | | | | | |
|---|---|---|---|---|---|
| Administration group | Tumor volume ($mm^3$) Day 0 | Tumor volume ($mm^3$) Day 28 | T/C (%) | TGI (%) | p value |
| Vehicle | 151 ± 13 | 906 ± 82 | — | — | — |
| ADC-1, 3 mg/kg | 151 ± 11 | 355 ± 80 | 38.20 | 72.94 | 0.005 |
| ADC-2, 3 mg/kg | 151 ± 12 | 116 ± 21 | 12.72 | 104.54 | 0.001 |
| ADC-3, 3 mg/kg | 151 ± 13 | 225 ± 51 | 23.44 | 90.25 | 0.001 |
| DS1062a, 3 mg/kg | 151 ± 12 | 540 ± 74 | 58.49 | 48.52 | 0.049 |

Conclusions

After 28 days of administration, ADC-2 3 mg/kg group (T/C=12.72%, TGI=104.54%, p=0.001) and DS1062a 3 mg/kg group (T/C=58.49%, TGI=48.52%, p=0.049), with mean tumor volumes of 116 $mm^3$ and 540 $mm^3$, respectively, indicated that the ADC-2 3 mg/kg group could significantly inhibit tumor growth.

Figure 12:
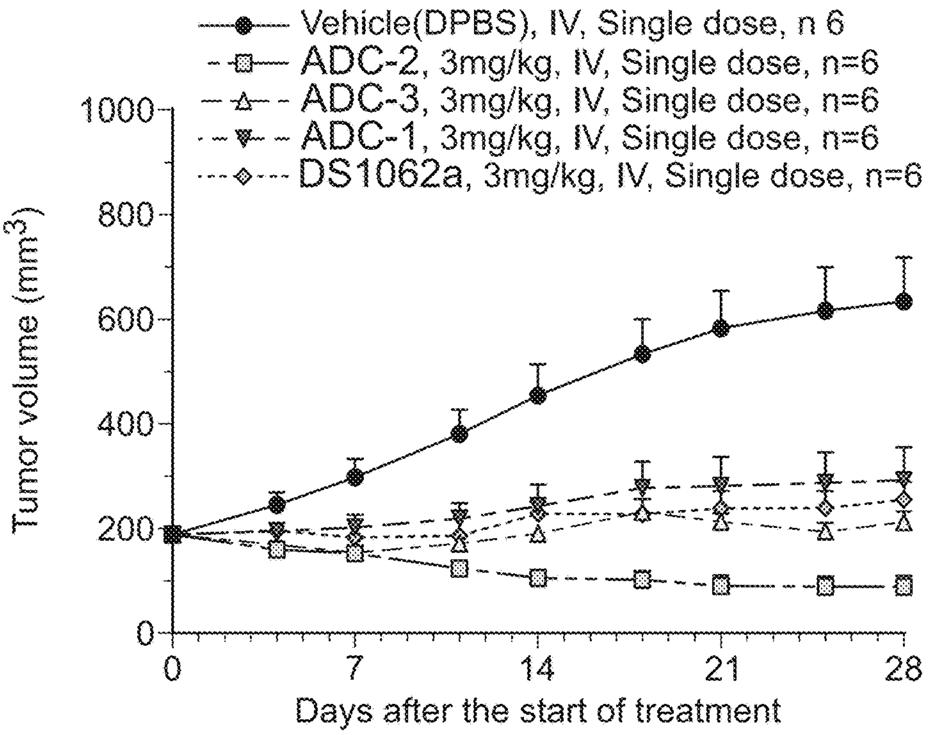
FIG. 12 shows the inhibitory effect of ADC-2, ADC-3 and ADC-1 on NCI-N87 mouse xenograft tumor.

Effect example 3.2.2 In vivo efficacy evaluation of ADC-2 and ADC-3 on NCI-N87 gastric cancer cells The BxPC-3 pancreatic cancer cells in Example 3.2.1 were replaced with NCI-N87 gastric cancer cells, and 8 days after cell inoculation, when the average tumor volume was about 188 $mm^3$, animals were randomly divided into vehicle control group, DS1062a 3 mg/kg group, ADC-1 3 mg/kg group, ADC-2 3 mg/kg group and ADC-3 3 mg/kg group, with 6 animals in each group. In vivo efficacy evaluation of ADC-2 was evaluated using the similar process as effect example 3.2.1, and the results are as shown in FIG. 12 and table 17

TABLE 17

| Inhibitory effect of ADC-2 on NCI-N87 mouse xenograft tumor | | | | | |
|---|---|---|---|---|---|
| Administration group | Tumor volume ($mm^3$) Day 0 | Tumor volume ($mm^3$) Day 28 | T/C (%) | TGI (%) | p value |
| Vehicle | 189 ± 8 | 634 ± 84 | — | — | — |
| ADC-2, 3 mg/kg | 188 ± 11 | 89 ± 21 | 14.08 | 122.25 | <0.001 |
| ADC-3, 3 mg/kg | 188 ± 9 | 212 ± 21 | 33.43 | 94.72 | <0.001 |
| ADC-1, 3 mg/kg | 189 ± 10 | 293 ± 63 | 46.15 | 76.62 | <0.001 |
| DS1062a, 3 mg/kg | 188 ± 11 | 255 ± 35 | 40.30 | 84.96 | <0.001 |

Conclusions

After 28 days of administration, ADC-2 3 mg/kg group (T/C=14.08%, TGI=122.25%, p<0.001), ADC-3 3 mg/kg group (T/C=33.43%, TGI=94.72%, p<0.001), ADC-1 3 mg/kg group (T/C=46.15%, TGI=76.62%, p<0.001) and DS1062a 3 mg/kg group (T/C=40.30%, TGI=84.96%, p<0.001), with mean tumor volumes of 89, 212, 293 and 255 $mm^3$, respectively, indicated that all the tested drugs can significantly inhibit NCI-N87 tumor growth.

Figure 13A:
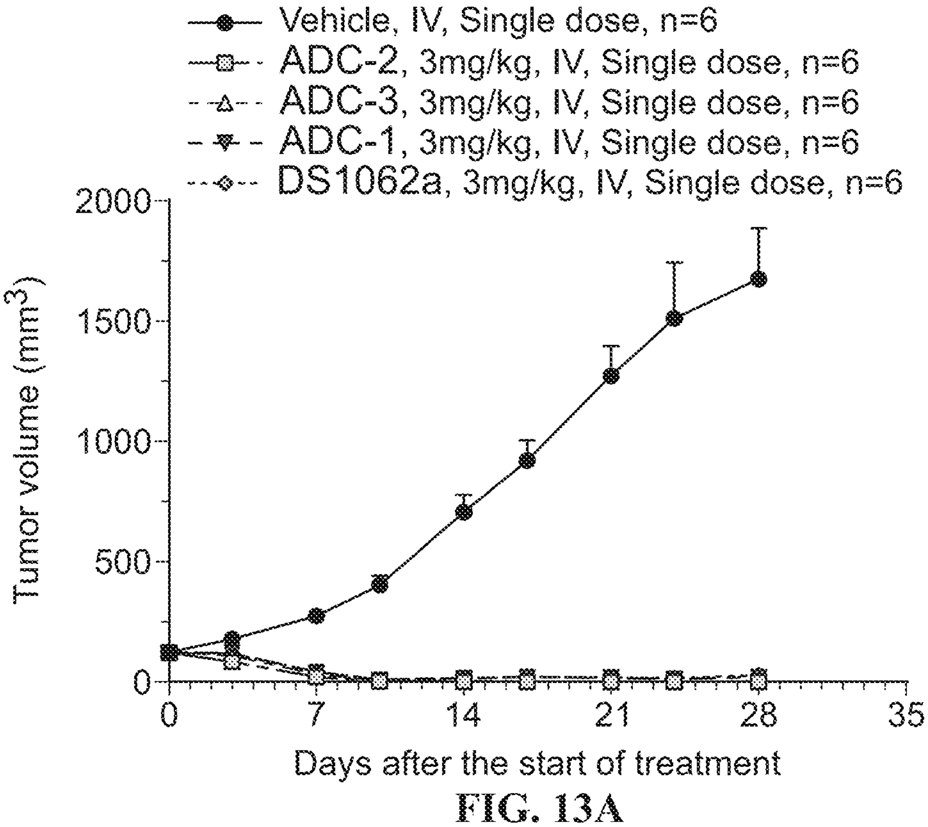
FIG. 13A shows the inhibitory effect of ADC-2, ADC-3 and ADC-1 on FaDu mouse xenograft tumor.

Effect Example 3.2.3 In Vivo Efficacy Evaluation of ADC-2 and ADC-3 on Human Pharyngeal Squamous Cells Carcinoma FaDu The BxPC-3 cells in Example 3.2.1 were replaced with human pharyngeal squamous cells carcinoma FaDu, and 11 days after cell inoculation, when the average tumor volume was about 123 $mm^3$, animals were randomly divided into vehicle control group, DS1062a 3 mg/kg group, ADC-1 3 mg/kg group, ADC-2 3 mg/kg group and ADC-2 3 mg/kg group, with 6 animals in each group. In vivo efficacy evaluation of ADC-2 was evaluated using the similar process as effect example 3.2.1, and the results are as shown in FIG. 13A and table 18.

TABLE 18

Inhibitory effect of ADC-2 on FaDu mouse xenograft tumor

| Administration group | Tumor volume ($mm^3$) Day 0 | Tumor volume ($mm^3$) Day 28 | T/C (%) | TGI (%) | p value |
|---|---|---|---|---|---|
| Vehicle | 123 ± 12 | 1,676 ± 211 | — | — | — |
| ADC-2, 3 mg/kg | 123 ± 12 | 0 ± 0 | 0.00 | 107.90 | 0.003 |
| ADC-3, 3 mg/kg | 123 ± 10 | 4 ± 3 | 0.25 | 107.63 | 0.003 |
| ADC-1, 3 mg/kg | 123 ± 13 | 21 ± 6 | 1.23 | 106.59 | 0.003 |
| DS1062a, 3 mg/kg | 123 ± 13 | 28 ± 14 | 1.68 | 106.11 | 0.003 |

Conclusions

After 28 days of administration, ADC-2 3 mg/kg group (T/C=0.00%, TGI=107.90%, p=0.003), ADC-3 3 mg/kg group (T/C=0.25%, TGI=107.63%, p=0.003), ADC-1 3 mg/kg group (T/C=1.23%, TGI=106.59%, p=0.003) and DS1062a 3 mg/kg group (T/C=1.68%, TGI=106.11%, p=0.003), with mean tumor volumes of 0, 4, 21 and 28 $mm^3$, respectively, indicated that all the tested drugs could significantly inhibit FaDu tumor growth. In addition, at the end of the experiment, 6 mice in the ADC-2 3 mg/kg group and 3 mice in the ADC-3 3 mg/kg group had complete tumor regression, respectively.

Effect Example 3.2.4 In Vivo Efficacy Evaluation of ADC-2 on MDA-MB-468

The MDA-MB-468 tumor cells (ATCC, HTB-132) were maintained in vitro as a monolayer culture in L-15 medium supplemented with 10% fetal bovine serum and 1% Anti-biotic-Antimycotic at 37° C. in an atmosphere of 0% $CO_2$ in air. The cells growing in an exponential growth phase will be harvested and counted for tumor inoculation. For in vivo anti-tumor efficacy study, $10\times10^6$ MDA-MB-468 human breast cancer cells (Trop2 positive) in 0.2 mL of PBS with Matrigel (1:1) were inoculated subcutaneously in the right flank in BALB/c Nude mice. After 24 days, when tumor volume reached 187 $mm^3$ on average, the tumor bearing mice were assigned and administrated intravenously of ADC-2 at 0.5 mg/kg, 1.5 mg/kg and 4.5 mg/kg, Trodelvy at 4.5 mg/kg and DS1062a at 4.5 mg/kg. The tumor volume was measured twice weekly with a caliper. T/C and TGI values were calculated using tumor volume.

Conclusions

Figure 13B:
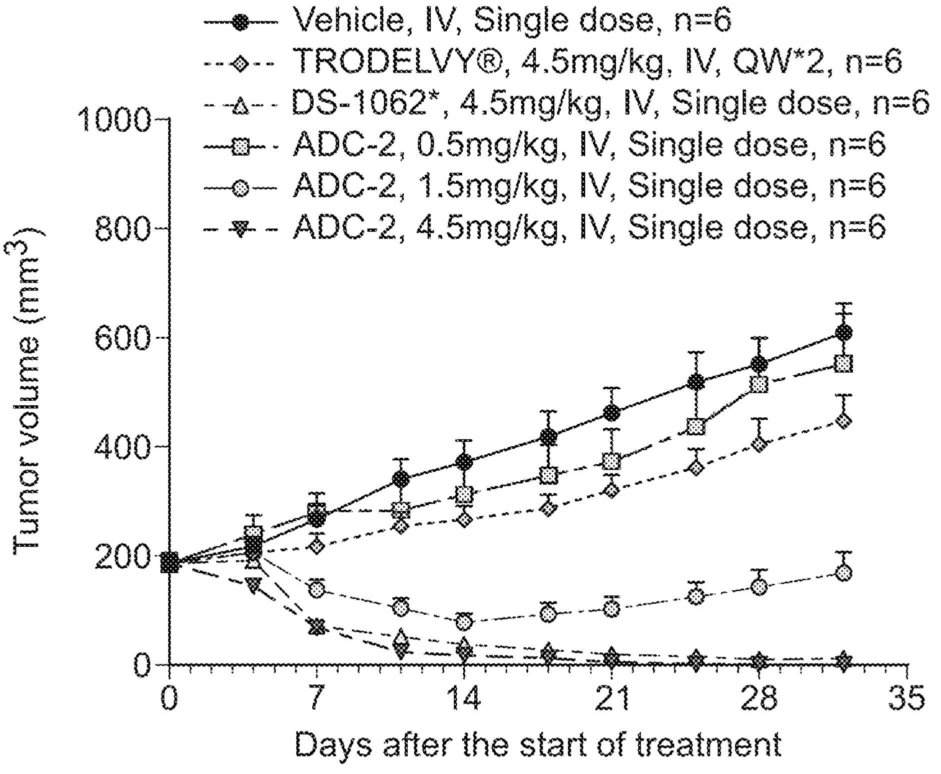
FIG. 13B shows the inhibitory effect of ADC-2 on MDA-MB-468 mouse xenograft tumor.

After 35 days of administration, ADC-2 4.5 mg/kg group (T/C=0.00%, TGI=137.93%), DS1062a 4.5 mg/kg group (T/C=1.35%, TGI=136.06%) and Trodelvy 4.5 mg/kg group (T/C=78.73%). The results were as shown in FIG. 13B and Table below. ADC-2 showed significant better efficacy than Trodelvy and slight better efficacy than DS1062a.

Inhibitory effect of ADC-2 on MDA-MB-468 mouse xenograft tumor

| Treatment | N | Tumor volume ($mm^3$) on day 35 | T/C (%) | TGI (%) | p value |
|---|---|---|---|---|---|
| Vehicle | 6 | 678 ± 68 | — | — | — |
| Trodelvy, 4.5 mg/kg | 6 | 535 ± 60 | 78.73 | 29.24 | 0.701 |
| DS1062a, 4.5 mg/kg | 6 | 9 ± 9 | 1.35 | 136.06 | 0.001 |
| ADC-2, 0.5 mg/kg | 5 | 588 ± 85 | 86.04 | 18.65 | 0.975 |
| ADC-2, 1.5 mg/kg | 6 | 202 ± 41 | 29.77 | 96.85 | 0.004 |
| ADC-2, 4.5 mg/kg | 6 | 0 ± 0 | 0.00 | 137.93 | 0.002 |

Effect Example 3.3 In Vivo Efficacy Evaluation of ADC-5 and ADC-6

Figure 14:
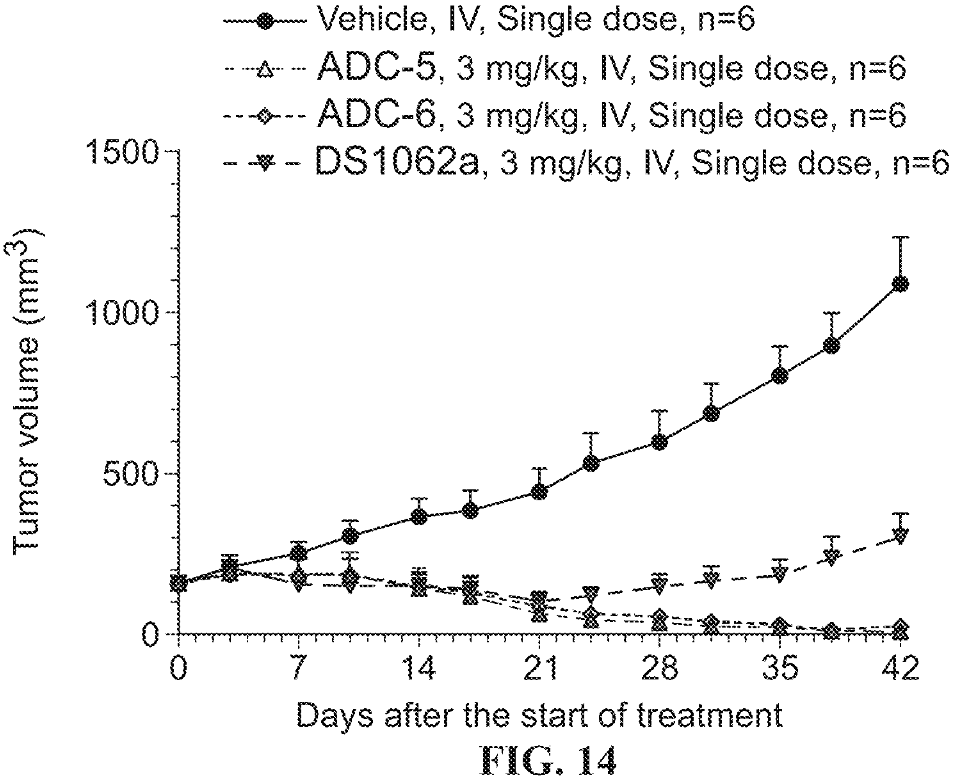
FIG. 14 shows the inhibitory effect of ADC-5 and ADC-6 on BxPC-3 mouse xenograft tumor.

Effect Example 3.3.1 In Vivo Efficacy Evaluation of ADC-5 and ADC-6 on BxPC-3 Pancreatic Cancer Cells 6 days after cell inoculation, when the average tumor volume was about 159 $mm^3$, animals were randomly divided into vehicle control group, ADC-5 3 mg/kg group, ADC-6 3 mg/kg group, and DS1062a 3 mg/kg group, with 6 animals in each group. In vivo efficacy evaluation of ADC-5 and ADC-6 was evaluated using the similar process as effect example 3.1.1, and the results are as shown in FIG. 14 and table 19.

TABLE 19

Inhibitory effects of ADC-5 and ADC-6 on BxPC-3 mouse xenograft tumor

| Administration group | Tumor volume ($mm^3$) Day 0 | Tumor volume ($mm^3$) Day 42 | T/C (%) | TGI (%) | p value |
|---|---|---|---|---|---|
| Vehicle | 159 ± 5 | 1,088 ± 145 | — | — | — |
| ADC-5, 3 mg/kg | 159 ± 7 | 8 ± 7 | 0.75 | 116.20 | 0.003 |
| ADC-6, 3 mg/kg | 159 ± 9 | 27 ± 11 | 2.48 | 114.17 | 0.003 |
| DS1062a, 3 mg/kg | 159 ± 11 | 302 ± 73 | 27.69 | 84.60 | 0.007 |

Conclusions

After 42 days of administration, ADC-5 3 mg/kg group (T/C=0.75%, TGI=116.20%, p=0.003), ADC-6 3 mg/kg group (T/C=2.48%, TGI=114.17%, p=0.003) and DS1062a 3 mg/kg groups (T/C=27.69%, TGI=84.60%, p=0.007), with mean tumor volumes of 8 $mm^3$, 27 $mm^3$ and 302 $mm^3$, respectively, indicated that all the tested drugs could significantly inhibit tumor growth; inhibitory effect of ADC-5 and ADC-6 were much better than inhibitory effect of DS1062a.

Figure 15:
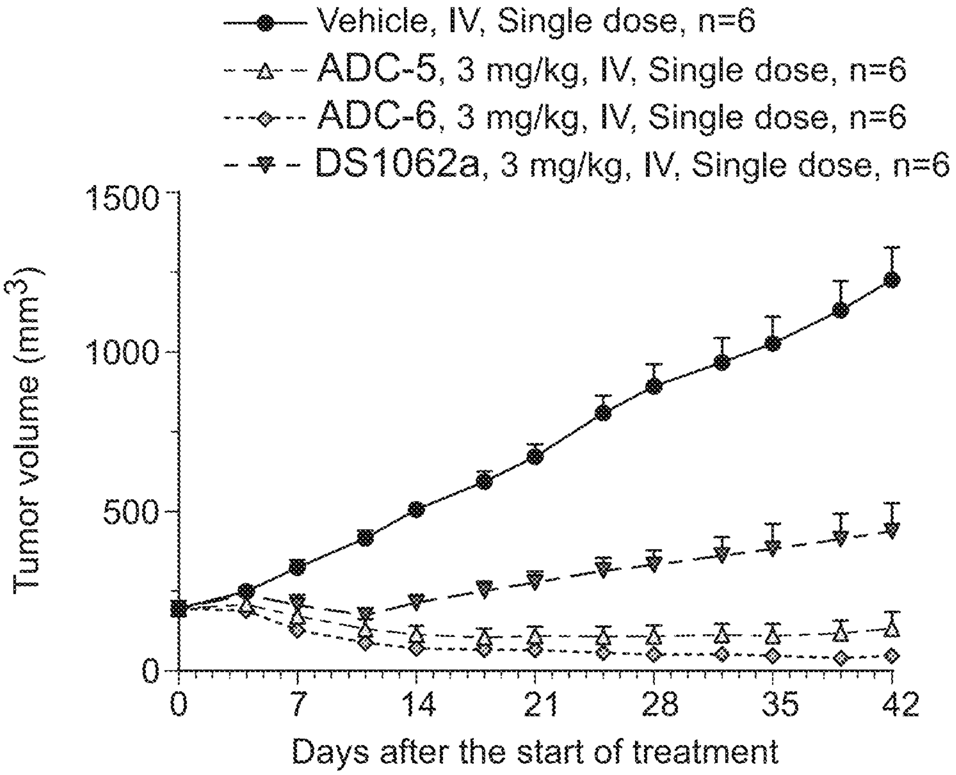
FIG. 15 shows the inhibitory effect of ADC-5 and ADC-6 on NCI-N87 mouse xenograft tumor.

Effect Example 3.3.2 In Vivo Efficacy Evaluation of ADC-5 and ADC-6 on NCI-N87 Gastric Cancer Cells The BxPC-3 pancreatic cancer cells in Example 3.3.1 were replaced with NCI-N87 gastric cancer cells, and 6 days after cell inoculation, when the average tumor volume was about 196 $mm^3$, animals were randomly divided into vehicle control group, ADC-5 3 mg/kg group, ADC-6 3 mg/kg group, and DS1062a 3 mg/kg group, with 6 animals in each group. In vivo efficacy evaluation of ADC-5 and ADC-6 was evaluated using the similar process as effect example 3.3.1, and the results are as shown in FIG. 15 and table 20.

TABLE 20

Inhibitory effects of ADC-5 and ADC-6 on NCI-N87 mouse xenograft tumor

| Administration group | Tumor volume ($mm^3$) Day 0 | Tumor volume ($mm^3$) Day 42 | T/C (%) | TGI (%) | p value |
|---|---|---|---|---|---|
| Vehicle | 196 ± 11 | 1,226 ± 102 | — | — | — |
| ADC-5, 3 mg/kg | 196 ± 15 | 133 ± 51 | 10.88 | 106.06 | <0.001 |
| ADC-6, 3 mg/kg | 196 ± 12 | 48 ± 19 | 3.89 | 114.36 | <0.001 |
| DS1062a, 3 mg/kg | 196 ± 14 | 437 ± 89 | 35.67 | 76.58 | <0.001 |

Conclusions

After 42 days of administration, ADC-5 3 mg/kg group (T/C=10.88%, TGI=106.06%, p<0.001), ADC-6 3 mg/kg group (T/C=3.89%, TGI=114.36%, p<0.001) and DS1062a 3 mg/kg groups (T/C=35.67%, TGI=76.58%, p<0.001), with mean tumor volumes of 133 $mm^3$, 48 $mm^3$ and 437 $mm^3$, respectively, indicated that all the tested drugs could significantly inhibit tumor growth; inhibitory effect of ADC-5 and ADC-6 were much better than inhibitory effect of DS1062a.

Figure 16:
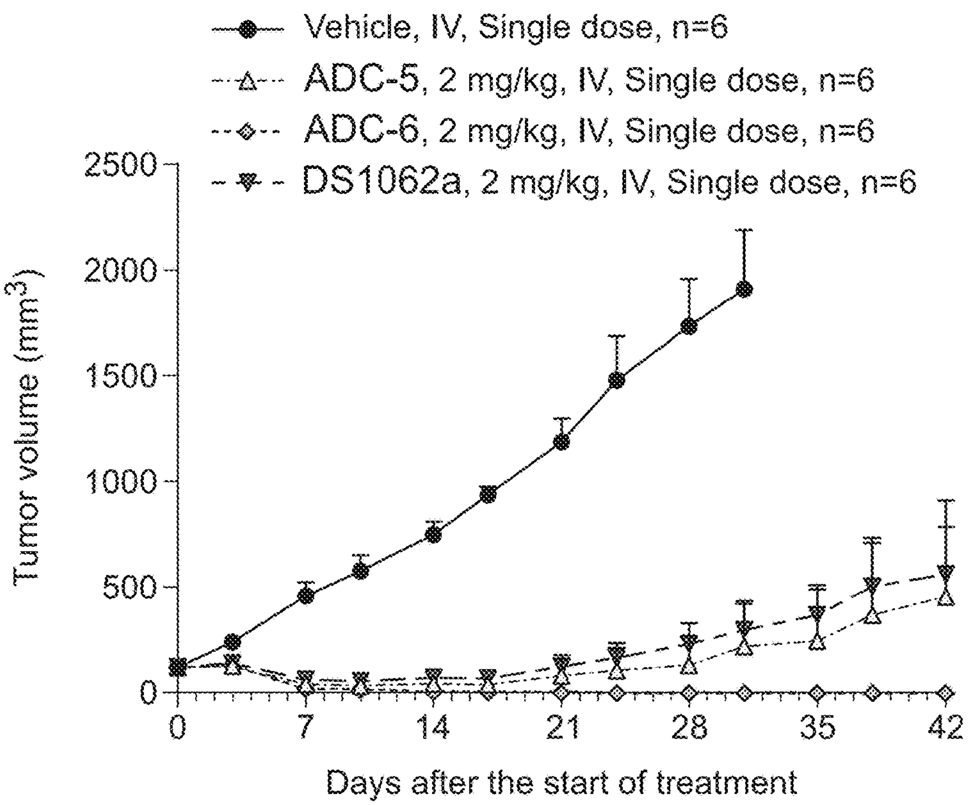
FIG. 16 shows the inhibitory effect of ADC-5 and ADC-6 on FaDu mouse xenograft tumor.

Effect Example 3.3.3 In Vivo Efficacy Evaluation of ADC-5 and ADC-6 on Human Pharyngeal Squamous Cells Carcinoma FaDu The BxPC-3 pancreatic cancer cells in Example 3.3.1 were replaced with human pharyngeal squamous cells carcinoma FaDu, and 10 days after cell inoculation, when the average tumor volume was about 119 $mm^3$, animals were randomly divided into vehicle control group, ADC-5 2 mg/kg group, ADC-6 2 mg/kg group, and DS1062a 2 mg/kg group, with 6 animals in each group. In vivo efficacy evaluation of ADC-5 and ADC-6 was evaluated using the similar process as effect example 3.3.1, and the results are as shown in FIG. 16 and table 21.

TABLE 21

Inhibitory effects of ADC-5 and ADC-6 on FaDu mouse xenograft tumor

| Administration group | Tumor volume ($mm^3$) Day 0 | Tumor volume ($mm^3$) Day 31 | T/C (%) | TGI (%) | p value |
|---|---|---|---|---|---|
| Vehicle | 119 ± 10 | 1,911 ± 279 | — | — | — |
| ADC-5, 2 mg/kg | 119 ± 11 | 217 ± 216 | 11.34 | 94.56 | 0.004 |
| ADC-6, 2 mg/kg | 119 ± 12 | 1 ± 0 | 0.05 | 106.60 | 0.004 |
| DS1062a, 2 mg/kg | 119 ± 11 | 296 ± 125 | 15.47 | 90.15 | 0.005 |

Conclusions

After 31 days of administration, ADC-5 2 mg/kg group (T/C=11.34%, TGI=94.56%, p=0.004), ADC-6 2 mg/kg group (T/C=0.05%, TGI=106.60%, p=0.004) and DS1062a 2 mg/kg groups (T/C=15.47%, TGI=90.15%, p=0.005), with mean tumor volumes of 217 $mm^3$, 1 $mm^3$ and 296 $mm^3$, respectively, indicated that all the tested drugs could significantly inhibit tumor growth; inhibitory effect of ADC-6 was much better than inhibitory effect of DS1062a.

Effect Example 4 the Serum Stability of ADC-1

Figure 17:
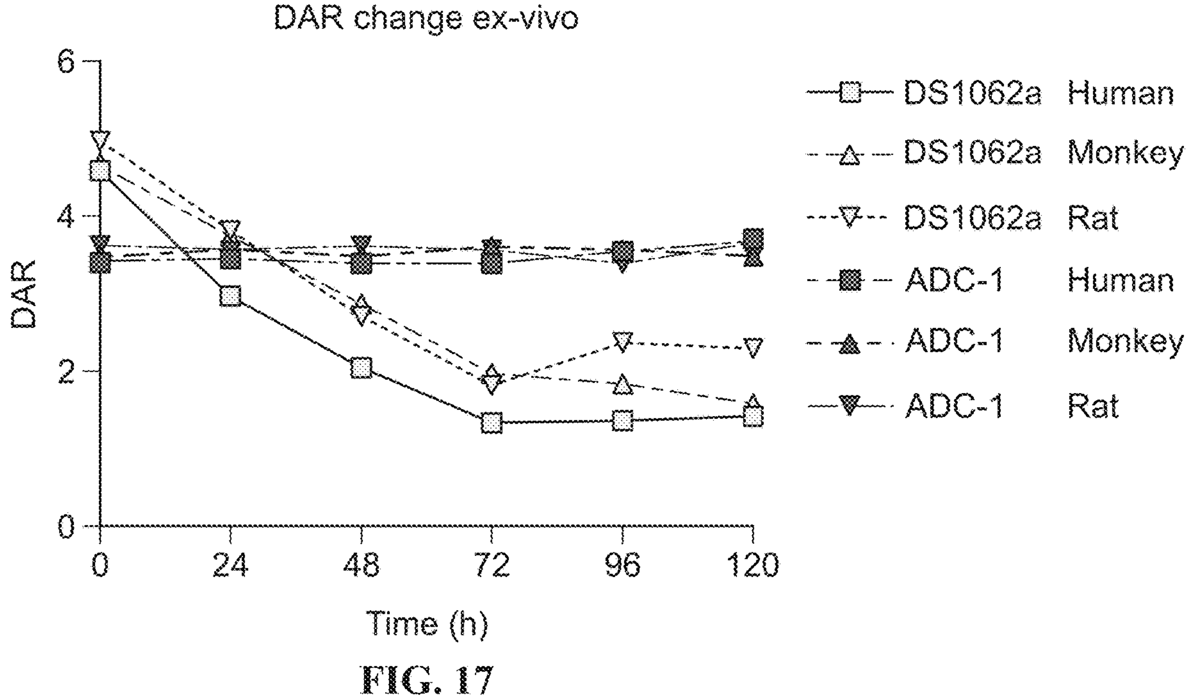
FIG. 17 shows the results of serum stability of ADC-1.

An appropriate amount of Trop 2 was bound to CNBr-activated agarose microspheres by covalent coupling to form immobilized antigens. After blocking, the stable samples pre-incubated with plasma were added in a certain proportion, and incubated with shaking. ADC-1 and DS1062a (ADC drugs) in the matrix will be specifically captured by the immobilized antigen to form a solid-phase antigen/antibody complex, and the unbound substances are removed by washing. After the incubation, N-glycosidase was used to excise the coupled sugar chain of the Fc region of the ADC drug antibody, and then the ADC was recovered by formic acid elution, and the DAR was detected by LC-MS. The results were as shown in FIG. 17.

CONCLUSION

The results showed that the serum stability of ADC-1 was significantly better than that of DS1062a.

The invention claimed is:

1. An antibody drug conjugate comprising an antibody, a linker, and a payload, wherein the antibody drug conjugate is represented by the following structural formula:

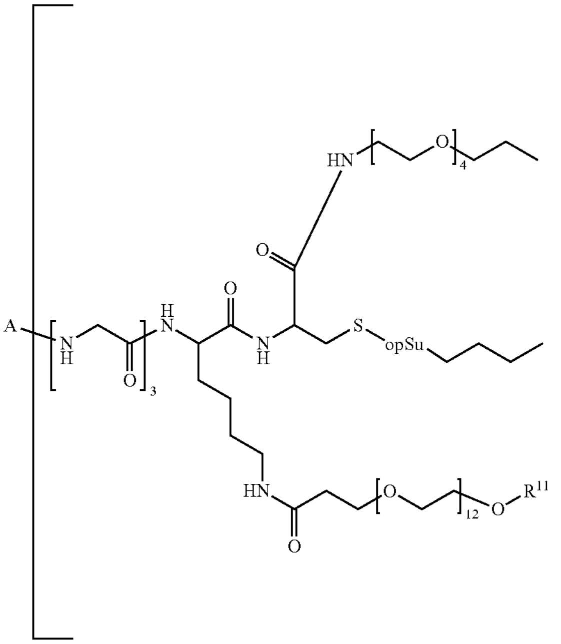

-continued

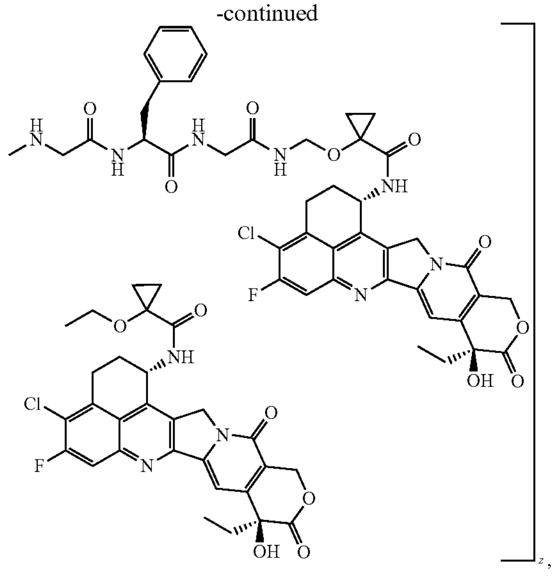

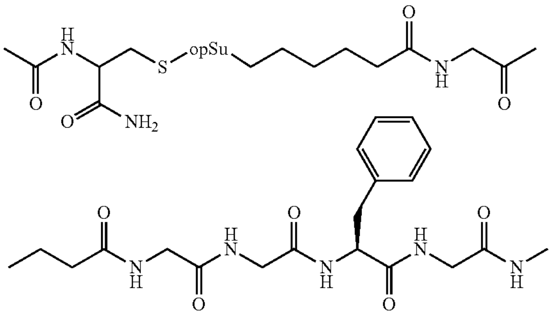

wherein A is an antibody GQhRS7, wherein the amino acid sequence of each heavy chain of the antibody is SEQ ID NO: 30, wherein the amino acid sequence of each light chain of the antibody is SEQ ID NO: 40 modified by deletion of GG in the LPETGG sequence, and wherein the T of the LPET is connected to the linker; and wherein each occurrence of opSu is independently a structure selected from

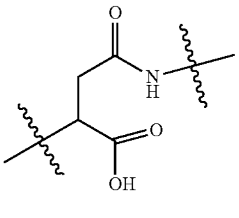

and

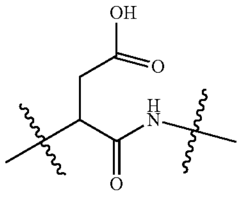

.

2. A pharmaceutical composition comprising an effective amount of the antibody drug conjugate of claim 1 and a pharmaceutically acceptable carrier, excipient or diluent.

* * * * *

SEQUENCE LISTING

```
Sequence total quantity: 41
SEQ ID NO: 1            moltype =   length =
SEQUENCE: 1
000

SEQ ID NO: 2            moltype = AA  length = 17
FEATURE                 Location/Qualifiers
source                  1..17
                        mol_type = protein
                        organism = synthetic construct
VARIANT                 5
                        note = X is Y, H or D
```

```
VARIANT                 6
                        note = X is T or S
VARIANT                 8
                        note = X is E or V
VARIANT                 10
                        note = X is T or K
VARIANT                 12
                        note = X is T or A
VARIANT                 13
                        note = X is D or E
SEQUENCE: 2
WINTXXGXPX YXXDFKG                                                    17

SEQ ID NO: 3            moltype = AA  length = 12
FEATURE                 Location/Qualifiers
source                  1..12
                        mol_type = protein
                        organism = synthetic construct
VARIANT                 1
                        note = X is G or S
SEQUENCE: 3
XGFGSSYWYF DV                                                         12

SEQ ID NO: 4            moltype = AA  length = 5
FEATURE                 Location/Qualifiers
source                  1..5
                        mol_type = protein
                        organism = synthetic construct
SEQUENCE: 4
NYGMN                                                                 5

SEQ ID NO: 5            moltype = AA  length = 5
FEATURE                 Location/Qualifiers
source                  1..5
                        mol_type = protein
                        organism = synthetic construct
SEQUENCE: 5
TAGMQ                                                                 5

SEQ ID NO: 6            moltype = AA  length = 5
FEATURE                 Location/Qualifiers
source                  1..5
                        mol_type = protein
                        organism = synthetic construct
SEQUENCE: 6
AAGMN                                                                 5

SEQ ID NO: 7            moltype = AA  length = 5
FEATURE                 Location/Qualifiers
source                  1..5
                        mol_type = protein
                        organism = synthetic construct
SEQUENCE: 7
NAGMN                                                                 5

SEQ ID NO: 8            moltype = AA  length = 17
FEATURE                 Location/Qualifiers
source                  1..17
                        mol_type = protein
                        organism = synthetic construct
SEQUENCE: 8
WINTYTGEPT YTDDFKG                                                    17

SEQ ID NO: 9            moltype = AA  length = 17
FEATURE                 Location/Qualifiers
source                  1..17
                        mol_type = protein
                        organism = synthetic construct
SEQUENCE: 9
WINTHSGVPK YAEDFKG                                                    17

SEQ ID NO: 10           moltype = AA  length = 17
FEATURE                 Location/Qualifiers
source                  1..17
                        mol_type = protein
                        organism = synthetic construct
SEQUENCE: 10
WINTDSGEPT YTDDFKG                                                    17
```

-continued

```
SEQ ID NO: 11          moltype = AA  length = 12
FEATURE                Location/Qualifiers
source                 1..12
                       mol_type = protein
                       organism = synthetic construct
SEQUENCE: 11
GGFGSSYWYF DV                                                      12

SEQ ID NO: 12          moltype = AA  length = 12
FEATURE                Location/Qualifiers
source                 1..12
                       mol_type = protein
                       organism = synthetic construct
SEQUENCE: 12
SGFGSSYWYF DV                                                      12

SEQ ID NO: 13          moltype = AA  length = 11
FEATURE                Location/Qualifiers
source                 1..11
                       mol_type = protein
                       organism = synthetic construct
SEQUENCE: 13
KASQDVSIAV A                                                       11

SEQ ID NO: 14          moltype = AA  length = 11
FEATURE                Location/Qualifiers
source                 1..11
                       mol_type = protein
                       organism = synthetic construct
SEQUENCE: 14
KASQDVSTAV A                                                       11

SEQ ID NO: 15          moltype = AA  length = 7
FEATURE                Location/Qualifiers
source                 1..7
                       mol_type = protein
                       organism = synthetic construct
SEQUENCE: 15
SASYRYT                                                            7

SEQ ID NO: 16          moltype = AA  length = 9
FEATURE                Location/Qualifiers
source                 1..9
                       mol_type = protein
                       organism = synthetic construct
SEQUENCE: 16
QQHYITPLT                                                          9

SEQ ID NO: 17          moltype = AA  length = 30
FEATURE                Location/Qualifiers
source                 1..30
                       mol_type = protein
                       organism = synthetic construct
SEQUENCE: 17
QVQLQQSGSE LKKPGASVKV SCKASGYTFT                                   30

SEQ ID NO: 18          moltype = AA  length = 14
FEATURE                Location/Qualifiers
source                 1..14
                       mol_type = protein
                       organism = synthetic construct
SEQUENCE: 18
WVKQAPGQGL KWMG                                                    14

SEQ ID NO: 19          moltype = AA  length = 32
FEATURE                Location/Qualifiers
source                 1..32
                       mol_type = protein
                       organism = synthetic construct
SEQUENCE: 19
RFAFSLDTSV STAYLQISSL KADDTAVYFC AR                                32

SEQ ID NO: 20          moltype = AA  length = 11
FEATURE                Location/Qualifiers
source                 1..11
                       mol_type = protein
                       organism = synthetic construct
SEQUENCE: 20
WGQGSLVTVS S                                                       11
```

```
SEQ ID NO: 21          moltype = AA  length = 121
FEATURE                Location/Qualifiers
source                 1..121
                       mol_type = protein
                       organism = synthetic construct
SEQUENCE: 21
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
S                                                                 121

SEQ ID NO: 22          moltype = AA  length = 121
FEATURE                Location/Qualifiers
source                 1..121
                       mol_type = protein
                       organism = synthetic construct
SEQUENCE: 22
QVQLVQSGAE VKKPGASVKV SCKASGYTFT TAGMQWVRQA PGQGLEWMGW INTHSGVPKY  60
AEDFKGRVTI SADTSTSTAY LQLSSLKSED TAVYYCARSG FGSSYWYFDV WGQGTLVTVS  120
S                                                                 121

SEQ ID NO: 23          moltype = AA  length = 121
FEATURE                Location/Qualifiers
source                 1..121
                       mol_type = protein
                       organism = synthetic construct
SEQUENCE: 23
QVQLQQSGSE LKKPGASVKV SCKASGYTFT NAGMNWVKQA PGQGLKWMGW INTDSGEPTY  60
TDDFKGRFAF SLDTSVSTAY LQISSLKADD TAVYFCARGG FGSSYWYFDV WGQGSLVTVS  120
S                                                                 121

SEQ ID NO: 24          moltype = AA  length = 121
FEATURE                Location/Qualifiers
source                 1..121
                       mol_type = protein
                       organism = synthetic construct
SEQUENCE: 24
QVQLQQSGSE LKKPGASVKV SCKASGYTFT AAGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
S                                                                 121

SEQ ID NO: 25          moltype = AA  length = 121
FEATURE                Location/Qualifiers
source                 1..121
                       mol_type = protein
                       organism = synthetic construct
SEQUENCE: 25
QVQLQQSGSE LKKPGASVKV SCKASGYTFT NYGMNWVKQA PGQGLKWMGW INTDSGEPTY  60
TDDFKGRFAF SLDTSVSTAY LQISSLKADD TAVYFCARGG FGSSYWYFDV WGQGSLVTVS  120
S                                                                 121

SEQ ID NO: 26          moltype = AA  length = 110
FEATURE                Location/Qualifiers
source                 1..110
                       mol_type = protein
                       organism = synthetic construct
SEQUENCE: 26
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV            110

SEQ ID NO: 27          moltype = AA  length = 110
FEATURE                Location/Qualifiers
source                 1..110
                       mol_type = protein
                       organism = synthetic construct
SEQUENCE: 27
DIQMTQSPSS LSASVGDRVT ITCKASQDVS TAVAWYQQKP GKAPKLLIYS ASYRYTGVPS  60
RFSGSGSGTD FTLTISSLQP EDFAVYYCQQ HYITPLTFGQ GTKLEIKRTV            110

SEQ ID NO: 28          moltype = AA  length = 330
FEATURE                Location/Qualifiers
source                 1..330
                       mol_type = protein
                       organism = synthetic construct
SEQUENCE: 28
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
```

-continued

```
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 29          moltype = AA  length = 104
FEATURE                Location/Qualifiers
source                 1..104
                       mol_type = protein
                       organism = synthetic construct
SEQUENCE: 29
AAPSVFIFPP SDEQLKSGTA SVVCLLNNFY PREAKVQWKV DNALQSGNSQ ESVTEQDSKD  60
STYSLSSTLT LSKADYEKHK VYACEVTHQG LSSPVTKSFN RGEC                   104

SEQ ID NO: 30          moltype = AA  length = 451
FEATURE                Location/Qualifiers
source                 1..451
                       mol_type = protein
                       organism = synthetic construct
SEQUENCE: 30
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 31          moltype = AA  length = 451
FEATURE                Location/Qualifiers
source                 1..451
                       mol_type = protein
                       organism = synthetic construct
SEQUENCE: 31
QVQLQQSGSE LKKPGASVKV SCKASGYTFT NAGMNWVKQA PGQGLKWMGW INTDSGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 32          moltype = AA  length = 451
FEATURE                Location/Qualifiers
source                 1..451
                       mol_type = protein
                       organism = synthetic construct
SEQUENCE: 32
QVQLQQSGSE LKKPGASVKV SCKASGYTFT AAGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 33          moltype = AA  length = 451
FEATURE                Location/Qualifiers
source                 1..451
                       mol_type = protein
                       organism = synthetic construct
SEQUENCE: 33
QVQLVQSGAE VKKPGASVKV SCKASGYTFT TAGMQWVRQA PGQGLEWMGW INTHSGVPKY  60
AEDFKGRVTI SADTSTSTAY LQLSSLKSED TAVYYCARSG FGSSYWYFDV WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 34          moltype = AA  length = 214
FEATURE                Location/Qualifiers
source                 1..214
                       mol_type = protein
                       organism = synthetic construct
SEQUENCE: 34
DIQLTQSPSS LSASVGDRVS ITCKASQDVS IAVAWYQQKP GKAPKLLIYS ASYRYTGVPD  60
```

-continued

```
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 35           moltype = AA  length = 214
FEATURE                 Location/Qualifiers
source                  1..214
                        mol_type = protein
                        organism = synthetic construct
SEQUENCE: 35
DIQMTQSPSS LSASVGDRVT ITCKASQDVS TAVAWYQQKP GKAPKLLIYS ASYRYTGVPS  60
RFSGSGSGTD FTLTISSLQP EDFAVYYCQQ HYITPLTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 36           moltype = AA  length = 457
FEATURE                 Location/Qualifiers
source                  1..457
                        mol_type = protein
                        organism = synthetic construct
SEQUENCE: 36
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG ALPETGG                           457

SEQ ID NO: 37           moltype = AA  length = 457
FEATURE                 Location/Qualifiers
source                  1..457
                        mol_type = protein
                        organism = synthetic construct
SEQUENCE: 37
QVQLQQSGSE LKKPGASVKV SCKASGYTFT NAGMNWVKQA PGQGLKWMGW INTDSGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG ALPETGG                           457

SEQ ID NO: 38           moltype = AA  length = 457
FEATURE                 Location/Qualifiers
source                  1..457
                        mol_type = protein
                        organism = synthetic construct
SEQUENCE: 38
QVQLQQSGSE LKKPGASVKV SCKASGYTFT AAGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG ALPETGG                           457

SEQ ID NO: 39           moltype = AA  length = 457
FEATURE                 Location/Qualifiers
source                  1..457
                        mol_type = protein
                        organism = synthetic construct
SEQUENCE: 39
QVQLVQSGAE VKKPGASVKV SCKASGYTFT TAGMQWVRQA PGQGLEWMGW INTHSGVPKY  60
AEDFKGRVTI SADTSTSTAY LQLSSLKSED TAVYYCARSG FGSSYWYFDV WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG ALPETGG                           457

SEQ ID NO: 40           moltype = AA  length = 222
FEATURE                 Location/Qualifiers
source                  1..222
                        mol_type = protein
```

-continued

```
                        organism = synthetic construct
SEQUENCE: 40
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGALPET GG                    222

SEQ ID NO: 41           moltype = AA  length = 222
FEATURE                 Location/Qualifiers
source                  1..222
                        mol_type = protein
                        organism = synthetic construct
SEQUENCE: 41
DIQMTQSPSS LSASVGDRVT ITCKASQDVS TAVAWYQQKP GKAPKLLIYS ASYRYTGVPS  60
RFSGSGSGTD FTLTISSLQP EDFAVYYCQQ HYITPLTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGALPET GG                    222
```